(12) United States Patent
Wolf et al.

(10) Patent No.: US 6,579,663 B2
(45) Date of Patent: Jun. 17, 2003

(54) ORGANOMETALLIC MONOACYLARYLPHOSPHINES

(75) Inventors: Jean-Pierre Wolf, Maisprach (CH); Beat Michael Aebli, Basel (CH); Gebhard Hug, Rheinfelden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/037,111

(22) Filed: Oct. 22, 2001

(65) Prior Publication Data

US 2002/0107413 A1 Aug. 8, 2002

Related U.S. Application Data

(62) Division of application No. 09/776,657, filed on Feb. 5, 2001, now Pat. No. 6,399,805.

(30) Foreign Application Priority Data

Feb. 8, 2000 (CH) .............................................. 0255/00

(51) Int. Cl.⁷ .............................. G03F 7/027; C08F 2/46
(52) U.S. Cl. .................... 430/281.1; 430/325; 430/923; 522/18; 522/64
(58) Field of Search ..................... 522/18, 64; 430/325, 430/270.1, 281.1, 923

(56) References Cited

U.S. PATENT DOCUMENTS

| | | | |
|---|---|---|---|
| 4,792,632 A | 12/1988 | Ellrich et al. | 568/15 |
| 5,218,009 A | 6/1993 | Rutsch et al. | 522/16 |
| 5,399,770 A | 3/1995 | Leppard et al. | 568/15 |
| 5,504,236 A | 4/1996 | Fischer et al. | 558/134 |
| 5,534,559 A | 7/1996 | Leppard et al. | 522/64 |
| 5,767,169 A * | 6/1998 | Leppard et al. | 522/64 |
| 6,251,963 B1 * | 6/2001 | Kohler et al. | 522/64 |
| 6,306,555 B1 * | 10/2001 | Schulz et al. | 430/270.1 |

FOREIGN PATENT DOCUMENTS

| | | |
|---|---|---|
| GB | 2292740 | 3/1996 |
| GB | 2310855 | 9/1997 |
| WO | 00/32612 | 6/2000 |

OTHER PUBLICATIONS

Chem. Abstr. 113:40826 of J. Organometa. Chem. by Issleib et al., 382, (1,2), pp. 53–60, (1990).
Chem. Abstr. 99:105512 of DE 3139984 (1983).
Chem. Abstr. 133:43973 of JP 2000169511 (2000).
Derwent Abstr. 91348 for EP 0040721 (Mar. 1984).
Chem Abstr. 125:58878 of Tetrahedron:Assymetry by Kolodiazhnyl et al., 7(4), pp. 967–970, (1996).
Chem. Abstr. 110:232783 of WO 88/08434 (1988).
C. Liotta et al., Tetrahedron Letters, vol. 25, No. 12, pp. 1249–1252 (1984).
K. Issleib et al., Zeitschrift fur Naturforschung, Teil B, vol. 22b, No. 7, 1967, pp. 784–785.
Chem. Abstr. 1968:59656 for K. Issleib et al., Z. Naturforsch., b: Anorg. Chem., Org, Chem., Biochem., Biophys., Biol. (1967), vol. 22 (7), pp. 784–785.

* cited by examiner

Primary Examiner—Rosemary Ashton
(74) Attorney, Agent, or Firm—David R. Crichton

(57) ABSTRACT

Compounds of the formula I

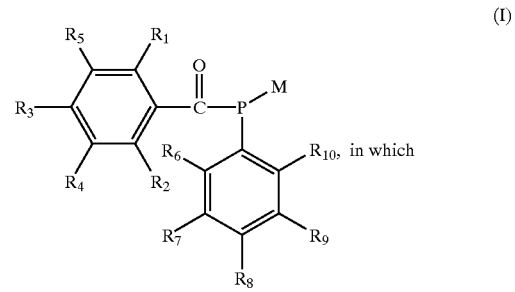

in which $R_1$ and $R_2$ independently of one another are $C_1$–$C_{20}$alkyl, $OR_{11}$, $CF_3$ or halogen; $R_3$, $R_4$ and $R_5$ independently of one another are hydrogen, $C_1$–$C_{20}$alkyl, $OR_{11}$ or halogen; $R_6$, $R_7$, $R_8$, $R_9$ and $R_{10}$ independently of one another are hydrogen, $C_1$–$C_{20}$alkyl; $C_2$–$C_{20}$alkyl which is interrupted once or more than once by nonconsecutive O atoms and which is unsubstituted or substituted by OH and/or SH; or $R_6$, $R_7$, $R_8$, $R_9$ and $R_{10}$ are $OR_{11}$, $SR_{11}$, $N(R_{12})(R_{13})$, phenyl or halogen; $R_{11}$ is $C_1$–$C_{20}$alkyl, $C_3$–$C_8$cycloalkyl, phenyl, benzyl or $C_2$–$C_{20}$alkyl which is interrupted once or more than once by O or S and which is unsubstituted or substituted by OH and/or SH; $R_{12}$ and $R_{13}$ independently of one another are hydrogen, $C_1$14 $C_{20}$alkyl, $C_3$–$C_8$cycloalkyl, phenyl, benzyl or $C_2$-$C_{20}$alkyl which is interrupted once or more than once by nonconsecutive O atoms and which is unsubstituted or substituted by OH and/or SH; or $R_{12}$ and $R_{13}$ together are $C_3$–$C_5$alkylene which can be interrupted by O, S or $NR_{14}$; $R_{14}$ is hydrogen, phenyl, $C_1$–$C_{12}$alkyl or $C_2$–$C_{12}$alkyl which is interrupted once or more than once by O or S and which is unsubstituted or substituted by OH and/or SH; and M is hydrogen, Li, Na or K; are valuable intermediates for the preparation of unsymmetrical bisacylphosphine oxides and monoacylphosphine oxides.

8 Claims, No Drawings

ORGANOMETALLIC MONOACYLARYLPHOSPHINES

This application is a DIVISIONAL of application Ser. No. 09/776,657 filed Feb. 5, 2001 now U.S. Pat. No. 6,399,805.

The present application relates to organometallic monoacylarylphosphines, to the preparation thereof, and to the use thereof as starting materials for the preparation of acylphosphines, acylphosphine oxides or acylphosphine sulfides.

Various metalated phosphines have become known as intermediates in the preparation of acylphosphine oxides. Thus, for example, in EP 40721, acylphosphines are obtained by reaction of acyl halides with metalated diorganophosphines or silylated phosphines or diorganophosphines.

By oxidation of the acyldiorganophosphines, the corresponding acylphosphine oxide photoinitiators can be prepared therefrom. Swiss Patent Application No 2376/98 discloses a one-pot process for the preparation of bisacylphosphine oxides in which dichloroorganophosphines are metalated, then reacted with acyl halides to give the corresponding acylphosphines and then, by oxidation or sulfurization, the bisacylphosphine oxides or bisacylphosphine sulfides are obtained.

Arylacylphosphines and the corresponding metalated compounds are not known in the prior art.

U.S. Pat. No. 5,399,770 discloses a bisacylphosphine oxide having two different acyl groups, and U.S. Pat. No. 5,218,009 specifically discloses a monoacylphosphine oxide having two different non-acyl substituents on the phosphorus atom.

For the technology, readily accessible starting materials for the preparation of acylphosphine oxides and acylphosphine sulfides are of great importance. Of particular interest are starting materials which permit the preparation of "unsymmetrical" bisacylphosphine oxides and bisacylphosphine sulfides, i.e. those with two different acyl groups, in a simple manner.

A process for the preparation of metalated arylacylphosphines which are suitable as starting materials for the preparation of acylphosphine oxide or acylphosphine sulfide photoinitiators has been found. The phosphines, phosphine oxides and phosphine sulfides obtained are novel.

The invention provides compounds of the formula I

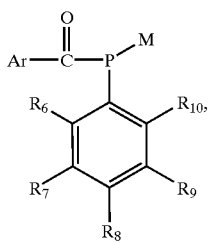

(I)

in which

Ar is a group

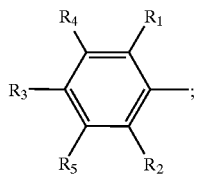

or Ar is cyclopentyl, cyclohexyl, naphthyl, biphenylyl, anthracyl or an O—, S— or N-containing 5- or 6-membered heterocyclic ring, where the radicals cyclopentyl, cyclohexyl, naphthyl, biphenylyl, anthracyl or O—, S— or N-containing 5- or 6-membered heterocyclic ring are unsubstituted or substituted by halogen, $C_1$–$C_4$alkyl and/or $C_1$–$C_4$alkoxy;

$R_1$ and $R_2$ independently of one another are $C_1$–$C_{20}$alkyl, $OR_{11}$, $CF_3$ or halogen;

$R_3$, $R_4$ and $R_5$ independently of one another are hydrogen, $C_1$–$C_{20}$alkyl, $OR_{11}$ or halogen; or in each case two of the radicals $R_1$, $R_2$, $R_3$, $R_4$ and/or $R_5$ together form $C_1$–$C_{20}$alkylene, which can be interrupted by O, S or $NR_{14}$;

$R_6$, $R_7$, $R_8$, $R_9$ and $R_{10}$ independently of one another are hydrogen, $C_1$–$C_{20}$alkyl; $C_2$–$C_{20}$alkyl which is interrupted once or more than once by nonconsecutive O atoms and which is unsubstituted or substituted by OH and/or SH; or $R_6$, $R_7$, $R_8$, $R_9$ and $R_{10}$ $OR_{11}$, phenyl or halogen;

$R_{11}$ is hydrogen, $C_1$–$C_{20}$alkyl, $C_2$–$C_{20}$alkenyl, $C_3$–$C_8$cycloalkyl, phenyl, benzyl or $C_2$–$C_{20}$alkyl which is interrupted once or more than once by O or S and which is unsubstituted or is substituted by OH and/or SH;

$R_{14}$ is hydrogen, phenyl, $C_1$–$C_{12}$alkyl or $C_2$–$C_{12}$alkyl which is interrupted once or more than once by O or S and which is unsubstituted or substituted by OH and/or SH; and M is hydrogen, Li, Na or K.

$C_1$–$C_{24}$alkyl is linear or branched and is, for example, $C_2$–$C_{24}$alkyl, $C_1$–$C_{20}$alkyl, $C_1$–$C_{18}$alkyl, $C_1$–$C_{12}$alkyl, $C_1$–$C_8$alkyl, $C_1$–$C_6$alkyl or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl, icosyl or tetraicosyl.

For example, $R_1$, $R_2$, $R_3$, $R_1'$, $R_2'$ and $R_3'$ are $C_1$–$C_8$alkyl, in particular $C_1$–$C_6$alkyl, preferably $C_1$–$C_4$alkyl, particularly preferably methyl.

$C_1$–$C_{20}$alkyl, $C_1$–$C_{18}$alkyl, $C_1$–$C_{12}$alkyl, $C_1$–$C_6$alkyl and $C_1$–$C_4$alkyl are likewise linear or branched and have, for example, the meanings given above apart from the corresponding number of carbon atoms.

$R_5$, $R_6$, $R_7$, $R_8$, $R_9$, $R_{10}$, $R_{11}$, $R_{12}$, $R_{13}$, $R_{19}$, $R_{20}$, $R_{21}$, $R_{22}$ and $R_{23}$ are, for example $C_1$–$C_8$alkyl, in particular $C_1$–$C_6$alkyl, preferably $C_1$–$C_4$alkyl, for example methyl or butyl.

$C_2$–$C_{24}$alkyl which is interrupted once or more than once by O, S or $NR_{14}$ is, for example, interrupted 1–9 times, e.g. 1–7 times or once or twice, by O, S or $NR_{14}$. If the radicals are interrupted by two or more O, S or $NR_{14}$, then the O atoms, S atoms or $NR_{14}$ groups are in each case separated from one another by at least one methylene group. The O atoms, S atoms or $NR_{14}$ groups are thus not directly consecutive. The alkyl radical can be linear or branched. For example, structural units such as —$CH_2$—O—$CH_3$, —$CH_2CH_2$—O—$CH_2CH_3$, —[$CH_2CH_2O$]$_z$—$CH_3$, where z=1 to 9, —($CH_2CH_2O$)$_7$$CH_2CH_3$, —$CH_2$—CH($CH_3$)—O—$CH_2$—$CH_2CH_3$, —$CH_2$—CH($CH_3$)—O—$CH_2$—$CH_3$, —$CH_2SCH_3$ or —$CH_2$—N($CH_3$)$_2$ arise.

$C_2$–$C_{20}$alkyl, $C_2$–$C_{18}$alkyl, $C_2$–$C_{12}$alkyl which are interrupted by O and optionally by S are likewise linear or branched and can, for example, have the meanings given above apart from the given number of carbon atoms. Here too, the O atoms are not consecutive.

$C_1$–$C_{18}$haloalkyl is $C_1$–$C_{18}$alkyl as described above which is mono- or polysubstituted by halogen. This is, for example, perfluorinated $C_1$–$C_{18}$alkyl. Examples are chloromethyl, trichloromethyl, trifluoromethyl or 2-bromopropyl, in particular trifluoromethyl or trichloromethyl.

$C_3$–$C_{24}$cycloalkyl, e.g. $C_5$–$C_{12}$cycloalkyl, $C_3$–$C_{12}$cycloalkyl, $C_3$–$C_8$cycloalkyl, stands both for individual alkyl ring systems and also bridged alkyl ring systems. Furthermore, the radicals can also contain linear or branched alkyl groups (as described above apart from the corresponding number of carbon atoms). Examples are cyclopropyl, cyclopentyl, cyclohexyl, cyclooctyl, cyclododecyl, cycloicosyl, adamantyl, in particular cyclopentyl and cyclohexyl, preferably cyclohexyl. Further examples are

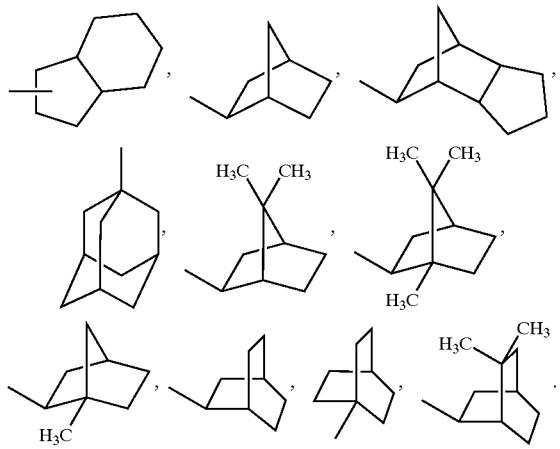

$C_3$–$C_8$cycloalkyl, e.g. $C_3$–$C_6$cycloalkyl, can have the meanings given above apart from the corresponding number of carbon atoms.

$C_3$–$C_{18}$cycloalkyl substituted by $C_1$–$C_{20}$alkyl, $OR_{11}$, $CF_3$ or halogen is preferably tri- or disubstituted in the 2,4,6- or 2,6-positions respectively, of the cycloalkyl ring. Preference is given to 2,4,6-trimethylcyclohexyl and 2,6-dimethoxycyclohexyl.

$C_2$–$C_{24}$alkenyl radicals are mono- or polyunsaturated, and are linear or branched and are, for example, $C_2$–$C_{18}$alkenyl, $C_2$–$C_8$alkenyl, $C_2$–$C_6$alkenyl or $C_2$–$C_4$alkenyl. Examples are vinyl, allyl, methallyl, 1,1-dimethylallyl, 1-butenyl, 2-butenyl, 1,3-pentadienyl, 1-hexenyl, 1-octenyl, decenyl or dodecenyl, in particular allyl. $C_2$–$C_{18}$alkenyl has the same meanings as given above apart from the corresponding number of carbon atoms.

If $C_2$–$C_{24}$alkenyl radicals are interrupted, for example, by O, then the following structures are, for example, included: —$(CH_2)_y$—O—$(CH_2)_x$—CH=$CH_2$, —$(CH_2)_y$—O—$(CH_2)_x$—C($CH_3$)=$CH_2$ or —$(CH_2)_y$—O—CH=$CH_2$, where x and y independently of one another are a number from 1 to 21.

$C_3$–$C_{24}$cycloalkenyl, e.g. $C_5$–$C_{12}$cycloalkenyl, $C_3$–$C_{12}$cycloalkenyl, $C_3$–$C_8$cycloalkenyl, stands both for individual alkyl ring systems and also bridged alkyl ring systems and can be mono- or polyunsaturated, e.g. mono- or diunsaturated. Furthermore, the radicals can also contain linear or branched alkyl groups (as described above apart from the corresponding number of carbon atoms). Examples are cyclopropenyl, cyclopentenyl, cyclohexenyl, cyclooctenyl, cyclododecenyl, cycloicosenyl, in particular cyclopentenyl and cyclohexenyl, preferably cyclohexenyl.

$C_6$–$C_{14}$aryl is, for example, $C_6$–$C_{10}$aryl. Examples are phenyl, naphthyl, biphenylyl, anthracyl or phenanthryl, preferably phenyl or naphthyl, in particular phenyl.

$C_7$–$C_{24}$arylalkyl is, for example, $C_7$–$C_{16}$arylalkyl, $C_7$–$C_{11}$arylalkyl. The alkyl radical in this group can either be linear or branched. Examples are benzyl, phenylethyl, α-methylbenzyl, phenylpentyl, phenylhexyl, α,α-dimethylbenzyl, naphthylmethyl, naphthylethyl, naphthyleth-1-yl or naphthyl-1-methyl-eth-1-yl, in particular benzyl. Substituted $C_7$–$C_{24}$arylalkyl is substituted one to four times, e.g. once, twice or three times, in particular once or twice, on the aryl ring.

$C_8$–$C_{24}$arylcycloalkyl is e.g. $C_9$–$C_{16}$arylcycloalkyl, $C_9$–$C_{13}$arylcycloalkyl and is cycloalkyl which is fused with one or more aryl rings. Examples are

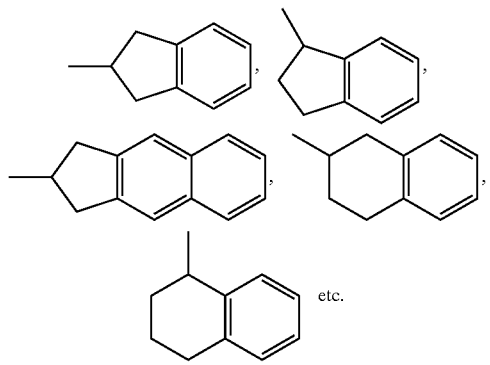

etc.

$C_1$–$C_{12}$alkylthio stands for linear or branched radicals and is, for example, $C_1$–$C_8$alkylthio, $C_1$–$C_6$alkylthio or $C_1$–$C_4$alkylthio. Examples are methylthio, ethylthio, propylthio, isopropylthio, n-butylthio, sec-butylthio, isobutylthio, tert-butylthio, pentylthio, hexylthio, heptylthio, 2,4,4-trimethylpentylthio, 2-ethylhexylthio, octylthio, nonylthio, decylthio or dodecylthio, in particular methylthio, ethylthio, propylthio, isopropylthio, n-butylthio, sec-butylthio, isobutylthio, tert-butylthio, preferably methylthio.

$C_1$–$C_8$alkylthio is likewise linear or branched and has, for example, the meanings given above apart from the corresponding number of carbon atoms.

$C_1$–$C_{24}$alkylene is linear or branched and is, for example, $C_1$–$C_{20}$alkylene, $C_1$–$C_{12}$alkylene, $C_1$–$C_8$alkylene, $C_2$–$C_8$alkylene, $C_1$–$C_4$alkylene, for example methylene, ethylene, propylene, isopropylene, n-butylene, sec-butylene, isobutylene, tert-butylene, pentylene, hexylene, heptylene, octylene, nonylene, decylene, dodecylene, tetradecylene, heptadecylene, octadecylene, icosylene or e.g. $C_1$–$C_{12}$alkylene, for example ethylene, decylene,

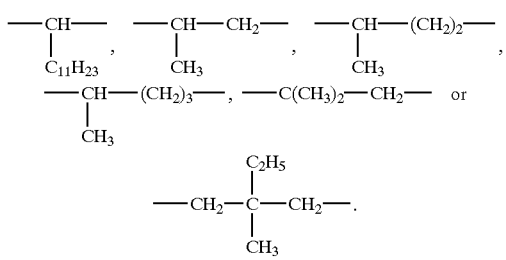

$C_2$–$C_{18}$alkylene is also linear or branched, e.g. $C_2$–$C_8$alkylene or $C_2$–$C_4$alkylene and has the meanings given above apart from the corresponding number of carbon atoms.

If $C_2$–$C_{18}$alkylene is interrupted once or more than once by O, S, or $NR_{14}$, then it is, for example, interrupted 1–9 times, e.g. 1–7 times or once or twice by O, S or $NR_{14}$, and, for example, structural units such as —$CH_2$—O—$CH_2$—, —$CH_2CH_2$—O—$CH_2CH_2$—, —[$CH_2CH_2$O]$_z$—, where z=1 to 9, —($CH_2CH_2$O)$_7CH_2CH_2$—, —$CH_2$—CH($CH_3$)—O—$CH_2$—CH($CH_3$)—, —$CH_2$—S—$CH_2$—, —$CH_2CH_2$—S—$CH_2CH_2$—, —$CH_2CH_2CH_2$—S—$CH_2CH_2CH_2$—, —($CH_2$)$_3$—S—($CH_2$)$_3$—S—($CH_2$)$_3$—, —$CH_2$—($NR_{14}$)—$CH_2$— or —$CH_2CH_2$—($NR_{14}$)—$CH_2CH_2$— arise. The alkylene radicals can be linear or branched and, if the alkylene radicals are interrupted by two or more O, S or $NR_{14}$ groups, then the O, S and $NR_{14}$ are not consecutive, but in each case are separated from one another by at least one methylene group.

$C_2$–$C_{24}$alkenylene is mono- or polyunsaturated and linear or branched and e.g. $C_2$–$C_{18}$-alkenylene or $C_2$–$C_8$alkenylene. Examples are ethenylene, propenylene, butenylene, pentenylene, hexenylene, octenylene, e.g. 1-propenylene, 1-butenylene, 3-butenylene, 2-butenylene, 1,3-pentadienylene, 5-hexenylene or 7-octenylene.

$C_2$–$C_{24}$alkenylene, interrupted once or more than once by O, S, $NR_{14}$, is mono- or polyunsaturated and linear or branched and is, for example, interrupted 1–9 times, e.g. 1–7 times or once or twice, by O, S or $NR_{14}$, where in the case of two or more O, S or $NR_{14}$, these are in each case separated from one another by at least one methylene group. Here, the meanings for $C_2$–$C_{24}$alkenylene are as defined above.

$C_4$–$C_{18}$cycloalkylene is linear or branched and can be either an individual ring or bridged alkyl rings. It is e.g. $C_4$–$C_{12}$cycloalkylene or $C_4$–$C_8$cycloalkylene, for example cyclopentylene, cyclohexylene, cyclooctylene, cyclododecylene, in particular cyclopentylene and cyclohexylene, preferably cyclohexylene. However, $C_4$–$C_{18}$cycloalkylene likewise stands for structural units such as

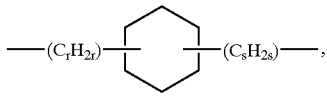

in which r and s independently of one another are 0–12 and the sum r+s is $\leq 12$, or

in which r and s independently of one another are 0–13 and the sum r+s is $\leq 13$.

$C_4$–$C_{18}$cycloalkylene interrupted once or more than once by O, S or $NR_{14}$ stands for cycloalkylene units as described above which can be interrupted either in the ring unit or in the side-chain unit e.g. 1–9 times, 1–7 times or once or twice, by O, S or $NR_{14}$.

$C_3$–$C_{24}$cycloalkenylene is linear or branched and can be either a single ring or bridged rings and is mono- or polyunsaturated. It is e.g. $C_3$–$C_{12}$cycloalkenylene or $C_3$–$C_8$cycloalkenylene, for example cyclopentenylene, cyclohexenylene, cyclooctenylene, cyclododecenylene, in particular cyclopentenylene and cyclohexenylene, preferably cyclohexenylene. $C_3$–$C_{24}$cycloalkenylene also, however, stands for structural units such as

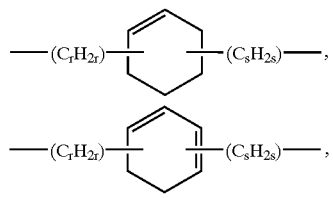

in which r and s independently of another are 0–12 and the sum r+s is $\leq 12$, or

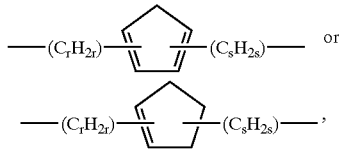

in which r and s independently of one another are 0–13 and the sum r+s is $\leq 13$.

$C_5$–$C_{18}$cycloalkenylene has the meanings given above for $C_3$–$C_{24}$cycloalkenylene apart from the corresponding number of carbon atoms.

$C_3$–$C_{24}$cycloalkenylene interrupted once or more than once by O, S or $NR_{14}$ stands for cycloalkenylene units as described above which can be interrupted either in the ring unit or in the side-chain unit e.g. 1–9 times, 1–7 times or once or twice by O, S or $NR_{14}$. Examples are

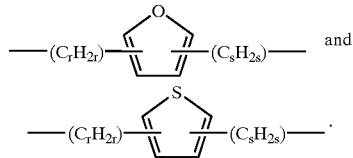

Halogen is fluorine, chlorine, bromine or iodine, in particular fluorine, chlorine and bromine, preferably chlorine. $R_1$, $R_1'$, $R_2$, $R_2'$, $R_3$ and $R_3'$ as halogen are, in particular, chlorine.

If in each case two of the radicals $R_1$, $R_2$, $R_3$, $R_4$ or $R_5$ or in each case two of the radicals $R_1'$, $R_2'$, $R_3'$, $R_4'$ or $R_5'$ form $C_1$–$C_{12}$alkylene, then, for example, the following structures

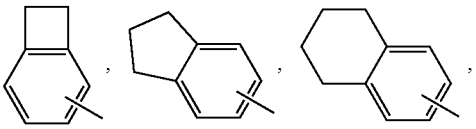

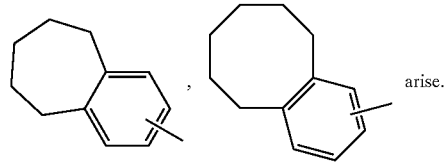

arise.

As a(n) O—, S— or N-containing 5- or 6-membered heterocyclic ring, Ar is e.g. furyl, thienyl, pyrrolyl, oxinyl, dioxinyl or pyridyl. Said heterocyclic radicals can be mono- or polysubstituted, e.g. monosubstituted or disubstituted, by halogen, linear or branched $C_1$–$C_4$alkyl, such as methyl, ethyl, propyl, butyl, and/or $C_1$–$C_4$alkoxy. Examples thereof are dimethylpyridyl, dimethylpyrrolyl or methylfuryl.

Ar is, for example, 2-methylnaphth-2-yl, 2-methoxynaphth-2-yl, 1,3-dimethylnaphth-2-yl, 2,8- dimethylnaphth-1-yl, 1,3-dimethoxynaphth-2-yl, 1,3-dichloronaphth-2-yl, 2,8-dimethoxynaphth-1-yl, 2,4,6-trimethylpyrid-3-yl, 2,4-dimethoxyfuran-3-yl or 2,4,5-trimethylthien-3-yl.

Preference is given to compounds of the formula I in which Ar is a radical

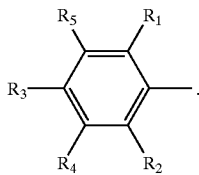

"Styryl" and "methylstyryl" are

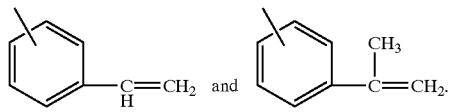

"—N=C=A" is a group —NCO or —NCS.

Cycloalkyl substituted by —N=C=A and $C_1$–$C_4$alkyl is for example isophoroneisocyanate.

In connection with the present application, the term "and/or" means that not only one of the defined alternatives (substituents), but likewise two or more different defined alternatives (substituents) together, i.e. mixtures of different alternatives (substituents) may be present. The term "at least" is intended to define one or more than one, e.g. one or two or three, preferably one or two.

Of particular interest are compounds of the formula I, in which $R_1$ and $R_2$ independently of one another are $C_1$–$C_4$alkyl, $C_1$–$C_4$alkoxy, Cl or $CF_3$, in particular methyl or methoxy.

$R_1$ and $R_2$ are preferably identical.

$R_1$ and $R_2$ are preferably $C_1$–$C_4$alkyl or $C_1$–$C_4$alkoxy.

$R_3$, $R_4$ and $R_5$ in the compounds of the formula I are, in particular, independently of one another hydrogen, $C_1$–$C_4$alkyl, Cl or $C_1$–$C_4$alkoxy, in particular hydrogen, methyl or methoxy. $R_3$ is preferably $C_1$–$C_4$alkyl, or $C_1$–$C_4$alkoxy, in particular methyl, methoxy or hydrogen, and $R_4$ and $R_5$ are hydrogen.

$R_6$, $R_7$, $R_8$, $R_9$ and $R_{10}$ in the compounds of the formula I are, in particular, independently of one another hydrogen, $C_1$–$C_{12}$alkyl; $OR_{11}$, phenyl or halogen, preferably $C_1$–$C_4$alkyl, $C_1$–$C_4$alkoxy, phenyl or halogen. $R_6$, $R_7$, $R_8$, $R_9$ and $R_{10}$ in the compounds of the formula I are preferably hydrogen, $C_1$–$C_4$alkyl, $C_1$–$C_4$alkoxy, in particular hydrogen.

$R_{11}$ in the compounds of the formula I is, for example, hydrogen, $C_1$–$C_{12}$alkyl, cyclopentyl, cyclohexyl, phenyl, benzyl or $C_2$–$C_{12}$alkyl which is interrupted once or more than once by O or S, preferably $C_1$–$C_4$alkyl, cyclopentyl, cyclohexyl, phenyl or benzyl.

Compounds in which $R_{12}$ and $R_{13}$ are e.g. hydrogen, $C_1$–$C_4$alkyl, phenyl or benzyl or $C_2$–$C_{12}$alkyl which is interrupted once or more than once by nonconsecutive O atoms and which is unsubstituted or is substituted by OH and/or SH; or $R_{12}$ and $R_{13}$ together are piperidino, morpholino, or piperazino are likewise of interest. $R_{12}$ and $R_{13}$ are preferably $C_1$–$C_4$alkyl, or $R_{12}$ and $R_{13}$ are together morpholino.

$R_{14}$ in the compounds of the formula I is, in particular, hydrogen, phenyl, $C_1$–$C_4$alkyl or $C_2$–$C_4$alkyl which is interrupted once or more than once by O or S and which is unsubstituted or is substituted by OH and/or SH, preferably hydrogen and $C_1$–$C_4$alkyl.

M in the compounds of the formula I is preferably hydrogen or Li, in particular Li.

Of particular interest are compounds of the formula I in which $R_1$ and $R_2$ independently of one another are $C_1$–$C_{12}$alkyl, $OR_{11}$, $CF_3$ or halogen;

$R_3$, $R_4$ and $R_5$ independently of one another are hydrogen, $C_1$–$C_{12}$alkyl, $OR_{11}$ or halogen;

$R_6$, $R_7$, $R_8$, $R_9$ and $R_{10}$ independently of one another are hydrogen, $C_1$–$C_{12}$alkyl, $OR_{11}$, phenyl or halogen;

$R_{11}$ is hydrogen, $C_1$–$C_{12}$alkyl, cyclohexyl, cyclopentyl, phenyl or benzyl;

$R_{14}$ is hydrogen or $C_1$–$C_{12}$alkyl; and

M is hydrogen or Li.

Examples of compounds of the formula I are lithium 2,6-dimethylbenzoylphenylphosphine; lithium 2,6-diethylbenzoylphenylphosphine; lithium 2,4,6-trimethylbenzoylphenylphosphine; lithium 2,3,4,5,6-pentamethylbenzoylphenylphosphine; lithium 2,3,5,6-tetramethylbenzoylphenylphosphine; lithium 2,4,6-triisopropylbenzoylphenylphosphine; lithium 2,4,5,6-tetramethylbenzoylphenylphosphine; lithium 2,4,6-tri-tert-butylbenzoylphenylphosphine; lithium 2,6-dimethyl-4-tert-butylbenzoylphenylphosphine; lithium 2,6-diphenoxymethylbenzoylphenylphosphine; lithium 2,3,6-trimethylbenzoylphenylphosphine; lithium 2,3,4,6-tetramethylbenzoylphenylphosphine; lithium 2-phenyl-6-methylbenzoylphenylphosphine; lithium 2,4,6-trimethoxybenzoylphenylphosphine; lithium 2,4-dimethoxybenzoylphenylphosphine; lithium 2,3,6-trimethoxybenzoylphenylphosphine; lithium 2,6-diethoxybenzoylphenylphosphine; lithium 2,6-dimethoxy-3,5-dimethylbenzoylphenylphosphine; lithium 2,6-dimethoxy-4-methylbenzoylphenylphosphine; lithium 2,6-dimethoxy-3-bromobenzoylphenylphosphine; lithium 2,6-dimethoxy-3-chlorobenzoylphenylphosphine; lithium 2,6-dimethoxy-3-chloro-5-bromobenzoylphenylphosphine; lithium 2,6-dimethoxy-3,5-dichlorobenzoylphenylphosphine; lithium 2,3,6-trimethoxy-5-bromobenzoylphenylphosphine; lithium 2,6-dichlorobenzoylphenylphosphine; lithium 2,4,6-trichlorobenzoylphenylphosphine; lithium 2,3,6-trichlorobenzoylphenylphosphine; lithium 2,3,5,6-tetrachlorobenzoylphenylphosphine; lithium 2,3,4,5,6-pentachlorobenzoylphenylphosphine; lithium 2,6-dichloro-3-methylbenzoylphenylphosphine; lithium 2-chloro-6-methylbenzoylphenylphosphine; lithium 2-methoxy-3,6-dichlorobenzoylphenylphosphine; lithium 2-methoxy-6-chlorobenzoylphenylphosphine; lithium 2,6-bis(trifluoromethyl)-benzoylphenylphosphine; lithium 2-chloro-6-methylthiobenzoylphenylphosphine; lithium 2,6-dibromobenzoylphenylphosphine; lithium 2,4,6-trimethylbenzoyl-4-methylphenylphosphine; lithium 2,4,6-trimethylbenzoyl-2-methylphenylphosphine; lithium 2,4,6-trimethylbenzoyl-2,4-dimethylphenylphosphine; lithium 2,4,6-trimethylbenzoyl-2,6-dimethylphenylphosphine; lithium 2,4,6-trimethylbenzoyl-2,5-dimethylphenylphosphine; lithium 2,4,6-trimethylbenzoyl-2,4,6-trimethylphenylphosphine; lithium 2,4,6-trimethylbenzoyl-2,6-dimethyl-4-tert-butylphenylphosphine; lithium 2,4,6-trimethylbenzoyl-2,5-diisopropylphenylphosphine; lithium 2,4,6-trimethylbenzoyl-4-phenylphenylphosphine; lithium 2,4,6-trimethylbenzoyl-2-phenylphenylphosphine; lithium 2,4,6- trimethylbenzoyl-4-methoxyphenylphosphine; lithium 2,4,6-trimethylbenzoyl-4-ethoxyphenylphosphine; lithium 2,4,6-trimethylbenzoyl-4-propoxyphenylphosphine; lithium 2,4,6-trimethylbenzoyl-4-butoxyphenylphosphine; lithium 2,4,6-trimethylbenzoyl-4-pentoxyphenylphosphine; lithium 2,4,6-trimethylbenzoyl-4-hexoxyphenylphosphine; lithium 2,4,6-trimethylbenzoyl-4-isopropoxyphenylphosphine; lithium 2,4,6-trimethylbenzoyl-4-isobutoxyphenylphosphine; lithium 2,4,6-trimethylbenzoyl-4-tert-butoxyphenylphosphine; lithium 2,4,6-trimethylbenzoyl-4-(2-ethylhexoxy)phenylphosphine; lithium 2,4,6-trimethylbenzoyl-4-(1-methylpropoxy)phenylphosphine; lithium 2,4,6-trimethylbenzoyl-4-amyloxyphenylphosphine; lithium 2,4,6-trimethylbenzoyl-4-isopentoxyphenylphosphine; lithium 2,4,6-trimethylbenzoyl-4-benzyloxyphenylphosphine; lithium 2,4,6-trimethylbenzoyl-4-phenyloxyphenylphosphine; lithium 2,4,6-trimethylbenzoyl-4-methoxyethoxyphenylphosphine; lithium 2,4,6-trimethylbenzoyl-4-ethoxyethoxyphenylphosphine; lithium 2,4,6-trimethylbenzoyl-2,4-dimethoxyphenylphosphine; lithium 2,4,6-trimethylbenzoyl-2,4-diethoxyphenylphosphine; lithium 2,4,6-trimethylbenzoyl-2,4-dipropoxyphenylphosphine; lithium 2,4,6-trimethylbenzoyl-2,4-dibutoxyphenylphosphine; lithium 2,4,6-trimethylbenzoyl-2,4-dipentoxyphenylphosphine; lithium 2,4,6-trimethylbenzoyl-2,4-dihexoxyphenylphosphine; lithium 2,4,6-trimethylbenzoyl-2,4-diisopropoxyphenylphosphine; lithium 2,4,6-trimethylbenzoyl-2,4-diisobutoxyphenylphosphine; lithium 2,4,6-trimethylbenzoyl-2,4-di-tert-butoxyphenylphosphine; lithium 2,4,6-trimethylbenzoyl-2,4-di(2-ethylhexoxy)phenylphosphine; lithium 2,4,6-trimethylbenzoyl-2,4-di(1-methylpropoxy)phenylphosphine; lithium 2,4,6-trimethylbenzoyl-2,4-diamyloxyphenylphosphine; lithium 2,4,6-trimethylbenzoyl-2,4-diisopentoxyphenylphosphine; lithium 2,4,6-trimethylbenzoyl-2,4-dibenzyloxyphenylphosphine; lithium 2,4,6-trimethylbenzoyl-2,4-diphenoxyphenylphosphine; lithium 2,4,6-trimethylbenzoyl-2,4-dimethoxyethoxyphenylphosphine; lithium 2,4,6-trimethylbenzoyl-2,4-diethoxyethoxyphenylphosphine; lithium 2,4,6-trimethylbenzoyl-2,4,6-trimethoxyphenylphosphine; lithium 2,4,6-trimethylbenzoyl-2,4,6-triethoxyphenylphosphine; lithium 2,4,6-trimethylbenzoyl-2,4,6-tripropoxyphenylphosphine; lithium 2,4,6-trimethylbenzoyl-2,4,6-tributoxyphenylphosphine; lithium 2,4,6-trimethylbenzoyl-2,4,6-tripentoxyphenylphosphine; lithium 2,4,6-trimethylbenzoyl-2,4,6-trihexoxyphenylphosphine; lithium 2,4,6-trimethylbenzoyl-2,4,6-triisopropoxyphenylphosphine; lithium 2,4,6-trimethylbenzoyl-2,4,6-triisobutoxyphenylphosphine; lithium 2,4,6-trimethylbenzoyl-2,4,6-tri-tert-butoxyphenylphosphine; lithium 2,4,6-trimethylbenzoyl-2,4,6-tri(2-ethylhexoxy)phenylphosphine; lithium 2,4,6-trimethylbenzoyl-2,4,6-tri(1-methylpropoxy)phenylphosphine; lithium 2,4,6-trimethylbenzoyl-2,4,6-triamyloxyphenylphosphine; lithium 2,4,6-trimethylbenzoyl-2,4,6-triisopentoxyphenylphosphine; lithium 2,4,6-trimethylbenzoyl-2,4,6-tribenzyloxyphenylphosphine; lithium 2,4,6-trimethylbenzoyl-2,4,6-triphenoxyphenylphosphine; lithium 2,4,6-trimethylbenzoyl-2,4,6-trimethoxyethoxyphenylphosphine; lithium 2,4,6-trimethylbenzoyl-2,4,6-triethoxyethoxyphenylphosphine; lithium 2,4,6-trimethylbenzoyl-2-methyl-4-methoxyphenylphosphine; lithium 2,4,6-trimethylbenzoyl-2-methyl-4-ethoxyphenylphosphine; lithium 2,4,6-trimethylbenzoyl-2-methyl-4-propoxyphenylphosphine; lithium 2,4,6-trimethylbenzoyl-2-methyl-4-butoxyphenylphosphine; lithium 2,4,6-trimethylbenzoyl-2-methyl-4-pentoxyphenylphosphine; lithium 2,4,6-trimethylbenzoyl-2-methyl-4-hexoxyphenylphosphine; lithium 2,4,6-trimethylbenzoyl-2-methyl-4-isopropoxyphenylphosphine; lithium 2,4,6-trimethylbenzoyl-2-methyl-4-isobutoxyphenylphosphine; lithium 2,4,6-trimethylbenzoyl-2-methyl-4-tert-butoxyphenylphosphine; lithium 2,4,6-trimethylbenzoyl-2-methyl-4-(2-ethylhexoxy)phenylphosphine; lithium 2,4,6-trimethylbenzoyl-2-methyl-4-(1-methylpropoxy)phenylphosphine; lithium 2,4,6-trimethylbenzoyl-2-methyl-4-amyloxyphenylphosphine; lithium 2,4,6-trimethylbenzoyl-2-methyl-4-isopentoxyphenylphosphine; lithium 2,4,6-trimethylbenzoyl-2-methyl-4-benzyloxyphenylphosphine; lithium 2,4,6-trimethylbenzoyl-2-methyl-4-phenoxyphenylphosphine; lithium 2,4,6-trimethylbenzoyl-2-methyl-4-methoxyethoxyphenylphosphine; lithium 2,4,6-trimethylbenzoyl-2-methyl-4-ethoxyethoxyphenylphosphine; lithium 2,6-dimethylbenzoyl-4-methylphenylphosphine; lithium 2,6-dimethylbenzoyl-2-methylphenylphosphine; lithium 2,6-dimethylbenzoyl-2,4-dimethylphenylphosphine; lithium 2,6-dimethylbenzoyl-2,6-dimethylphenylphosphine; lithium 2,6-dimethylbenzoyl-2,5-dimethylphenylphosphine; lithium 2,6-dimethylbenzoyl-2,4,6-trimethylphenylphosphine; lithium 2,6-dimethylbenzoyl-2,6-dimethyl-4-tert-butylphenylphosphine; lithium 2,6-dimethylbenzoyl-2,5-diisopropylphenylphosphine; lithium 2,6-dimethylbenzoyl-4-phenylphenylphosphine; lithium 2,6-dimethylbenzoyl-2-phenylphenylphosphine; lithium 2,6-dimethylbenzoyl-4-methoxyphenylphosphine; lithium 2,6-dimethylbenzoyl-4-ethoxyphenylphosphine; lithium 2,6-dimethylbenzoyl-4-propoxyphenylphosphine; lithium 2,6-dimethylbenzoyl-4-butoxyphenylphosphine; lithium 2,6-dimethylbenzoyl-4-pentoxyphenylphosphine; lithium 2,6-dimethylbenzoyl-4-hexoxyphenylphosphine; lithium 2,6-dimethylbenzoyl-4-isopropoxyphenylphosphine; lithium 2,6-dimethylbenzoyl-4-isobutoxyphenylphosphine; lithium 2,6-dimethylbenzoyl-4-tert-butoxyphenylphosphine; lithium 2,6-dimethylbenzoyl-4-(2-ethylhexoxy)phenylphosphine; lithium 2,6-dimethylbenzoyl-4-(1-methylpropoxy)phenylphosphine; lithium 2,6-dimethylbenzoyl-4-amyloxyphenylphosphine; lithium 2,6-dimethylbenzoyl-4-isopentoxyphenylphosphine; lithium 2,6-dimethylbenzoyl-4-benzyloxyphenylphosphine; lithium 2,6-dimethylbenzoyl-4-phenoxyphenylphosphine; lithium 2,6-dimethylbenzoyl-4-methoxyethoxyphenylphosphine; lithium 2,6-dimethylbenzoyl-4-ethoxyethoxyphenylphosphine; lithium 2,6-dimethylbenzoyl-2,4-dimethoxyphenylphosphine; lithium 2,6-dimethylbenzoyl-2,4-diethoxyphenylphosphine; lithium 2,6-dimethylbenzoyl-2,4-dipropoxyphenylphosphine; lithium 2,6-dimethylbenzoyl-2,4-dibutoxyphenylphosphine; lithium 2,6-dimethylbenzoyl-2,4-dipentoxyphenylphosphine; lithium 2,6-dimethylbenzoyl-2,4-dihexoxyphenylphosphine; lithium 2,6-dimethylbenzoyl-2,4-diisopropoxyphenylphosphine; lithium 2,6-dimethylbenzoyl-2,4-diisobutoxyphenylphosphine; lithium 2,6-dimethylbenzoyl-2,4-di-tert-butoxyphenylphosphine; lithium 2,6-dimethylbenzoyl-2,4-di(2-ethylhexoxy)phenylphosphine; lithium 2,6-dimethylbenzoyl-2,4-di(1-methylpropoxy)phenylphosphine; lithium 2,6- dimethylbenzoyl-2,4-diamyloxyphenylphosphine; lithium 2,6-dimethylbenzoyl-2,4-diisopentoxyphenylphosphine; lithium 2,6-dimethylbenzoyl-2,4-dibenzyloxyphenylphosphine; lithium 2,6-dimethylbenzoyl-2,4-diphenoxyphenylphosphine; lithium 2,6-dimethylbenzoyl-2,4-dimethoxyethoxyphenylphosphine; lithium 2,6-dimethylbenzoyl-2,4-diethoxyethoxyphenylphosphine; lithium 2,6-dimethylbenzoyl-2,4,6-trimethoxyphenylphosphine; lithium 2,6-dimethylbenzoyl-2,4,6-triethoxyphenylphosphine; lithium 2,6-dimethylbenzoyl-2,4,6-tripropoxyphenylphosphine; lithium 2,6-dimethylbenzoyl-2,4,6-tributoxyphenylphosphine; lithium 2,6-dimethylbenzoyl-2,4,6-tripentoxyphenylphosphine; lithium 2,6-dimethylbenzoyl-2,4,6-trihexoxyphenylphosphine; lithium 2,6-dimethylbenzoyl-2,4,6-triisopropoxyphenylphosphine; lithium 2,6-dimethylbenzoyl-2,4,6-triisobutoxyphenylphosphine; lithium 2,6-dimethylbenzoyl-2,4,6-tri-tert-butoxyphenylphosphine; lithium 2,6-dimethylbenzoyl-2,4,6-tri(2-ethylhexoxy)phenylphosphine; lithium 2,6-dimethylbenzoyl-2,4,6-tri(1-methylpropoxy)phenylphosphine; lithium 2,6-dimethylbenzoyl-2,4,6-triamyloxyphenylphosphine; lithium 2,6-dimethylbenzoyl-2,4,6-triisopentoxyphenylphosphine; lithium 2,6-dimethylbenzoyl-2,4,6-tribenzyloxyphenylphosphine; lithium 2,6-dimethylbenzoyl-2,4,6-triphenoxyphenylphosphine; lithium 2,6-dimethylbenzoyl-2,4,6-trimethoxyethoxyphenylphosphine; lithium 2,6-dimethylbenzoyl-2,4,6-triethoxyethoxyphenylphosphine; lithium 2,6-dimethylbenzoyl-2-methyl-4-methoxyphenylphosphine; lithium 2,6-dimethylbenzoyl-2-methyl-4-ethoxyphenylphosphine; lithium 2,6-dimethylbenzoyl-2-methyl-4-propoxyphenylphosphine; lithium 2,6-dimethylbenzoyl-2-methyl-4-butoxyphenylphosphine; lithium 2,6-dimethylbenzoyl-2-methyl-4-pentoxyphenylphosphine; lithium 2,6-dimethylbenzoyl-2-methyl-4-hexoxyphenylphosphine; lithium 2,6-dimethylbenzoyl-2-methyl-4-isopropoxyphenylphosphine; lithium 2,6-dimethylbenzoyl-2-methyl-4-isobutoxyphenylphosphine; lithium 2,6-dimethylbenzoyl-2-methyl-4-tert-butoxyphenylphosphine; lithium 2,6-dimethylbenzoyl-2-methyl-4-(2-ethylhexoxy)phenylphosphine; lithium 2,6-dimethylbenzoyl-2-methyl-4-(1-methylpropoxy)phenylphosphine; lithium 2,6-dimethylbenzoyl-2-methyl-4-amyloxyphenylphosphine; lithium 2,6-dimethylbenzoyl-2-methyl-4-isopentoxyphenylphosphine; lithium 2,6-dimethylbenzoyl-2-methyl-4-benzyloxyphenylphosphine; lithium 2,6-dimethylbenzoyl-2-methyl-4-phenoxyphenylphosphine; lithium 2,6-dimethylbenzoyl-2-methyl-4-methoxyethoxyphenylphosphine; lithium 2,6-dimethylbenzoyl-2-methyl-4-ethoxyethoxyphenylphosphine; lithium 2,6-dimethoxybenzoyl-4-methylphenylphosphine; lithium 2,6-dimethoxybenzoyl-2-methylphenylphosphine; lithium 2,6-dimethoxybenzoyl-2,4-dimethylphenylphosphine; lithium 2,6-dimethoxybenzoyl-2,6-dimethylphenylphosphine; lithium 2,6-dimethoxybenzoyl-2,5-dimethylphenylphosphine; lithium 2,6-dimethoxybenzoyl-2,4,6-trimethylphenylphosphine; lithium 2,6-dimethoxybenzoyl-2,6-dimethyl-4-tert-butylphenylphosphine; lithium 2,6-dimethoxybenzoyl-2,5-diisopropylphenylphosphine; lithium 2,6-dimethoxybenzoyl-4-phenylphenylphosphine; lithium 2,6-dimethoxybenzoyl-2-phenylphenylphosphine; lithium 2,6-dimethoxybenzoyl-4-methoxy-phenylphosphine; lithium 2,6-dimethoxybenzoyl-4-ethoxy-phenylphosphine; lithium 2,6-dimethoxybenzoyl-4-propoxy-phenylphosphine; lithium 2,6-dimethoxybenzoyl-4-butoxy-phenylphosphine; lithium 2,6-dimethoxybenzoyl-4-pentoxy-phenylphosphine; lithium 2,6-dimethoxybenzoyl-4-hexoxy-phenylphosphine; lithium 2,6-dimethoxybenzoyl-4-isopropoxy-phenylphosphine; lithium 2,6-dimethoxybenzoyl-4-isobutoxy-phenylphosphine; lithium 2,6-dimethoxybenzoyl-4-tert-butoxy-phenylphosphine; lithium 2,6-dimethoxybenzoyl-4-(2-ethylhexoxy)phenylphosphine; lithium 2,6-dimethoxybenzoyl-4-(1-methylpropoxy)phenylphosphine; lithium 2,6-dimethoxybenzoyl-4-amyloxyphenylphosphine; lithium 2,6-dimethoxybenzoyl-4-isopentoxyphenylphosphine; lithium 2,6-dimethoxybenzoyl-4-benzyloxyphenylphosphine; lithium 2,6-dimethoxybenzoyl-4-phenoxyphenylphosphine; lithium 2,6-dimethoxybenzoyl-4-methoxyethoxyphenylphosphine; lithium 2,6-dimethoxybenzoyl-4-ethoxyethoxyphenylphosphine; lithium 2,6-dimethoxybenzoyl-2,4-dimethoxyphenylphosphine; lithium 2,6-dimethoxybenzoyl-2,4-diethoxyphenylphosphine; lithium 2,6-dimethoxybenzoyl-2,4-dipropoxyphenylphosphine; lithium 2,6-dimethoxybenzoyl-2,4-dibutoxyphenylphosphine; lithium 2,6-dimethoxybenzoyl-2,4-dipentoxyphenylphosphine; lithium 2,6-dimethoxybenzoyl-2,4-dihexoxyphenylphosphine; lithium 2,6-dimethoxybenzoyl-2,4-diisopropoxyphenylphosphine; lithium 2,6-dimethoxybenzoyl-2,4-diisobutoxyphenylphosphine; lithium 2,6-dimethoxybenzoyl-2,4-di-tert-butoxyphenylphosphine; lithium 2,6-dimethoxybenzoyl-2,4-di(2-ethylhexoxy)-phenylphosphine; lithium 2,6-dimethoxybenzoyl-2,4-di(1-methylpropoxy)-phenylphosphine; lithium 2,6-dimethoxybenzoyl-2,4-diamyloxyphenylphosphine; lithium 2,6-dimethoxybenzoyl-2,4-diisopentoxyphenylphosphine; lithium 2,6-dimethoxybenzoyl-2,4-dibenzyloxyphenylphosphine; lithium 2,6-dimethoxybenzoyl-2,4-diphenoxyphenylphosphine; lithium 2,6-dimethoxybenzoyl-2,4-dimethoxyethoxyphenylphosphine; lithium 2,6-dimethoxybenzoyl-2,4-diethoxyethoxyphenylphosphine; lithium 2,6-dimethoxybenzoyl-2,4,6-trimethoxyphenylphosphine; lithium 2,6-dimethoxybenzoyl-2,4,6-triethoxyphenylphosphine; lithium 2,6-dimethoxybenzoyl-2,4,6-tripropoxyphenylphosphine; lithium 2,6-dimethoxybenzoyl-2,4,6-tributoxyphenylphosphine; lithium 2,6-dimethoxybenzoyl-2,4,6-tripentoxyphenylphosphine; lithium 2,6-dimethoxybenzoyl-2,4,6-trihexoxyphenylphosphine; lithium 2,6-dimethoxybenzoyl-2,4,6-triisopropoxyphenylphosphine; lithium 2,6-dimethoxybenzoyl-2,4,6-triisobutoxyphenylphosphine; lithium 2,6-dimethoxybenzoyl-2,4,6-tri-tert-butoxyphenylphosphine; lithium 2,6-dimethoxybenzoyl-2,4,6-tri(2-ethylhexoxy)-phenylphosphine; lithium 2,6-dimethoxybenzoyl-2,4,6-tri(1-methylpropoxy)-phenylphosphine; lithium 2,6-dimethoxybenzoyl-2,4,6-triamyloxyphenylphosphine; lithium 2,6-dimethoxybenzoyl-2,4,6-triisopentoxyphenylphosphine; lithium 2,6-dimethoxybenzoyl-2,4,6-tribenzyloxyphenylphosphine; lithium 2,6-dimethoxybenzoyl-2,4,6-triphenoxyphenylphosphine; lithium 2,6-dimethoxybenzoyl-2,4,6-trimethoxyethoxyphenylphosphine; lithium 2,6-dimethoxybenzoyl-2,4,6-triethoxyethoxyphenylphosphine; lithium 2,6-dimethoxybenzoyl-2-methyl-4- methoxyphenylphosphine; lithium 2,6-dimethoxybenzoyl-2-methyl-4-ethoxyphenylphosphine; lithium 2,6-dimethoxybenzoyl-2-methyl-4-propoxyphenylphosphine; lithium 2,6-dimethoxybenzoyl-2-methyl-4-butoxyphenylphosphine; lithium 2,6-dimethoxybenzoyl-2-methyl-4-pentoxyphenylphosphine; lithium 2,6-dimethoxybenzoyl-2-methyl-4-hexoxyphenylphosphine; lithium 2,6-dimethoxybenzoyl-2-methyl-4-isopropoxyphenylphosphine; lithium 2,6-dimethoxybenzoyl-2-methyl-4-isobutoxyphenylphosphine; lithium 2,6-dimethoxybenzoyl-2-methyl-4-tert-butoxyphenylphosphine; lithium 2,6-dimethoxybenzoyl-2-methyl-4-(2-ethylhexoxy)-phenylphosphine; lithium 2,6-dimethoxybenzoyl-2-methyl-4-(1-methylpropoxy)-phenylphosphine; lithium 2,6-dimethoxybenzoyl-2-methyl-4-amyloxyphenylphosphine; lithium 2,6-dimethoxybenzoyl-2-methyl-4-isopentoxyphenylphosphine; lithium 2,6-dimethoxybenzoyl-2-methyl-4-benzyloxyphenylphosphine; lithium 2,6-dimethoxybenzoyl-2-methyl-4-phenoxyphenylphosphine; lithium 2,6-dimethoxybenzoyl-2-methyl-4-methoxyethoxyphenylphosphine; lithium 2,6-dimethoxybenzoyl-2-methyl-4-ethoxyethoxyphenylphosphine; lithium 2,6-bis(trifluoromethyl)benzoyl-4-methylphenylphosphine; lithium 2,6-bis(trifluoromethyl)benzoyl-2-methylphenylphosphine; lithium 2,6-bis(trifluoromethyl)benzoyl-2,4-dimethylphenylphosphine; lithium 2,6-bis(trifluoromethyl)benzoyl-2,6-dimethylphenylphosphine; lithium 2,6-bis(trifluoromethyl)benzoyl-2,5-dimethylphenylphosphine; lithium 2,6-bis(trifluoromethyl)benzoyl-2,4,6-trimethylphenylphosphine; lithium 2,6-bis(trifluoromethyl)benzoyl-2,6-dimethyl-4-tert-butylphenylphosphine; lithium 2,6-bis(trifluoromethyl)benzoyl-2,5-diisopropylphenylphosphine; lithium 2,6-bis(trifluoromethyl)benzoyl-4-phenylphenylphosphine; lithium 2,6-bis(trifluoromethyl)benzoyl-2-phenylphenylphosphine; lithium 2,6-bis(trifluoromethyl)benzoyl-4-methoxyphenylphosphine; lithium 2,6-bis(trifluoromethyl)benzoyl-4-ethoxyphenylphosphine; lithium 2,6-bis(trifluoromethyl)benzoyl-4-propoxyphenylphosphine; lithium 2,6-bis(trifluoromethyl)benzoyl-4-butoxyphenylphosphine; lithium 2,6-bis(trifluoromethyl)benzoyl-4-pentoxyphenylphosphine; lithium 2,6-bis(trifluoromethyl)benzoyl-4-hexoxyphenylphosphine; lithium 2,6-bis(trifluoromethyl)benzoyl-4-isopropoxyphenylphosphine; lithium 2,6-bis(trifluoromethyl)benzoyl-4-isobutoxyphenylphosphine; lithium 2,6-bis(trifluoromethyl)benzoyl-4-tert-butoxyphenylphosphine; lithium 2,6-bis(trifluoromethyl)benzoyl-4-(2-ethylhexoxy)-phenylphosphine; lithium 2,6-bis(trifluoromethyl)benzoyl-4-(1-methylpropoxy)-phenylphosphine; lithium 2,6-bis(trifluoromethyl)benzoyl-4-amyloxyphenylphosphine; lithium 2,6-bis(trifluoromethyl)benzoyl-4-isopentoxyphenylphosphine; lithium 2,6-bis(trifluoromethyl)benzoyl-4-benzyloxyphenylphosphine; lithium 2,6-bis(trifluoromethyl)benzoyl-4-phenoxyphenylphosphine; lithium 2,6-bis(trifluoromethyl)benzoyl-4-methoxyethoxyphenylphosphine; lithium 2,6-bis(trifluoromethyl)benzoyl-4-ethoxyethoxyphenylphosphine; lithium 2,6-bis(trifluoromethyl)benzoyl-2,4-dimethoxyphenylphosphine; lithium 2,6-bis(trifluoromethyl)benzoyl-2,4-diethoxyphenylphosphine; lithium 2,6-bis(trifluoromethyl)benzoyl-2,4-dipropoxyphenylphosphine; lithium 2,6-bis(trifluoromethyl)benzoyl-2,4-dibutoxyphenylphosphine; lithium 2,6-bis(trifluoromethyl)benzoyl-2,4-dipentoxyphenylphosphine; lithium 2,6-bis(trifluoromethyl)benzoyl-2,4-dihexoxyphenylphosphine; lithium 2,6-bis(trifluoromethyl)benzoyl-2,4-diisopropoxyphenylphosphine; lithium 2,6-bis(trifluoromethyl)benzoyl-2,4-diisobutoxyphenylphosphine; lithium 2,6-bis(trifluoromethyl)benzoyl-2,4-di-tert-butoxyphenylphosphine; lithium 2,6-bis(trifiuoromethyl)benzoyl-2,4-di(2-ethylhexoxy)-phenylphosphine; lithium 2,6-bis(trifluoromethyl)benzoyl-2,4-di(1-methylpropoxy)-phenylphosphine; lithium 2,6-bis(trifluoromethyl)benzoyl-2,4-diamyloxyphenylphosphine; lithium 2,6-bis(trifluoromethyl)benzoyl-2,4-diisopentoxyphenylphosphine; lithium 2,6-bis(trifluoromethyl)benzoyl-2,4-dibenzyloxyphenylphosphine; lithium 2,6-bis(trifluoromethyl)benzoyl-2,4-diphenoxyphenylphosphine; lithium 2,6-bis(trifluoromethyl)benzoyl-2,4-dimethoxyethoxyphenylphosphine; lithium 2,6-bis(trifluoromethyl)benzoyl-2,4-diethoxyethoxyphenylphosphine; lithium 2,6-bis(trifluoromethyl)benzoyl-2,4,6-trimethoxyphenylphosphine; lithium 2,6-bis(trifluoromethyl)benzoyl-2,4,6-triethoxyphenylphosphine; lithium 2,6-bis(trifluoromethyl)benzoyl-2,4,6-tripropoxyphenylphosphine; lithium 2,6-bis(trifluoromethyl)benzoyl-2,4,6-tributoxyphenylphosphine; lithium 2,6-bis(trifluoromethyl)benzoyl-2,4,6-tripentoxyphenylphosphine; lithium 2,6-bis(trifluoromethyl)benzoyl-2,4,6-trihexoxyphenylphosphine; lithium 2,6-bis(trifluoromethyl)benzoyl-2,4,6-triisopropoxyphenylphosphine; lithium 2,6-bis(trifluoromethyl)benzoyl-2,4,6-triisobutoxyphenylphosphine; lithium 2-lithium 2,6-bis(trifluoromethyl)benzoyl-2,4,6-tri(2-ethylhexoxy)-phenylphosphine; lithium 2,6-bis(trifluoromethyl)-benzoyl-2,4,6-tri(2-methylpropoxy)-phenylphosphine; lithium 2,6-bis(trifluoromethyl)benzoyl-2,4,6-triamyloxyphenylphosphine; lithium 2,6-bis(trifluoromethyl)benzoyl-2,4,6-triisopentoxyphenylphosphine; lithium 2,6-bis(trifluoromethyl)benzoyl-2,4,6-tribenzyloxyphenylphosphine; lithium 2,6-bis(trifluoromethyl)benzoyl-2,4,6-triphenoxyphenylphosphine; lithium 2,6-bis(trifluoromethyl)benzoyl-2,4,6-trimethoxyethoxyphenylphosphine; lithium 2,6-bis(trifluoromethyl)benzoyl-2,4,6-triethoxyethoxyphenylphosphine; lithium 2,6-bis(trifluoromethyl)benzoyl-2-methyl-4-methoxyphenylphosphine; lithium 2,6-bis(trifluoromethyl)benzoyl-2-methyl-4-ethoxyphenylphosphine; lithium 2,6-bis(trifluoromethyl)benzoyl-2-methyl4-propoxyphenylphosphine; lithium 2,6-bis(trifluoromethyl)benzoyl-2-methyl-4-butoxyphenylphosphine; lithium 2,6-bis(trifluoromethyl)benzoyl-2-methyl-4-pentoxyphenylphosphine; lithium 2,6-bis(trifluoromethyl)benzoyl-2-methyl-4-hexoxyphenylphosphine; lithium 2,6-bis(trifluoromethyl)benzoyl-2-methyl-4-isopropoxyphenylphosphine; lithium 2,6-bis(trifluoromethyl)benzoyl-2-methyl-4-isobutoxyphenylphosphine; lithium 2,6-bis(trifluoromethyl)benzoyl-2-methyl-4-tert-butoxyphenylphosphine; lithium 2,6-bis(trifluoromethyl)benzoyl-2-methyl-4-(2-ethylhexoxy)-phenylphosphine; lithium 2,6-bis(trifluoromethyl)benzoyl-2-methyl-4-(1-methylpropoxy)-phenylphosphine; lithium 2,6-bis(trifluoromethyl)benzoyl-2-methyl-4-amyloxyphenylphosphine; lithium 2,6-bis (trifluoromethyl)benzoyl-2-methyl-4-isopentoxyphenylphosphine; lithium 2,6-bis(trifluoromethyl)benzoyl-2-methyl-4-benzyloxyphenylphosphine; lithium 2,6-bis(trifluoromethyl)benzoyl-2-methyl-4-phenoxyphenylphosphine; lithium 2,6-bis(trifluoromethyl)benzoyl-2-methyl-4-methoxyethoxyphenylphosphine; lithium 2,6-bis(trifluoromethyl)benzoyl-2-methyl-4-ethoxyethoxyphenylphosphine; lithium 2,6-dichlorobenzoyl-4-methylphenylphosphine; lithium 2,6-dichlorobenzoyl-2-methylphenylphosphine; lithium 2,6-dichlorobenzoyl-2,4-dimethylphenylphosphine; lithium 2,6-dichlorobenzoyl-2,6-dimethylphenylphosphine; lithium 2,6-dichlorobenzoyl-2,5-dimethylphenylphosphine; lithium 2,6-dichlorobenzoyl-2,4,6-trimethylphenylphosphine; lithium 2,6-dichlorobenzoyl-2,6-dimethyl-4-tert-butylphenylphosphine; lithium 2,6-dichlorobenzoyl-2,5-diisopropylphenylphosphine; lithium 2,6-dichlorobenzoyl-4-phenylphenylphosphine; lithium 2,6-dichlorobenzoyl-2-phenylphenylphosphine; lithium 2,6-dichlorobenzoyl-4-methoxyphenylphosphine; lithium 2,6-dichlorobenzoyl-4-ethoxyphenylphosphine; lithium 2,6-dichlorobenzoyl-4-propoxyphenylphosphine; lithium 2,6-dichlorobenzoyl-4-butoxyphenylphosphine; lithium 2,6-dichlorobenzoyl-4-pentoxyphenylphosphine; lithium 2,6-dichlorobenzoyl-4-hexoxyphenylphosphine; lithium 2,6-dichlorobenzoyl-4-isopropoxyphenylphosphine; lithium 2,6-dichlorobenzoyl-4-isobutoxyphenylphosphine; lithium 2,6-dichlorobenzoyl-4-tert-butoxyphenylphosphine; lithium 2,6-dichlorobenzoyl-4-(2-ethylhexoxy)phenylphosphine; lithium 2,6-dichlorobenzoyl-4-(1-methylpropoxy)phenylphosphine; lithium 2,6-dichlorobenzoyl-4-amyloxyphenylphosphine; lithium 2,6-dichlorobenzoyl-4-isopentoxyphenylphosphine; lithium 2,6-dichlorobenzoyl-4-benzyloxyphenylphosphine; lithium 2,6-dichlorobenzoyl-4-phenoxyphenylphosphine; lithium 2,6-dichlorobenzoyl-4-methoxyethoxyphenylphosphine; lithium 2,6-dichlorobenzoyl-4-ethoxyethoxyphenylphosphine; lithium 2,6-dichlorobenzoyl-2,4-dimethoxyphenylphosphine; lithium 2,6-dichlorobenzoyl-2,4-diethoxyphenylphosphine; lithium 2,6-dichlorobenzoyl-2,4-dipropoxyphenylphosphine; lithium 2,6-dichlorobenzoyl-2,4-dibutoxyphenylphosphine; lithium 2,6-dichlorobenzoyl-2,4-dipentoxyphenylphosphine; lithium 2,6-dichlorobenzoyl-2,4-dihexoxyphenylphosphine; lithium 2,6-dichlorobenzoyl-2,4-diisopropoxyphenylphosphine; lithium 2,6-dichlorobenzoyl-2,4-diisobutoxyphenylphosphine; lithium 2,6-dichlorobenzoyl-2,4-di-tert-butoxyphenylphosphine; lithium 2,6-dichlorobenzoyl-2,4-di(2-ethylhexoxy)phenylphosphine; lithium 2,6-dichlorobenzoyl-2,4-di(1-methylpropoxy)phenylphosphine; lithium 2,6-dichlorobenzoyl-2,4-diamyloxyphenylphosphine; lithium 2,6-dichlorobenzoyl-2,4-diisopentoxyphenylphosphine; lithium 2,6-dichlorobenzoyl-2,4-dibenzyloxyphenylphosphine; lithium 2,6-dichlorobenzoyl-2,4-diphenoxyphenylphosphine; lithium 2,6-dichlorobenzoyl-2,4-dimethoxyethoxyphenylphosphine; lithium 2,6-dichlorobenzoyl-2,4-diethoxyethoxyphenylphosphine; lithium 2,6-dichlorobenzoyl-2,4,6-trimethoxyphenylphosphine; lithium 2,6-dichlorobenzoyl-2,4,6-triethoxyphenylphosphine; lithium 2,6-dichlorobenzoyl-2,4,6-tripropoxyphenylphosphine; lithium 2,6-dichlorobenzoyl-2,4,6-tributoxyphenylphosphine; lithium 2,6-dichlorobenzoyl-2,4,6-tripentoxyphenylphosphine; lithium 2,6-dichlorobenzoyl-2,4,6-trihexoxyphenylphosphine; lithium 2,6-dichlorobenzoyl-2,4,6-triisopropoxyphenylphosphine; lithium 2,6-dichlorobenzoyl-2,4,6-triisobutoxyphenylphosphine; lithium 2,6-dichlorobenzoyl-2,4,6-tri-tert-butoxyphenylphosphine; lithium 2,6-dichlorobenzoyl-2,4,6-tri(2-ethylhexoxy)phenylphosphine; lithium 2,6-dichlorobenzoyl-2,4,6-tri(1-methylpropoxy)phenylphosphine; lithium 2,6-dichlorobenzoyl-2,4,6-triamyloxyphenylphosphine; lithium 2,6-dichlorobenzoyl-2,4,6-triisopentoxyphenylphosphine; lithium 2,6-dichlorobenzoyl-2,4,6-tribenzyloxyphenylphosphine; lithium 2,6-dichlorobenzoyl-2,4,6-triphenoxyphenylphosphine; lithium 2,6-dichlorobenzoyl-2,4,6-trimethoxyethoxyphenylphosphine; lithium 2,6-dichlorobenzoyl-2,4,6-triethoxyethoxyphenylphosphine; lithium 2,6-dichlorobenzoyl-2-methyl-4-methoxyphenylphosphine; lithium 2,6-dichlorobenzoyl-2-methyl-4-ethoxyphenylphosphine; lithium 2,6-dichlorobenzoyl-2-methyl-4-propoxyphenylphosphine; lithium 2,6-dichlorobenzoyl-2-methyl-4-butoxyphenylphosphine; lithium 2,6-dichlorobenzoyl-2-methyl-4-pentoxyphenylphosphine; lithium 2,6-dichlorobenzoyl-2-methyl-4-hexoxyphenylphosphine; lithium 2,6-dichlorobenzoyl-2-methyl-4-isopropoxyphenylphosphine; lithium 2,6-dichlorobenzoyl-2-methyl-4-isobutoxyphenylphosphine; lithium 2,6-dichlorobenzoyl-2-methyl-4-tert-butoxyphenylphosphine; lithium 2,6-dichlorobenzoyl-2-methyl-4-(2-ethylhexoxy)phenylphosphine; lithium 2,6-dichlorobenzoyl-2-methyl-4-(1-methylpropoxy)phenylphosphine; lithium 2,6-dichlorobenzoyl-2-methyl-4-amyloxyphenylphosphine; lithium 2,6-dichlorobenzoyl-2-methyl-4-isopentoxyphenylphosphine; lithium 2,6-dichlorobenzoyl-2-methyl-4-benzyloxyphenylphosphine; lithium 2,6-dichlorobenzoyl-2-methyl-4-phenoxyphenylphosphine; lithium 2,6-dichlorobenzoyl-2-methyl-4-methoxyethoxyphenylphosphine; lithium 2,6-dichlorobenzoyl-2-methyl-4-ethoxyethoxyphenylphosphine; lithium 2,3,4,6-tetramethylbenzoyl-4-methylphenylphosphine; lithium 2,3,4,6-tetramethylbenzoyl-2-methylphenylphosphine; lithium 2,3,4,6-tetramethylbenzoyl-2,4-dimethylphenylphosphine; lithium 2,3,4,6-tetramethylbenzoyl-2,6-dimethylphenylphosphine; lithium 2,3,4,6-tetramethylbenzoyl-2,5-dimethylphenylphosphine; lithium 2,3,4,6-tetramethylbenzoyl-2,4,6-trimethylphenylphosphine; lithium 2,3,4,6-tetramethylbenzoyl-2,6-dimethyl-4-tert-butylphenylphosphine; lithium 2,3,4,6-tetramethylbenzoyl-2,5-diisopropylphenylphosphine; lithium 2,3,4,6-tetramethylbenzoyl-4-phenylphenylphosphine; lithium 2,3,4,6-tetramethylbenzoyl-2-phenylphenylphosphine; lithium 2,3,4,6-tetramethylbenzoyl-4-methoxyphenylphosphine; lithium 2,3,4,6-tetramethylbenzoyl-4-ethoxyphenylphosphine; lithium 2,3,4,6-tetramethylbenzoyl-4-propoxyphenylphosphine; lithium 2,3,4,6-tetramethylbenzoyl-4-butoxyphenylphosphine; lithium 2,3,4,6-tetramethylbenzoyl-4-pentoxyphenylphosphine; lithium 2,3,4,6-tetramethylbenzoyl-4-hexoxyphenylphosphine; lithium 2,3,4,6-tetramethylbenzoyl-4-isopropoxyphenylphosphine; lithium 2,3,4,6-tetramethylbenzoyl-4-isobutoxyphenylphosphine; lithium 2,3,4,6-tetramethylbenzoyl-4-tert-butoxyphenylphosphine; lithium 2,3,4,6-tetramethylbenzoyl-4-(2-ethylhexoxy)phenylphosphine; lithium 2,3,4,6-tetramethylbenzoyl-4-(1-methylpropoxy)phenylphosphine; lithium 2,3,4,6-tetramethylbenzoyl-4-amyloxyphenylphosphine; lithium 2,3,4,6-tetramethylbenzoyl-4-isopentoxyphenylphosphine; lithium 2,3,4,6-tetramethylbenzoyl-4-benzyloxyphenylphosphine; lithium 2,3,4,6-tetramethylbenzoyl-4-phenoxyphenylphosphine; lithium 2,3,4,6-tetramethylbenzoyl-4-methoxyethoxyphenylphosphine; lithium 2,3,4,6-tetramethylbenzoyl-4-ethoxyethoxyphenylphosphine; lithium 2,3,4,6-tetramethylbenzoyl-2,4-dimethoxyphenylphosphine; lithium 2,3,4,6-tetramethylbenzoyl-2,4-diethoxyphenylphosphine; lithium 2,3,4,6-tetramethylbenzoyl-2,4-dipropoxyphenylphosphine; lithium 2,3,4,6-tetramethylbenzoyl-2,4-dibutoxyphenylphosphine; lithium 2,3,4,6-tetramethylbenzoyl-2,4-dipentoxyphenylphosphine; lithium 2,3,4,6-tetramethylbenzoyl-2,4-dihexoxyphenylphosphine; lithium 2,3,4,6-tetramethylbenzoyl-2,4-diisopropoxyphenylphosphine; lithium 2,3,4,6-tetramethylbenzoyl-2,4-diisobutoxyphenylphosphine; lithium 2,3,4,6-tetramethylbenzoyl-2,4-di-tert-butoxyphenylphosphine; lithium 2,3,4,6-tetramethylbenzoyl-2,4-di(2-ethylhexoxy)phenylphosphine; lithium 2,3,4,6-tetramethylbenzoyl-2,4-di(1-methylpropoxy)phenylphosphine; lithium 2,3,4,6-tetramethylbenzoyl-2,4-diamyloxyphenylphosphine; lithium 2,3,4,6-tetramethylbenzoyl-2,4-diisopentoxyphenylphosphine; lithium 2,3,4,6-tetramethylbenzoyl-2,4-dibenzyloxyphenylphosphine; lithium 2,3,4,6-tetramethylbenzoyl-2,4-diphenoxyphenylphosphine; lithium 2,3,4,6-tetramethylbenzoyl-2,4-dimethoxyethoxyphenylphosphine; lithium 2,3,4,6-tetramethylbenzoyl-2,4-diethoxyethoxyphenylphosphine; lithium 2,3,4,6-tetramethylbenzoyl-2,4,6-trimethoxyphenylphosphine; lithium 2,3,4,6-tetramethylbenzoyl-2,4,6-triethoxyphenylphosphine; lithium 2,3,4,6-tetramethylbenzoyl-2,4,6-tripropoxyphenylphosphine; lithium 2,3,4,6-tetramethylbenzoyl-2,4,6-tributoxyphenylphosphine; lithium 2,3,4,6-tetramethylbenzoyl-2,4,6-tripentoxyphenylphosphine; lithium 2,3,4,6-tetramethylbenzoyl-2,4,6-trihexoxyphenylphosphine; lithium 2,3,4,6-tetramethylbenzoyl-2,4,6-triisopropoxyphenylphosphine; lithium 2,3,4,6-tetramethylbenzoyl-2,4,6-triisobutoxyphenylphosphine; lithium 2,3,4,6-tetramethylbenzoyl-2,4,6-tri-tert-butoxyphenylphosphine; lithium 2,3,4,6-tetramethylbenzoyl-2,4,6-tri(2-ethylhexoxy)phenylphosphine; lithium 2,3,4,6-tetramethylbenzoyl-2,4,6-tri(1-methylpropoxy)phenylphosphine; lithium 2,3,4,6-tetramethylbenzoyl-2,4,6-triamyloxyphenylphosphine; lithium 2,3,4,6-tetramethylbenzoyl-2,4,6-triisopentoxyphenylphosphine; lithium 2,3,4,6-tetramethylbenzoyl-2,4,6-tribenzyloxyphenylphosphine; lithium 2,3,4,6-tetramethylbenzoyl-2,4,6-triphenoxyphenylphosphine; lithium 2,3,4,6-tetramethylbenzoyl-2,4,6-trimethoxyethoxyphenylphosphine; lithium 2,3,4,6-tetramethylbenzoyl-2,4,6-triethoxyethoxyphenylphosphine; lithium 2,3,4,6-tetramethylbenzoyl-2-methyl-4-methoxyphenylphosphine; lithium 2,3,4,6-tetramethylbenzoyl-2-methyl-4-ethoxyphenylphosphine; lithium 2,3,4,6-tetramethylbenzoyl-2-methyl-4-propoxyphenylphosphine; lithium 2,3,4,6-tetramethylbenzoyl-2-methyl-4-butoxyphenylphosphine; lithium 2,3,4,6-tetramethylbenzoyl-2-methyl-4-pentoxyphenylphosphine; lithium 2,3,4,6-tetramethylbenzoyl-2-methyl-4-hexoxyphenylphosphine; lithium 2,3,4,6-tetramethylbenzoyl-2-methyl-4-isopropoxyphenylphosphine; lithium 2,3,4,6-tetramethylbenzoyl-2-methyl-4-isobutoxyphenylphosphine; lithium 2,3,4,6-tetramethylbenzoyl-2-methyl-4-tert-butoxyphenylphosphine; lithium 2,3,4,6-tetramethylbenzoyl2-methyl-4-(2-ethylhexoxy)phenylphosphine; lithium 2,3,4,6-tetramethylbenzoyl-2-methyl-4-(1-methylpropoxy)phenylphosphine; lithium 2,3,4,6-tetramethylbenzoyl-2-methyl-4-amyloxyphenylphosphine; lithium 2,3,4,6-tetramethylbenzoyl-2-methyl-4-isopentoxyphenylphosphine; lithium 2,3,4,6-tetramethylbenzoyl-2-methyl-4-benzyloxyphenylphosphine; lithium 2,3,4,6-tetramethylbenzoyl-2-methyl-4-phenoxyphenylphosphine; lithium 2,3,4,6-tetramethylbenzoyl-2-methyl-4-methoxyethoxyphenylphosphine; lithium 2,3,4,6-tetramethylbenzoyl-2-methyl-4-ethoxyethoxyphenylphosphine; lithium 2,4,6-trimethoxybenzoyl-4-methylphenylphosphine; lithium 2,4,6-trimethoxybenzoyl-2-methylphenylphosphine; lithium 2,4,6-trimethoxybenzoyl-2,4-dimethylphenylphosphine; lithium 2,4,6-trimethoxybenzoyl-2,6-dimethylphenylphosphine; lithium 2,4,6-trimethoxybenzoyl-2,5-dimethylphenylphosphine; lithium 2,4,6-trimethoxybenzoyl-2,4,6-trimethylphenylphosphine; lithium 2,4,6-trimethoxybenzoyl-2,6-dimethyl-4-tert-butylphenylphosphine; lithium 2,4,6-trimethoxybenzoyl-2,5-diisopropylphenylphosphine; lithium 2,4,6-trimethoxybenzoyl-4-phenylphenylphosphine; lithium 2,4,6-trimethoxybenzoyl-2-phenylphenylphosphine; lithium 2,4,6-trimethoxybenzoyl-4-methoxyphenylphosphine; lithium 2,4,6-trimethoxybenzoyl-4-ethoxyphenylphosphine; lithium 2,4,6-trimethoxybenzoyl-4-propoxyphenylphosphine; lithium 2,4,6-trimethoxybenzoyl-4-butoxyphenylphosphine; lithium 2,4,6-trimethoxybenzoyl-4-pentoxyphenylphosphine; lithium 2,4,6-trimethoxybenzoyl-4-hexoxyphenylphosphine; lithium 2,4,6-trimethoxybenzoyl-4-isopropoxyphenylphosphine; lithium 2,4,6-trimethoxybenzoyl-4-isobutoxyphenylphosphine; lithium 2,4,6-trimethoxybenzoyl-4-tert-butoxyphenylphosphine; lithium 2,4,6-trimethoxybenzoyl-4-(2-ethylhexoxy)phenylphosphine; lithium 2,4,6-trimethoxybenzoyl-4-(1-methylpropoxy)phenylphosphine; lithium 2,4,6-trimethoxybenzoyl-4-amyloxyphenylphosphine; lithium 2,4,6-trimethoxybenzoyl-4-isopentoxyphenylphosphine; lithium 2,4,6-trimethoxybenzoyl-4-benzyloxyphenylphosphine; lithium 2,4,6-trimethoxybenzoyl-4-phenoxyphenylphosphine; lithium 2,4,6-trimethoxybenzoyl-4-methoxyethoxyphenylphosphine; lithium 2,4,6-trimethoxybenzoyl-4-ethoxyethoxyphenylphosphine; lithium 2,4,6-trimethoxybenzoyl-2,4-dimethoxyphenylphosphine; lithium 2,4,6-trimethoxybenzoyl-2,4-diethoxyphenylphosphine; lithium 2,4,6-trimethoxybenzoyl-2,4-dipropoxyphenylphosphine; lithium 2,4,6-trimethoxybenzoyl-2,4-dibutoxyphenylphosphine; lithium 2,4,6-trimethoxybenzoyl-2,4-dipentoxyphenylphosphine; lithium 2,4,6-trimethoxybenzoyl-2,4-dihexoxyphenylphosphine; lithium 2,4,6-trimethoxybenzoyl-2,4-diisopropoxyphenylphosphine; lithium 2,4,6-trimethoxybenzoyl-2,4-diisobutoxyphenylphosphine; lithium 2,4,6-trimethoxybenzoyl-2,4-di-tert-butoxyphenylphosphine; lithium 2,4,6-trimethoxybenzoyl-2,4-di(2-ethylhexoxy)phenylphosphine; lithium 2,4,6-trimethoxybenzoyl-2,4-di(1-methylpropoxy)

phenylphosphine; lithium 2,4,6-trimethoxybenzoyl-2,4-diamyloxyphenylphosphine; lithium 2,4,6-trimethoxybenzoyl-2,4-diisopentoxyphenylphosphine; lithium 2,4,6-trimethoxybenzoyl-2,4-dibenzyloxyphenylphosphine; lithium 2,4,6-trimethoxybenzoyl-2,4-diphenoxyphenylphosphine; lithium 2,4,6-trimethoxybenzoyl-2,4-dimethoxyethoxyphenylphosphine; lithium 2,4,6-trimethoxybenzoyl-2,4-diethoxyethoxyphenylphosphine; lithium 2,4,6-trimethoxybenzoyl-2,4,6-trimethoxyphenylphosphine; lithium 2,4,6-trimethoxybenzoyl-2,4,6-triethoxyphenylphosphine; lithium 2,4,6-trimethoxybenzoyl-2,4,6-tripropoxyphenylphosphine; lithium 2,4,6-trimethoxybenzoyl-2,4,6-tributoxyphenylphosphine; lithium 2,4,6-trimethoxybenzoyl-2,4,6-tripentoxyphenylphosphine; lithium 2,4,6-trimethoxybenzoyl-2,4,6-trihexoxyphenylphosphine; lithium 2,4,6-trimethoxybenzoyl-2,4,6-triisopropoxyphenylphosphine; lithium 2,4,6-trimethoxybenzoyl-2,4,6-triisobutoxyphenylphosphine; lithium 2,4,6-trimethoxybenzoyl-2,4,6-tri-tert-butoxyphenylphosphine; lithium 2,4,6-trimethoxybenzoyl-2,4,6-tri(2-ethylhexoxy)phenylphosphine; lithium 2,4,6-trimethoxybenzoyl-2,4,6-tri(1-methylpropoxy)phenylphosphine; lithium 2,4,6-trimethoxybenzoyl-2,4,6-triamyloxyphenylphosphine; lithium 2,4,6-trimethoxybenzoyl-2,4,6-triisopentoxyphenylphosphine; lithium 2,4,6-trimethoxybenzoyl-2,4,6-tribenzyloxyphenylphosphine; lithium 2,4,6-trimethoxybenzoyl-2,4,6-triphenoxyphenylphosphine; lithium 2,4,6-trimethoxybenzoyl-2,4,6-trimethoxyethoxyphenylphosphine; lithium 2,4,6-trimethoxybenzoyl-2,4,6-triethoxyethoxyphenylphosphine; lithium 2,4,6-trimethoxybenzoyl-2-methyl-4-methoxyphenylphosphine; lithium 2,4,6-trimethoxybenzoyl-2-methyl-4-ethoxyphenylphosphine; lithium 2,4,6-trimethoxybenzoyl-2-methyl-4-propoxyphenylphosphine; lithium 2,4,6-trimethoxybenzoyl-2-methyl-4-butoxyphenylphosphine; lithium 2,4,6-trimethoxybenzoyl-2-methyl-4-pentoxyphenylphosphine; lithium 2,4,6-trimethoxybenzoyl-2-methyl-4-hexoxyphenylphosphine; lithium 2,4,6-trimethoxybenzoyl-2-methyl-4-isopropoxyphenylphosphine; lithium 2,4,6-trimethoxybenzoyl-2-methyl-4-isobutoxyphenylphosphine; lithium 2,4,6-trimethoxybenzoyl-2-methyl-4-tert-butoxyphenylphosphine; lithium 2,4,6-trimethoxybenzoyl-2-methyl-4-(2-ethylhexoxy)phenylphosphine; lithium 2,4,6-trimethoxybenzoyl-2-methyl-4-(1-methylpropoxy)phenylphosphine; lithium 2,4,6-trimethoxybenzoyl-2-methyl-4-amyloxyphenylphosphine; lithium 2,4,6-trimethoxybenzoyl-2-methyl-4-isopentoxyphenylphosphine; lithium 2,4,6-trimethoxybenzoyl-2-methyl-4-benzyloxyphenylphosphine; lithium 2,4,6-trimethoxybenzoyl-2-methyl-4-phenoxyphenylphosphine; lithium 2,4,6-trimethoxybenzoyl-2-methyl-4-methoxyethoxyphenylphosphine; lithium 2,4,6-trimethoxybenzoyl-2-methyl-4-ethoxyethoxyphenylphosphine; lithium 2,6-dimethyl-4-tert-butylbenzoyl-4-methylphenylphosphine; lithium 2,6-dimethyl-4-tert-butylbenzoyl-2-methylphenylphosphine; lithium 2,6-dimethyl-4-tert-butylbenzoyl-2,4-dimethylphenylphosphine; lithium 2,6-dimethyl-4-tert-butylbenzoyl-2,6-dimethylphenylphosphine; lithium 2,6-dimethyl-4-tert-butylbenzoyl-2,5-dimethylphenylphosphine; lithium 2,6-dimethyl-4-tert-butylbenzoyl-2,4,6-trimethylphenylphosphine; lithium 2,6-dimethyl-4-tert-butylbenzoyl-2,6-dimethyl-4-tert-butylphenylphosphine; lithium 2,6-dimethyl-4-tert-butylbenzoyl-2,5-diisopropylphenylphosphine; lithium 2,6-dimethyl-4-tert-butylbenzoyl-4-phenylphenylphosphine; lithium 2,6-dimethyl-4-tert-butylbenzoyl-2-phenylphenylphosphine; lithium 2,6-dimethyl-4-tert-butylbenzoyl-4-methoxyphenylphosphine; lithium 2,6-dimethyl-4-tert-butylbenzoyl-4-ethoxyphenylphosphine; lithium 2,6-dimethyl-4-tert-butylbenzoyl-4-propoxyphenylphosphine; lithium 2,6-dimethyl-4-tert-butylbenzoyl-4-butoxyphenylphosphine; lithium 2,6-dimethyl-4-tert-butylbenzoyl-4-pentoxyphenylphosphine; lithium 2,6-dimethyl-4-tert-butylbenzoyl-4-hexoxyphenylphosphine; lithium 2,6-dimethyl-4-tert-butylbenzoyl-4-isopropoxyphenylphosphine; lithium 2,6-dimethyl-4-tert-butylbenzoyl-4-isobutoxyphenylphosphine; lithium 2,6-dimethyl-4-tert-butylbenzoyl-4-tert-butoxyphenylphosphine; lithium 2,6-dimethyl-4-tert-butylbenzoyl-4-(2-ethylhexoxy)phenylphosphine; lithium 2,6-dimethyl-4-tert-butylbenzoyl-4-(1-methylpropoxy)phenylphosphine, lithium 2,6-dimethyl-4-tert-butylbenzoyl-4-amyloxyphenylphosphine; lithium 2,6-dimethyl-4-tert-butylbenzoyl-4-isopentoxyphenylphosphine; lithium 2,6-dimethyl-4-tert-butylbenzoyl-4-benzyloxyphenylphosphine; lithium 2,6-dimethyl-4-tert-butylbenzoyl-4-phenoxyphenylphosphine; lithium 2,6-dimethyl-4-tert-butylbenzoyl-4-methoxyethoxyphenylphosphine; lithium 2,6-dimethyl-4-tert-butylbenzoyl-4-ethoxyethoxyphenylphosphine; lithium 2,6-dimethyl-4-tert-butylbenzoyl-2,4-dimethoxyphenylphosphine; lithium 2,6-dimethyl-4-tert-butylbenzoyl-2,4-diethoxyphenylphosphine; lithium 2,6-dimethyl-4-tert-butylbenzoyl-2,4-dipropoxyphenylphosphine; lithium 2,6-dimethyl-4-tert-butylbenzoyl-2,4-dibutoxyphenylphosphine; lithium 2,6-dimethyl-4-tert-butylbenzoyl-2,4-dipentoxyphenylphosphine; lithium 2,6-dimethyl-4-tert-butylbenzoyl-2,4-dihexoxyphenylphosphine; lithium 2,6-dimethyl-4-tert-butylbenzoyl-2,4-diisopropoxyphenylphosphine; lithium 2,6-dimethyl-4-tert-butylbenzoyl-2,4-diisobutoxyphenylphosphine; lithium 2,6-dimethyl-4-tert-butylbenzoyl-2,4-di-tert-butoxyphenylphosphine; lithium 2,6-dimethyl-4-tert-butylbenzoyl-2,4-di(2-ethylhexoxy)phenylphosphine; lithium 2,6-dimethyl-4-tert-butylbenzoyl-2,4-di(1-methylpropoxy)phenylphosphine; lithium 2,6-dimethyl-4-tert-butylbenzoyl-2,4-diamyloxyphenylphosphine; lithium 2,6-dimethyl-4-tert-butylbenzoyl-2,4-diisopentoxyphenylphosphine; lithium 2,6-dimethyl-4-tert-butylbenzoyl-2,4-dibenzyloxyphenylphosphine; lithium 2,6-dimethyl-4-tert-butylbenzoyl-2,4-diphenoxyphenylphosphine; lithium 2,6-dimethyl-4-tert-butylbenzoyl-2,4-dimethoxyethoxyphenylphosphine; lithium 2,6-dimethyl-4-tert-butylbenzoyl-2,4-diethoxyethoxyphenylphosphine; lithium 2,6-dimethyl-4-tert-butylbenzoyl-2,4,6-trimethoxyphenylphosphine; lithium 2,6-dimethyl-4-tert-butylbenzoyl-2,4,6-triethoxyphenylphosphine; lithium 2,6-dimethyl-4-tert-butylbenzoyl-2,4,6-tripropoxyphenylphosphine; lithium 2,6-dimethyl-4-tert-butylbenzoyl-2,4,6-tributoxyphenylphosphine; lithium 2,6-dimethyl-4-tert-butylbenzoyl-2,4,6-tripentoxyphenylphosphine; lithium 2,6-dimethyl-4-tert-butylbenzoyl-2,4,6-trihexoxyphenylphosphine; lithium 2,6-dimethyl-4-tert-butylbenzoyl-2,4,6-triisopropoxyphenylphosphine; lithium 2,6-dimethyl-4-tert-butylbenzoyl-2,4,6- triisobutoxyphenylphosphine; lithium 2,6-dimethyl-4-tert-butylbenzoyl-2,4,6-tri-tert-butoxyphenylphosphine; lithium 2,6-dimethyl-4-tert-butylbenzoyl-2,4,6-tri(2-ethylhexoxy) phenylphosphine; lithium 2,6-dimethyl-4-tert-butylbenzoyl-2,4,6-tri(1-methylpropoxy)phenylphosphine; lithium 2,6-dimethyl-4-tert-butylbenzoyl-2,4,6-triamyloxyphenylphosphine; lithium 2,6-dimethyl-4-tert-butylbenzoyl-2,4,6-triisopentoxyphenylphosphine; lithium 2,6-dimethyl-4-tert-butylbenzoyl-2,4,6-tribenzyloxyphenylphosphine; lithium 2,6-dimethyl-4-tert-butylbenzoyl-2,4,6-triphenoxyphenylphosphine; lithium 2,6-dimethyl-4-tert-butylbenzoyl-2,4,6-triphenoxyphenylphosphine; lithium 2,6-dimethyl-4-tert-butylbenzoyl-2,4,6-triethoxyethoxyphenylphosphine; lithium 2,6-dimethyl-4-tert-butylbenzoyl-2-methyl-4-methoxyphenylphosphine; lithium 2,6-dimethyl-4-tert-butylbenzoyl-2-methyl-4-ethoxyphenylphosphine; lithium 2,6-dimethyl-4-tert-butylbenzoyl-2-methyl-4-propoxyphenylphosphine; lithium 2,6-dimethyl-4-tert-butylbenzoyl-2-methyl-4-butoxyphenylphosphine; lithium 2,6-dimethyl-4-tert-butylbenzoyl-2-methyl-4-pentoxyphenylphosphine; lithium 2,6-dimethyl-4-tert-butylbenzoyl-2-methyl-4-hexoxyphenylphosphine; lithium 2,6-dimethyl-4-tert-butylbenzoyl-2-methyl-4-isopropoxyphenylphosphine; lithium 2,6-dimethyl-4-tert-butylbenzoyl-2-methyl-4-isobutoxyphenylphosphine; lithium 2,6-dimethyl-4-tert-butylbenzoyl-2-methyl-4-tert-butoxyphenylphosphine; lithium 2,6-dimethyl-4-tert-butylbenzoyl-2-methyl-4-(2-ethylhexoxy)phenylphosphine; lithium 2,6-dimethyl-4-tert-butylbenzoyl-2-methyl-4-(1-methylpropoxy)phenylphosphine; lithium 2,6-dimethyl-4-tert-butylbenzoyl-2-methyl-4-amyloxyphenylphosphine; lithium 2,6-dimethyl-4-tert-butylbenzoyl-2-methyl-4-isopentoxyphenylphosphine; lithium 2,6-dimethyl-4-tert-butylbenzoyl-2-methyl-4-benzyloxyphenylphosphine; lithium 2,6-dimethyl-4-tert-butylbenzoyl-2-methyl-4-phenoxyphenylphosphine; lithium 2,6-dimethyl-4-tert-butylbenzoyl-2-methyl-4-methoxyethoxyphenylphosphine; lithium 2,6-dimethyl-4-tert-butylbenzoyl-2-methyl-4-ethoxyethoxyphenylphosphine; lithium 2-chloro-6-methylbenzoyl-4-methylphenylphosphine; lithium 2-chloro-6-methylbenzoyl-2-methylphenylphosphine; lithium 2-chloro-6-methylbenzoyl-2,4-dimethylphenylphosphine; lithium 2-chloro-6-methylbenzoyl-2,6-dimethylphenylphosphine; lithium 2-chloro-6-methylbenzoyl-2,5-dimethylphenylphosphine; lithium 2-chloro-6-methylbenzoyl-2,4,6-trimethylphenylphosphine; lithium 2-chloro-6-methylbenzoyl-2,6-dimethyl-4-tert-butylphenylphosphine; lithium 2-chloro-6-methylbenzoyl-2,5-diisopropylphenylphosphine; lithium 2-chloro-6-methylbenzoyl-4-phenylphenylphosphine; lithium 2-chloro-6-methylbenzoyl-2-phenylphenylphosphine; lithium 2-chloro-6-methylbenzoyl-4-methoxyphenylphosphine; lithium 2-chloro-6-methylbenzoyl-4-ethoxyphenylphosphine; lithium 2-chloro-6-methylbenzoyl-4-propoxyphenylphosphine; lithium 2-chloro-6-methylbenzoyl-4-butoxyphenylphosphine; lithium 2-chloro-6-methylbenzoyl-4-pentoxyphenylphosphine; lithium 2-chloro-6-methylbenzoyl-4-hexoxyphenylphosphine; lithium 2-chloro-6-methylbenzoyl-4-isopropoxyphenylphosphine; lithium 2-chloro-6-methylbenzoyl-4-isobutoxyphenylphosphine; lithium 2-chloro-6-methylbenzoyl-4-tert-butoxyphenylphosphine; lithium 2-chloro-6-methylbenzoyl-4-(2-ethylhexoxy)phenylphosphine; lithium 2-chloro-6-methylbenzoyl-4-(1-methylpropoxy) phenylphosphine; lithium 2-chloro-6-methylbenzoyl-4-amyloxyphenylphosphine; lithium 2-chloro-6-methylbenzoyl-4-isopentoxyphenylphosphine; lithium 2-chloro-6-methylbenzoyl-4-benzyloxyphenylphosphine; lithium 2-chloro-6-methylbenzoyl-4-phenoxyphenylphosphine; lithium 2-chloro-6-methylbenzoyl-4-methoxyethoxyphenylphosphine; lithium 2-chloro-6-methylbenzoyl-4-ethoxyethoxyphenylphosphine; lithium 2-chloro-6-methylbenzoyl-2,4-dimethoxyphenylphosphine; lithium 2-chloro-6-methylbenzoyl-2,4-diethoxyphenylphosphine; lithium 2-chloro-6-methylbenzoyl-2,4-dipropoxyphenylphosphine; lithium 2-chloro-6-methylbenzoyl-2,4-dibutoxyphenylphosphine; lithium 2-chloro-6-methylbenzoyl-2,4-dipentoxyphenylphosphine; lithium 2-chloro-6-methylbenzoyl-2,4-dihexoxyphenylphosphine; lithium 2-chloro-6-methylbenzoyl-2,4-diisopropoxyphenylphosphine; lithium 2-chloro-6-methylbenzoyl-2,4-diisobutoxyphenylphosphine; lithium 2-chloro-6-methylbenzoyl-2,4-di-tert-butoxyphenylphosphine; lithium 2-chloro-6-methylbenzoyl-2,4-di(2-ethylhexoxy) phenylphosphine; lithium 2-chloro-6-methylbenzoyl-2,4-di(1-methylpropoxy)phenylphosphine; lithium 2-chloro-6-methylbenzoyl-2,4-diamyloxyphenylphosphine; lithium 2-chloro-6-methylbenzoyl-2,4-diisopentoxyphenylphosphine; lithium 2-chloro-6-methylbenzoyl-2,4-dibenzyloxyphenylphosphine; lithium 2-chloro-6-methylbenzoyl-2,4-diphenoxyphenylphosphine; lithium 2-chloro-6-methylbenzoyl-2,4-dimethoxyethoxyphenylphosphine; lithium 2-chloro-6-methylbenzoyl-2,4-diethoxyethoxyphenylphosphine; lithium 2-chloro-6-methylbenzoyl-2,4,6-trimethoxyphenylphosphine; lithium 2-chloro-6-methylbenzoyl-2,4,6-triethoxyphenylphosphine; lithium 2-chloro-6-methylbenzoyl-2,4,6-tripropoxyphenylphosphine; lithium 2-chloro-6-methylbenzoyl-2,4,6-tributoxyphenylphosphine; lithium 2-chloro-6-methylbenzoyl-2,4,6-tripentoxyphenylphosphine; lithium 2-chloro-6-methylbenzoyl-2,4,6-trihexoxyphenylphosphine; lithium 2-chloro-6-methylbenzoyl-2,4,6-triisopropoxyphenylphosphine; lithium 2-chloro-6-methylbenzoyl-2,4,6-triisobutoxyphenylphosphine; lithium 2-chloro-6-methylbenzoyl-2,4,6-tri-tert-butoxyphenylphosphine; lithium 2-chloro-6-methylbenzoyl-2,4,6-tri(2-ethylhexoxy)phenylphosphine; lithium 2-chloro-6-methylbenzoyl-2,4,6-tri(1-methylpropoxy)phenylphosphine; lithium 2-chloro-6-methylbenzoyl-2,4,6-triamyloxyphenylphosphine; lithium 2-chloro-6-methylbenzoyl-2,4,6-triisopentoxyphenylphosphine; lithium 2-chloro-6-methylbenzoyl-2,4,6-tribenzyloxyphenylphosphine; lithium 2-chloro-6-methylbenzoyl-2,4,6-triphenoxyphenylphosphine; lithium 2-chloro-6-methylbenzoyl-2,4,6-trimethoxyethoxyphenylphosphine; lithium 2-chloro-6-methylbenzoyl-2,4,6-triethoxyethoxyphenylphosphine; lithium 2-chloro-6-methylbenzoyl-2-methyl-4-methoxyphenylphosphine; lithium 2-chloro-6-methylbenzoyl-2-methyl-4-ethoxyphenylphosphine; lithium 2-chloro-6-methylbenzoyl-2-methyl-4-propoxyphenylphosphine; lithium 2-chloro-6-methylbenzoyl-2-methyl-4-butoxyphenylphosphine; lithium 2-chloro-6-methylbenzoyl-2-methyl-4-pentoxyphenylphosphine; lithium 2-chloro-6-methylbenzoyl-2-methyl-4-hexoxyphenylphosphine; lithium 2-chloro-6-methylbenzoyl-2-methyl-4- isopropoxyphenylphosphine; lithium 2-chloro-6-methylbenzoyl-2-methyl-4-isobutoxyphenylphosphine; lithium 2-chloro-6-methylbenzoyl-2-methyl-4-tert-butoxyphenylphosphine; lithium 2-chloro-6-methylbenzoyl-2-methyl-4-(2-ethylhexoxy)phenylphosphine; lithium 2-chloro-6-methylbenzoyl-2-methyl-4-(1-methylpropoxy)phenylphosphine; lithium 2-chloro-6-methylbenzoyl-2-methyl-4-amyloxyphenylphosphine; lithium 2-chloro-6-methylbenzoyl-2-methyl-4-isopentoxyphenylphosphine; lithium 2-chloro-6-methylbenzoyl-2-methyl-4-benzyloxyphenylphosphine; lithium 2-chloro-6-methylbenzoyl-2-methyl-4-phenoxyphenylphosphine; lithium 2-chloro-6-methylbenzoyl-2-methyl-4-methoxyethoxyphenylphosphine; lithium 2-chloro-6-methylbenzoyl-2-methyl-4-ethoxyethoxyphenylphosphine; lithium 2-chloro-6-methoxybenzoyl-4-methylphenylphosphine; lithium 2-chloro-6-methoxybenzoyl-2-methylphenylphosphine; lithium 2-chloro-6-methoxybenzoyl-2,4-dimethylphenylphosphine; lithium 2-chloro-6-methoxybenzoyl-2,6-dimethylphenylphosphine; lithium 2-chloro-6-methoxybenzoyl-2,5-dimethylphenylphosphine; lithium 2-chloro-6-methoxybenzoyl-2,4,6-trimethylphenylphosphine; lithium 2-chloro-6-methoxybenzoyl-2,6-dimethyl-4-tert-butylphenylphosphine; lithium 2-chloro-6-methoxybenzoyl-2,5-diisopropylphenylphosphine; lithium 2-chloro-6-methoxybenzoyl-4-phenylphenylphosphine; lithium 2-chloro-6-methoxybenzoyl-2-phenylphenylphosphine; lithium 2-chloro-6-methoxybenzoyl-4-methoxyphenylphosphine; lithium 2-chloro-6-methoxybenzoyl-4-ethoxyphenylphosphine; lithium 2-chloro-6-methoxybenzoyl-4-propoxyphenylphosphine; lithium 2-chloro-6-methoxybenzoyl-4-butoxyphenylphosphine; lithium 2-chloro-6-methoxybenzoyl-4-pentoxyphenylphosphine; lithium 2-chloro-6-methoxybenzoyl-4-hexoxyphenylphosphine; lithium 2-chloro-6-methoxybenzoyl-4-isopropoxyphenylphosphine; lithium 2-chloro-6-methoxybenzoyl-4-isobutoxyphenylphosphine; lithium 2-chloro-6-methoxybenzoyl-4-tert-butoxyphenylphosphine; lithium 2-chloro-6-methoxybenzoyl-4-(2-ethylhexoxy)phenylphosphine; lithium 2-chloro-6-methoxybenzoyl-4-(1-methylpropoxy)phenylphosphine; lithium 2-chloro-6-methoxybenzoyl-4-amyloxyphenylphosphine; lithium 2-chloro-6-methoxybenzoyl-4-isopentoxyphenylphosphine; lithium 2-chloro-6-methoxybenzoyl-4-benzyloxyphenylphosphine; lithium 2-chloro-6-methoxybenzoyl-4-phenoxyphenylphosphine; lithium 2-chloro-6-methoxybenzoyl-4-methoxyethoxyphenylphosphine; lithium 2-chloro-6-methoxybenzoyl-4-ethoxyethoxyphenylphosphine; lithium 2-chloro-6-methoxybenzoyl-2,4-dimethoxyphenylphosphine; lithium 2-chloro-6-methoxybenzoyl-2,4-diethoxyphenylphosphine; lithium 2-chloro-6-methoxybenzoyl-2,4-dipropoxyphenylphosphine; lithium 2-chloro-6-methoxybenzoyl-2,4-dibutoxyphenylphosphine; lithium 2-chloro-6-methoxybenzoyl-2,4-dipentoxyphenylphosphine; lithium 2-chloro-6-methoxybenzoyl-2,4-dihexoxyphenylphosphine; lithium 2-chloro-6-methoxybenzoyl-2,4-diisopropoxyphenylphosphine; lithium 2-chloro-6-methoxybenzoyl-2,4-diisobutoxyphenylphosphine; lithium 2-chloro-6-methoxybenzoyl-2,4-di-tert-butoxyphenylphosphine; lithium 2-chloro-6-methoxybenzoyl-2,4-di(2-ethylhexoxy)phenylphosphine; lithium 2-chloro-6-methoxybenzoyl-2,4-di(1-methylpropoxy)phenylphosphine; lithium 2-chloro-6-methoxybenzoyl-2,4-diamyloxyphenylphosphine; lithium 2-chloro-6-methoxybenzoyl-2,4-diisopentoxyphenylphosphine; lithium 2-chloro-6-methoxybenzoyl-2,4-dibenzyloxyphenylphosphine; lithium 2-chloro-6-methoxybenzoyl-2,4-diphenoxyphenylphosphine; lithium 2-chloro-6-methoxybenzoyl-2,4-dimethoxyethoxyphenylphosphine; lithium 2-chloro-6-methoxybenzoyl-2,4-diethoxyethoxyphenylphosphine; lithium 2-chloro-6-methoxybenzoyl-2,4,6-trimethoxyphenylphosphine; lithium 2-chloro-6-methoxybenzoyl-2,4,6-triethoxyphenylphosphine; lithium 2-chloro-6-methoxybenzoyl-2,4,6-tripropoxyphenylphosphine; lithium 2-chloro-6-methoxybenzoyl-2,4,6-tributoxyphenylphosphine; lithium 2-chloro-6-methoxybenzoyl-2,4,6-tripentoxyphenylphosphine; lithium 2-chloro-6-methoxybenzoyl-2,4,6-trihexoxyphenylphosphine; lithium 2-chloro-6-methoxybenzoyl-2,4,6-triisopropoxyphenylphosphine; lithium 2-chloro-6-methoxybenzoyl-2,4,6-triisobutoxyphenylphosphine; lithium 2-chloro-6-methoxybenzoyl-2,4,6-tri-tert-butoxyphenylphosphine; lithium 2-chloro-6-methoxybenzoyl-2,4,6-tri(2-ethylhexoxy)phenylphosphine; lithium 2-chloro-6-methoxybenzoyl-2,4,6-tri(-methylpropoxy)phenylphosphine; lithium 2-chloro-6-methoxybenzoyl-2,4,6-triamyloxyphenylphosphine; lithium 2-chloro-6-methoxybenzoyl-2,4,6-triisopentoxyphenylphosphine; lithium 2-chloro-6-methoxybenzoyl-2,4,6-tribenzyloxyphenylphosphine; lithium 2-chloro-6-methoxybenzoyl-2,4,6-triphenoxyphenylphosphine; lithium 2-chloro-6-methoxybenzoyl-2,4,6-trimethoxyethoxyphenylphosphine; lithium 2-chloro-6-methoxybenzoyl-2,4,6-triethoxyethoxyphenylphosphine; lithium 2-chloro-6-methoxybenzoyl-2-methyl-4-methoxyphenylphosphine; lithium 2-chloro-6-methoxybenzoyl-2-methyl-4-ethoxyphenylphosphine; lithium 2-chloro-6-methoxybenzoyl-2-methyl-4-propoxyphenylphosphine; lithium 2-chloro-6-methoxybenzoyl-2-methyl-4-butoxyphenylphosphine; lithium 2-chloro-6-methoxybenzoyl-2-methyl-4-pentoxyphenylphosphine; lithium 2-chloro-6-methoxybenzoyl-2-methyl-4-hexoxyphenylphosphine; lithium 2-chloro-6-methoxybenzoyl-2-methyl-4-isopropoxyphenylphosphine; lithium 2-chloro-6-methoxybenzoyl-2-methyl-4-isobutoxyphenylphosphine; lithium 2-chloro-6-methoxybenzoyl-2-methyl-4-tert-butoxyphenylphosphine; lithium 2-chloro-6-methoxybenzoyl-2-methyl-4-(2-ethylhexoxy)phenylphosphine; lithium 2-chloro-6-methoxybenzoyl-2-methyl-4-(1-methylpropoxy)phenylphosphine; lithium 2-chloro-6-methoxybenzoyl-2-methyl-4-amyloxyphenylphosphine; lithium 2-chloro-6-methoxybenzoyl-2-methyl-4-isopentoxyphenylphosphine; lithium 2-chloro-6-methoxybenzoyl-2-methyl-4-benzyloxyphenylphosphine; lithium 2-chloro-6-methoxybenzoyl-2-methyl-4-phenoxyphenylphosphine; lithium 2-chloro-6-methoxybenzoyl-2-methyl-4-methoxyethoxyphenylphosphine; lithium 2-chloro-6-methoxybenzoyl-2-methyl-4-ethoxyethoxyphenylphosphine, lithium 1,3-dimethylnaphthoylphenylphosphine, lithium 2,8-dimethylnaphthoylphenylphosphine, lithium 1,3-dimethoxynaphthoylphenylphosphine, lithium 2,8-dichloronaphthoylphenylphosphine, lithium 2,8-dimethoxynaphthoylphenylphosphine, lithium 2,4,6-trimethylpyridoylphenylphosphine, lithium 2,4-dimethoxyfuranoylphenylphosphine, lithium 1,3-dimethylnaphthoylphenylphosphine, lithium 2,4,5-trimethylthienoylphenylphosphine.

The compounds of the formula I are, for example, selectively obtained by reaction of acyl halides (IV) with dimetalated arylphosphines (V):

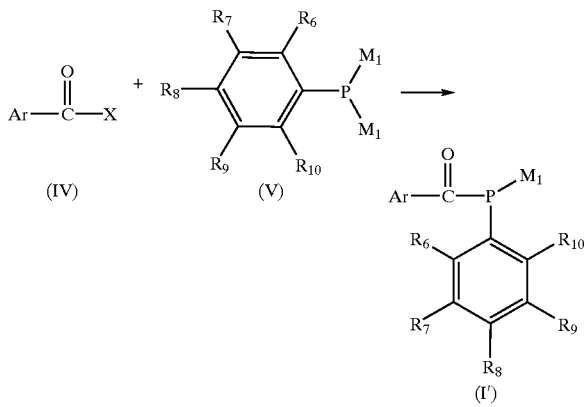

Ar, $R_6$, $R_7$, $R_8$, $R_9$ and $R_{10}$ have the meanings described above. X is Cl or Br and $M_1$ is Na, Li or K.

The starting materials are advantageously reacted in the molar ratio 1:1. A slight excess of one or other of the components, e.g. up to 20%, is not, however, critical. In this case too the desired product is formed, although the proportion of undesired byproduct may be influenced.

The reaction is advantageously carried out in a solvent. In particular, as solvents, it is possible to use ethers which are liquid at atmospheric pressure and room temperature. Examples are dimethyl ether, diethyl ether, methyl propyl ether, 1,2-dimethoxyethane, bis-(2-methoxyethyl)ether, dioxane or tetrahydrofuran. Preference is given to using tetrahydrofuran.

The reaction temperatures are advantageously –60° C. to +120° C., e.g. –40° C. to 100° C., for example –20° C. to +80° C.

It is advisable to stir the reaction mixture.

It is advantageous to initially introduce the compound of the formula V and to add dropwise the compound of the formula IV at the temperatures given above.

Here, the compound of the formula IV can be added without a diluent or else diluted with the reaction solvent.

If desired, the course of the reaction can be monitored using methods customary in the art, for example NMR, for example $^{31}$P-NMR, chromatography (thin-layer, HPLC, GC) etc. In the reactions described above, it is essential to work in an inert gas atmosphere, e.g. with a protective gas such as argon or nitrogen, in order to exclude atmospheric oxygen.

In order to prepare compounds of the formula I in which M is hydrogen, the reaction given above is followed by a hydrolysis step:

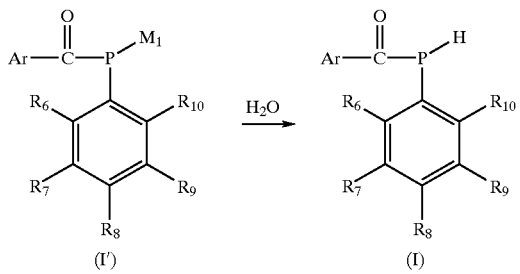

The procedure for such hydrolysis reactions is known to the person skilled in the art and is carried out under generally customary conditions. The hydrolysis of metalated primary and secondary phosphines is described, for example, in Houben-Weyl, XII/1, pages 56–57. Likewise conceivable is the preparation of compounds of the formula (I) by reaction between a compound of the formula (IV) and an alkylphosphine compound in the presence of an acid-binding agent, such as barium carbonate, calcium carbonate or potassium carbonate, as described, for example, in Houben-Weyl, XII1, pages 73–74 or in K. Issleib and R. Kümmel, Z. Naturf. B (1967), 22, 784.

The compounds of the formula I according to the invention are identified by $^{31}$P-NMR spectroscopy and are stable in the solution under inert gas at room temperature for a number of weeks.

The invention also provides a process for the selective preparation of compounds of the formula I by
(1) reaction of an acyl halide of the formula IV

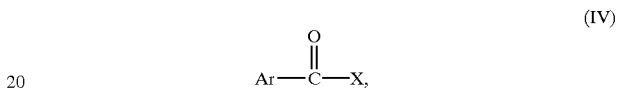

in which
Ar is as defined in claim 1, and
X is Cl or Br;
with a dimetalated arylphosphine of the formula V

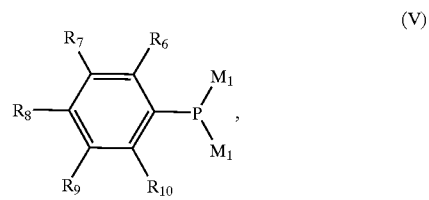

in which
$R_6$, $R_7$, $R_8$, $R_9$ and $R_{10}$ are as defined in claim 1; and
$M_1$ is Na, Li or K;
in the molar ratio 1:1; and
(2) where appropriate, subsequent hydrolysis if compounds of the formula I in which M is hydrogen are to be obtained.

The acyl halides (IV) used as starting material are known substances, some of which are available commercially, or can be prepared by analogy with known compounds. The preparation of the metalated arylphosphines (V) can, for example, be carried out by reacting suitable phosphorus halides (preparation of which is known and disclosed, for example, by W. Davies in J. Chem. Soc. (1935), 462 and J. Chem. Soc. (1944), 276 with the corresponding alkali metal:

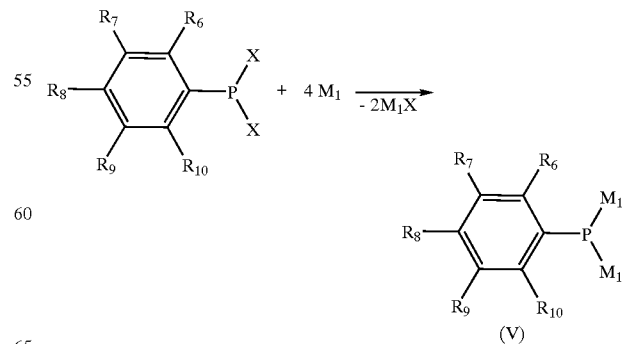

$R_6$–$R_{10}$ have the meaning given above.

Suitable as metal ($M_1$) are lithium, sodium or potassium. The use of mixtures of these metals is also possible. 4 to 8 molar equivalents of the alkaline metal are advantageously used. The reaction is advantageously carried out in a solvent. In particular, as solvents, it is possible to use ethers which are liquid at atmospheric pressure and room temperature. Examples are dimethyl ether, diethyl ether, methyl propyl ether, 1,2-dimethoxyethane, bis(2-methoxyethyl)ether, dioxane or tetrahydrofuran. Preference is given to using tetrahydrofuran. The reaction temperatures are advantageously −60° C. to +120° C. The reaction is, where appropriate, carried out with the addition of a catalyst. Suitable catalysts are aromatic hydrocarbons with or without heteroatoms, for example naphthalene, anthracene, phenanthrene, biphenyl, terphenyl, quaterphenyl, triphenylene, trans-1,2-diphenylethene, pyrene, perylene, acenaphthalene, decacyclene, quinoline, N-ethylcarbazole, dibenzothiophene or dibenzofuran.

For the preparation of the compounds of the formula I according to the invention in the process according to the invention, the thus obtained compounds of the formulae (V) can be further used without isolation.

Another conceivable method for the preparation of metalated arylphosphines is, for example, the reaction of suitable arylphosphines with the corresponding alkali metal hydride or an alkyllithium compound with the exclusion of air in an inert solvent at temperatures of e.g. −80° C. to +120° C. Advantageously, 2 to 4 mol equivalents of the alkali metal hydrides or alkyllithium compound are used. Suitable solvents are e.g. ethers as described above, or inert solvents, such as alkanes, cycloalkanes, or aromatic solvents such as toluene, xylene, mesitylene.

Suitable aryl phosphines can be prepared by reduction of the corresponding aryldichlorophosphines [Ar—P—$Cl_2$], arylphosphonic esters [Ar—P—O(OR')$_2$] and arylphosphonous esters [Ar—P(OR')$_2$] using $LiAlH_4$; $SiHCl_3$; $Ph_2SiH_2$ (Ph=phenyl); a) LiH, b) $H_2O$; a) Li/tetrahydrofuran, b) $H_2O$ or a) Na/toluene, b) $H_2O$. These methods are described, for example, in U.S. Pat. No. 6,020,528 (col. 5–6). Hydrogenations using $LiAlH_4$ are given, for example, in Helv. Chim. Acta 1966, No. 96, 842.

The compounds of the formula I are particularly suitable for the preparation of unsymmetrical mono- and bisacylphosphines, mono- and bisacylphosphine oxides, and mono- and bisacylphosphine sulfides. "Unsymmetrical" means in this connection that in the bisacylphosphines, bisacylphosphine oxides and bisacylphosphine sulfides, two different acyl groups are present, and in the monoacylphosphines, monoacylphosphine oxides and monoacylphosphine sulfides, in addition to the acyl group, two different radicals are bonded to the phosphorus atom.

Such "unsymmetrical" mono- and bisacylphosphines, mono- and bisacylphosphine oxides, and mono- and bisacylphosphine sulfides are, with a few exceptions, novel.

Accordingly, the invention also provides compounds of the formula II

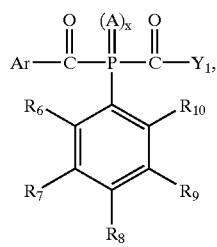

(II)

wherein
A is O or S;
x is 0 or 1;

Ar is a group

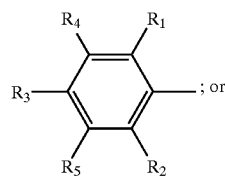

; or

Ar is cyclopentyl, cyclohexyl, naphthyl, biphenylyl, anthracyl or an O—, S— or N-containing 5- or 6-membered heterocyclic ring, where the radicals cyclopentyl, cyclohexyl, naphthyl, biphenylyl, anthracyl or an O—, S— or N-containing 5- or 6-membered heterocyclic ring are unsubstituted or substituted by halogen, $C_1$–$C_4$alkyl and/or $C_1$–$C_4$alkoxy;

$R_1$ and $R_2$ independently of one another are $C_1$–$C_{20}$alkyl, $OR_{11}$, $CF_3$ or halogen;

$R_3$, $R_4$ and $R_5$ independently of one another are hydrogen, $C_1$–$C_{20}$alkyl, $OR_{11}$, or halogen; or in each case two of the radicals $R_1$, $R_2$, $R_3$, $R_4$ and/or $R_5$ together form $C_1$–$C_{20}$alkylene which can be interrupted by O, S or $NR_{14}$;

$R_6$, $R_7$, $R_8$, $R_9$ and $R_{10}$ independently of one another are hydrogen, $C_1$–$C_{20}$alkyl; $C_2$–$C_{20}$alkyl, which is interrupted once or more than once by nonconsecutive O atoms and which can be substituted by OH and/or SH; or $R_6$, $R_7$, $R_8$, $R_9$ and $R_{10}$ are $OR_{11}$, phenyl or halogen;

$R_{11}$ is hydrogen, $C_1$–$C_{20}$alkyl, $C_2$–$C_{20}$alkenyl, $C_3$–$C_8$cycloalkyl, phenyl, benzyl or $C_2$–$C_{20}$alkyl which is interrupted once or more than once by nonconsecutive O atoms and which is unsubstituted or substituted by OH and/or SH;

$Y_1$ is $C_1$–$C_{18}$alkyl which is unsubstituted or substituted by one or more phenyl; $C_1$–$C_{18}$-halogenoalkyl; $C_2$–$C_{18}$alkyl which is interrupted once or more than once by O or S and which can be substituted by OH and/or SH; unsubstituted $C_3$–$C_{18}$cycloalkyl or $C_3$–$C_{18}$cycloalkyl substituted by $C_1$–$C_{20}$alkyl, $OR_{11}$, $CF_3$ or halogen; $C_2$–$C_{18}$alkenyl; naphthyl, biphenylyl, anthracyl or an O—, S— or N-containing 5- or 6-membered heterocyclic ring, where the radicals naphthyl, biphenylyl, anthracyl or an O—, S— or N-containing 5- or 6-membered heterocyclic ring are unsubstituted or are substituted by halogen, $C_1$–$C_4$alkyl and/or $C_1$–$C_4$alkoxy;

or $Y_1$ is $OR_{11}$, $N(R_{16})(R_{17})$,

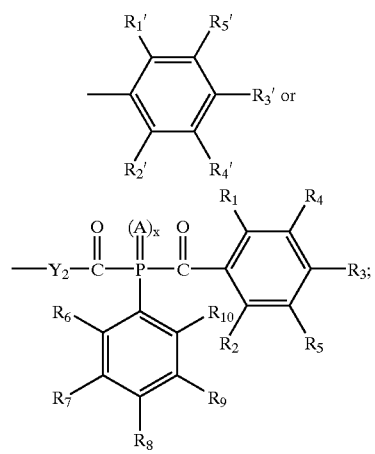

$Y_2$ is a direct bond, $C_1$–$C_{18}$alkylene optionally substituted by phenyl; unsubstituted $C_4$–$C_{18}$-cycloalkylene or $C_4$–$C_{18}$cycloalkylene substituted by $C_1$–$C_{12}$alkyl, OR$_{11}$, halogen and/or phenyl; unsubstituted C$_5$–C$_{18}$cycloalkenylene or C$_5$–C$_{18}$cycloalkenylene substituted by C$_1$–C$_{12}$alkyl, OR$_{11}$, halogen and/or phenyl; unsubstituted phenylene or phenylene substituted one to four times by C$_1$–C$_{12}$alkyl, OR$_{11}$, halogen, —(CO)OR$_{14}$, —(CO)N(R$_{12}$)(R$_{13}$) and/or phenyl;

or Y$_2$ is a radical

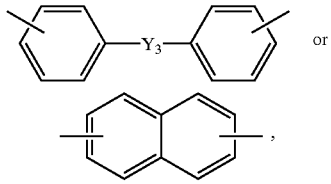

where these radicals are unsubstituted or are substituted one to four times on one or both aromatic ring(s) by C$_1$–C$_{12}$alkyl, OR$_{11}$, halogen and/or phenyl;

Y$_3$ is O, S, SO, SO$_2$, CH$_2$, C(CH$_3$)$_2$, CHCH$_3$, C(CF$_3$)$_2$, (CO), or a direct bond;

R$_{12}$ and R$_{13}$ independently of one another are hydrogen, C$_1$–C$_{20}$alkyl, C$_3$–C$_8$cycloalkyl, phenyl, benzyl or C$_2$–C$_{20}$alkyl which is interrupted once or more than once by O or S and which is unsubstituted or substituted by OH and/or SH; or R$_{12}$ and R$_{13}$ together are C$_3$–C$_5$alkylene which can be interrupted by O, S or NR$_{14}$;

R$_{14}$ is hydrogen, phenyl, C$_1$–C$_{12}$alkyl or C$_2$–C$_{12}$alkyl which is interrupted once or more than once by O or S and which can be substituted by OH and/or SH;

R$_1$' and R$_2$' independently of one another have the same meanings as given for R$_1$ and R$_2$; and R$_3$', R$_4$' and R$_5$' independently of one another have the same meanings as given for R$_3$, R$_4$ and R$_5$;

with the proviso that if Y$_1$ is a radical

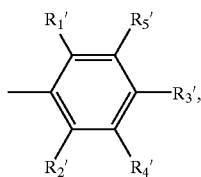

naphthyl, biphenylyl, anthracyl or an O—, S— or N-containing 5- or 6-membered heterocyclic ring, this is not identical to the other benzoyl group on the phosphorus atom.

In the compounds of the formula II, the preferred meanings of the radicals R$_1$, R$_2$, R$_3$, R$_4$, R$_5$, R$_6$, R$_7$, R$_8$, R$_9$ and R$_{10}$ are analogous to those given above for the compounds of the formula I. Preferred R$_1$', R$_2$', R$_3$', R$_4$' and R$_5$' likewise correspond to those given for the radicals R$_1$, R$_2$, R$_3$, R$_4$, R$_5$, R$_6$, R$_7$, R$_8$, R$_9$ and R$_{10}$.

In the compounds of the formula II, x is preferably 1. In particular, A is oxygen.

Of particular importance are compounds of the formula II in which Y$_1$ is C$_1$–C$_{12}$alkyl, in particular branched C$_1$–C$_{12}$alkyl; unsubstituted C$_3$–C$_{18}$cycloalkyl or C$_3$–C$_{18}$cycloalkyl substituted by C$_1$–C$_{20}$alkyl, OR$_{11}$, CF$_3$ or halogen; or is

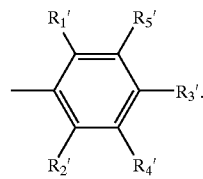

Y$_1$ as C$_1$–C$_{12}$alkyl is preferably branched in the α-position relative to the bond to the CO group. The carbon atom in the α-position relative to the CO group is preferably a tertiary carbon atom.

The preferred meanings for R$_1$', R$_2$', R$_3$', R$_4$' and R$_5$' are analogous to those preferred meanings of R$_1$, R$_2$, R$_3$, R$_4$ and R$_5$ given above for formula I.

Also of interest are compounds of the formula II in which R$_1$, R$_2$ and R$_3$ are C$_1$–C$_4$alkyl, in particular methyl; R$_1$' and R$_2$' are C$_1$–C$_4$alkoxy, in particular methoxy, or chlorine; and R$_4$, R$_5$, R$_3$', R$_4$' and R$_5$' are hydrogen.

In preferred compounds of the formula II,

A is oxygen and x is 1;

R$_1$ and R$_2$ are C$_1$–C$_4$alkyl, C$_1$–C$_4$alkoxy, Cl or CF$_3$;

R$_3$ is hydrogen, C$_1$–C$_4$alkyl or C$_1$–C$_4$alkoxy;

R$_4$ and R$_5$ are hydrogen;

R$_6$, R$_7$, R$_8$, R$_9$ and R$_{10}$ independently of one another are hydrogen, C$_1$–C$_{12}$alkyl; OR$_{11}$, phenyl or halogen;

R$_{11}$ is hydrogen, C$_1$–C$_{12}$alkyl, cyclohexyl, cyclopentyl, phenyl or benzyl;

Y$_1$ is C$_1$–C$_{12}$alkyl which is unsubstituted or substituted by one or more phenyl; or Y$_1$ is

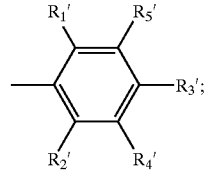

R$_{12}$ and R$_{13}$ independently of one another are, C$_1$–C$_{12}$alkyl, cyclopentyl, cyclohexyl, phenyl, benzyl or C$_2$–C$_{12}$alkyl which is interrupted once or more than once by nonconsecutive O atoms and which is unsubstituted or substituted by OH and/or SH; or R$_{12}$ and R$_{13}$ together are piperidino, morpholino or piperazino;

R$_{14}$ is hydrogen or C$_1$–C$_{12}$alkyl;

R$_1$' and R$_2$' have the same meanings as given for R$_1$ and R$_2$; and

R$_3$', R$_4$' and R$_5$' independently of one another have the same meanings as given for R$_3$, R$_4$ and R$_5$.

Examples of preferred compounds of the formula II are 2,4,6-trimethylbenzoyl-2,6-dimethylbenzoylphenylphosphine oxide; 2,4,6-trimethylbenzoyl-2,6-diethylbenzoylphenylphosphine oxide; 2,4,6-trimethylbenzoyl-2,3,4,5,6-pentamethylbenzoylphenylphosphine oxide; 2,4,6-trimethylbenzoyl-2,3,5,6-tetramethylbenzoylphenylphosphine oxide; 2,4,6-trimethylbenzoyl-2,4,6-triisopropylbenzoylphenylphosphine oxide; 2,4,6-trimethylbenzoyl-2,4,5,6-tetramethylbenzoylphenylphosphine oxide; 2,4,6-trimethylbenzoyl-2,4,6-tri-tert-butylbenzoylphenylphosphine oxide; 2,4,6- trimethylbenzoyl-2,6-dimethyl-4-tert-butylbenzoylphenylphosphine oxide; 2,4,6-trimethylbenzoyl-2,6-diphenoxymethylbenzoylphenylphosphine oxide; 2,4,6-trimethylbenzoyl-2,3,6-trimethylbenzoylphenylphosphine oxide; 2,4,6-trimethylbenzoyl-2,3,4,6-tetramethylbenzoylphenylphosphine oxide; 2,4,6-trimethylbenzoyl-2-phenyl-6-methylbenzoylphenylphosphine oxide; 2,4,6-trimethylbenzoyl-2,4,6-trimethoxybenzoylphenylphosphine oxide; 2,4,6-trimethylbenzoyl-2,4-dimethoxybenzoylphenylphosphine oxide; 2,4,6-trimethylbenzoyl-2,3,6-trimethoxybenzoylphenylphosphine oxide; 2,4,6-trimethylbenzoyl-2,6-diethoxybenzoylphenylphosphine oxide; 2,4,6-trimethylbenzoyl-2,6-dimethoxy-3,5-dimethylbenzoylphenylphosphine oxide; 2,4,6-trimethylbenzoyl-2,6-dimethoxy-4-methylbenzoylphenylphosphine oxide; 2,4,6-trimethylbenzoyl-2,6-dimethoxy-3-bromobenzoylphenylphosphine oxide; 2,4,6-trimethylbenzoyl-2,6-dimethoxy-3-chlorobenzoylphenylphosphine oxide; 2,4,6-trimethylbenzoyl-2,6-dimethoxy-3-chloro-5-bromobenzoylphenylphosphine oxide; 2,4,6-trimethylbenzoyl-2,6-dimethoxy-3,5-dichlorobenzoylphenylphosphine oxide; 2,4,6-trimethylbenzoyl-2,3,6-trimethoxy-5-bromobenzoylphenylphosphine oxide; 2,4,6-trimethylbenzoyl-2,6-dichlorobenzoylphenylphosphine oxide; 2,4,6-trimethylbenzoyl-2,4,6-trichlorobenzoylphenylphosphine oxide; 2,4,6-trimethylbenzoyl-2,3,6-trichlorobenzoylphenylphosphine oxide; 2,4,6-trimethylbenzoyl-2,3,5,6-tetrachlorobenzoylphenylphosphine oxide; 2,4,6-trimethylbenzoyl-2,3,4,5,6-pentachlorobenzoylphenylphosphine oxide; 2,4,6-trimethylbenzoyl-2,6-dichloro-3-methylbenzoylphenylphosphine oxide; 2,4,6-trimethylbenzoyl-2-chloro-6-methylbenzoylphenylphosphine oxide; 2,4,6-trimethylbenzoy,-2-methoxy-3,6-dichlorobenzoylphenylphosphine oxide; 2,4,6-trimethylbenzoyl -2-methoxy-6-chlorobenzoylphenylphosphine oxide; 2,4,6-trimethylbenzoyl-2,6-bis(trifluoromethyl)benzoylphenylphosphine oxide; 2,4,6-trimethylbenzoyl-2-chloro-6-methylthiobenzoylphenylphosphine oxide; 2,4,6-trimethylbenzoyl-2,6-dibromobenzoylphenylphosphine oxide; 2,6-dimethoxybenzoyl-2,6-dimethylbenzoylphenylphosphine oxide; 2,6-dimethoxybenzoyl-2,6-diethylbenzoylphenylphosphine oxide; 2,6-dimethoxybenzoyl-2,4,6-trimethylbenzoylphenylphosphine oxide; 2,6-dimethoxybenzoyl-2,3,4,5,6-pentamethylbenzoylphenylphosphine oxide; 2,6-dimethoxybenzoyl-2,3,5,6-tetramethylbenzoylphenylphosphine oxide; 2,6-dimethoxybenzoyl-2,4,6-triisopropylbenzoylphenylphosphine oxide; 2,6-dimethoxybenzoyl-2,4,5,6-tetramethylbenzoylphenylphosphine oxide; 2,6-dimethoxybenzoyl-2,4,6-tri-tert-butylbenzoylphenylphosphine oxide; 2,6-dimethoxybenzoyl-2,6-dimethyl-4-tert-butylbenzoylphenylphosphine oxide; 2,6-dimethoxybenzoyl-2,6-diphenoxymethylbenzoylphenylphosphine oxide; 2,6-dimethoxybenzoyl-2,3,6-trimethylbenzoylphenylphosphine oxide; 2,6-dimethoxybenzoyl-2,3,4,6-tetramethylbenzoylphenylphosphine oxide; 2,6-dimethoxybenzoyl-2-phenyl-6-methylbenzoylphenylphosphine oxide; 2,6-dimethoxybenzoyl-2,4,6-trimethoxybenzoylphenylphosphine oxide; 2,6-dimethoxybenzoyl-2,4-dimethoxybenzoylphenylphosphine oxide; 2,6-dimethoxybenzoyl-2,3,6-trimethoxybenzoylphenylphosphine oxide; 2,6-dimethoxybenzoyl-2,6-diethoxybenzoylphenylphosphine oxide; 2,6-dimethoxybenzoyl-2,6-dimethoxy-3,5-dimethylbenzoylphenylphosphine oxide; 2,6-dimethoxybenzoyl-2,6-dimethoxy-4-methylbenzoylphenylphosphine oxide; 2,6-dimethoxybenzoyl-2,6-dimethoxy-3-bromobenzoylphenylphosphine oxide; 2,6-dimethoxybenzoyl-2,6-dimethoxy-3-chlorobenzoylphenylphosphine oxide; 2,6-dimethoxybenzoyl-2,6-dimethoxy-3-chloro-5-bromobenzoylphenylphosphine oxide; 2,6-dimethoxybenzoyl-2,6-dimethoxy-3,5-dichlorobenzoylphenylphosphine oxide; 2,6-dimethoxybenzoyl-2,3,6-trimethoxy-5-bromobenzoylphenylphosphine oxide; 2,6-dimethoxybenzoyl-2,6-dichlorobenzoylphenylphosphine oxide; 2,6-dimethoxybenzoyl-2,4,6-trichlorobenzoylphenylphosphine oxide; 2,6-dimethoxybenzoyl-2,3,6-trichlorobenzoylphenylphosphine oxide; 2,6-dimethoxybenzoyl-2,3,5,6-tetrachlorobenzoylphenylphosphine oxide; 2,6-dimethoxybenzoyl-2,3,4,5,6-pentachlorobenzoylphenylphosphine oxide; 2,6-dimethoxybenzoyl-2,6-dichloro-3-methylbenzoylphenylphosphine oxide; 2,6-dimethoxybenzoyl-2-chloro-6-methylbenzoylphenylphosphine oxide; 2,6-dimethoxybenzoyl-2-methoxy-3,6-dichlorobenzoylphenylphosphine oxide; 2,6-dimethoxybenzoyl-2-methoxy-6-chlorobenzoylphenylphosphine oxide; 2,6-dimethoxybenzoyl-2,6-bis(trifluoromethyl)benzoylphenylphosphine oxide; 2,6-dimethoxybenzoyl-2-chloro-6-methylthiobenzoylphenylphosphine oxide; 2,6-dimethoxybenzoyl-2,6-dibromobenzoylphenylphosphine oxide; 2,6-dichlorobenzoyl-2,6-dimethylbenzoylphenylphosphine oxide; 2,6-dichlorobenzoyl-2,6-diethylbenzoylphenylphosphine oxide; 2,6-dichlorobenzoyl-2,4,6-trimethylbenzoylphenylphosphine oxide; 2,6-dichlorobenzoyl-2,3,4,5,6-pentamethylbenzoylphenylphosphine oxide; 2,6-dichlorobenzoyl-2,3,5,6-tetramethylbenzoylphenylphosphine oxide; 2,6-dichlorobenzoyl-2,4,6-triisopropylbenzoylphenylphosphine oxide; 2,6-dichlorobenzoyl-2,4,5,6-tetramethylbenzoylphenylphosphine oxide; 2,6-dichlorobenzoyl-2,4,6-tri-tert-butylbenzoylphenylphosphine oxide; 2,6-dichlorobenzoyl-2,6-dimethyl-4-tert-butylbenzoylphenylphosphine oxide; 2,6-dichlorobenzoyl-2,6-diphenoxymethylbenzoylphenylphosphine oxide; 2,6-dichlorobenzoyl-2,3,6-trimethylbenzoylphenylphosphine oxide; 2,6-dichlorobenzoyl-2,3,4,6-tetramethylbenzoylphenylphosphine oxide; 2,6-dichlorobenzoyl-2-phenyl-6- methylbenzoylphenylphosphine oxide; 2,6-dichlorobenzoyl-2,4,6-trimethoxybenzoylphenylphosphine oxide; 2,6-dichlorobenzoyl-2,4-dimethoxybenzoylphenylphosphine oxide; 2,6-dichlorobenzoyl-2,3,6-trimethoxybenzoylphenylphosphine oxide; 2,6-dichlorobenzoyl-2,6-diethoxybenzoylphenylphosphine oxide; 2,6-dichlorobenzoyl-2,6-dimethoxy-3,5-dimethylbenzoylphenylphosphine oxide; 2,6-dichlorobenzoyl-2,6-dimethoxy-4-methylbenzoylphenylphosphine oxide; 2,6-dichlorobenzoyl-2,6-dimethoxy-3-bromobenzoylphenylphosphine oxide; 2,6-dichlorobenzoyl-2,6-dimethoxy-3-chlorobenzoylphenylphosphine oxide; 2,6-dichlorobenzoyl-2,6-dimethoxy-3-chloro-5-bromobenzoylphenylphosphine oxide; 2,6-dichlorobenzoyl-2,6-dimethoxy-3,5-dichlorobenzoylphenylphosphine oxide; 2,6-dichlorobenzoyl-2,3,6-trimethoxy-5-bromobenzoylphenylphosphine oxide; 2,6-dichlorobenzoyl-2,4,6-trichlorobenzoylphenylphosphine oxide; 2,6-dichlorobenzoyl-2,3,6-trichlorobenzoylphenylphosphine oxide; 2,6-dichlorobenzoyl-2,3,5,6-tetrachlorobenzoylphenylphosphine oxide; 2,6-dichlorobenzoyl-2,3,4,5,6-pentachlorobenzoylphenylphosphine oxide; 2,6-dichlorobenzoyl-2,6-dichloro-3-methylbenzoylphenylphosphine oxide; 2,6-dichlorobenzoyl-2-chloro-6-methylbenzoylphenylphosphine oxide; 2,6-dichlorobenzoyl-2-methoxy-3,6-dichlorobenzoylphenylphosphine oxide; 2,6-dichlorobenzoyl-2-methoxy-6-chlorobenzoylphenylphosphine oxide; 2,6-dichlorobenzoyl-2,6-bis(trifluoromethyl)benzoylphenylphosphine oxide; 2,6-dichlorobenzoyl-2-chloro-6-methylthiobenzoylphenylphosphine oxide; 2,6-dichlorobenzoyl-2,6-dibromobenzoylphosphine oxide; 2,6-bis(trifluoromethyl)benzoyl-2,6-dimethylbenzoylphenylphosphine oxide; 2,6-bis(trifluoromethyl)benzoyl-2,6-diethylbenzoylphenylphosphine oxide; 2,6-bis(trifluoromethyl)benzoyl-2,4,6-trimethylbenzoylphenylphosphine oxide; 2,6-bis(trifluoromethyl)benzoyl-2,3,4,5,6-pentamethylbenzoylphenylphosphine oxide; 2,6-bis(trifluoromethyl)benzoyl-2,3,5,6-tetramethylbenzoylphenylphosphine oxide; 2,6-bis(trifluoromethyl)benzoyl-2,4,6-triisopropylbenzoylphenylphosphine oxide; 2,6-bis(trifluoromethyl)benzoyl-2,4,5,6-tetramethylbenzoylphenylphosphine oxide; 2,6-bis(trifluoromethyl)benzoyl-2,4,6-tri-tert-butylbenzoylphenylphosphine oxide; 2,6-bis(trifluoromethyl)benzoyl-2,6-dimethyl-4-tert-butylbenzoylphenylphosphine oxide; 2,6-bis(trifluoromethyl)benzoyl-2,6-diphenoxymethylbenzoylphenylphosphine oxide; 2,6-bis(trifluoromethyl)benzoyl-2,3,6-trimethylbenzoylphenylphosphine oxide; 2,6-bis(trifluoromethyl)benzoyl-2,3,4,6-tetramethylbenzoyl phenylphosphine oxide; 2,6-bis(trifluoromethyl)benzoyl-2-phenyl-6-methylbenzoylphenylphosphine oxide; 2,6-bis(trifluoromethyl)benzoyl-2,4,6-trimethoxybenzoylphenylphosphine oxide; 2,6-bis(trifluoromethyl)benzoyl-2,4-dimethoxybenzoylphenylphosphine oxide; 2,6-bis(trifluoromethyl)benzoyl-2,3,6-trimethoxybenzoylphenyl oxide; 2,6-bis(trifluoromethyl)benzoyl-2,6-diethoxybenzoylphenylphosphine oxide; 2,6-bis(trifluoromethyl)benzoyl-2,6-diethoxybenzoylphenylphosphine oxide; 2,6-bis(trifluoromethyl)benzoyl-2,6-dimethoxy-4-methylbenzoylphenylphosphine oxide; 2,6-bis(trifluoromethyl)benzoyl-2,6-dimethoxy-3-bromobenzoylphenylphosphine oxide; 2,6-bis(trifluoromethyl)benzoyl-2,6-dimethoxy-3-chlorobenzoylphenylphosphine oxide; 2,6-bis(trifluoromethyl)benzoyl-2,6-dimethoxy-3-chloro-5-bromobenzoylphenylphosphine oxide; 2,6-bis(trifluoromethyl)benzoyl-2,6-dimethoxy-3,5-dichlorobenzoylphenylphosphine oxide; 2,6-bis(trifluoromethyl)benzoyl-2,3,6-trimethoxy-5-bromobenzoylphenylphosphine oxide; 2,6-bis(trifluoromethyl)benzoyl-2,6-dichlorobenzoylphenylphosphine oxide; 2,6-bis(trifluoromethyl)benzoyl-2,4,6-trichlorobenzoylphenylphosphine oxide; 2,6-bis(trifluoromethyl)benzoyl-2,3,6-trichlorobenzoylphenylphosphine oxide; 2,6-bis(trifluoromethyl)benzoyl-2,3,5,6-tetrachlorobenzoylphenylphosphine oxide; 2,6-bis(trifluoromethyl)benzoyl-2,3,4,5,6-pentachlorobenzoylphenylphosphine oxide; 2,6-bis(trifluoromethyl)benzoyl-2,6-dichloro-3-methylbenzoylphenylphosphine oxide; 2,6-bis(trifluoromethyl)benzoyl-2-chloro-6-methylbenzoylphenylphosphine oxide; 2,6-bis(trifluoromethyl)benzoyl-2-methoxy-3,6-dichlorobenzoylphenylphosphine oxide; 2,6-bis(trifluoromethyl)benzoyl-2-methoxy-6-chlorobenzoylphenylphosphine oxide; 2,6-bis(trifluoromethyl)benzoyl-2-chloro-6-methylthiobenzoylphenylphosphine oxide; 2,6-bis(trifluoromethyl)benzoyl-2,6-dibromobenzoylphenylphosphine oxide; 2,6-dimethylbenzoyl-2,6-diethylbenzoylphenylphosphine oxide; 2,6-dimethylbenzoyl-2,4,6-trimethylbenzoylphenylphosphine oxide; 2,6-dimethylbenzoyl-2,3,4,5,6-pentamethylbenzoylphenylphosphine oxide; 2,6-dimethylbenzoyl-2,3,5,6-tetramethylbenzoylphenylphosphine oxide; 2,6-dimethylbenzoyl-2,4,6-triisopropylbenzoylphenylphosphine oxide; 2,6-dimethylbenzoyl-2,4,5,6-tetramethylbenzoylphenylphosphine oxide; 2,6-dimethylbenzoyl-2,4,6-tri-tert-butylbenzoylphenylphosphine oxide; 2,6-dimethylbenzoyl-2,6-dimethyl-4-tert-butylbenzoylphenylphosphine oxide; 2,6-dimethylbenzoyl-2,6-diphenoxymethylbenzoylphenylphosphine oxide; 2,6-dimethylbenzoyl-2,3,6-trimethylbenzoylphenylphosphine oxide; 2,6-dimethylbenzoyl-2,3,4,6-tetramethylbenzoylphenylphosphine oxide; 2,6-dimethylbenzoyl-2-phenyl-6-methylbenzoylphenylphosphine oxide; 2,6-dimethylbenzoyl-2,4,6-trimethoxybenzoylphenylphosphine oxide; 2,6-dimethylbenzoyl-2,4-dimethoxybenzoylphenylphosphine oxide; 2,6-dimethylbenzoyl-2,3,6-trimethoxybenzoylphenylphosphine oxide; 2,6-dimethylbenzoyl-2,6-diethoxybenzoylphenylphosphine oxide; 2,6-dimethylbenzoyl-2,6-dimethoxy-3,5-dimethylbenzoylphenylphosphine oxide; 2,6- dimethylbenzoyl-2,6-dimethoxy-4-methylbenzoylphenylphosphine oxide; 2,6-dimethylbenzoyl-2,6-dimethoxy-3-bromobenzoylphenylphosphine oxide; 2,6-dimethylbenzoyl-2,6-dimethoxy-3-chlorobenzoylphenylphosphine oxide; 2,6-dimethylbenzoyl-2,6-dimethoxy-3-chloro-5-bromobenzoylphenylphosphine oxide; 2,6-dimethylbenzoyl-2,6-dimethoxy-3,5-dichlorobenzoylphenylphosphine oxide; 2,6-dimethylbenzoyl-2,3,6-trimethoxy-5-bromobenzoylphenylphosphine oxide; 2,6-dimethylbenzoyl-2,6-dichlorobenzoylphenylphosphine oxide; 2,6-dimethylbenzoyl-2,4,6-trichlorobenzoylphenylphosphine oxide; 2,6-dimethylbenzoyl-2,3,6-trichlorobenzoylphenylphosphine oxide; 2,6-dimethylbenzoyl-2,3,5,6-tetrachlorobenzoylphenylphosphine oxide; 2,6-dimethylbenzoyl-2,3,4,5,6-pentachlorobenzoylphenylphosphine oxide; 2,6-dimethylbenzoyl-2,6-dichloro-3-methylbenzoylphenylphosphine oxide; 2,6-dimethylbenzoyl-2-chloro-6-methylbenzoylphenylphosphine oxide; 2,6-dimethylbenzoyl-2-methoxy-3,6-dichlorobenzoylphenylphosphine oxide; 2,6-dimethylbenzoyl-2-methoxy-6-chlorobenzoylphenylphosphine oxide; 2,6-dimethylbenzoyl-2,6-bis(trifluoromethyl)benzoylphenylphosphine oxide; 2,6-dimethylbenzoyl-2-chloro-6-methylthiobenzoylphenylphosphine oxide; 2,6-dimethylbenzoyl-2,6-dibromobenzoylphenylphosphine oxide; 2,3,4,6-tetramethylbenzoyl-2,6-dimethylbenzoylphenylphosphine oxide; 2,3,4,6-tetramethylbenzoyl-2,6-diethylbenzoylphenylphosphine oxide; 2,3,4,6-tetramethylbenzoyl-2,4,6-trimethylbenzoylphenylphosphine oxide; 2,3,4,6-tetramethylbenzoyl-2,3,4,5,6-pentamethylbenzoylphenylphosphine oxide; 2,3,4,6-tetramethylbenzoyl-2,3,5,6-tetramethylbenzoylphenylphosphine oxide; 2,3,4,6-tetramethylbenzoyl-2,4,6-triisopropylbenzoylphenylphosphine oxide; 2,3,4,6-tetramethylbenzoyl-2,4,5,6-tetramethylbenzoylphenylphosphine oxide; 2,3,4,6-tetramethylbenzoyl-2,4,6-tri-tert-butylbenzoylphenylphosphine oxide; 2,3,4,6-tetramethylbenzoyl-2,6-dimethyl-4-tert-butylbenzoylphenylphosphine oxide; 2,3,4,6-tetramethylbenzoyl-2,6-diphenoxymethylbenzoylphenylphosphine oxide; 2,3,4,6-tetramethylbenzoyl-2,3,6-trimethylbenzoylphenylphosphine oxide; 2,3,4,6-tetramethylbenzoyl-2,3,4,6-tetramethylbenzoylphenylphosphine oxide; 2,3,4,6-tetramethylbenzoyl-2-phenyl-6-methylbenzoylphenylphosphine oxide; 2,3,4,6-tetramethylbenzoyl-2,4,6-trimethoxybenzoylphenylphosphine oxide; 2,3,4,6-tetramethylbenzoyl-2,4-dimethoxybenzoylphenylphosphine oxide; 2,3,4,6-tetramethylbenzoyl-2,3,6-trimethoxybenzoylphenylphosphine oxide; 2,3,4,6-tetramethylbenzoyl-2,6-diethoxybenzoylphenylphosphine oxide; 2,3,4,6-tetramethylbenzoyl-2,6-dimethoxy-3,5-dimethylbenzoylphenylphosphine oxide; 2,3,4,6-tetramethylbenzoy-2,6-dimethoxy-4-methylbenzoylphenylphosphine oxide; 2,3,4,6-tetramethylbenzoyl-2,6-dimethoxy-3-bromobenzoylphenylphosphine oxide; 2,3,4,6-tetramethylbenzoyl-2,6-dimethoxy-3-chlorobenzoylphenylphosphine oxide; 2,3,4,6-tetramethylbenzoyl-2,6-dimethoxy-3-chloro-5-bromobenzoylphenylphosphine oxide; 2,3,4,6-tetramethylbenzoyl-2,6-dimethoxy-3,5-dichlorobenzoylphenylphosphine oxide; 2,3,4,6-tetramethylbenzoyl-2,3,6-trimethoxy-5-bromobenzoylphenylphosphine oxide; 2,3,4,6-tetramethylbenzoyl-2,6-dichlorobenzoylphenylphosphine oxide; 2,3,4,6-tetramethylbenzoyl-2,4,6-trichlorobenzoylphenylphosphine oxide; 2,3,4,6-tetramethylbenzoyl-2,3,6-trichlorobenzoylphenylphosphine oxide; 2,3,4,6-tetramethylbenzoyl-2,3,5,6-tetrachlorobenzoylphenylphosphine oxide; 2,3,4,6-tetramethylbenzoyl-2,3,4,5,6-pentachlorobenzoylphenylphosphine oxide; 2,3,4,6-tetramethylbenzoyl-2,6-dichloro-3-methylbenzoylphenylphosphine oxide; 2,3,4,6-tetramethylbenzoyl-2-chloro-6-methylbenzoylphenylphosphine oxide; 2,3,4,6-tetramethylbenzoyl-2-methoxy-3,6-dichlorobenzoylphenylphosphine oxide; 2,3,4,6-tetramethylbenzoyl-2-methoxy-6-chlorobenzoylphenyloxide; 2,3,4,6-tetramethylbenzoyl-2-chloro-6methylthiobenzoylphenylphosphine oxide; 2,3,4,6-tetramethylbenzoyl-2,6-dibromobenzoylphenylphosphine oxide; 2,4,6-trimethoxybenzoyl-2,6-dipmethylobenzoylphenylphosphine oxide; 2,4,6-trimethoxybenzoyl-2,6-diethylbenzoylphenylphosphine oxide; 2,4,6-trimethoxybenzoyl-2,4,6-trimethylbenzoylphenylphosphine oxide; 2,4,6-trimethoxybenzoyl-2,3,4,5,6-pentamethylbenzoylphenylphosphine oxide; 2,4,6-trimethoxybenzoyl2,3,5,6-tetramethylbenzoylphenylphosphine oxide; 2,4,6-trimethoxybenzoyl-2,4,6-triisopropylbenzoylphenylphosphine oxide; 2,4,6-trimethoxybenzoyl-2,4,5,6-tetramethylbenzoylphenylphosphine oxide; 2,4,6-trimethoxybenzoyl-2,4,6-tri-tert-butylbenzoylphenylphosphine oxide; 2,4,6-trimethoxybenzoyl-2,6-dimethyl-4-tert-butylbenzoylphenylphosphine oxide; 2,4,6-trimethoxybenzoyl-2,6-diphenoxymethylbenzoylphenylphosphine; oxide; 2,4,6-trimethoxybenzoyl-2,3,6-trimethylbenzoylphenylphosphine oxide; 2,4,6-trimethoxybenzoyl-2,3,4,6-tetramethylbenzoylphenylphosphine oxide; 2,4,6-trimethoxybenzoyl-2-phenyl-6-methylbenzoylphenylphosphine oxide; 2,4,6-trimethoxybenzoyl-2,4-dimethoxybenzoylphenylphosphine oxide; 2,4,6-trimethoxybenzoyl-2,3,6-trimethoxybenzoylphenylphosphine oxide; 2,4,6trimethoxybenzoyl-2,6-diethoxybenzoylphenylphosphine oxide; 2,4,6-trimethoxybenzoyl-2,6-dimethoxy-3,5-dimethylbenzoylphenylphosphine oxide; 2,4,6-trimethoxybenzoyl-2,6-dimethoxy-4-methylbenzoylphenylphosphine oxide; 2,4,6-trimethoxybenzoyl-2,6-dimethoxy-3-bromobenzoylphenylphosphine oxide; 2,4,6-trimethoxybenzoyl-2,6-dimethoxy-3-chlorobenzoylphenylphosphine oxide; 2,4,6-trimethoxybenzoyl-2,6-dimethoxy-3-chloro-5-bromobenzoylphenylphosphine oxide; 2,4,6-trimethoxybenzoyl-2,6-dimethoxy-3,5-dichlorobenzoylphenylphosphine oxide; 2,4,6- trimethoxybenzoyl-2,3,6-trimethoxy-5-bromobenzoylphenylphosphine oxide; 2,4,6-trimethoxybenzoyl-2,6-dichlorobenzoylphenylphosphine oxide; 2,4,6-trimethoxybenzoyl-2,4,6-trichlorobenzoylphenylphosphine oxide; 2,4,6-trimethoxybenzoyl-2,3,6-trichlorobenzoylphenylphosphine oxide; 2,4,6-trimethoxybenzoyl-2,3,5,6-tetrachlorobenzoylphenylphosphine oxide; 2,4,6-trimethoxybenzoyl-2,3,4,5,6-pentachlorobenzoylphenylphosphine oxide; 2,4,6-trimethoxybenzoyl-2,6-dichloro-3-methylbenzoylphenylphosphine oxide; 2,4,6-trimethoxybenzoyl-2-chloro-6-methylbenzoylphenylphosphine oxide; 2,4,6-trimethoxybenzoyl-2-methoxy-3,6-dichlorobenzoylphenylphosphine oxide; 2,4,6-trimethoxybenzoyl-2-methoxy-6-chlorobenzoylphenylphosphine oxide; 2,4,6-trimethoxybenzoyl-2,6-bis(trifluoromethyl)benzoylphenylphosphine oxide; 2,4,6-trimethoxybenzoyl-2-chloro-6-methylthiobenzoylphenylphosphine oxide; 2,4,6-trimethoxybenzoyl-2,6-dibromobenzoylphenylphosphine oxide; 2,6-dimethyl-4-tert-butylbenzoyl-2,6-dimethylbenzoylphenylphosphine oxide; 2,6-dimethyl-4-tert-butylbenzoyl-2,6-diethylbenzoylphenylphosphine oxide; 2,6-dimethyl-4-tert-butylbenzoyl-2,4,6-trimethylbenzoylphenylphosphine oxide; 2,6-dimethyl-4-tert-butylbenzoyl-2,3,4,5,6-pentamethylbenzoylphenylphosphine oxide; 2,6-dimethyl-4-tert-butylbenzoyl-2,3,5,6-tetramethylbenzoylphenylphosphine oxide; 2,6-dimethyl-4-tert-butylbenzoyl-2,4,6-triisopropylbenzoylphenylphosphine oxide; 2,6-dimethyl-4-tert-butylbenzoyl-2,4,5,6-tetramethylbenzoylphenylphosphine oxide; 2,6-dimethyl-4-tert-butylbenzoyl-2,4,6-tri-tert-butylbenzoylphenylphosphine oxide; 2,6-dimethyl-4-tert-butylbenzoyl-2,6-dimethyl-4-tert-butylbenzoylphenylphosphine oxide; 2,6-dimethyl-4-tert-butylbenzoyl-2,6-diphenoxymethylbenzoylphenylphosphine oxide; 2,6-dimethyl-4-tert-butylbenzoyl-2,3,6-trimethylbenzoylphenylphosphine oxide; 2,6-dimethyl-4-tert-butylbenzoyl-2,3,4,6-tetramethylbenzoylphenylphosphine oxide; 2,6-dimethyl-4-tert-butylbenzoyl-2-phenyl-6-methylbenzoylphenylphosphine oxide; 2,6-dimethyl-4-tert-butylbenzoyl-2,4,6-trimethoxybenzoylphenylphosphine oxide; 2,6-dimethyl-4-tert-butylbenzoyl-2,4-dimethoxybenzoylphenylphosphine oxide; 2,6-dimethyl-4-tert-butylbenzoyl-2,3,6-trimethoxybenzoylphenylphosphine oxide; 2,6-dimethyl-4-tert-butylbenzoyl-2,6-diethoxybenzoylphenylphosphine oxide; 2,6-dimethyl-4-tert-butylbenzoyl-2,6-dimethoxy-3,5-dimethylbenzoylphenylphosphine oxide; 2,6-dimethyl-4-tert-butylbenzoyl-2,6-dimethoxy-4-methylbenzoylphenylphosphine oxide; 2,6-dimethyl-4-tert-butylbenzoyl-2,6-dimethoxy-3-bromobenzoylphenylphosphine oxide; 2,6-dimethyl-4-tert-butylbenzoyl-2,6-dimethoxy-3-chlorobenzoylphenylphosphine oxide; 2,6-dimethyl-4-tert-butylbenzoyl-2,6-dimethoxy-3-chloro-5-bromobenzoylphenylphosphine oxide; 2,6-dimethyl-4-tert-butylbenzoyl-2,6-dimethoxy-3,5-dichlorobenzoylphenylphosphine oxide; 2,6-dimethyl-4-tert-butylbenzoyl-2,3,6-trimethoxy-5-bromobenzoylphenylphosphine oxide; 2,6-dimethyl-4-tert-butylbenzoyl-2,6-dichlorobenzoylphenylphosphine oxide; 2,6-dimethyl-4-tert-butylbenzoyl-2,4,6-trichlorobenzoylphenylphosphine oxide; 2,6-dimethyl-4-tert-butylbenzoyl-2,3,6-trichlorobenzoylphenylphosphine oxide; 2,6-dimethyl-4-tert-butylbenzoyl-2,3,5,6-tetrachlorobenzoylphenylphosphine oxide; 2,6-dimethyl-4-tert-butylbenzoyl-2,3,4,5,6-pentachlorobenzoylphenylphosphine oxide; 2,6-dimethyl-4-tert-butylbenzoyl-2,6-dichloro-3-methylbenzoylphenylphosphine oxide; 2,6-dimethyl-4-tert-butylbenzoyl-2-chloro-6-methylbenzoylphenylphosphine oxide; 2,6-dimethyl-4-tert-butylbenzoyl-2-methoxy-3,6-dichlorobenzoylphenylphosphine oxide; 2,6-dimethyl-4-tert-butylbenzoyl-2-methoxy-6-chlorobenzoylphenylphosphine oxide; 2,6-dimethyl-4-tert-butylbenzoyl-2,6-bis(trifluoromethyl)benzoylphenylphosphine oxide; 2,6-dimethyl-4-tert-butylbenzoyl-2-chloro-6-methylthiobenzoylphenylphosphine oxide; 2,6-dimethyl-4-tert-butylbenzoyl-2,6-dibromobehzoylphenylphosphine oxide; 2-chloro-6-methylbenzoyl-2,6-dimethylbenzoylphenylphosphine oxide; 2-chloro-6-methylbenzoyl-2,6-diethylbenzoylphenylphosphine oxide; 2-chloro-6-methylbenzoyl-2,4,6-trimethylbenzoylphenylphosphine oxide; 2-chloro-6-methylbenzoyl-2,3,4,5,6-pentamethylbenzoylphenylphosphine oxide; 2-chloro-6-methylbenzoyl-2,3,5,6-tetramethylbenzoylphenylphosphine oxide; 2-chloro-6-methylbenzoyl-2,4,6-triisopropylbenzoylphenylphosphine oxide; 2-chloro-6-methylbenzoyl-2,4,5,6-tetramethylbenzoylphenylphosphine oxide; 2-chloro-6-methylbenzoyl-2,4,6-tri-tert-butylbenzoylphenylphosphine oxide; 2-chloro-6-methylbenzoyl-2,6-dimethyl-4-tert-butylbenzoylphenylphosphine oxide; 2-chloro-6-methylbenzoyl-2,6-diphenoxymethylbenzoylphenylphosphine oxide; 2-chloro-6-methylbenzoyl-2,3,6-trimethylbenzoylphenylphosphine oxide; 2-chloro-6-methylbenzoyl-2,3,4,6-tetramethylbenzoylphenylphosphine oxide; 2-chloro-6-methylbenzoyl-2-phenyl-6-methylbenzoylphenylphosphine oxide; 2-chloro-6-methylbenzoyl-2,4,6-trimethoxybenzoylphenylphosphine oxide; 2-chloro-6-methylbenzoyl-2,4-dimethoxybenzoylphenylphosphine oxide; 2-chloro-6-methylbenzoyl-2,3,6-trimethoxybenzoylphenylphosphine oxide; 2-chloro-6-methylbenzoyl-2,6-diethoxybenzoylphenylphosphine oxide; 2-chloro-6-methylbenzoyl-2,6-dimethoxy-3,5-dimethylbenzoylphenylphosphine oxide; 2-chloro-6-methylbenzoyl-2,6-dimethoxy-4-methylbenzoylphenylphosphine oxide; 2-chloro-6-methylbenzoyl-2,6-dimethoxy-3-bromobenzoylphenylphosphine oxide; 2-chloro-6-methylbenzoyl-2,6-dimethoxy-3-chlorobenzoylphenylphosphine oxide; 2-chloro-6-methylbenzoyl-2,6-dimethoxy-3-chloro-5-bromobenzoylphenylphosphine oxide; 2-chloro-6-methylbenzoyl-2,6-dimethoxy-3,5-dichlorobenzoylphenylphosphine oxide; 2-chloro-6-methylbenzoyl-2,3,6-trimethoxy-5-bromobenzoylphenylphosphine oxide; 2-chloro-6-methylbenzoyl-2,6-dichlorobenzoylphenylphosphine oxide; 2-chloro-6-methylbenzoyl-2,4,6-trichlorobenzoylphenylphosphine oxide; 2-chloro-6-methylbenzoyl-2,3,6-trichlorobenzoylphenylphosphine oxide; 2-chloro-6-methylbenzoyl-2,3,5,6-tetrachlorobenzoylphenylphosphine oxide; 2-chloro-6- methylbenzoyl-2,3,4,5,6-pentachlorobenzoylphenylphosphine oxide; 2-chloro-6-methylbenzoyl-2,6-dichloro-3-methylbenzoylphenylphosphine oxide; 2-chloro-6-methylbenzoyl-2-methoxy-3,6-dichlorobenzoylphenylphosphine oxide; 2-chloro-6-methylbenzoyl-2-methoxy-6-chlorobenzoylphenylphosphine oxide; 2-chloro-6-methylbenzoyl-2,6-bis(trifluoromethyl)benzoylphenylphosphine oxide; 2-chloro-6-methylbenzoyl-2-chloro-6-methylthiobenzoylphenylphosphine oxide; 2-chloro-6-methylbenzoyl-2,6-dibromobenzoylphenylphosphine oxide; 2-chloro-6-methoxybenzoyl-2,6-dimethylbenzoylphenylphosphine oxide; 2-chloro-6-methoxybenzoyl-2,6-diethylbenzoylphenylphosphine oxide; 2-chloro-6-methoxybenzoyl-2,4,6-trimethylbenzoylphenylphosphine oxide; 2-chloro-6-methoxybenzoyl-2,3,4,5,6-pentamethylbenzoylphenylphosphine oxide; 2-chloro-6-methoxybenzoyl-2,3,5,6-tetramethylbenzoylphenylphosphine oxide; 2-chloro-6-methoxybenzoyl-2,4,6-triisopropylbenzoylphenylphosphine oxide; 2-chloro-6-methoxybenzoyl-2,4,5,6-tetramethylbenzoylphenylphosphine oxide; 2-chloro-6-methoxybenzoyl-2,4,6-tri-tert-butylbenzoylphenylphosphine oxide; 2-chloro-6-methoxybenzoyl-2,6-dimethyl-4-tert-butylbenzoylphenylphosphine oxide; 2-chloro-6-methoxybenzoyl-2,6-diphenoxymethylbenzoylphenylphosphine oxide; 2-chloro-6-methoxybenzoyl-2,3,6-trimethylbenzoylphenylphosphine oxide; 2-chloro-6-methoxybenzoyl-2,3,4,6-tetramethylbenzoylphenylphosphine oxide; 2-chloro-6-methoxybenzoyl-2-phenyl-6-methylbenzoylphenylphosphine oxide; 2-chloro-6-methoxybenzoyl-2,4,6-trimethoxybenzoylphenylphosphine oxide; 2-chloro-6-methoxybenzoyl-2,4-dimethoxybenzoylphenylphosphine oxide; 2-chloro-6-methoxybenzoyl-2,3,6-trimethoxybenzoylphenylphosphine oxide; 2-chloro-6-methoxybenzoyl-2,6-diethoxybenzoylphenylphosphine oxide; 2-chloro-6-methoxybenzoyl-2,6-dimethoxy-3,5-dimethylbenzoylphenylphosphine oxide; 2-chloro-6-methoxybenzoyl-2,6-dimethoxy-4-methylbenzoylphenylphosphine oxide; 2-chloro-6-methoxybenzoyl-2,6-dimethoxy-3-bromobenzoylphenylphosphine oxide; 2-chloro-6-methoxybenzoyl-2,6-dimethoxy-3-chlorobenzoylphenylphosphine oxide; 2-chloro-6-methoxybenzoyl-2,6-dimethoxy-3-chloro-5-bromobenzoylphenylphosphine oxide; 2-chloro-6-methoxybenzoyl-2,6-dimethoxy-3,5-dichlorobenzoylphenylphosphine oxide; 2-chloro-6-methoxybenzoyl-2,3,6-trimethoxy-5-bromobenzoylphenylphosphine oxide; 2-chloro-6-methoxybenzoyl-2,6-dichlorobenzoylphenylphosphine oxide; 2-chloro-6-methoxybenzoyl-2,4,6-trichlorobenzoylphenylphosphine oxide; 2-chloro-6-methoxybenzoyl-2,3,6-trichlorobenzoylphenylphosphine oxide; 2-chloro-6-methoxybenzoyl-2,3,5,6-tetrachlorobenzoylphenylphosphine oxide; 2-chloro-6-methoxybenzoyl-2,3,4,5,6-pentachlorobenzoylphenylphosphine oxide; 2-chloro-6-methoxybenzoyl-2,6-dichloro-3-methylbenzoylphenylphosphine oxide; 2-chloro-6-methoxybenzoyl-2-chloro-6-methylbenzoylphenylphosphine oxide; 2-chloro-6-methoxybenzoyl-2-methoxy-3,6-dichlorobenzoylphenylphosphine oxide; 2-chloro-6-methoxybenzoyl-2,6-bis(trifluoromethyl)benzoylphenylphosphine oxide; 2-chloro-6-methoxybenzoyl-2-chloro-6-methylthiobenzoylphenylphosphine oxide; 2-chloro-6-methoxybenzoyl-2,6-dibromobenzoylphenylphosphine oxide.

The compounds of the formula II where x=0 (formula II') are obtained by reacting an arylacrylphosphine of the formula I with an acid halide of the formula (IV):

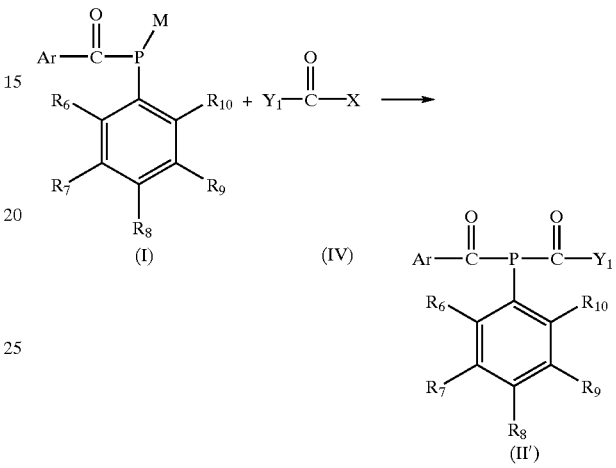

The meanings of the radicals Ar, $R_6$–$R_{10}$, M, X, A, x and $Y_1$ are as described above. The starting materials are advantageously reacted in a molar ratio of 1:1. A slight excess of one or other of the components, e.g. up to 20%, is, however, not critical. The desired product forms in this case too, although the portion of undesired byproduct can be influenced. The reaction conditions for this reaction correspond to those given above in connection with the preparation of the compounds of the formula I.

Compounds of the formula II where x=1 and A is oxygen are prepared by oxidation of the compounds of the formula (II'), and compounds of the formula II where A is sulfur are prepared by sulfurization of the compounds of the formula II':

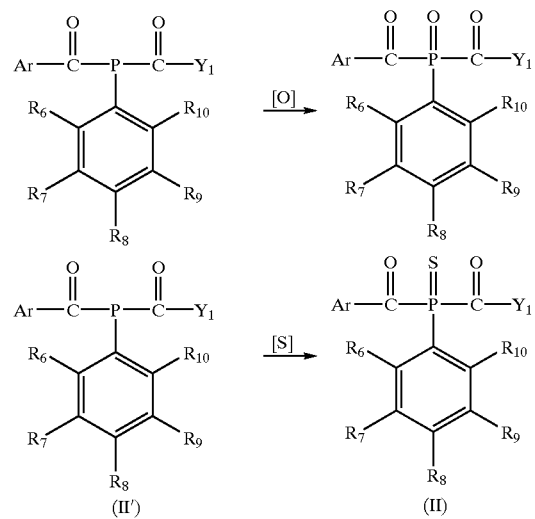

Prior to the oxidation or sulfurization, the phosphine II' can be isolated by customary separation methods familiar to the person skilled in the art, although the reaction can also be carried out immediately after the previous reaction step without isolation of the phosphine. During the preparation of the oxide, the oxidation of the phosphine is carried out using oxidizing agents customary in the art. Suitable oxidizing agents are primarily hydrogen peroxide and organic peroxy compounds, for example peracetic acid or t-butyl hydroperoxide, air or pure oxygen.

The oxidation is advantageously carried out in solution. Suitable solvents are aromatic hydrocarbons, for example benzene, toluene, m-xylene, p-xylene, ethylbenzene or mesitylene, or aliphatic hydrocarbons, e.g. alkanes and alkane mixtures, such as petroleum ether, hexane or cyclohexane. Further suitable examples are dimethyl ether, diethyl ether, methyl propyl ether, 1,2-dimethoxyethane, bis(2-methoxyethyl)ether, dioxane or tetrahydrofuran. Preference is given to using toluene.

The reaction temperature during the oxidation is advantageously kept between 0° and 120° C., preferably between 200 and 80° C.

The reaction products of the formula (II) can be isolated and purified by customary processing measures familiar to the person skilled in the art.

The preparation of the respective sulfide is carried out by reaction with sulfur. The bisacylphosphines (II') are here reacted with an equimolar to 2-fold molar amount of elemental sulfur e.g. without a diluent or optionally in a suitable inert organic solvent. Examples of suitable solvents are those described for the oxidation reaction. It is, however, also possible to use, for example, aliphatic or aromatic ethers, for example dibutyl ether, dioxane, diethylene glycol dimethyl ether or diphenyl ether at temperatures of from 200 to 250° C., preferably 60° to 120° C. The resulting bisacylphosphine sulfide, or its solution is advantageously freed from any elemental sulfur which may still be present by filtration. Following removal of the solvent, the bisacylphosphine sulfide can be isolated in pure form by distillation, recrystallization or chromatographic separation methods.

It is advantageous to carry out all of the reactions described above with the exclusion of air in an inert gas atmosphere, e.g. under nitrogen or argon gas. Moreover, stirring of the respective reaction mixture is advantageously appropriate.

The invention likewise provides a process for the preparation of the compounds of the formula II, from compounds of the formula I as starting materials, by (1) reaction of an acyl halide of the formula IV

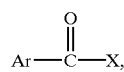

(IV)

in which
Ar is as defined above, and
X is Cl or Br;
with a dimetalated arylphosphine of the formula V

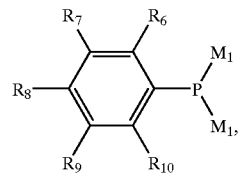

(V)

in which
$R_6$, $R_7$, $R_8$, $R_9$ and $R_{10}$ are as defined above; and
$M_1$ is Na, Li or K;
in the molar ratio of approximately 1:1;

(2) subsequent reaction of the product with an acyl halide of the formula IVa

(IVa)

in which
$Y_1$ is as defined above; and
X is as defined above;
with the proviso that the acyl halide of the formula IV is not identical to the acyl halide of the formula IVa;
in the molar ratio of approximately 1:1; and, (3) if compounds of the formula II in which A is oxygen or sulfur are to be obtained, subsequent oxidation or sulfurization of the resulting phosphine compounds.

Furthermore, the compounds of the formula II can also be prepared by reacting the compound of the formula I with phosgene, analogously to the description in "W. A. Henderson et al., J. Am. Chem. Soc. 1960, 82, 5794" or "GB 904 086" or in "Organic Phosphorous Compounds, Editors: R. M. Kosolapoff and L. Maier, Wiley-Interscience 1972, Vol.1, page 28" or "Houben-Weyl, Methoden der Organischen Chemie, Vol. XII/1, page 201", to give the corresponding phosphinechloride (Ii). Compounds of the formula (Ii) can, as described in "Organic Phosphorous Compounds, Editors: R. M. Kosolapoff and L. Maier, Wiley-Interscience 1972, Vol.4, pages 268–269", be reacted with alcohols to give compounds of the formula (Iii), which are then reacted directly with an acyl halide of the formula IVa, in analogy with the description in U.S. Pat. No. 4,324,744 (by Michaelis-Arbuzov reaction), to give compounds of the formula II. In this case, the oxidation step is superfluous.

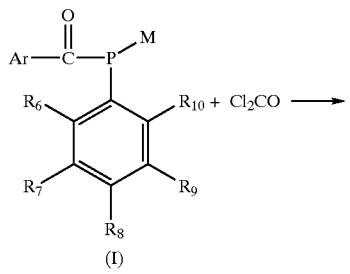

(I)

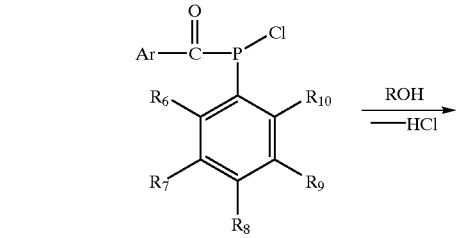

(Ii)

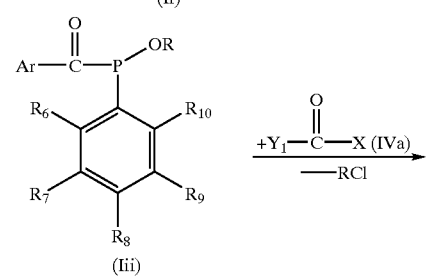

(Iii)

-continued

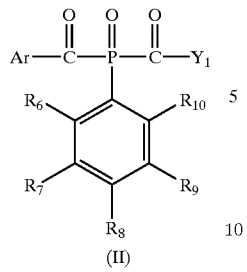

(II)

Ar and $Y_1$ are as defined in claims 1 and 2, although Ar and $Y_1$ are not the same radical; X is Cl or Br; M and $R_6$ are likewise as defined in claim 1, and R is any alcohol radical, e.g. $C_1$–$C_{12}$alkyl, $C_5$–$C_8$cycloalkyl, for example cyclopentyl or cyclohexyl, or benzyl.

Compounds of the formula (Iii) can be oxidized using suitable oxidizing agents, such as peroxo acids, hydrogen peroxide or hydrogen peroxide/urea, to give the corresponding phosphinic esters (Iiii):

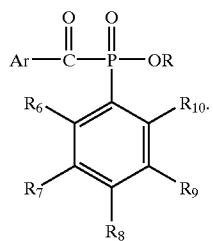

(Iiii)

This preparation process is novel.

The invention thus also provides a process for the preparation of compounds of the formula II in which A is oxygen and x is 1, by (1) reaction of the compounds of the formula (I),

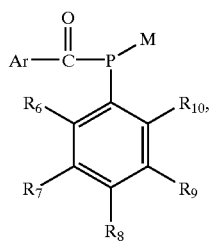

(I)

in which
Ar, M, $R_6$, $R_7$, $R_8$, $R_9$ and $R_{10}$ are as defined above, with phosgene to give the corresponding phosphine chloride (Ii)

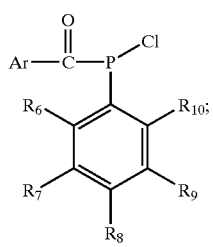

(Ii)

(2) subsequent reaction with an alcohol to give the compound of the formula (Iii)

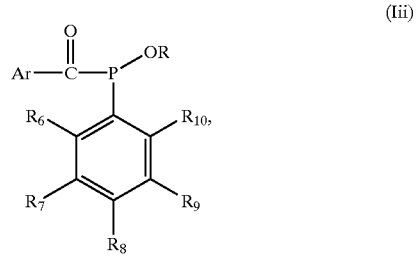

(Iii)

in which
R is the radical of an alcohol, in particular $C_1$–$C_{12}$alkyl, $C_5$–$C_8$cycloalkyl or benzyl; and (3) reaction of the resulting compound of the formula (Iii) with an acyl halide

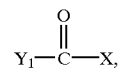

in which
$Y_1$ is as defined above, but is not identical to Ar from the formula (I), and
X is Cl or Br,
to give the compound of the formula II.

As already mentioned, slightly unsymmetrical monoacylphosphines, monoacylphosphine oxides or monoacylphosphine sulfides can also be obtained from the compounds of the formula I.

The invention thus also provides compounds of the formula III

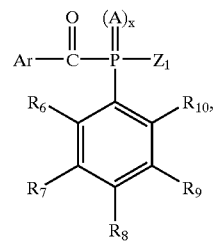

(III)

in which
A is O or S;
x is 0 or 1;
Ar is a group

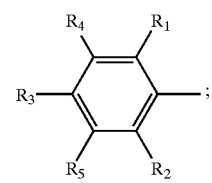

or Ar is cyclopentyl, cyclohexyl, naphthyl, biphenylyl, anthracyl or an O—, S— or N-containing 5- or 6-membered heterocyclic ring, where the radicals cyclopentyl, cyclohexyl, naphthyl, biphenylyl, anthracyl or O—, S— or N-containing 5- or 6-membered heterocyclic ring are unsubstituted or are substituted by halogen, $C_1$–$C_4$alkyl and/or $C_1$–$C_4$alkoxy;

$R_1$ and $R_2$ independently of one another are $C_1$–$C_{20}$alkyl, $OR_{11}$, $CF_3$ or halogen;

$R_3$, $R_4$ and $R_5$ independently of one another are hydrogen, $C_1$–$C_{20}$alkyl, $OR_{11}$ or halogen or in each case two of the radicals $R_1$, $R_2$, $R_3$, $R_4$ and/or $R_5$ together form a $C_1$–$C_{20}$alkylene which can be interrupted by O, S or $NR_{14}$;

$R_6$, $R_7$, $R_8$, $R_9$ and $R_{10}$ independently of one another are hydrogen, $C_1$–$C_{20}$alkyl; $C_2$–$C_{20}$alkyl which is interrupted once or more than once by nonconsecutive O atoms and which is unsubstituted or substituted by OH and/or SH; or $R_6$, $R_7$, $R_8$, $R_9$ and $R_{10}$ are $OR_{11}$; halogen or unsubstituted phenyl or phenyl substituted once or more than once by $C_1$–$C_4$alkyl;

$R_{11}$ is hydrogen, $C_1$–$C_{20}$alkyl, $C_2$–$C_{20}$alkenyl, $C_3$–$C_8$cycloalkyl, phenyl, benzyl or $C_2$–$C_{20}$alkyl which is interrupted once or more than once by nonconsecutive O atoms and which is unsubstituted or substituted by OH and/or SH;

$Z_1$ is $C_1$–$C_{24}$alkyl which is unsubstituted or substituted once or more than once by $OR_{15}$, $SR_{15}$, $N(R_{16})(R_{17})$, phenyl, halogen, CN, NCO, 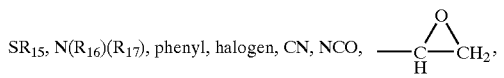

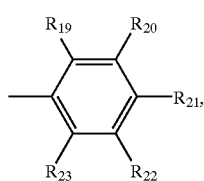

cycloalkyl or $C_3$–$C_{24}$cycloalkyl substituted by $C_1$–$C_{20}$alkyl, $OR_{11}$, $CF_3$ or halogen; unsubstituted $C_2$–$C_{24}$alkenyl or $C_2$–$C_{24}$-alkenyl substituted by $C_6$–$C_{12}$aryl, CN, (CO)$OR_{15}$ or (CO)$N(R_{18})_2$; or $Z_1$ is $C_3$–$C_{24}$cycloalkenyl or is one of the radicals (f)

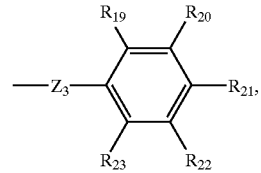

(g)

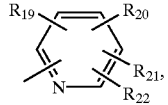

(h)

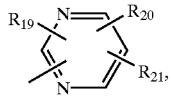

(i)

(k)

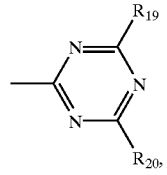

(l)

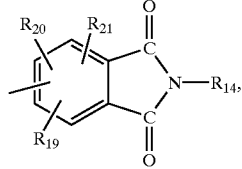

(m)

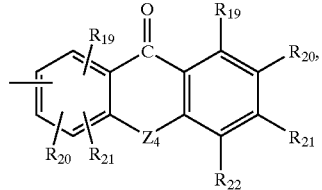

(n)

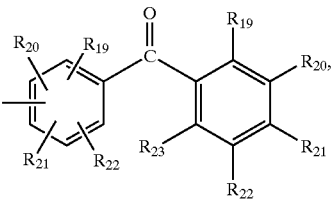

(o)

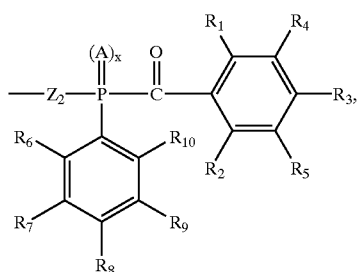

(p)

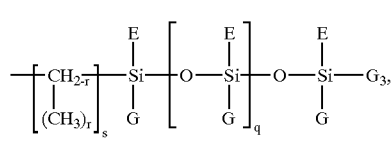

-continued

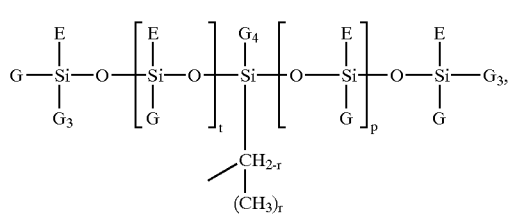  (q)

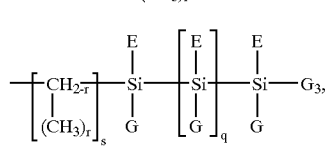  (t)

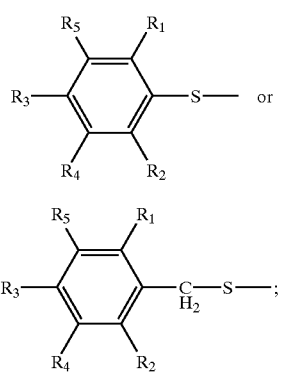

(v)

(w)

or $Z_1$ is $C_1$–$C_{24}$alkylthio, in which the alkyl radical is uninterrupted or is interrupted once or more than once by nonconsecutive O or S, and is unsubstituted or substituted by $OR_{15}$, $SR_{15}$ and/or halogen;

$A_1$ is O, S or $NR_{18a}$;

$Z_2$ is $C_1$–$C_{24}$alkylene; $C_2$–$C_{24}$alkylene interrupted once or more than once by O, S, or $NR_{14}$; $C_2$–$C_{24}$alkenylene; $C_2$–$C_{24}$alkenylene interrupted once or more than once by O, S, or $NR_{14}$; $C_3$–$C_{24}$cycloalkylene; $C_3$–$C_{24}$cycloalkylene interrupted once or more than once by O, S, or $NR_{14}$; $C_3$–$C_{24}$cycloalkenylene; $C_3$–$C_{24}$cycloalkenylene interrupted once or more than once by O, S, or $NR_{14}$;

where the radicals $C_1$–$C_{24}$alkylene, $C_2$–$C_{24}$alkylene, $C_2$–$C_{24}$alkenylene, $C_3$–$C_{24}$cycloalkylene and $C_3$–$C_{24}$cycloalkenylene are unsubstituted or are substituted by $OR_{11}$, $SR_{11}$, $N(R_{12})(R_{13})$ and/or halogen; or $Z_2$ is one of the radicals

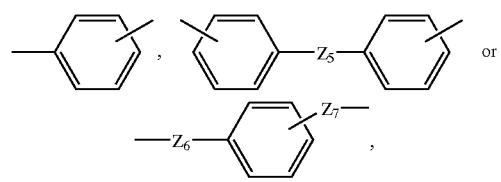

where these radicals are unsubstituted or are substituted on the aromatic by $C_1$–$C_{20}$alkyl; $C_2$–$C_{20}$alkyl which is interrupted once or more than once by non-consecutive O atoms and which is unsubstituted or substituted by OH and/or SH; $OR_{11}$, $SR_{11}$, $N(R_{12})(R_{13})$, phenyl, halogen, $NO_2$, CN, (CO)—$OR_{18}$, (CO)—$R_{18}$, (CO)—$N(R_{18})_2$, $SO_2R_{24}$, $OSO_2R_{24}$, $CF_3$ and/or $CCl_3$; or $Z_2$ is a group (r)

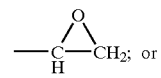  or (u)

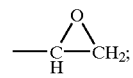

$Z_3$ is $CH_2$, $CHCH_3$ or $C(CH_3)_2$;

$Z_4$ is S, O, $CH_2$, C=O, $NR_{14}$ or a direct bond;

$Z_5$ is S, O, $CH_2$, $CHCH_3$, $C(CH_3)_2$, $C(CF_3)_2$, CO, SO, $SO_2$;

$Z_6$ and $Z_7$ independently of one another are $CH_2$, $CHCH_3$ or $C(CH_3)_2$;

r is 0, 1 or 2;

s is a number from 1 to 12;

q is a number from 0 to 50;

t and p are each a number from 0 to 20;

E, G, $G_3$ and $G_4$ independently of one another are unsubstituted $C_1$–$C_{12}$alkyl or $C_1$–$C_{12}$alkyl substituted by halogen, or are unsubstituted phenyl or phenyl substituted by one or more $C_1$–$C_4$alkyl;

$R_{11a}$ is $C_1$–$C_{20}$alkyl substituted once or more than once by $OR_{15}$, halogen or $$-\underset{H}{\overset{O}{C}}-CH_2; \text{ or}$$

is $C_2$–$C_{20}$alkyl interrupted once or more than once by nonconsecutive O atoms and which optionally is substituted once or more than once by $OR_{15}$, halogen or $$-\underset{H}{\overset{O}{C}}-CH_2;$$

or is $C_2$–$C_{20}$alkenyl or $C_3$–$C_{12}$alkynyl; or is $C_3$–$C_{12}$cycloalkyl substituted once or more than once by $C_1$–$C_6$alkyl or halogen; or is $C_6$–$C_{12}$aryl optionally substituted once or more than once by halogen, $NO_2$, $C_1$–$C_6$alkyl, $OR_{11}$ or $C(O)OR_{18}$; or is $C_7$–$C_{16}$arylalkyl or $C_8$–$C_{16}$arylcycloalkyl;

$R_{14}$ is hydrogen, phenyl, $C_1$–$C_{12}$alkoxy, $C_1$–$C_{12}$alkyl or $C_2$–$C_{12}$alkyl which is interrupted once or more than once by O or S and which is unsubstituted or substituted by OH and/or SH;

$R_{15}$ has one of the meanings given for $R_{11}$ or is a radical

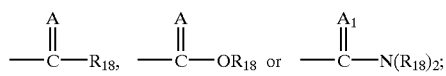

$R_{16}$ and $R_{17}$ independently of one another have one of the meanings given for $R_{12}$ or are a radical

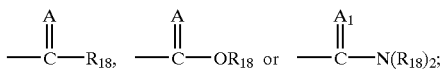

R$_{18}$ is hydrogen, C$_1$–C$_{24}$alkyl, C$_2$–C$_{12}$alkenyl, C$_3$–C$_8$cycloalkyl, phenyl, benzyl; C$_2$–C$_{20}$alkyl which is interrupted once or more than once by O or S and which is unsubstituted or substituted by OH;

R$_{18a}$ and R$_{18b}$ independently of one another are hydrogen, C$_1$–C$_{20}$alkyl which is substituted once or more than once by OR$_{15}$, halogen, styryl, methylstyryl, —N=C=A or

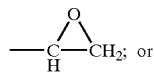

are C$_2$–C$_{20}$alkyl which is interrupted once or more than once by nonconsecutive O atoms and which optionally is substituted once or more than once by OR$_{15}$, halogen, styryl, methylstyryl or

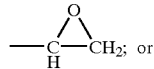

are C$_2$–C$_{12}$alkenyl; or are C$_5$–C$_{12}$cycloalkyl substituted by —N=C=A or —CH$_2$—N=C=A and optionally additionally once or more than once substituted by C$_1$–C$_4$alkyl; or are C$_6$–C$_{12}$aryl optionally once or more than once substituted by halogen, NO$_2$, C$_1$–C$_6$alkyl, C$_2$–C$_4$alkenyl, OR$_{11}$, —N=C=A, —CH$_2$—N=C=A or C(O)OR$_{18}$; or are C$_7$–C$_{16}$arylalkyl; or both groups R$_{18a}$ and R$_{18b}$ together are C$_8$–C$_{16}$arylcycloalkyl; or R$_{18a}$ and R$_{18b}$ independently of one another are

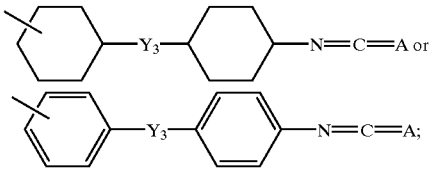

Y$_3$ is O, S, SO, SO$_2$, CH$_2$, C(CH$_3$)$_2$, CHCH$_3$, C(CF$_3$)$_2$, (CO), or a direct bond;

R$_{19}$, R$_{20}$, R$_{21}$, R$_{22}$ and R$_{23}$ have one of the meanings given for R$_6$ or are NO$_2$, CN, SO$_2$R$_{24}$, OSO$_2$R$_{24}$, CF$_3$, CCl$_3$ or halogen;

R$_{24}$ is C$_1$–C$_{12}$alkyl, halogen-substituted C$_1$–C$_{12}$alkyl, phenyl, or phenyl substituted by OR$_{15}$ and/or SR$_{15}$;

with the proviso that if Z$_1$ is a radical

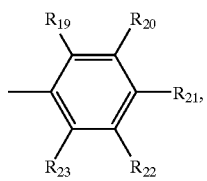

this is not identical to the other aromatic radical

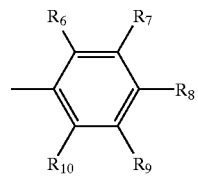

on the phosphorus atom.

In the compounds of the formula III, the preferred meanings of the radicals R$_1$, R$_2$, R$_3$, R$_4$, R$_5$, R$_6$, R$_7$, R$_8$, R$_9$ and R$_{10}$ are analogous to those given above for the compounds of the formula I.

Preferred R$_{19}$, R$_{20}$, R$_{21}$, R$_{22}$ and R$_{23}$ are defined identically to the preferred R$_6$, R$_7$, R$_8$, R$_9$ and R$_{10}$ in formula I.

A in formula III is, in particular, oxygen and x is preferably 1.

Preference is given to compounds of the formula III in which A is O; and x is 1; R$_1$ and R$_2$ independently of one another are C$_1$–C$_{12}$alkyl, C$_1$–C$_{12}$alkoxy, CF$_3$ or halogen; R$_3$, R$_4$ and R$_5$ independently of one another are hydrogen, C$_1$–C$_{12}$alkyl, C$_1$–C$_{12}$alkoxy or halogen; R$_6$, R$_7$, R$_8$, R$_9$ and R$_{10}$ independently of one another are hydrogen, C$_1$–C$_{12}$alkyl; C$_2$–C$_{12}$alkyl which is interrupted once or more than once by nonconsecutive O atoms and which is unsubstituted or substituted by OH and/or SH; or R$_6$, R$_7$, R$_8$, R$_9$ and R$_{10}$ are OR$_{11}$, SR$_{11}$, N(R$_{12}$)(R$_{13}$), phenyl or halogen; R$_{11}$ is C$_1$–C$_{12}$alkyl, C$_3$–C$_8$cycloalkyl, phenyl, benzyl or C$_2$–C$_{12}$alkyl which is interrupted once or more than once by nonconsecutive O atoms and which is unsubstituted or substituted by OH and/or SH; R$_{12}$ and R$_{13}$ independently of one another are hydrogen, C$_1$–C$_4$alkyl, C$_3$–C$_6$cycloalkyl, phenyl, benzyl or C$_2$–C$_{12}$alkyl which is interrupted once or more than once by O or S and which is unsubstituted or substituted by OH and/or SH; or R$_{12}$ and R$_{13}$ together are piperidino, morpholino or piperazino; Z$_1$ is C$_1$–C$_{18}$alkyl which is unsubstituted or mono- or polysubstituted by OR$_{15}$, SR$_{15}$, N(R$_{16}$)(R$_{17}$), phenyl, halogen, CN, NCO,

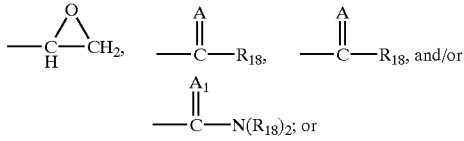

Z$_1$ is C$_2$–C$_{18}$alkyl which is interrupted once or more than once by O, S or NR$_{14}$ and which is unsubstituted or substituted by OR$_{15}$, SR$_{15}$, N(R$_{16}$)(R$_{17}$), phenyl, halogen,

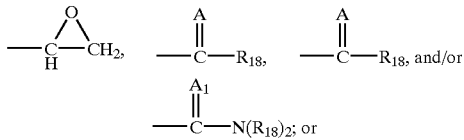

Z$_1$ is C$_1$–C$_{18}$alkoxy which is substituted once or more than once by phenyl, CN, NCO,

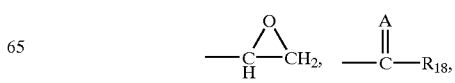

-continued

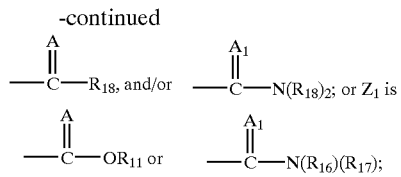

or $Z_1$ is unsubstituted $C_3$–$C_{12}$cycloalkyl or $C_3$–$C_{12}$cycloalkyl substituted by $C_1$–$C_{20}$alkyl, $OR_{11}$, $CF_3$ or halogen; unsubstituted $C_2$–$C_{12}$alkenyl or $C_2$–$C_{12}$alkenyl substituted by phenyl, naphthyl, biphenylyl; or is $C_3$–$C_{12}$cycloalkenyl, or $Z_1$ is one of the radicals (f), (g), (h), (i), (k), (l), (m), (n), (o), (p) (q) or (t); $Z_2$ is $C_1$–$C_{18}$alkylene; $C_2$–$C_{12}$alkylene interrupted once or more than once by O, S, or $NR_{14}$, $C_2$–$C_{12}$alkenylene; $C_2$–$C_{12}$alkenylene interrupted once or more than once by O, S, or $NR_{14}$; $C_3$–$C_{12}$cycloalkylene; $C_3$–$C_{12}$cycloalkylene interrupted once or more than once by O, S, or $NR_{14}$; $C_3$–$C_{12}$cycloalkylene; $C_3$–$C_{12}$cycloalkenylene interrupted once or more than once by O, S, or $NR_{14}$; where the radicals $C_1$–$C_{18}$alkylene, $C_2$–$C_{12}$alkylene, $C_2$–$C_{12}$alkenylene, $C_3$–$C_{12}$cycloalkylene and $C_3$–$C_{12}$cycloalkenylene are unsubstituted or are substituted by $OR_{11}$, $SR_{11}$, $N(R_{12})(R_{13})$ and/or halogen; or $Z_2$ is one of the radicals

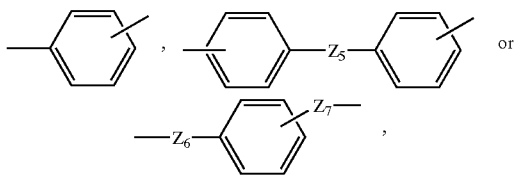

these radicals being unsubstituted or substituted on the aromatic by $C_1$–$C_{12}$alkyl; $C_2$–$C_{12}$alkyl which is interrupted once or more than once by nonconsecutive O atoms and which is unsubstituted or substituted by OH and/or SH; $OR_{11}$, $SR_{11}$, $N(R_{12})(R_{13})$, phenyl, halogen, $NO_2$, CN, (CO)—$OR_{18}$, (CO)—$R_{18}$, (CO)—$N(R_{18})_2$, $SO_2R_{24}$, and/or $CF_3$; or $Z_2$ is a group (r); $Z_3$ is $CH_2$, $CHCH_3$ or $C(CH_3)_2$; $Z_4$ is S, O, $CH_2$, C=O, $NR_{14}$ or a direct bond; $Z_5$ is S, O, $CH_2$, $CHCH_3$, $C(CH_3)_2$, $C(CF_3)_2$, CO, SO, $SO_2$; $Z_6$ and $Z_7$ independently of one another are $CH_2$, $CHCH_3$ or $C(CH_3)_2$; r is 0, 1 or 2; s is a number from 1 to 12; q is a number from 0 to 50; t and p are in each case a number from 0 to 20; E, G, $G_3$ and $G_4$ independently of one another are $C_1$–$C_{12}$alkyl, or are unsubstituted phenyl or phenyl substituted by one or more $C_1$–$C_4$alkyl; $R_{14}$ is hydrogen, phenyl, $C_1$–$C_4$alkyl or $C_1$–$C_4$alkoxy, $R_{15}$ has one of the meanings given for $R_{11}$ or is a radical

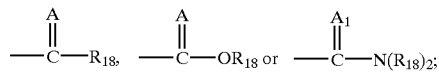

$R_{16}$ and $R_{17}$ independently of one another have one of the meanings given for $R_{12}$ or are a radical

$R_{18}$ is hydrogen, $C_1$–$C_{24}$alkyl, $C_2$–$C_{12}$alkenyl, $C_3$–$C_8$cycloalkyl, phenyl, benzyl; $C_2$–$C_{20}$alkyl which is interrupted once or more than once by O or S and which is unsubstituted or substituted by OH; $R_{19}$, $R_{20}$, $R_{21}$, $R_{22}$ and $R_{23}$ have one of the meanings given for $R_6$ or are $NO_2$, CN, $SO_2R_{24}$, $CF_3$, or halogen; $R_{24}$ is $C_1$–$C_{12}$alkyl, halogen-substituted $C_1$–$C_{12}$alkyl, phenyl, or is phenyl substituted by $OR_{15}$ and/or $SR_{15}$.

In the compounds of the formula III, $R_6$, $R_7$, $R_8$, $R_9$ and $R_{10}$ are preferably hydrogen, $C_1$–$C_8$alkyl, $C_1$–$C_8$alkoxy or chlorine, in particular hydrogen.

$R_{12}$ and $R_{13}$ in the compounds of the formula III are preferably $C_1$–$C_4$alkyl, $C_1$–$C_4$alkoxy or $R_{12}$ and $R_{13}$ together form a morpholino ring.

Also of interest are compounds of the formula III in which A is O; and x is 1; $R_1$ and $R_2$ independently of one another are $C_1$–$C_4$alkyl, $C_1$–$C_4$alkoxy, $CF_3$ or halogen; $R_3$, $R_4$ and $R_5$ independently of one another are hydrogen, $C_1$–$C_4$alkyl, $C_1$–$C_4$alkoxy or chlorine; $R_6$, $R_7$, $R_8$, $R_9$ and $R_{10}$ independently of one another are hydrogen, $C_1$–$C_8$alkoxy, $C_1$–$C_6$alkyl; or $R_6$, $R_7$, $R_8$, $R_9$ and $R_{10}$ are phenyl or halogen; $R_{11}$ is $C_1$–$C_8$alkyl, cyclopentyl, cyclohexyl, phenyl, benzyl or $C_2$–$C_6$alkyl which is interrupted once or twice by nonconsecutive O atoms and which is unsubstituted or substituted by OH; $Z_1$ is $C_1$–$C_{12}$alkyl which is unsubstituted or is mono- or polysubstituted by $OR_{15}$, $SR_{15}$, $N(R_{16})(R_{17})$, phenyl, halogen, CN, NCO,

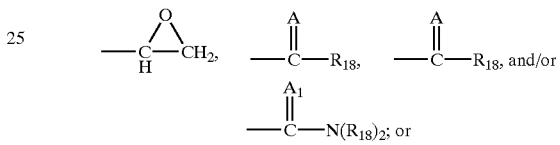

$Z_1$ is $C_2$–$C_{12}$alkyl which is interrupted once or more than once by O, S or $NR_{14}$ and which is unsubstituted or substituted by $OR_{15}$, $SR_{15}$, $N(R_{16})(R_{17})$, phenyl, halogen,

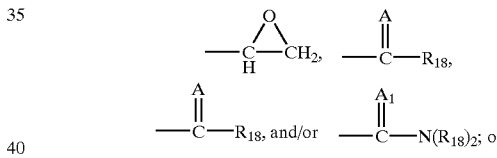

$Z_1$ is $C_1$–$C_{12}$alkoxy which is mono- or polysubstituted by phenyl, CN, NCO,

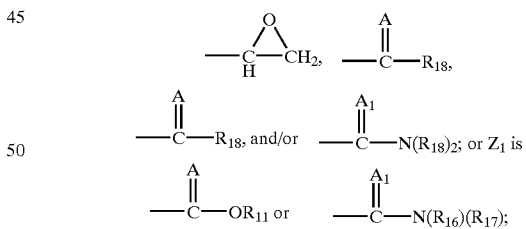

or $Z_1$ is in each case unsubstituted or $C_1$–$C_{20}$alkyl-, $OR_{11}$—, $CF_3$— or halogen-substituted cyclopentyl or cyclohexyl; or $Z_1$ is unsubstituted $C_2$–$C_{12}$alkenyl or $C_2$–$C_{12}$alkenyl substituted by phenyl, biphenylyl or naphthyl; or $C_5$–$C_{12}$cycloalkenyl is or stands for one of the radicals (f), (g), (h), (i), (k), (l), (m), (n), (o), (p) (q) or (t); $Z_2$ is $C_1$–$C_{12}$alkylene; $C_2$–$C_{12}$alkenyl interrupted once or more than once by O; $C_2$–$C_{12}$alkenylene; $C_2$–$C_{12}$alkenylene interrupted once or than once by O; $C_5$–$C_8$cycloalkylene; $C_3$–$C_5$cycloalkylene interrupted by O, S, or $NR_{14}$; $C_5$–$C_8$cycloalkenylene; $C_3$–$C_5$cycloalkenylene interrupted by O, S, or $NR_{14}$; where the radicals $C_1$–$C_{12}$alkylene, $C_2$–$C_{12}$alkylene, $C_2$–$C_{12}$alkenylene, $C_5$–$C_8$-cycloalkylene and $C_3$–$C_8$-cycloalkenylene are unsubstituted or are substituted by $OR_{11}$; or $Z_2$ is one of the radicals

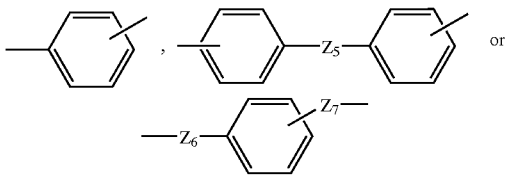

where these radicals are unsubstituted or are substituted on the aromatic by $C_1$–$C_4$alkyl, $OR_{11}$, phenyl, (CO)—$OR_{18}$, (CO)—$R_{18}$ and/or (CO)—$N(R_{18})_2$; or $Z_2$ is a group (r); $Z_3$ is $CH_2$, $CHCH_3$ or $C(CH_3)_2$; $Z_4$ is S, O, $CH_2$, C=O, $NR_{14}$ or a direct bond; $Z_5$ is O, $CH_2$, $CHCH_3$, $C(CH_3)_2$, $C(CF_3)_2$; $Z_6$ and $Z_7$ independently of one another are $CH_2$, $CHCH_3$ or $C(CH_3)_2$; r is 0, 1 or 2; s is a number from 1 to 12; q is a number from 0 to 50; t and p are in each case a number from 0 to 20; E, G, $G_3$ and $G_4$ independently of one another are $C_1$–$C_{12}$alkyl, or are unsubstituted phenyl or phenyl substituted by one or more $C_1$–$C_4$alkyl; $R_{14}$ is hydrogen, phenyl or $C_1$–$C_4$alkyl; $R_{15}$ has one of the meanings given for $R_{11}$ or is a radical

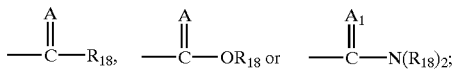

$R_{16}$ and $R_{17}$ independently of one another have one of the meanings given for $R_{12}$ or are a radical

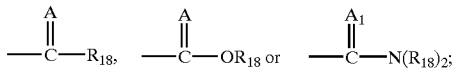

$R_{18}$ is hydrogen, $C_1$–$C_{24}$alkyl, $C_2$–$C_{12}$alkenyl, $C_3$–$C_8$cycloalkyl, phenyl, benzyl, $C_2$–$C_{20}$alkyl which is interrupted once or more than once by O or S and which is optionally substituted by OH; $R_{19}$, $R_{20}$, $R_{21}$, $R_{22}$ and $R_{23}$ have one of the meanings given for $R_6$, or are $NO_2$, CN, $CF_3$ or halogen.

Examples of compounds of the formula III according to the invention are 2,4,6-trimethylbenzoylphenylmethylphosphine oxide; 2,4,6-trimethylbenzoylphenylethylphosphine oxide; 2,4,6-trimethylbenzoylphenylpropylphosphine oxide; 2,4,6-trimethylbenzoylphenylbutylphosphine oxide; 2,4,6-trimethylbenzoylphenylpentylphosphine oxide; 2,4,6-trimethylbenzoylphenylhexylphosphine oxide; 2,4,6-trimethylbenzoylphenylheptylphosphine oxide; 2,4,6-trimethylbenzoylphenyloctylphosphine oxide; 2,4,6-trimethylbenzoylphenyldodecylphosphine oxide; 2,4,6-trimethylbenzoylphenylisopropylphosphine oxide; 2,4,6-trimethylbenzoylphenylisobutylphosphine oxide; 2,4,6-trimethylbenzoylphenylamylphosphine oxide; 2,4,6-trimethylbenzoylphenyl-2-ethylhexylphosphine oxide; 2,4,6-trimethylbenzoylphenyl-tert-butyl-phosphine oxide; 2,4,6-trimethylbenzoylphenyl-1-methylpropylphosphine oxide; 2,4,6-trimethylbenzoylphenylisopentylphosphine oxide; 2,4,6-trimethylbenzoylphenylmethoxyethoxy-phosphine oxide; 2,4,6-trimethylbenzoylphenylbenzylphosphine oxide; 2,4,6-trimethylbenzoylphenyl-2,4,4-trimethylpentylphosphine oxide; 2,4,6-trimethylbenzoylphenyl-2-propionic methyl ester phosphine oxide; 2,4,6-trimethylbenzoylphenyl-2-propionic ethyl ester phosphine oxide; 2,4,6-trimethylbenzoylphenyl-2-propionic propyl ester phosphine oxide; 2,4,6-trimethylbenzoylphenyl-2-propionic butyl ester phosphine oxide; 2,4,6-trimethylbenzoylphenyl-2-propionic pentyl ester phosphine oxide; 2,4,6-trimethylbenzoylphenyl-2-propionic hexyl ester phosphine oxide; 2,4,6-trimethylbenzoylphenyl-2-propionic octyl ester phosphine oxide; 2,4,6-trimethylbenzoylphenyl-2-propionic decyl ester phosphine oxide; 2,4,6-trimethylbenzoylphenyl-2-propionic dodecyl ester phosphine oxide; 2,4,6-trimethylbenzoylphenyl-2-propionic isopropyl ester phosphine oxide; 2,4,6-trimethylbenzoylphenyl-2-propionic isobutyl ester phosphine oxide; 2,4,6-trimethylbenzoylphenyl-2-propionic amyl ester phosphine oxide; 2,4,6-trimethylbenzoylphenyl-2-propionic 2-ethylhexyl ester phosphine oxide; 2,4,6-trimethylbenzoylphenyl-2-propionic tert-butyl ester phosphine oxide; 2,4,6-trimethylbenzoylphenyl-2-propionic 1-methylpropyl ester phosphine oxide; 2,4,6-trimethylbenzoylphenyl-2-propionic isopentyl ester phosphine oxide; 2,4,6-trimethylbenzoylphenyl-2-propionic methoxyethoxy ester phosphine oxide; 2,4,6-trimethylbenzoylphenyl-2-propionic benzyl ester phosphine oxide; 2,4,6-trimethylbenzoylphenyl-2-propionic 2,4,4-trimethylpentyl ester phosphine oxide; 2,4,6-trimethylbenzoylphenylacetic methyl ester phosphine oxide; 2,4,6-trimethylbenzoylphenylacetic ethyl ester phosphine oxide; 2,4,6-trimethylbenzoylphenylacetic propyl ester phosphine oxide; 2,4,6-trimethylbenzoylphenylacetic butyl ester phosphine oxide; 2,4,6-trimethylbenzoylphenylacetic pentyl ester phosphine oxide; 2,4,6-trimethylbenzoylphenylacetic hexyl ester phosphine oxide; 2,4,6-trimethylbenzoylphenylacetic octyl ester phosphine oxide; 2,4,6-trimethylbenzoylphenylacetic decyl ester phosphine oxide; 2,4,6-trimethylbenzoylphenylacetic dodecyl ester phosphine oxide; 2,4,6-trimethylbenzoylphenylacetic isopropyl ester phosphine oxide; 2,4,6-trimethylbenzoylphenylacetic isobutyl ester phosphine oxide; 2,4,6-trimethylbenzoylphenylacetic amyl ester phosphine oxide; 2,4,6-trimethylbenzoylphenylacetic 2-ethylhexyl ester phosphine oxide; 2,4,6-trimethylbenzoylphenylacetic tert-butyl ester phosphine oxide; 2,4,6-trimethylbenzoylphenylacetic 1-methyl propyl ester phosphine oxide; 2,4,6-trimethylbenzoylphenylacetic isopentyl ester phosphine oxide; 2,4,6-trimethylbenzoylphenylacetic methoxyethoxy ester phosphine oxide; 2,4,6-trimethylbenzoylphenylacetic benzyl ester phosphine oxide; 2,4,6-trimethylbenzoylphenylacetic 2,4,4-trimethylpentyl ester phosphine oxide; 2,6-dimethylbenzoylphenylmethylphosphine oxide; 2,6-dimethylbenzoylphenylethylphosphine oxide; 2,6-dimethylbenzoylphenylpropylphosphine oxide; 2,6-dimethylbenzoylphenylbutylphosphine oxide; 2,6-dimethylbenzoylphenylpentylphosphine oxide; 2,6-dimethylbenzoylphenylhexylphosphine oxide; 2,6-dimethylbenzoylphenylheptylphosphine oxide; 2,6-dimethylbenzoylphenyloctylphosphine oxide; 2,6-dimethylbenzoylphenyldodecylphosphine oxide; 2,6-dimethylbenzoylphenylisopropylphosphine oxide; 2,6-dimethylbenzoylphenylisobutylphosphine oxide; 2,6-dimethylbenzoylphenylamylphosphine oxide; 2,6-dimethylbenzoylphenyl-2-ethylhexylphosphine oxide; 2,6-dimethylbenzoylphenyl-tert-butylphosphine oxide; 2,6-dimethylbenzoylphenyl-1-methylpropylphosphine oxide; 2,6-dimethylbenzoylphenylisopentylphosphine oxide; 2,6-dimethylbenzoylphenylmethoxyethoxyphosphine oxide; 2,6-dimethylbenzoylphenylbenzylphosphine oxide; 2,6-dimethylbenzoylphenyl 2,4,4-trimethylpentylphosphine oxide; 2,6-dimethylbenzoylphenyl-2-propionic methyl ester phosphine oxide; 2,6-dimethylbenzoylphenyl-2-propionic ethyl ester phosphine oxide; 2,6-dimethylbenzoylphenyl-2-propionic propyl ester phosphine oxide; 2,6-dimethylbenzoylphenyl-2-propionic butyl ester phosphine oxide; 2,6-dimethylbenzoylphenyl-2-propionic pentyl ester phosphine oxide; 2,6-dimethylbenzoylphenyl-2-propionic hexyl ester phosphine oxide; 2,6-dimethylbenzoylphenyl-2-propionic octyl ester phosphine oxide; 2,6-dimethylbenzoylphenyl-2-propionic decyl ester phosphine oxide; 2,6-dimethylbenzoylphenyl-2-propionic dodecyl ester phosphine oxide; 2,6-dimethylbenzoylphenyl-2-propionic isopropyl ester phosphine oxide; 2,6-dimethylbenzoylphenyl-2-propionic isobutyl ester phosphine oxide; 2,6-dimethylbenzoylphenyl-2-propionic amyl ester phosphine oxide; 2,6-dimethylbenzoylphenyl-2-propionic 2-ethylhexyl ester phosphine oxide; 2,6-dimethylbenzoylphenyl-2-propionic tert-butyl ester phosphine oxide; 2,6-dimethylbenzoylphenyl-2-propionic 1-methylpropyl ester phosphine oxide; 2,6-dimethylbenzoylphenyl-2-propionic isopentyl ester phosphine oxide; 2,6-dimethylbenzoylphenyl-2-propionic methoxyethoxy ester phosphine oxide; 2,6-dimethylbenzoylphenyl-2-propionic benzyl ester phosphine oxide; 2,6-dimethylbenzoylphenyl-2-propionic 2,4,4-trimethylpentyl ester phosphine oxide; 2,6-dimethylbenzoylphenylacetic methyl ester phosphine oxide; 2,6-dimethylbenzoylphenylacetic ethyl ester phosphine oxide; 2,6-dimethylbenzoylphenylacetic propyl ester phosphine oxide; 2,6-dimethylbenzoylphenylacetic butyl ester phosphine oxide; 2,6-dimethylbenzoylphenylacetic pentyl ester phosphine oxide; 2,6-dimethylbenzoylphenylacetic hexyl ester phosphine oxide; 2,6-dimethylbenzoylphenylacetic octyl ester phosphine oxide; 2,6-dimethylbenzoylphenylacetic decyl ester phosphine oxide; 2,6-dimethylbenzoylphenylacetic dodecyl ester phosphine oxide; 2,6-dimethylbenzoylphenylacetic isopropyl ester phosphine oxide; 2,6-dimethylbenzoylphenylacetic isobutyl ester phosphine oxide; 2,6-dimethylbenzoylphenylacetic amyl ester phosphine oxide; 2,6-dimethylbenzoylphenylacetic 2-ethylhexyl ester phosphine oxide; 2,6-dimethylbenzoylphenylacetic tert-butyl ester phosphine oxide; 2,6-dimethylbenzoylphenylacetic 1-methylpropyl ester phosphine oxide; 2,6-dimethylbenzoylphenylacetic isopentyl ester phosphine oxide; 2,6-dimethylbenzoylphenylacetic methoxyethoxy ester phosphine oxide; 2,6-dimethylbenzoylphenylacetic benzyl ester phosphine oxide; 2,6-dimethylbenzoylphenylacetic 2,4,4-trimethylpentyl ester phosphine oxide; 2,6-dimethoxybenzoylphenylmethylphosphine oxide; 2,6-dimethoxybenzoylphenylethylphosphine oxide; 2,6-dimethoxybenzoylphenylpropylphosphine oxide; 2,6-dimethoxybenzoylphenylbutylphosphine oxide; 2,6-dimethoxybenzoylphenylpentylphosphine oxide; 2,6-dimethoxybenzoylphenylhexylphosphine oxide; 2,6-dimethoxybenzoylphenylheptylphosphine oxide; 2,6-dimethoxybenzoylphenyloctylphosphine oxide; 2,6-dimethoxybenzoylphenyldodecylphosphine oxide; 2,6-dimethoxybenzoylphenylisopropylphosphine oxide; 2,6-dimethoxybenzoylphenylisobutylphosphine oxide; 2,6-dimethoxybenzoylphenylamylphosphine oxide; 2,6-dimethoxybenzoylphenyl-2-ethylhexylphosphine oxide; 2,6-dimethoxybenzoylphenyl-tert-butylphosphine oxide; 2,6-dimethoxybenzoylphenyl-1-methylpropylphosphine oxide; 2,6-dimethoxybenzoylphenyl-isopentylphosphine oxide; 2,6-dimethoxybenzoylphenylmethoxyethoxyphosphine oxide; 2,6-dimethoxybenzoylphenylbenzylphosphine oxide; 2,6-dimethoxybenzoylphenyl-2,4,4-trimethylpentylphosphine oxide; 2,6-dimethoxybenzoylphenyl-2-propionic methyl ester phosphine oxide; 2,6-dimethoxybenzoylphenyl-2-propionic ethyl ester phosphine oxide; 2,6-dimethoxybenzoylphenyl-2-propionic propyl ester phosphine oxide; 2,6-dimethoxybenzoylphenyl-2-propionic butyl ester phosphine oxide; 2,6-dimethoxybenzoylphenyl-2-propionic pentyl ester phosphine oxide; 2,6-dimethoxybenzoylphenyl-2-propionic hexyl ester phosphine oxide; 2,6-dimethoxybenzoylphenyl-2-propionic octyl ester phosphine oxide; 2,6-dimethoxybenzoylphenyl-2-propionic decyl ester phosphine oxide; 2,6-dimethoxybenzoylphenyl-2-propionic dodecyl ester phosphine oxide; 2,6-dimethoxybenzoylphenyl-2-propionic isopropyl ester phosphine oxide; 2,6-dimethoxybenzoylphenyl-2-propionic isobutyl ester phosphine oxide; 2,6-dimethoxybenzoylphenyl-2-propionic amyl ester phosphine oxide; 2,6-dimethoxybenzoylphenyl-2-propionic 2-ethylhexyl ester phosphine oxide; 2,6-dimethoxybenzoylphenyl-2-propionic tert-butyl ester phosphine oxide; 2,6-dimethoxybenzoylphenyl-2-propionic 1-methylpropyl ester phosphine oxide; 2,6-dimethoxybenzoylphenyl-2-propionic isopentyl ester phosphine oxide; 2,6-dimethoxybenzoylphenyl-2-propionic methoxyethoxy ester phosphine oxide; 2,6-dimethoxybenzoylphenyl-2-propionic benzyl ester phosphine oxide; 2,6-dimethoxybenzoylphenyl-2-propionic 2,4,4-trimethylpentyl ester phosphine oxide; 2,6-dimethoxybenzoylphenylacetic methyl ester phosphine oxide; 2,6-dimethoxybenzoylphenylacetic ethyl ester phosphine oxide; 2,6-dimethoxybenzoylphenylacetic propyl ester phosphine oxide; 2,6-dimethoxybenzoylphenylacetic butyl ester phosphine oxide; 2,6-dimethoxybenzoylphenylacetic pentyl ester phosphine oxide; 2,6-dimethoxybenzoylphenylacetic hexyl ester phosphine oxide; 2,6-dimethoxybenzoylphenylacetic octyl ester phosphine oxide; 2,6-dimethoxybenzoylphenylacetic decyl ester phosphine oxide; 2,6-dimethoxybenzoylphenylacetic dodecyl ester phosphine oxide; 2,6-dimethoxybenzoylphenylacetic isopropyl ester phosphine oxide; 2,6-dimethoxybenzoylphenylacetic isobutyl ester phosphine oxide; 2,6-dimethoxybenzoylphenylacetic amyl ester phosphine oxide; 2,6-dimethoxybenzoylphenylacetic 2-ethylhexyl ester phosphine oxide; 2,6-dimethoxybenzoylphenylacetic tert-butyl ester phosphine oxide; 2,6-dimethoxybenzoylphenylacetic 1-methylpropyl ester phosphine oxide; 2,6-dimethoxybenzoylphenylacetic isopentyl ester phosphine oxide; 2,6-dimethoxybenzoylphenylacetic methoxyethoxy ester phosphine oxide; 2,6-dimethoxybenzoylphenylacetic benzyl ester phosphine oxide; 2,6-dimethoxybenzoylphenylacetic 2,4,4-trimethylpentyl ester phosphine oxide; 2,6-bis(trifluoromethyl)benzoylphenylmethylphosphine oxide; 2,6-bis(trifluoromethyl)benzoylphenylethylphosphine oxide; 2,6-bis(trifluoromethyl)benzoylphenylpropylphosphine oxide; 2,6-bis(trifluoromethyl)benzoylphenylbutylphosphine oxide; 2,6-bis(trifluoromethyl)benzoylphenylpentylphosphine oxide; 2,6-bis(trifluoromethyl)benzoylphenylhexylphosphine oxide; 2,6-bis(trifluoromethyl)benzoylphenylheptylphosphine oxide; 2,6-bis(trifluoromethyl)benzoylphenyloctylphosphine oxide; 2,6-bis(trifluoromethyl)benzoylphenyldodecylphosphine oxide; 2,6-bis(trifluoromethyl)benzoylphenylisopropylphosphine oxide; 2,6-bis(trifluoromethyl)

benzoylphenylisobutylphosphine oxide; 2,6-bis(trifluoromethyl)benzoylphenylamylphosphine oxide; 2,6-bis(trifluoromethyl)benzoylphenyl-2-ethylhexylphosphine oxide; 2,6-bis(trifluoromethyl)benzoylphenyl-tert-butylphosphine oxide; 2,6-bis(trifluoromethyl)benzoylphenyl-1-methylpropylphosphine oxide; 2,6-bis(trifluoromethyl)benzoylphenylisopentylphosphine oxide; 2,6-bis(trifluoromethyl)benzoylphenylmethoxyethoxyphosphine oxide; 2,6-bis(trifluoromethyl)benzoylphenylbenzylphosphine oxide; 2,6-bis(trifluoromethyl)benzoylphenyl-2,4,4-trimethylpentylphosphine oxide; 2,6-bis(trifluoromethyl)benzoylphenyl-2-propionic methyl ester phosphine oxide; 2,6-bis(trifluoromethyl)benzoylphenyl-2-propionic ethyl ester phosphine oxide; 2,6-bis(trifluoromethyl)benzoylphenyl-2-propionic propyl ester phosphine oxide; 2,6-bis(trifluoromethyl)benzoylphenyl-2-propionic butyl ester phosphine oxide; 2,6-bis(trifluoromethyl)benzoylphenyl-2-propionic pentyl ester phosphine oxide; 2,6-bis(trifluoromethyl)benzoylphenyl-2-propionic hexyl ester phosphine oxide; 2,6-bis(trifluoromethyl)benzoylphenyl-2-propionic octyl ester phosphine oxide; 2,6-bis(trifluoromethyl)benzoylphenyl-2-propionic decyl ester phosphine oxide; 2,6-bis(trifluoromethyl)benzoylphenyl-2-propionic dodecyl ester phosphine oxide; 2,6-bis(trifluoromethyl)benzoylphenyl-2-propionic isopropyl ester phosphine oxide; 2,6-bis(trifluoromethyl)benzoylphenyl-2-propionic isobutyl ester phosphine oxide; 2,6-bis(trifluoromethyl)benzoylphenyl-2-propionic amyl ester phosphine oxide; 2,6-bis(trifluoromethyl)benzoylphenyl-2-propionic 2-ethylhexyl ester phosphine oxide; 2,6-bis(trifluoromethyl)benzoylphenyl-2-propionic tert-butyl ester phosphine oxide; 2,6-bis(trifluoromethyl)benzoylphenyl-2-propionic 1-methylpropyl ester phosphine oxide; 2,6-bis(trifluoromethyl)benzoylphenyl-2-propionic isopentyl ester phosphine oxide; 2,6-bis(trifluoromethyl)benzoylphenyl-2-propionic methoxyethoxy ester phosphine oxide; 2,6-bis(trifluoromethyl)benzoylphenyl-2-propionic benzyl ester phosphine oxide; 2,6-bis(trifluoromethyl)benzoylphenyl-2-propionic 2,4,4-trimethylpentyl ester phosphine oxide; 2,6-bis(trifluoromethyl)benzoylphenylacetic methyl ester phosphine oxide; 2,6-bis(trifluoromethyl)benzoylphenylacetic ethyl ester phosphine oxide; 2,6-bis(trifluoromethyl)benzoylphenylacetic propyl ester phosphine oxide; 2,6-bis(trifluoromethyl)benzoylphenylacetic butyl ester phosphine oxide; 2,6-bis(trifluoromethyl)benzoylphenylacetic pentyl ester phosphine oxide; 2,6-bis(trifluoromethyl)benzoylphenylacetic hexyl ester phosphine oxide; 2,6-bis(trifluoromethyl)benzoylphenylacetic octyl ester phosphine oxide; 2,6-bis(trifluoromethyl)benzoylphenylacetic decyl ester phosphine oxide; 2,6-bis(trifluoromethyl)benzoylphenylacetic dodecyl ester phosphine oxide; 2,6-bis(trifluoromethyl)benzoylphenylacetic isopropyl ester phosphine oxide; 2,6-bis(trifluoromethyl)benzoylphenylacetic isobutyl ester phosphine oxide; 2,6-bis(trifluoromethyl)benzoylphenylacetic amyl ester phosphine oxide; 2,6-bis(trifluoromethyl)benzoylphenylacetic 2-ethylhexyl ester phosphine oxide; 2,6-bis(trifluoromethyl)benzoylphenylacetic tert-butyl ester phosphine oxide; 2,6-bis(trifluoromethyl)benzoylphenylacetic 1-methyl-propyl ester phosphine oxide; 2,6-bis(trifluoromethyl)benzoylphenylacetic isopentyl ester phosphine oxide; 2,6-bis(trifluoromethyl)benzoylphenylacetic methoxyethoxy ester phosphine oxide; 2,6-bis(trifluoromethyl)benzoylphenylacetic benzyl ester phosphine oxide; 2,6-bis(trifluoromethyl)benzoylphenylacetic 2,4,4-trimethylpentyl ester phosphine oxide; 2,6-dichlorobenzoylphenylmethylphosphine oxide; 2,6-dichlorobenzoylphenylethylphosphine oxide; 2,6-dichlorobenzoylphenylpropylphosphine oxide; 2,6-dichlorobenzoylphenylbutylphosphine oxide; 2,6-dichlorobenzoylphenylpentylphosphine oxide; 2,6-dichlorobenzoylphenylhexylphosphine oxide; 2,6-dichlorobenzoylphenylheptylphosphine oxide; 2,6-dichlorobenzoylphenyloctylphosphine oxide; 2,6-dichlorobenzoylphenyldodecylphosphine oxide; 2,6-dichlorobenzoylphenylisopropylphosphine oxide; 2,6-dichlorobenzoylphenylisobutylphosphine oxide; 2,6-dichlorobenzoylphenylamylphosphine oxide; 2,6-dichlorobenzoylphenyl-2-ethylhexylphosphine oxide; 2,6-dichlorobenzoylphenyl-tert-butylphosphine oxide; 2,6-dichlorobenzoylphenyl-1-methylpropylphosphine oxide; 2,6-dichlorobenzoylphenylisopentylphosphine oxide; 2,6-dichlorobenzoylphenylmethoxyethoxy-phosphine oxide; 2,6-dichlorobenzoylphenylbenzylphosphine oxide; 2,6-dichlorobenzoylphenyl-2,4,4-trimethylpentylphosphine oxide; 2,6-dichlorobenzoylphenyl-2-propionic methyl ester phosphine oxide; 2,6-dichlorobenzoylphenyl-2-propionic ethyl ester phosphine oxide; 2,6-dichlorobenzoylphenyl-2-propionic propyl ester phosphine oxide; 2,6-dichlorobenzoylphenyl-2-propionic butyl ester phosphine oxide; 2,6-dichlorobenzoylphenyl-2-propionic pentyl ester phosphine oxide; 2,6-dichlorobenzoylphenyl-2-propionic hexyl ester phosphine oxide; 2,6-dichlorobenzoylphenyl-2-propionic octyl ester phosphine oxide; 2,6-dichlorobenzoylphenyl-2-propionic decyl ester phosphine oxide; 2,6-dichlorobenzoylphenyl-2-propionic dodecyl ester phosphine oxide; 2,6-dichlorobenzoylphenyl-2-propionic isopropyl ester phosphine oxide; 2,6-dichlorobenzoylphenyl-2-propionic isobutyl ester phosphine oxide; 2,6-dichlorobenzoylphenyl-2-propionic amyl ester phosphine oxide; 2,6-dichlorobenzoylphenyl-2-propionic 2-ethylhexyl ester phosphine oxide; 2,6-dichlorobenzoylphenyl-2-propionic tert-butyl ester phosphine oxide; 2,6-dichlorobenzoylphenyl-2-propionic 1-methylpropyl ester phosphine oxide; 2,6-dichlorobenzoylphenyl-2-propionic isopentyl ester phosphine oxide; 2,6-dichlorobenzoylphenyl-2-propionic methoxyethoxy ester phosphine oxide; 2,6-dichlorobenzoylphenyl-2-propionic benzyl ester phosphine oxide; 2,6-dichlorobenzoylphenyl-2-propionic 2,4,4-trimethylpentyl ester phosphine oxide; 2,6-dichlorobenzoylphenylacetic methyl ester phosphine oxide; 2,6-dichlorobenzoylphenylacetic ethyl ester phosphine oxide; 2,6-dichlorobenzoylphenylacetic propyl ester phosphine oxide; 2,6-dichlorobenzoylphenylacetic butyl ester phosphine oxide; 2,6-dichlorobenzoylphenylacetic pentyl ester phosphine oxide; 2,6-dichlorobenzoylphenylacetic hexyl ester phosphine oxide; 2,6-dichlorobenzoylphenylacetic octyl ester phosphine oxide; 2,6-dichlorobenzoylphenylacetic decyl ester phosphine oxide; 2,6-dichlorobenzoylphenylacetic dodecyl ester phosphine oxide; 2,6-dichlorobenzoylphenylacetic isopropyl ester phosphine oxide; 2,6-dichlorobenzoylphenylacetic isobutyl ester phosphine oxide; 2,6-dichlorobenzoylphenylacetic amyl ester phosphine oxide; 2,6-dichlorobenzoylphenylacetic 2-ethylhexyl ester phosphine oxide; 2,6-dichlorobenzoylphenylacetic tert-butyl ester phosphine oxide; 2,6-dichlorobenzoylphenylacetic 1-methylpropyl ester phosphine oxide; 2,6-dichlorobenzoylphenylacetic isopentyl ester phosphine oxide; 2,6-dichlorobenzoylphenylacetic methoxyethoxy ester phosphine oxide; 2,6-dichlorobenzoylphenylacetic benzyl ester phosphine oxide; 2,6- dichlorobenzoylphenylacetic 2,4,4-trimethylpentyl ester phosphine oxide; 2,3,4,6-tetramethylbenzoylphenylmethylphosphine oxide; 2,3,4,6-tetramethylbenzoylphenylethylphosphine oxide; 2,3,4,6-tetramethylbenzoylphenylpropylphosphine oxide; 2,3,4,6-tetramethylbenzoylphenylbutylphosphine oxide; 2,3,4,6-tetramethylbenzoylphenylpentylphosphine oxide; 2,3,4,6-tetramethylbenzoylphenylhexylphosphine oxide; 2,3,4,6-tetramethylbenzoylphenylheptylphosphine oxide; 2,3,4,6-tetramethylbenzoylphenyloctylphosphine oxide; 2,3,4,6-tetramethylbenzoylphenyldodecylphosphine oxide; 2,3,4,6-tetramethylbenzoylphenylisopropylphosphine oxide; 2,3,4,6-tetramethylbenzoylphenylisobutylphosphine oxide; 2,3,4,6-tetramethylbenzoylphenylamylphosphine oxide; 2,3,4,6-tetramethylbenzoylphenyl-2-ethylhexylphosphine oxide; 2,3,4,6-tetramethylbenzoylphenyl-tert-butyl-phosphine oxide; 2,3,4,6-tetramethylbenzoylphenyl-1-methylpropylphosphine oxide; 2,3,4,6-tetramethylbenzoylphenylisopentylphosphine oxide; 2,3,4,6-tetramethylbenzoylphenyl-methoxyethoxyphosphine oxide; 2,3,4,6-tetramethylbenzoylphenylbenzylphosphine oxide; 2,3,4,6-tetramethylbenzoylphenyl-2,4,4-trimethylpentylphosphine oxide; 2,3,4,6-tetramethylbenzoylphenyl-2-propionic methyl ester phosphine oxide; 2,3,4,6-tetramethylbenzoylphenyl-2-propionic ethyl ester phosphine oxide; 2,3,4,6-tetramethylbenzoylphenyl-2-propionic propyl ester phosphine oxide; 2,3,4,6-tetramethylbenzoylphenyl-2-propionic butyl ester phosphine oxide; 2,3,4,6-tetramethylbenzoylphenyl-2-propionic pentyl ester phosphine oxide; 2,3,4,6-tetramethylbenzoylphenyl-2-propionic hexyl ester phosphine oxide; 2,3,4,6-tetramethylbenzoylphenyl-2-propionic octyl ester phosphine oxide; 2,3,4,6-tetramethylbenzoylphenyl-2-propionic decyl ester phosphine oxide; 2,3,4,6-tetramethylbenzoylphenyl-2-propionic dodecyl ester phosphine oxide; 2,3,4,6-tetramethylbenzoylphenyl-2-propionic isopropyl ester phosphine oxide; 2,3,4,6-tetramethylbenzoylphenyl-2-propionic isobutyl ester phosphine oxide; 2,3,4,6-tetramethylbenzoylphenyl-2-propionic amyl ester phosphine oxide; 2,3,4,6-tetramethylbenzoylphenyl-2-propionic 2-ethylhexyl ester phosphine oxide; 2,3,4,6-tetramethylbenzoylphenyl-2-propionic tert-butyl ester phosphine oxide; 2,3,4,6-tetramethylbenzoylphenyl-2-propionic 1-methylpropyl ester phosphine oxide; 2,3,4,6-tetramethylbenzoylphenyl 2-propionic isopentyl ester phosphine oxide; 2,3,4,6-tetramethylbenzoylphenyl-2-propionic methoxyethoxy ester phosphine oxide; 2,3,4,6-tetramethylbenzoylphenyl-2-propionic benzyl ester phosphine oxide; 2,3,4,6-tetramethylbenzoylphenyl-2-propionic 2,4,4-trimethylpentyl ester phosphine oxide; 2,3,4,6-tetramethylbenzoylphenylacetic methyl ester phosphine oxide; 2,3,4,6-tetramethylbenzoylphenylacetic ethyl ester phosphine oxide; 2,3,4,6-tetramethylbenzoylphenylacetic propyl ester phosphine oxide; 2,3,4,6-tetramethylbenzoylphenylacetic butyl ester phosphine oxide; 2,3,4,6-tetramethylbenzoylphenylacetic pentyl ester phosphine oxide; 2,3,4,6-tetramethylbenzoylphenylacetic hexyl ester phosphine oxide; 2,3,4,6-tetramethylbenzoylphenylacetic octyl ester phosphine oxide; 2,3,4,6-tetramethylbenzoylphenylacetic decyl ester phosphine oxide; 2,3,4,6-tetramethylbenzoylphenylacetic dodecyl ester phosphine oxide; 2,3,4,6-tetramethylbenzoylphenylacetic isopropyl ester phosphine oxide; 2,3,4,6-tetramethylbenzoylphenylacetic isobutyl ester phosphine oxide; 2,3,4,6-tetramethylbenzoylphenylacetic amyl ester phosphine oxide; 2,3,4,6-tetramethylbenzoylphenylacetic 2-ethylhexyl ester phosphine oxide; 2,3,4,6-tetramethylbenzoylphenylacetic tert-butyl ester phosphine oxide; 2,3,4,6-tetramethylbenzoylphenylacetic 1-methylpropyl ester phosphine oxide; 2,3,4,6-tetramethylbenzoylphenylacetic isopentyl ester phosphine oxide; 2,3,4,6-tetramethylbenzoylphenylacetic methoxyethoxy ester phosphine oxide; 2,3,4,6-tetramethylbenzoylphenylacetic benzyl ester phosphine oxide; 2,3,4,6-tetramethylbenzoylphenylacetic 2,4,4-trimethylpentyl ester phosphine oxide; 2,4,6-trimethoxybenzoylphenylmethylphosphine oxide; 2,4,6-trimethoxybenzoylphenylethylphosphine oxide; 2,4,6-trimethoxybenzoylphenylpropylphosphine oxide; 2,4,6-trimethoxybenzoylphenylbutylphosphine oxide; 2,4,6-trimethoxybenzoylphenylpentylphosphine oxide; 2,4,6-trimethoxybenzoylphenylhexylphosphine oxide; 2,4,6-trimethoxybenzoylphenylheptylphosphine oxide; 2,4,6-trimethoxybenzoylphenyloctylphosphine oxide; 2,4,6-trimethoxybenzoylphenyldodecylphosphine oxide; 2,4,6-trimethoxybenzoylphenylisopropylphosphine oxide; 2,4,6-trimethoxybenzoylphenylisobutylphosphine oxide; 2,4,6-trimethoxybenzoylphenylamylphosphine oxide; 2,4,6-trimethoxybenzoylphenyl-2-ethylhexylphosphine oxide; 2,4,6-trimethoxybenzoylphenyl-tert-butylphosphine oxide; 2,4,6-trimethoxybenzoylphenyl-1-methylpropylphosphine oxide; 2,4,6-trimethoxybenzoylphenyl-isopentylphosphine oxide; 2,4,6-trimethoxybenzoylphenylmethoxyethoxyphosphine oxide; 2,4,6-trimethoxybenzoylphenylbenzylphosphine oxide; 2,4,6-trimethoxybenzoylphenyl-2,4,4-trimethylpentylphosphine oxide; 2,4,6-trimethoxybenzoylphenyl-2-propionic methyl ester phosphine oxide; 2,4,6-trimethoxybenzoylphenyl-2-propionic ethyl ester phosphine oxide; 2,4,6-trimethoxybenzoylphenyl-2-propionic propyl ester phosphine oxide; 2,4,6-trimethoxybenzoylphenyl-2-propionic butyl ester phosphine oxide; 2,4,6-trimethoxybenzoylphenyl-2-propionic pentyl ester phosphine oxide; 2,4,6-trimethoxybenzoylphenyl-2-propionic hexyl ester phosphine oxide; 2,4,6-trimethoxybenzoylphenyl-2-propionic octyl ester phosphine oxide; 2,4,6-trimethoxybenzoylphenyl-2-propionic decyl ester phosphine oxide; 2,4,6-trimethoxybenzoylphenyl-2-propionic dodecyl ester phosphine oxide; 2,4,6-trimethoxybenzoylphenyl-2-propionic isopropyl ester phosphine oxide; 2,4,6-trimethoxybenzoylphenyl-2-propionic isobutyl ester phosphine oxide; 2,4,6-trimethoxybenzoylphenyl-2-propionic amyl ester phosphine oxide; 2,4,6-trimethoxybenzoylphenyl-2-propionic 2-ethylhexyl ester phosphine oxide; 2,4,6-trimethoxybenzoylphenyl-2-propionic tert-butyl ester phosphine oxide; 2,4,6-trimethoxybenzoylphenyl-2-propionic 1-methylpropyl ester phosphine oxide; 2,4,6-trimethoxybenzoylphenyl-2-propionic isopentyl ester phosphine oxide; 2,4,6-trimethoxybenzoylphenyl-2-propionic methoxyethoxy ester phosphine oxide; 2,4,6-trimethoxybenzoylphenyl-2-propionic benzyl ester phosphine oxide; 2,4,6-trimethoxybenzoylphenyl-2-propionic 2,4,4-trimethylpentyl ester phosphine oxide; 2,4,6-trimethoxybenzoylphenylacetic methyl ester phosphine oxide; 2,4,6-trimethoxybenzoylphenylacetic ethyl ester phosphine oxide; 2,4,6-trimethoxybenzoylphenylacetic propyl ester phosphine oxide; 2,4,6-trimethoxybenzoylphenylacetic butyl ester phosphine oxide; 2,4,6-trimethoxybenzoylphenylacetic pentyl ester phosphine oxide; 2,4,6-trimethoxybenzoylphenylacetic hexyl ester phosphine oxide; 2,4,6-trimethoxybenzoylphenylacetic octyl ester phosphine oxide; 2,4,6-trimethoxybenzoylphenylacetic decyl ester phosphine oxide; 2,4,6-trimethoxybenzoylphenylacetic dodecyl ester phosphine oxide; 2,4,6-trimethoxybenzoylphenylacetic isopropyl ester phosphine oxide; 2,4,6-trimethoxybenzoylphenylacetic isobutyl ester phosphine oxide; 2,4,6-trimethoxybenzoylphenylacetic amyl ester phosphine oxide; 2,4,6-trimethoxybenzoylphenylacetic 2-ethylhexyl ester phosphine oxide; 2,4,6-trimethoxybenzoylphenylacetic tert-butyl ester phosphine oxide; 2,4,6-trimethoxybenzoylphenylacetic 1-methylpropyl ester phosphine oxide; 2,4,6-trimethoxybenzoylphenylacetic isopentyl ester phosphine oxide; 2,4,6-trimethoxybenzoylphenylacetic methoxyethoxy ester phosphine oxide; 2,4,6-trimethoxybenzoylphenylacetic benzyl ester phosphine oxide; 2,4,6-trimethoxybenzoylphenylacetic 2,4,4-trimethylpentyl ester phosphine oxide; 2,6-dimethyl-4-tert-butylbenzoylphenylmethylphosphine oxide; 2,6-dimethyl-4-tert-butylbenzoylphenylethylphosphine oxide; 2,6-dimethyl-4-tert-butylbenzoylphenylpropylphosphine oxide; 2,6-dimethyl-4-tert-butylbenzoylphenylbutylphosphine oxide; 2,6-dimethyl-4-tert-butylbenzoylphenylpentylphosphine oxide; 2,6-dimethyl-4-tert-butylbenzoylphenylhexylphosphine oxide; 2,6-dimethyl-4-tert-butylbenzoylphenylheptylphosphine oxide; 2,6-dimethyl-4-tert-butylbenzoylphenyloctylphosphine oxide; 2,6-dimethyl-4-tert-butylbenzoylphenyldodecylphosphine oxide; 2,6-dimethyl-4-tert-butylbenzoylphenylisopropylphosphine oxide; 2,6-dimethyl-4-tert-butylbenzoylphenylisobutylphosphine oxide; 2,6-dimethyl-4-tert-butylbenzoylphenylamylphosphine oxide; 2,6-dimethyl-4-tert-butylbenzoylphenyl-2-ethylhexylphosphine oxide; 2,6-dimethyl-4-tert-butylbenzoylphenyl-tert-butylphosphine oxide; 2,6-dimethyl-4-tert-butyl-benzoylphenyl-1-methylpropylphosphine oxide; 2,6-dimethyl-4-tert-butylbenzoylphenylisopentylphosphine oxide; 2,6-dimethyl-4-tert-butylbenzoylphenylisopentylphosphine oxide; 2,6-dimethyl-4-tert-butylbenzoylphenylbenzylphosphine oxide; 2,6-dimethyl-4-tert-butylbenzoylphenyl-2,4,4-trimethylpentylphosphine oxide; 2,6-dimethyl-4-tert-butylbenzoylphenyl-2-propionic methyl ester phosphine oxide; 2,6-dimethyl-4-tert-butylbenzoylphenyl-2-propionic ethyl ester phosphine oxide; 2,6-dimethyl-4-tert-butylbenzoylphenyl-2-propionic propyl ester phosphine oxide; 2,6-dimethyl-4-tert-butylbenzoylphenyl-2-propionic butyl ester phosphine oxide; 2,6-dimethyl-4-tert-butylbenzoylphenyl-2-propionic pentyl ester phosphine oxide; 2,6-dimethyl-4-tert-butylbenzoylphenyl-2-propionic hexyl ester phosphine oxide; 2,6-dimethyl-4-tert-butylbenzoylphenyl-2-propionic octyl ester phosphine oxide; 2,6-dimethyl-4-tert-butylbenzoylphenyl-2-propionic decyl ester phosphine oxide; 2,6-dimethyl-4-tert-butylbenzoylphenyl-2-propionic dodecyl ester phosphine oxide; 2,6-dimethyl-4-tert-butylbenzoylphenyl-2-propionic isopropyl ester phosphine oxide; 2,6-dimethyl-4-tert-butylbenzoylphenyl-2-propionic isobutyl ester phosphine oxide; 2,6-dimethyl-4-tert-butylbenzoylphenyl-2-propionic amyl ester phosphine oxide; 2,6-dimethyl-4-tert-butylbenzoylphenyl-2-propionic 2-ethylhexyl ester phosphine oxide; 2,6-dimethyl-4-tert-butylbenzoylphenyl-2-propionic tert-butyl ester phosphine oxide; 2,6-dimethyl-4-tert-butylbenzoylphenyl-2-propionic 1-methylpropyl ester phosphine oxide; 2,6-dimethyl-4-tert-butylbenzoylphenyl-2-propionic isopentyl ester phosphine oxide; 2,6-dimethyl-4-tert-butylbenzoylphenyl-2-propionic methoxyethoxy ester phosphine oxide; 2,6-dimethyl-4-tert-butylbenzoylphenyl-2-propionic benzyl ester phosphine oxide; 2,6-dimethyl-4-tert-butylbenzoylphenyl-2-propionic 2,4,4-trimethylpentyl ester phosphine oxide; 2,6-dimethyl-4-tert-butylbenzoylphenylacetic methyl ester phosphine oxide; 2,6-dimethyl-4-tert-butylbenzoylphenylacetic ethyl ester phosphine oxide; 2,6-dimethyl-4-tert-butylbenzoylphenylacetic propyl ester phosphine oxide; 2,6-dimethyl-4-tert-butylbenzoylphenylacetic butyl ester phosphine oxide; 2,6-dimethyl-4-tert-butylbenzoylphenylacetic pentyl ester phosphine oxide; 2,6-dimethyl-4-tert-butylbenzoylphenylacetic hexyl ester phosphine oxide; 2,6-dimethyl-4-tert-butylbenzoylphenylacetic octyl ester phosphine oxide; 2,6-dimethyl-4-tert-butylbenzoylphenylacetic decyl ester phosphine oxide; 2,6-dimethyl-4-tert-butylbenzoylphenylacetic dodecyl ester phosphine oxide; 2,6-dimethyl-4-tert-butylbenzoylphenylacetic isopropyl ester phosphine oxide; 2,6-dimethyl-4-tert-butylbenzoylphenylacetic isobutyl ester phosphine oxide; 2,6-dimethyl-4-tert-butylbenzoylphenylacetic amyl ester phosphine oxide; 2,6-dimethyl-4-tert-butylbenzoylphenylacetic 2-ethylhexyl ester phosphine oxide; 2,6-dimethyl-4-tert-butylbenzoylphenylacetic tert-butyl ester phosphine oxide; 2,6-dimethyl-4-tert-butylbenzoylphenylacetic 1-methylpropyl ester phosphine oxide; 2,6-dimethyl-4-tert-butylbenzoylphenylacetic isopentyl ester phosphine oxide; 2,6-dimethyl-4-tert-butylbenzoylphenylacetic methoxyethoxy ester phosphine oxide; 2,6-dimethyl-4-tert-butylbenzoylphenylacetic benzyl ester phosphine oxide; 2,6-dimethyl-4-tert-butylbenzoylphenylacetic 2,4,4-trimethylpentyl ester phosphine oxide; 2-chloro-6-methylbenzoylphenylmethylphosphine oxide; 2-chloro-6-methylbenzoylphenylethylphosphine oxide; 2-chloro-6-methylbenzoylphenylpropylphosphine oxide; 2-chloro-6-methylbenzoylphenylbutylphosphine oxide; 2-chloro-6-methylbenzoylphenylpentylphosphine oxide; 2-chloro-6-methylbenzoylphenylhexylphosphine oxide; 2-chloro-6-methylbenzoylphenylheptylphosphine oxide; 2-chloro-6-methylbenzoylphenyloctylphosphine oxide; 2-chloro-6-methylbenzoylphenyldodecylphosphine oxide; 2-chloro-6-methylbenzoylphenylisopropylphosphine oxide; 2-chloro-6-methylbenzoylphenylisobutylphosphine oxide; 2-chloro-6-methylbenzoylphenylamylphosphine oxide; 2-chloro-6-methylbenzoylphenyl-2-ethylhexylphosphine oxide; 2-chloro-6-methylbenzoylphenyl-tert-butylphosphine oxide; 2-chloro-6-methylbenzoylphenyl-1-methylpropylphosphine oxide; 2-chloro-6-methylbenzoylphenylisopentylphosphine oxide; 2-chloro-6-methylbenzoylphenylmethoxyethoxyphosphine oxide; 2-chloro-6-methylbenzoylphenyl-benzylphosphine oxide; 2-chloro-6-methylbenzoylphenyl-2,4,4-trimethylpentylphosphine oxide; 2-chloro-6-methylbenzoylphenyl-2-propionic methyl ester phosphine oxide; 2-chloro-6-methylbenzoylphenyl-2-propionic ethyl ester phosphine oxide; 2-chloro-6-methylbenzoylphenyl-2-propionic propyl ester phosphine oxide; 2-chloro-6-methylbenzoylphenyl-2-propionic butyl ester phosphine oxide; 2-chloro-6-methylbenzoylphenyl-2-propionic pentyl ester phosphine oxide; 2-chloro-6-methylbenzoylphenyl-2-propionic hexyl ester phosphine oxide; 2-chloro-6-methylbenzoylphenyl-2-propionic octyl ester phosphine oxide; 2-chloro-6-methylbenzoylphenyl-2-propionic decyl ester phosphine oxide; 2-chloro-6-methylbenzoylphenyl-2-propionic dodecyl ester phosphine oxide; 2-chloro-6- methylbenzoylphenyl-2-propionic isopropyl ester phosphine oxide; 2-chloro-6-methylbenzoylphenyl-2-propionic isobutyl ester phosphine oxide; 2-chloro-6-methylbenzoylphenyl-2-propionic amyl ester phosphine oxide; 2-chloro-6-methylbenzoylphenyl-2-propionic 2-ethyahexyl ester phosphine oxide; 2-chloro-6-methylbenzoylphenyl-2-propionic tert-butyl ester phosphine oxide; 2-chloro-6-methylbenzoylphenyl-2-propionic 1-methylpropyl ester phosphine oxide; 2-chloro-6-methylbenzoylphenyl-2-propionic isopentyl ester phosphine oxide; 2-chloro-6-methylbenzoylphenyl-2-propionic methoxyethoxy ester phosphine oxide; 2-chloro-6-methylbenzoylphenyl-2-propionic benzyl ester phosphine oxide; 2-chloro-6-methylbenzoylphenyl-2-propionic 2,4,4-trimethylpentyl ester phosphine oxide; 2-chloro-6-methylbenzoylphenylacetic methyl ester phosphine oxide; 2-chloro-6-methylbenzoylphenylacetic ethyl ester phosphine oxide; 2-chloro-6-methylbenzoylphenylacetic propyl ester phosphine oxide; 2-chloro-6-methylbenzoylphenylacetic butyl ester phosphine oxide; 2-chloro-6-methylbenzoylphenylacetic pentyl ester phosphine oxide; 2-chloro-6-methylbenzoylphenylacetic hexyl ester phosphine oxide; 2-chloro-6-methylbenzoylphenylacetic octyl ester phosphine oxide; 2-chloro-6-methylbenzoylphenylacetic decyl ester phosphine oxide; 2-chloro-6-methylbenzoylphenylacetic dodecyl ester phosphine oxide; 2-chloro-6-methylbenzoylphenylacetic isopropyl ester phosphine oxide; 2-chloro-6-methylbenzoylphenylacetic isobutyl ester phosphine oxide; 2-chloro-6-methylbenzoylphenylacetic amyl ester phosphine oxide; 2-chloro-6-methylbenzoylphenylacetic 2-ethylhexyl ester phosphine oxide; 2-chloro-6-methylbenzoylphenylacetic tert-butyl ester phosphine oxide; 2-chloro-6-methylbenzoylphenylacetic 1-methylpropyl ester phosphine oxide; 2-chloro-6-methylbenzoylphenylacetic isopentyl ester phosphine oxide; 2-chloro-6-methylbenzoylphenylacetic methoxyethoxy ester phosphine oxide; 2-chloro-6-methylbenzoylphenylacetic benzyl ester phosphine oxide; 2-chloro-6-methylbenzoylphenylacetic 2,4,4-trimethylpentyl ester phosphine oxide; 2-chloro-6-methoxybenzoylphenylmethylphosphine oxide; 2-chloro-6-methoxybenzoylphenylethylphosphine oxide; 2-chloro-6-methoxybenzoylphenylpropylphosphine oxide; 2-chloro-6-methoxybenzoylphenylbutylphosphine oxide; 2-chloro-6-methoxybenzoylphenylpentylphosphine oxide; 2-chloro-6-methoxybenzoylphenylhexylphosphine oxide; 2-chloro-6-methoxybenzoylphenylheptylphosphine oxide; 2-chloro-6-methoxybenzoylphenyloctylphosphine oxide; 2-chloro-6-methoxybenzoylphenyldodecylphosphine oxide; 2-chloro-6-methoxybenzoylphenylisopropylphosphine oxide; 2-chloro-6-methoxybenzoylphenylisobutylphosphine oxide; 2-chloro-6-methoxybenzoylphenylamylphosphine oxide; 2-chloro-6-methoxybenzoylphenyl-2-ethylhexylphosphine oxide; 2-chloro-6-methoxybenzoylphenyl-tert-butylphosphine oxide; 2-chloro-6-methoxybenzoylphenyl-1-methylpropylphosphine oxide; 2-chloro-6-methoxybenzoylphenylisopentylphosphine oxide; 2-chloro-6-methoxybenzoylphenylmethoxyethoxyphosphine oxide; 2-chloro-6-methoxybenzoylphenylbenzylphosphine oxide; 2-chloro-6-methoxybenzoylphenyl-2,4,4-trimethylpentylphosphine oxide; 2-chloro-6-methoxybenzoylphenyl-2-propionic methyl ester phosphine oxide; 2-chloro-6-methoxybenzoylphenyl-2-propionic ethyl ester phosphine oxide; 2-chloro-6-methoxybenzoylphenyl-2-propionic propyl ester phosphine oxide; 2-chloro-6-methoxybenzoylphenyl-2-propionic butyl ester phosphine oxide; 2-chloro-6-methoxybenzoylphenyl-2-propionic pentyl ester phosphine oxide; 2-chloro-6-methoxybenzoylphenyl-2-propionic hexyl ester phosphine oxide; 2-chloro-6-methoxybenzoylphenyl-2-propionic octyl ester phosphine oxide; 2-chloro-6-methoxybenzoylphenyl-2-propionic decyl ester phosphine oxide; 2-chloro-6-methoxybenzoylphenyl-2-propionic dodecyl ester phosphine oxide; 2-chloro-6-methoxybenzoylphenyl-2-propionic isopropyl ester phosphine oxide; 2-chloro-6-methoxybenzoylphenyl-2-propionic isobutyl ester phosphine oxide; 2-chloro-6-methoxybenzoylphenyl-2-propionic amyl ester phosphine oxide; 2-chloro-6-methoxybenzoylphenyl-2-propionic 2-ethylhexyl ester phosphine oxide; 2-chloro-6-methoxybenzoylphenyl-2-propionic tert-butyl ester phosphine oxide; 2-chloro-6-methoxybenzoylphenyl-2-propionic 1-methylpropyl ester phosphine oxide; 2-chloro-6-methoxybenzoylphenyl-2-propionic isopentyl ester phosphine oxide; 2-chloro-6-methoxybenzoylphenyl-2-propionic methoxyethoxy ester phosphine oxide; 2-chloro-6-methoxybenzoylphenyl-2-propionic benzyl ester phosphine oxide; 2-chloro-6-methoxybenzoylphenyl-2-propionic 2,4,4-trimethylpentyl ester phosphine oxide; 2-chloro-6-methoxybenzoylphenylacetic methyl ester phosphine oxide; 2-chloro-6-methoxybenzoylphenylacetic ethyl ester phosphine oxide; 2-chloro-6-methoxybenzoylphenylacetic propyl ester phosphine oxide; 2-chloro-6-methoxybenzoylphenylacetic butyl ester phosphine oxide; 2-chloro-6-methoxybenzoylphenylacetic pentyl ester phosphine oxide; 2-chloro-6-methoxybenzoylphenylacetic hexyl ester phosphine oxide; 2-chloro-6-methoxybenzoylphenylacetic octyl ester phosphine oxide; 2-chloro-6-methoxybenzoylphenylacetic decyl ester phosphine oxide; 2-chloro-6-methoxybenzoylphenylacetic dodecyl ester phosphine oxide; 2-chloro-6-methoxybenzoylphenylacetic isopropyl ester phosphine oxide; 2-chloro-6-methoxybenzoylphenylacetic isobutyl ester phosphine oxide; 2-chloro-6-methoxybenzoylphenylacetic amyl ester phosphine oxide; 2-chloro-6-methoxybenzoylphenylacetic 2-ethylhexyl ester phosphine oxide; 2-chloro-6-methoxybenzoylphenylacetic tert-butyl ester phosphine oxide; 2-chloro-6-methoxybenzoylphenylacetic 1-methylpropyl ester phosphine oxide; 2-chloro-6-methoxybenzoylphenylacetic isopentyl ester phosphine oxide; 2-chloro-6-methoxybenzoylphenylacetic methoxyethoxy ester phosphine oxide; 2-chloro-6-methoxybenzoylphenylacetic benzyl ester phosphine oxide; 2-chloro-6-methoxybenzoylphenylacetic 2,4,4-trimethylpentyl ester phosphine oxide.

The compounds of the formula III are obtained by reaction of a corresponding compound of the formula I with a compound $Z_1$—X (VI), where firstly the compound of the formula III in which x=0 (III') is prepared:

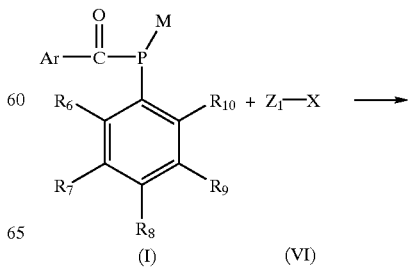

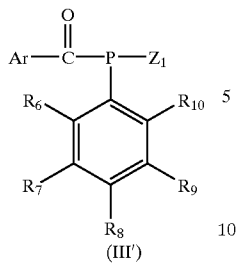

(III')

Ar, M, X, and $R_6$–$R_{10}$ are as defined above and in the claims. $Z_1$ is as defined in claim 3, with the exception of the groups (v), (w) and $C_1$–$C_{24}$alkylthio. (The preparation of compounds in which $Z_1$ is a group (v) or (w) or $C_1$–$C_{24}$alkylthio is described below.)

If compounds of the formula III where A=O or S are to be prepared, an oxidation or sulfurization of the compound of the formula (III') is then carried out, either after the compounds of the formula (III') have been separated off by customary methods, or without isolation thereof. The conditions for such reactions are analogous to those described for the preparation of the compounds of the formula II.

If a compound of the formula (III) in which $Z_1$ is a radical (v) or (w), or in which $Z_1$ is $C_1$–$C_{24}$alkylthio is desired, then the compound of the formula (I) is reacted with a compound of the formula $Z_1$—$SO_2$—X, where, without an intermediate stage, a compound of the formula (III) where A=O and x=1 is directly obtained. ($Z_1$ is defined as above, X is defined as in the claims.) The carrying out of the oxidation step is therefore unnecessary.

Similar reactions are described, for example, in Houben-Weyl, E2, Methoden der Organischen Chemie, 4$^{th}$ edition, pages 222–225.

If compounds of the formula (III) in which $Z_1$ is a radical (v) or (w) or $C_1$–$C_{24}$alkylthio and in which A is sulfur are to be prepared, then it is, for example, possible to convert the corresponding oxide compound as described above into the sulfide. This is possible, for example, by reacting the corresponding phosphine oxide with an excess of $P_2S_5$ or elemental sulfur in a high-boiling solvent. Such reactions, i.e. reactions in which a P=O bond is converted into a P=S bond, are described, for example, in L. Horner et al., Chem. Ber. 92, 2088 (1959) and U.S. Pat. No. 2,642,461. In principle, it is also possible to firstly reduce the corresponding phosphine oxide compound to give the respective phosphine and then to sulfurize the phosphine. I.e. the P=O bond is reduced to give the phosphine using a suitable reducing agent, and is then sulfurized with elemental sulfur to give the P=S bond. Reducing agents which may be used are, for example, $LiAlH_4$, $Ca(AlH_4)_2$, $CaH_2$ $AlH_3$, $SiHCl_3$, $PhSiH_3$ and the agents as described in "Organic Phosphorous Compounds, Wiley-Interscience 1972, Vol. 1, pages 45–46 and Vol.3, pages 408–413".

Compounds of the formula III, wherein $A_1$ is $NR_{18a}$, are for example prepared by reacting compounds of formula I with carbodiimides:

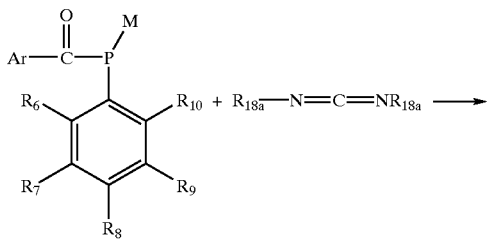

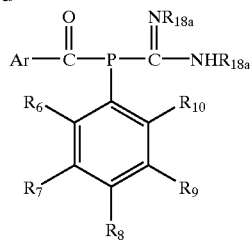

The invention provides a process for the preparation of compounds of the formula III from the novel starting materials of the formula I, (1) by reaction of an acyl halide of the formula IV

(IV)

in which

Ar is as defined above, and

X is Cl or Br;

with a dimetalated arylphosphine of the formula V

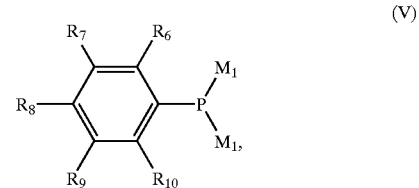

(V)

in which $R_6$, $R_7$, $R_8$, $R_9$ and $R_{10}$ are as defined above; and $M_1$ is Na, Li or K;

in the molar ratio of approximately 1:1;

(2) subsequent reaction of the product with a compound of the formula VI

$Z_1$—X   (VI), in which $Z_1$ is as defined above, with the exception of the groups (v), (w) and $C_1$–$C_{24}$alkylthio; and X is as defined above;

with the proviso that, if $Z_1$ is a radical

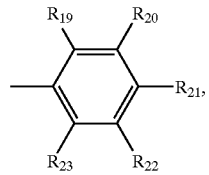

this radical is not identical to the radical

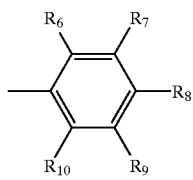

of the formula V;

in the molar ratio of approximately 1:1; and,
(3) if compounds of the formula III in which A is oxygen or sulfur are to be obtained, subsequent oxidation or sulfurization of the resulting phosphine compounds.

The compounds of the formula III in which $Z_1$ is $C_2$–$C_{24}$alkyl can, furthermore, be obtained by
(1) reaction of an acyl halide of the formula IV

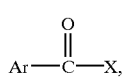
(IV)

in which

Ar is as defined above, and
X is Cl or Br;
with an unsymmetrical phosphine of the formula VII

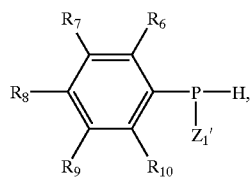
(VII)

in which $R_6$, $R_7$, $R_8$, $R_9$ and $R_{10}$ are as defined above, and
$Z_1'$ is $C_1$–$C_{24}$alkyl;
in the molar ratio of approximately 1:1, in the presence of a base, to give the corresponding acylphosphine; and
(2) subsequent oxidation or sulfurization of the acylphosphine thus obtained.

This preparation process is novel and likewise provided by the invention.

Suitable bases for this process are, for example, organo-lithium compounds, such as butyl-lithium, or organic nitrogen bases, for example tertiary amines or pyridine.

Furthermore, the compounds of the formula III can also be prepared by reacting the compound of the formula I with phosgene, analogous to the description in "W. A. Henderson et al., J. Am. Chem. Soc. 1960, 82, 5794" or "GB 904 086" or in "Organic Phosphorous Compounds, Editors: R. M. Kosolapoff and L. Maier, Wiley-Interscience 1972, Vol.1, page 28" or "Houben-Weyl, Methoden der Organischen Chemie, Vol. XII/1, page 201" to give the corresponding phosphine chloride (Ii). Compounds of the formula (Ii) can, as described in "Organic Phosphorous Compounds, Editors: R. M. Kosolapoff and L. Maier, Wiley-Interscience 1972, Vol.4, pages 268–269", be reacted with alcohols to give compounds of the formula (Iii), which are then directly reacted with an organohalide of the formula VI, in analogy to "K. Sasse in Houben-Weyl, Methoden der Organischen Chemie, Vol XII/1, page 433" (by Michaelis-Arbuzov reaction), to give compounds of the formula III. In this case, the oxidation or sulfurization step is superfluous.

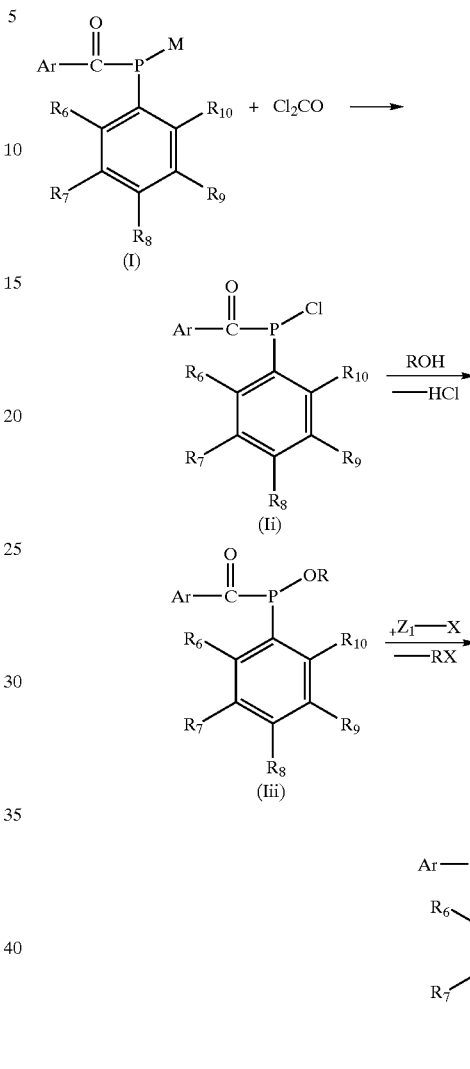

Ar is as described in claim 1 and $Z_1$ is as described in claim 3; X is Cl or Br; $R_6$ and M are likewise defined as in claim 1, and R is any alcohol radical, e.g. $C_1$–$C_{12}$alkyl, $C_5$–$C_8$cycloalkyl, for example cyclopentyl or cyclohexyl, or benzyl.

Compounds of the formula (Iii) can be oxidized using suitable oxidizing agents, such as peroxo acids, hydrogen peroxide or hydrogen peroxide/urea to give the corresponding phosphinic esters (Iiii):

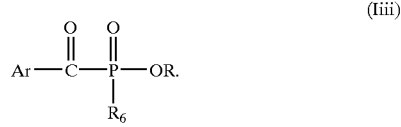
(Iiii)

The invention thus also provides a process for the preparation of compounds of the formula III in which A is oxygen and x is 1, by (1) reaction of a compound of the formula (I), according to claim 1

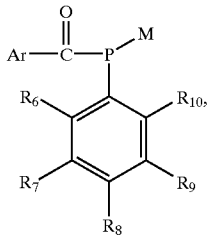

in which

Ar, M, $R_6$, $R_7$, $R_8$, $R_9$ and $R_{10}$ are as defined above, with phosgene to give corresponding phosphine chloride (Ii)

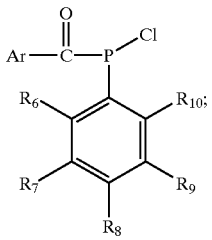

(2) subsequent reaction with an alcohol to give the compound of the formula (Iii)

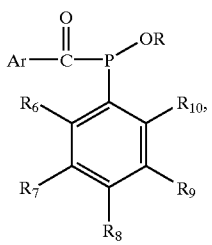

in which

R is the radical of an alcohol; and (3) reaction of the resulting compound of the formula (Iii) with an organohalide $$Z_1—X,$$

in which $Z_1$ is as defined above, but is not identical to Ar from the formula (I), and X is Cl or Br, to give the compound of the formula III.

It is also conceivable to obtain the compounds of the formula III according to the invention by another method. E.g. processes as described in U.S. Pat. No. 4,298,738 or U.S. Pat. No. 4,324,744 could be used.

The invention provides for the use of compounds of the formula I as starting materials for the preparation of mono- or bisacylphosphines, mono- or bisacylphosphine oxides or mono- or bisacylphosphine sulfides.

Also preferred are compounds of the formulae I, II and III,

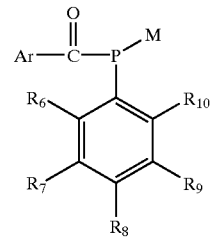

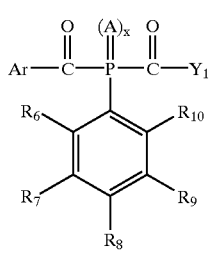

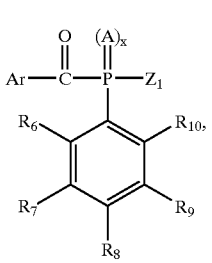

in which

Ar is a group

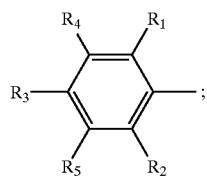

$R_1$ and $R_2$ independently of one another are $C_1$–$C_4$alkyl, $C_1$–$C_4$alkoxy or halogen;

$R_3$, $R_4$ and $R_5$ independently of one another are hydrogen or $C_1$–$C_4$alkyl;

$R_6$, $R_7$, $R_8$, $R_9$ and $R_{10}$ are hydrogen, $C_1$–$C_4$alkyl, $OR_{11}$ or phenyl;

$R_{11}$ is $C_1$–$C_4$alkyl, $C_2$–$C_8$alkenyl or benzyl;

M is hydrogen or Li;

A is O or S;

x is 1;

$Y_1$ is $C_1$–$C_4$alkyl which is unsubstituted or substituted by one or more phenyl; or $Y_1$ is naphthyl, anthracyl, $OR_{11}$, $N(R_{16})(R_{17})$, $OR_{11a}$, $N(R_{18a})(R_{18b})$,

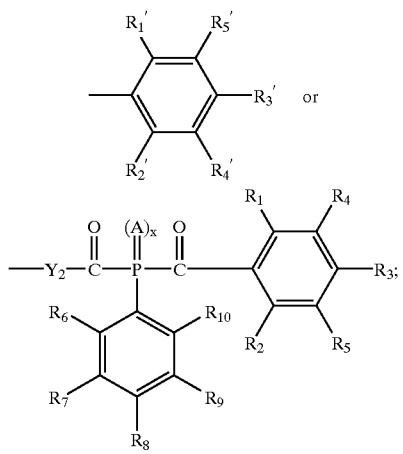 or

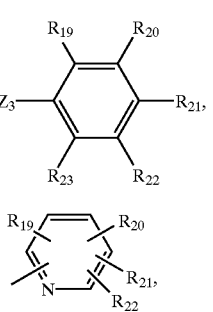

$Y_2$ is unsubstituted phenylene or phenylene substituted one to four times by $C_1$–$C_4$alkyl;

$R_1'$ and $R_2'$ independently of one another have the same meanings as given for $R_1$ and $R_2$; and $R_3'$, $R_4'$ and $R_5'$ independently of one another have the same meanings as given for $R_3$, $R_4$ and $R_5$;

with the proviso that if $Y_1$ is a radical

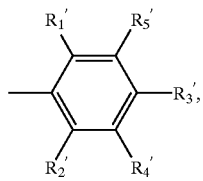

naphthyl or anthracyl, this is not identical to the other benzoyl group on the phosphorus atom;

$Z_1$ is $C_1$–$C_{12}$alkyl; $C_1$–$C_4$alkyl which is substituted by phenyl, halogen or

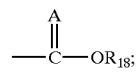

or $Z_1$ is unsubstituted $C_2$–$C_8$alkenyl or $C_2$–$C_8$alkenyl substituted by $C_6$–$C_{12}$aryl, CN, (CO)OR$_{15}$ or (CO)N(R$_{18}$)$_2$ or is (g)

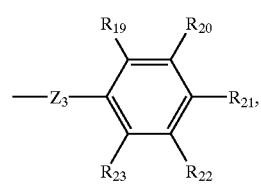

(h)

(k)

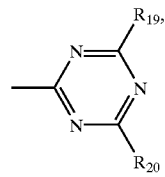

(m)

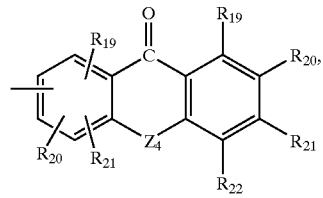

(p)

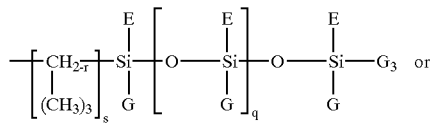  or (v)

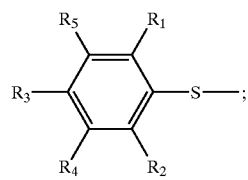

with the proviso that if $Z_1$ is a radical

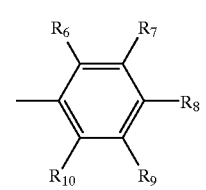

this is not identical to the other aromatic radical on the phosphorus atom;

$Z_3$ is CH$_2$;
$Z_4$ is S;
r is 0;
s is a number from 1 to 4;
q is a number from 0 to 4;

E, G, $G_3$ and $G_4$ independently of one another are unsubstituted $C_1$–$C_4$alkyl or are $C_1$–$C_4$alkyl substituted by chlorine;

$R_{11a}$ is $C_1$–$C_8$alkyl, substituted by $OR_{15}$, halogen or

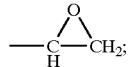

or is $C_2$–$C_6$alkenyl, $C_3$–$C_6$cycloalkyl or $C_7$–$C_{12}$arylalkyl; or is $C_6$–$C_{10}$aryl optionally once or more than once substituted by $C_1$–$C_4$alkyl;

$R_{15}$ is $C_1$–$C_8$alkyl or $(CO)R_{18}$;

$R_{16}$ and $R_{17}$ indepedently of one another are hydrogen, $C_1$–$C_8$alkyl; $C_2$–$C_6$alkenyl, $C_3$–$C_6$cycloalkyl, phenyl or benzyl; or $R_{16}$ and $R_{17}$ together are $C_3$–$C_5$alkylen optionally interrupted by O, S or $NR_{18}$;

$R_{18}$ is $C_1$–$C_8$alkyl or $C_1$–$C_8$alkenyl;

$R_{18a}$ and $R_{18b}$ independently of one another are $C_1$–$C_8$alkyl, substituted by $OR_{15}$, halogen, —N=C=A or

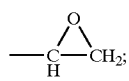

or are $C_2$–$C_8$alkenyl; or are $C_5$–$C_{12}$cycloalkyl substituted by —N=C=A or —$CH_2$—N=C=A and optionally additionally once or more than once substituted by methyl; or are $C_6$–$C_{10}$aryl optionall substituted by $C_1$–$C_4$alkyl and/or —N=C=A; or are $C_7$–$C_{12}$arylalkyl; $R_{19}$, $R_{20}$, $R_{21}$, $R_{22}$ and $R_{23}$ are hydrogen, $CF_3$, $CCl_3$ or halogen.

Likewise of interest are compounds of the formulae I, II and III in which $R_1$ and $R_2$ independently of one another are methyl, methoxy or chlorine;

$R_3$, $R_4$ and $R_5$ independently of one another are hydrogen or methyl;

$R_6$, $R_7$, $R_8$, $R_9$ and $R_{10}$ are hydrogen;

M is Li;

A is O;

x is 1;

$Y_1$ is $C_1$–$C_4$alkyl; or $Y_1$ is one of the radicals

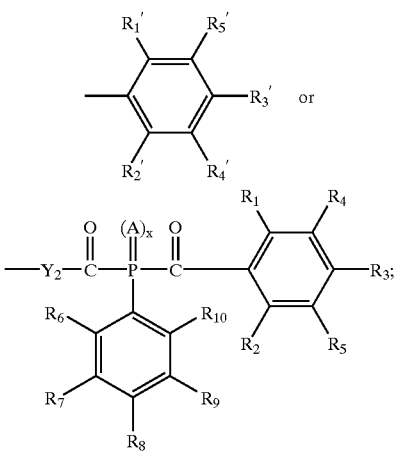

$Y_2$ is phenylene;

$R_1'$ and $R_2'$ independently of one another have the same meanings as given for $R_1$ and $R_2$; and $R_3'$, $R_4'$ and $R_5'$ independently of one another have the same meanings as given for $R_3$, $R_4$ and $R_5$;

with the proviso that if $Y_1$ is a radical

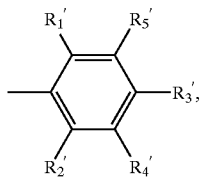

this is not identical to the other benzoyl group on the phosphorus atom;

$Z_1$ is $C_1$–$C_{12}$alkyl; $C_1$–$C_4$alkyl which is substituted by

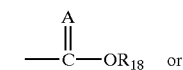

$Z_1$ is one of the radicals

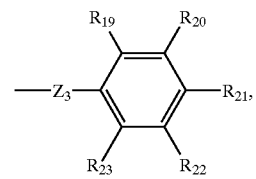

(g)

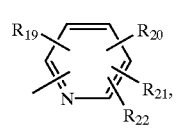

(h)

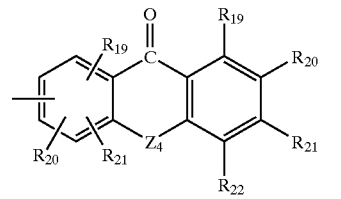

(m)

or

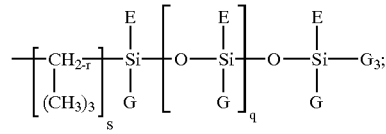

(p)

$Z_3$ is $CH_2$;

$Z_4$ is S;

r is 0;

s is a number from 1 to 4;

q is 0;

E, G, $G_3$ and $G_4$ independently of one another are unsubstituted or chlorine-substituted $C_1$–$C_4$alkyl;

$R_{18}$ is $C_1$–$C_8$alkyl;

$R_{19}$, $R_{20}$, $R_{21}$, $R_{22}$ and $R_{23}$ are hydrogen, $CF_3$, $CCl_3$ or halogen.

According to the invention, the compounds of the formulae II and III can be used as photoinitiators for the photopolymerization of ethylenically unsaturated compounds or mixtures which comprise such compounds.

This use can also take place in combination with another photoinitiator and/or other additives.

The invention thus also relates to photopolymerizable compositions comprising (a) at least one ethylenically unsaturated photopolymerizable compound and (b) as photoinitiator, at least one compound of the formula II and/or III, where the composition, in addition to the component (b), can also comprise other photoinitiators (c) and/or other additives (d).

Preference is given to using in these compositions compounds of the formula II or III in which x is 1, in particular those compounds in which x is 1 and A is oxygen.

The unsaturated compounds can contain one or more olefinic double bonds. They can be of low molecular weight (monomeric) or relatively high molecular weight (oligomeric). Examples of monomers with a double bond are alkyl or hydroxyalkyl acrylates or methacrylates, for example methyl acrylate, ethyl acrylate, butyl acrylate, 2-ethylhexyl acrylate or 2-hydroxyethyl acrylate, isobornyl acrylate, methyl methacrylate or ethyl methacrylate. Also of interest are silicon- or fluorine-modified resins, e.g. silicone acrylates. Further examples are acrylonitrile, acrylamide, methacrylamide, N-substituted (meth)acrylamides, vinyl esters, such as vinyl acetate, vinyl ethers, such as isobutyl vinyl ether, styrene, alkyl- and halostyrenes, N-vinylpyrrolidone, vinyl chloride or vinylidene chloride.

Examples of monomers having two or more double bonds are ethylene glycol diacrylate, propylene glycol diacrylate, neopentyl glycol diacrylate, hexamethylene glycol diacrylate or bisphenol A diacrylate, 4,4'-bis(2-acryloyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl)isocyanurate.

Examples of higher molecular weight (oligomeric) polyunsaturated compounds are acrylicized epoxy resins, polyurethanes, polyethers and polyesters which are acrylicized or contain vinyl ether or epoxy groups. Further examples of unsaturated oligomers are unsaturated polyester resins which are mostly prepared from maleic acid, phthalic acid and one or more diols and have molecular weights of from about 500 to 3,000. In addition, it is also possible to use vinyl ether monomers and oligomers, and maleate-terminated oligomers having polyester, polyurethane, polyether, polyvinyl ether and epoxy main chains. In particular, combinations of oligomers which carry vinyl ether groups and polymers as described in WO 90/01512 are highly suitable. However, copolymers of vinyl ether and maleic acid-functionalized monomers are also suitable. Such unsaturated oligomers may also be referred to as prepolymers.

Examples of particularly suitable compounds are esters of ethylenically unsaturated carboxylic acids and polyols or polyepoxides, and polymers containing ethylenically unsaturated groups in the chain or in side-groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and mixtures of one or more such polymers.

Examples of unsaturated carboxylic acids are acrylic acid, methacrylic acid, crotonic acid, itaconic acid, cinnamic acid, unsaturated fatty acids such as linolenic acid or oleic acid. Preference is given to acrylic acid and methacrylic acid.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on said polyols, particularly aromatic polyols and epichlorohydrins. In addition, polymers and copolymers which contain hydroxyl groups in the polymer chain or in side groups, for example polyvinyl alcohol and copolymers thereof or hydroxyalkyl polymethacrylates or copolymers thereof, are also suitable as polyols. Further suitable polyols are oligoesters containing hydroxyl end-groups.

Examples of aliphatic and cycloaliphatic polyols are alkylenediols having, preferably, 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of, preferably, 200 to 1,500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified using one or different unsaturated carboxylic acids, where the free hydroxyl groups in partial esters may be modified, e.g. etherified or esterified with other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and triacrylate, 1,4-cyclohexane diacrylate, bisacrylates and bismethacrylates of polyethylene glycol having molecular weights of from 200 to 1,500, or mixtures thereof.

Also suitable as component (a) are the amides of identical or different unsaturated carboxylic acids of aromatic, cycloaliphatic and aliphatic polyamines having, preferably, 2 to 6, particularly 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)ethane or di(β-aminopropoxy)ethane. Further suitable polyamines are polymers and copolymers with or without additional amino groups in the side chain and oligoamides containing amino end groups. Examples of such unsaturated amides are: methylenebisacrylamide, 1,6-hexamethylenebisacrylamide, diethylenetriaminetrismethacrylamide, bis(methacrylamidopropoxy)ethane, β-methacrylamidoethyl methacrylate, N[(β-hydroxyethoxy)ethyl]acrylamide.

Suitable unsaturated polyesters and polyamides are derived, for example, from maleic acid and diols or diamines. Some of the maleic acid may be replaced by other dicarboxylic acids. They can be used together with ethylenically unsaturated comonomers, e.g. styrene. The polyesters and polyamides may also be derived from dicarboxylic acids and ethylenically unsaturated diols or diamines, particularly from relatively long chain compounds containing, for example, 6 to 20 carbon atoms. Examples of polyurethanes are those constructed from saturated or unsaturated diisocyanates and unsaturated or saturated diols.

Polybutadiene and polyisoprene and copolymers thereof are known. Suitable comonomers are, for example, olefins, such as ethylene, propene, butene, hexene, (meth)acrylates, acrylonitrile, styrene or vinyl chloride. Polymers containing (meth)acrylate groups in the side chain are likewise known. These may, for example, be products of the reaction of novolak-based epoxy resins with (meth)acrylic acid, homo- or copolymers of vinyl alcohol or hydroxyalkyl derivatives thereof which have been esterified using (meth)acrylic acid, or homo- and copolymers of (meth)acrylates which have been esterified using hydroxyalkyl (meth)acrylates.

The photopolymerizable compounds may be used on their own or in any desired mixtures. Preference is given to using mixtures of polyol (meth)acrylates.

It is also possible to add binders to the compositions according to the invention; this is particularly advantageous if the photopolymerizable compounds are liquid or viscose substances. The amount of binder may, for example, be 5–95% by weight, preferably 10–90% by weight and particularly 40–90% by weight, based on the total solids. The binder is chosen depending on the field of application and on the properties required therefore, such as the facility for development in aqueous or organic solvent systems, adhesion to substrates and sensitivity to oxygen.

Examples of suitable binders are polymers having a molecular weight of from about 5,000–2,000,000, preferably 10,000–1,000,000. Examples are: homo- and copolymeric acrylates and methacrylates, e.g. copolymers of methyl methacrylate/ethyl acrylate/methacrylic acid, poly(alkyl methacrylates), poly(alkyl acrylates); cellulose esters and cellulose ethers, such as cellulose acetate, cellulose acetate butyrate, methylcellulose, ethylcellulose; polyvinylbutyral, polyvinylformal, cyclized rubber, polyethers, such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethyleneadipamide), and polyesters such as poly(ethylene glycol terephthalate) and poly(hexamethylene glycol succinate).

The unsaturated compounds can also be used in mixtures with non-photopolymerizable film-forming components. These may, for example, be physically drying polymers or solutions thereof in organic solvents, for example nitrocellulose or cellulose acetobutyrate. However, they may also be chemically or thermally curable resins, for example polyisocyanates, polyepoxides or melamine resins. The co-use of thermally curable resins is of importance for use in so-called hybrid systems, which are photopolymerized in a first stage and are crosslinked by thermal aftertreatment in a second stage.

The photoinitiators according to the invention are also suitable as initiators for the curing of oxidatively drying systems, as are described, for example, in Lehrbuch der Lacke und Beschichtungen Volume III, 296–328, Verlag W. A. Colomb in Heenemann GmbH, Berlin-Oberschwandorf (1976).

Apart from the photoinitiator, the photopolymerizable mixtures can also contain various additives (d). Examples thereof are thermal inhibitors, which are intended to prevent premature polymerization, for example hydroquinone, hydroquinone derivatives, p-methoxyphenol, β-naphthol or sterically hindered phenols, for example 2,6-di(tert-butyl)-p-cresol. To increase the storage stability in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. In order to exclude atmospheric oxygen during the polymerization, it is possible to add paraffin or similar wax-like substances which migrate to the surface at the start of the polymerization due to their lack of solubility in the polymers, and form a transparent surface layer which prevents the entry of air. It is likewise possible to apply an oxygen-impermeable layer. Light protection agents which may be used are UV absorbers, for example those of the hydroxyphenylbenzotriazol, hydroxyphenylbenzophenone, oxalamide or hydroxyphenyl-s-triazine type. The compounds can be used individually or as mixtures, with or without the use of sterically hindered amines (HALS).

Examples of such UV absorbers and light protection agents are 1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriole, 2-(3',5'-bis(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-yl phenol]; transesterification product of 2-[3'-tert-butyl-5'-(2-methoxycarbonylethyl)-2'-hydroxyphenyl]-benzotriazole with polyethylene glycol 300; [R—CH$_2$CH$_2$—COO(CH$_2$)$_3$]$_2$— where R=3'-tert-butyl-4'-hydroxy-5'-2H-benzotriazol-2-yl phenyl.
2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.
3. Esters of unsubstituted or substituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.
4. Acrylates, for example ethyl and isooctyl α-cyano-β,β-diphenylacrylate, methyl α-carbomethoxycinnamate, methyl and butyl α-cyano-β-methyl-p-methoxycinnamate, methyl α-carbomethoxy-p-methoxycinnamate and N-(β-carbomethoxy-β-cyanovinyl)-2-methylindoline.
5. Sterically hindered amines, for example bis(2,2,6,6-tetramethylpiperidyl)sebacate, bis(2,2,6,6-tetramethylpiperidyl)succinate, bis(1,2,2,6,6-pentamethylpiperidyl)sebacate, bis(1,2,2,6,6-pentamethylpiperidyl)n-butyl-3,5-di-tert-butyl-4-hydroxybenzylmalonate, the product of the condensation of 1-hydroxyethyl-2,2,6,6-tetramethyl-4-hydroxypiperidine and succinic acid, the product of the condensation of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)bis-(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, the product of the condensation of N,N'-bis(2,2,6,6-tetramethyl-4-piperidyl)hexamethylene-diamine and 4-morpholino-2,6-dichloro-1,3,5-triazine, the product of the condensation of 2-chloro-4,6-di(4-n-butylamino-2,2,6,6-tetramethylpiperidyl)1,3,5-triazine and 1,2-bis(3-aminopropylamino)ethane, the product of the condensation of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9,-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione, 2,4-bis[N-(1-cyclohexyloxy-2,2,6,6-tetramethylpiperidin-4-yl)-N-butylamino]-6-(2-hydroxyethyl)amino-1,3,5-triazine, the product of the condensation of 2,4-bis[1-cyclohexyloxy-2,2,6,6-tetramethylpiperidin-4-yl) butylamino]-6-chloro-s-triazine and N,N'-bis(3-aminopropyl)ethylenediamine.
6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and mixtures thereof with 2-ethoxy-2'-ethyl-5,4'-di-tert-butyloxanilide, and mixtures of o- and p-methoxy- and of o- and p-ethoxy-disubstituted oxanilides.
7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,5-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine and 2-[4-dodecyl/tridecyloxy(2-hydroxypropyl)oxy-2-hydroxyphenyl]-4,6-bis(2,4-dimethylphenyl)-1,3,5-triazine.
8. Phosphites and phosphonites, for example triphenyl phosphite, diphenyl alkylphosphites, phenyl dialkylphosphites, tris(nonylphenyl)phosphite, trilauryl phosphite, trioctadecyl phosphite, distearyl pentaerythritol diphosphite, tris(2,4-di-tert-butylphenyl)phosphite, diisodecylpentaerythritol diphosphite, bis(2,4-di-tert-butylphenyl)pentaerythritol diphosphite, bis(2,6-di-tert-butyl-4-methylphenyl)pentaerythritol diphosphite, bisisodecyloxy-pentaerythritol diphosphite, bis(2,4-di-tert-butyl-6-methylphenyl)pentaerythritol diphosphite, bis(2,4,6-tri-tert-butylphenyl)pentaerythritol diphosphite, tristearylsorbitol triphosphite, tetrakis-(2,4-di-tert-butylphenyl)-4,4'-biphenylenediphosphonite, 6-isooctyloxy-2,4,8,10-tetra-tert-butyl-12H-dibenz[d,g]-1,3,2-dioxaphosphocine, 6-fluoro-2,4,8,10-tetra-tert-butyl-12-methyl-dibenz[d,g]-1,3,2-dioxaphosphocine, bis (2,4-di-tert-butyl-6-methylphenyl)methylphosphite, and bis(2,4-di-tert-butyl-6-methylphenyl)ethylphosphite.

Examples of UV absorbers and light protection agents suitable as component (d) are also "Krypto-UVA", as are described, for example, in EP 180548. It is also possible to use latent UV absorbers, as described, for example, by Hida et al. in RadTech Asia 97, 1997, page 212.

It is also possible to use additives customary in the art, for example antistats, levelling auxiliaries and adhesion improvers.

To accelerate the photopolymerization it is possible to add, as further additives (d), a large number of amines, for example triethanolamine, N-methyldiethanolamine, ethyl p-dimethylaminobenzoate or Michlers ketone. The action of the amines can be intensified by the addition of aromatic ketones, e.g. of the benzophenone type. Examples of amines which can be used as oxygen scavengers are substituted N,N-dialkylanilines, as described in EP 339841. Other accelerators, coinitiators and autoxidators are thiols, thioethers, disulfides and phosphines, as described, for example, in EP 438123 and GB 2180358.

It is also possible to add chain transfer reagents customary in the art to the compositions according to the invention. Examples thereof are mercaptans, amines and benzothiazols.

The photopolymerization can also be accelerated by the addition of photosensitizers as further additives (d); these shift and/or broaden the spectral sensitivity. These are, in particular, aromatic carbonyl compounds, for example benzophenone, thioxanthone, in particular also isopropylthioxanthone, anthraquinone and 3-acylcoumarin derivatives, terphenyls, styryl ketones, and 3-(aroylmethylene)thiazolines, camphorquinone, but also eosin, rhodamine and erythrosine dyes.

As photosensitizers, it is also possible, for example, to consider the amines given above.

Further examples of such photosensitizers are

1. Thioxanthones thioxanthone, 2-isopropylthioxanthone, 2-chlorothioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di-[2-(2-methoxyethoxy)ethoxycarbonyl]thioxanthone, 1-ethoxycarbonyl-3-(1-methyl-1-morpholinoethyl)thioxanthone, 2-methyl-6-dimethoxymethylthioxanthone, 2-methyl-6-(1,1-dimethoxybenzyl)thioxanthone, 2-morpholinomethylthioxanthone, 2-methyl-6-morpholinomethylthioxanthone, n-allylthioxanthone-3,4-dicarboximide, n-octylthioxanthone-3,4-dicarboximide, N-(1,1,3,3-tetramethylbutyl)thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-polyethylene glycol ester, 2-hydroxy-3-(3,4-dimethyl-9-oxo-9H-thioxanthon-2-yloxy)-N,N,N-trimethyl-1-propanaminium chloride;

2. Benzophenones benzophenone, 4-phenylbenzophenone, 4-methoxybenzophenone, 4,4'-dimethoxybenzophenone, 4,4'-dimethylbenzophenone, 4,4'-dichlorobenzophenone, 4,4'-dimethylaminobenzophenone, 4,4'-diethylaminobenzophenone, 4-methylbenzophenone, 2,4,6-trimethylbenzophenone, 4-(4-methylthiophenyl)benzophenone, 3,3'-dimethyl-4-methoxybenzophenone, methyl-2-benzoylbenzoate, 4-(2-hydroxyethylthio)benzophenone, 4-(4-tolylthio)benzophenone, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl-1,4,7,10,13-pentaoxatridecyl)benzophenone, 4-benzoyl-N,N-dimethyl-N-[2-(1-oxo-2-propenyl)oxy]ethylbenzenemethanaminium chloride;

3. 3-Acylcoumarins 3-benzoylcoumarin, 3-benzoyl-7-methoxycoumarin, 3-benzoyl-5,7-di(propoxy)coumarin, 3-benzoyl-6,8-dichlorocoumarin, 3-benzoyl-6-chlorocoumarin, 3,3'-carbonylbis[5,7-di(propoxy)coumarin], 3,3'-carbonylbis(7-methoxycoumarin), 3,3'-carbonylbis(7-diethylaminocoumarin), 3-isobutyroylcoumarin, 3-benzoyl-5,7-dimethoxycoumarin, 3-benzoyl-5,7-diethoxycoumarin, 3-benzoyl-5,7-dibutoxycoumarin, 3-benzoyl-5,7-di(methoxyethoxy)coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)coumarin, 5,7-dimethoxy-3-(1-naphthoyl)coumarin, 3-benzoylbenzo[f]coumarin, 7-diethylamino-3-thienoylcoumarin, 3-(4-cyanobenzoyl)-5,7-dimethoxycoumarin;

4. 3-(Aroylmethylene)thiazolines

3-Methyl-2-benzoylmethylene-β-naphthothiazoline, 3-methyl-2-benzoylmethylenebenzothiazoline, 3-ethyl-2-propionylmethylene-β-naphthothiazoline;

5. Other Carbonyl Compounds

Acetophenone, 3-methoxyacetophenone, 4-phenylacetophenone, benzil, 2-acetylnaphthalene, 2-naphthaldehyde, 9,10-anthraquinone, 9-fluorenone, dibenzosuberone, xanthone, 2,5-bis(4-diethylaminobenzylidene)cyclopentanone, α-(para-dimethylaminobenzylidene)ketones, such as 2-(4-dimethylaminobenzylidene)indan-1-one or 3-(4-dimethylaminophenyl)-1-indan-5-ylpropenone, 3-phenylthiophthalimide, N-methyl-3,5-di(ethylthio)phthalimide.

The curing process can also be aided, in particular, by pigmented compositions (e.g. with titanium dioxide), also by the addition as additional additive (d) of a component which forms the radicals under thermal conditions, for example an azo compound, such as 2,2'-azobis-(4-methoxy-2,4-dimethylvaleronitrile), a triazene, diazo sulfide, pentazadiene or a peroxy compound, for example hydroperoxide or peroxycarbonate, e.g. t-butyl hydroperoxide, as described, for example, in EP 245639.

As further additive (d), the compositions according to the invention can also comprise a photoreproducible dye, for example xanthene, benzoxanthene, benzothioxanthene, thiazine, pyronine, porphyrin or acridine dyes, and/or a radiation-cleavable trihalomethyl compound. Similar compositions are described, for example, in EP 445624.

Depending on the intended use, further customary additives (d) are optical brighteners, fillers, pigments, both white and coloured pigments, dyes, antistats, wetting agents or levelling auxiliaries.

For the curing of thick and pigmented coatings, the addition of microglass beads or pulverized glass fibres, as described, for example, in U.S. Pat. No. 5,013,768, is suitable.

The formulations can also comprise dyes and/or white or coloured pigments. Depending on the intended use, it is possible to use both inorganic and organic pigments. Such additives are known to the person skilled in the art, examples being titanium dioxide pigments, e.g. of the rutile or anatase type, carbon black, zinc oxide, such as zinc white, iron oxides, such as iron oxide yellow, iron oxide red, chromium yellow, chromium green, nickel titanium yellow, ultramarine blue, cobalt blue, bismuth vanadate, cadmium yellow or cadmium red. Examples of organic pigments are mono- or bisazo pigments, and metal complexes thereof, phthalocyanine pigments, polycyclic pigments, for example perylene, anthraquinone, thioindigo, quinacridone or triphenylmethane pigments, and diketopyrrolopyrrole, isoindolinone, e.g. tetrachloroisoindolinone, isoindoline, dioxazine, benzimidazolone and quinophthalone pigments. The pigments can be used individually or else as mixtures in the formulations.

Depending on the intended use, the pigments are added to the formulations in amounts customary in the art, for example in an amount of from 0.1 to 60% by weight, 0.1 to 30% by weight or 10 to 30% by weight, based on the total composition.

The formulations can, for example, also comprise organic dyes from very diverse classes. Examples are azo dyes, methine dyes, anthraquinone dyes or metal complex dyes. Customary concentrations are, for example, 0.1 to 20%, in particular 1 to 5%, based on the total compositions.

Depending on the formulation used, compounds can also neutralize the acids, in particular amines are used as stabilizers. Suitable systems are described, for example, in JP-A 11-199610. Examples are pyridine and derivatives thereof, N-alkylanilines or N,N-dialkylanilines, pyrazine derivatives, pyrrol derivatives, etc.

The choice of additives depends on the field of application in question and the properties desired for this field. The above-described additives (d) are customary in the art and are accordingly used in amounts customary in the art.

The invention also provides compositions comprising, as components (a), at least one ethylenically unsaturated photopolymerizable compound which is emulsified or dissolved in water.

Such radiation-curable aqueous prepolymer dispersions are available commercially in many variations. This is understood as meaning a dispersion of water and at least one prepolymer dispersed therein. The concentration of the water in these systems is, for example, 2 to 80% by weight, in particular 30 to 60% by weight. The radiation-curable prepolymers or prepolymer mixture is present, for example, in concentrations of from 95 to 20% by weight, in particular 70 to 40% by weight. In these compositions, the total of the percentages given for water and prepolymers is in each case 100, the auxiliaries and additives being added in varying amounts, depending on the intended use.

The radiation-curable film-forming prepolymers which are dispersed, and often also dissolved, in water are mono- or polyfunctional ethylenically unsaturated prepolymers which can be initiated by free radicals and are known per se for aqueous prepolymer dispersions, which have, for example, a content of from 0.01 to 1.0 mol per 100 g of prepolymer of polymerizable double bonds, and also an average molecular weight of, for example, at least 400, in particular from 500 to 10,000. However, depending on the intended use, prepolymers with higher molecular weights are also suitable.

Polyesters containing polymerizable C—C double bonds and having an acid number of at most 10, polyethers containing polymerizable C—C double bonds, hydroxyl-containing products of the reaction of a polyepoxide containing at least two epoxide groups per molecule with at least one α,β-ethylenically unsaturated carboxylic acid, polyurethane (meth)acrylates, and acrylic copolymers containing α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions based on specific (meth) acrylic alkyl ester polymers are described in EP 41125, and suitable water-dispersible, radiation-curable prepolymers of urethane acrylates can be found in DE 2936039.

As further additives, these radiation-curable aqueous prepolymer dispersions can also comprise the above-described additional additives (d), i.e., for example, dispersion auxiliaries, emulsifiers, antioxidants, light stabilizers, dyes, pigments, fillers, e.g. talc, gypsum, silica, rutile, carbon black, zinc oxide, iron oxides, reaction accelerators, levelling agents, lubricants, wetting agents, thickeners, matting agents, antifoams and other auxiliaries customary in surface coating technology. Suitable dispersion auxiliaries are water-soluble high molecular weight organic compounds having polar groups, for example polyvinyl alcohols, polyvinylpyrrolidone or cellulose ethers. Emulsifiers which may be used are nonionic, and, where appropriate, also ionic, emulsifiers.

The photoinitiators of the formula II or III according to the invention can also be dispersed as such in aqueous solutions and added in this dispersed form to the mixtures to be cured. Treated with suitable nonionic or, where appropriate, also ionic, emulsifiers, the compounds of the formula II or III according to the invention can be incorporated by mixing and e.g. binding into water. This produces stable emulsions which can be used as such as photoinitiators, in particular for aqueous photocurable mixtures as described above.

In certain cases, it may be advantageous to use mixtures of two or more of the photoinitiators according to the invention. It is of course also possible to use mixtures with known photoinitiators, e.g. mixtures with camphorquinone, benzophenone, benzophenone derivatives, acetophenone, acetophenone derivatives, for example α-hydroxycycloalkyl phenyl ketones or 2-hydroxy-2-methyl-1-phenylpropanone, dialkoxyacetophenones, α-hydroxy or α-aminoacetophenones, for example 4-methylthiobenzoyl-1-methyl-1-morpholinoethane, 4-morpholinobenzoyl-1-benzyl-1-dimethylaminopropane, 4-aroyl-1,3-dioxolanes, benzoin alkyl ethers and benzil ketals, for example benzil dimethyl ketal, phenyl glyoxalates and derivatives thereof, dimeric phenyl glyoxalates, peresters, e.g. benzophenonetetracarboxylic peresters, as described, for example, in EP 126541, monoacylphosphine oxides, for example (2,4,6-trimethylbenzoyl)phenylphosphine oxide, bisacylphosphine oxides, for example bis(2,6-dimethoxybenzoyl)(2,4,4-trimethylpent-1-yl)phosphine oxide, bis-(2,4,6-trimethylbenzoyl)phenylphosphine oxide or bis(2,4,6-trimethylbenzoyl)(2,4-dipentoxyphenyl)phosphine oxide, trisacylphosphine oxides, halomethyltriazines, e.g. 2-[2-(4-methoxyphenyl)vinyl]-4,6-bistrichloromethyl-[1,3,5] triazine, 2-(4-methoxyphenyl)-4,6-bis-trichloromethyl-[1,3,5]triazine, 2-(3,4-dimethoxyphenyl)-4,6-bistrichloromethyl-[1,3,5]triazine, 2-methyl-4,6-bistrichloromethyl-[1,3,5] triazine, hexaarylbisimidazole/coinitiator systems, e.g. ortho-chlorohexaphenylbisimidazole in combination with 2-mercaptobenzothiazole; ferrocenium compounds or titanocenes, for example dicyclopentadienylbis-(2,6-difluoro-3-pyrrolophenyl)titanium. Coinitiators which may also be used are borate compounds.

In the case of the use of the photoinitiators according to the invention in hybrid systems, in this connection mixtures of free-radically and cationically curing systems are thus intended, in addition to the free-radical curing agents according to the invention, cationic photoinitiators, for example benzoyl peroxide (other suitable peroxides are described in U.S. Pat. No. 4,950,581, column 19, lines 17–25), aromatic sulfonium, phosphonium or iodonium salts, as described, for example in U.S. Pat. No. 4,950,581, column 18, line 60 to column 19, line 10, or cyclopentadienylareneiron(II) complex salts, e.g. ($\eta^6$-isopropylbenzene) ($\eta^5$-cyclopentadienyl)iron(II) hexafluorophosphate, are used.

The invention also provides compositions in which the additional photoinitiators (c) are compounds of the formula VIII, IX, X, XI or mixtures thereof,

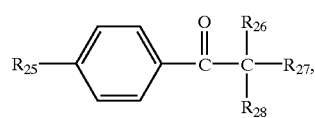

(VIII)

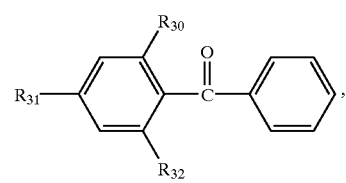

(IX)

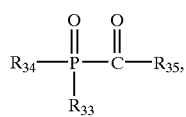
(X)

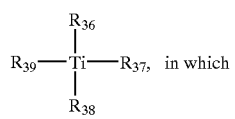
(XI)

$R_{25}$ is hydrogen, $C_1$–$C_{18}$alkyl, $C_1$–$C_{18}$alkoxy, —OCH$_2$CH$_2$—OR$_{29}$, morpholino, SCH$_3$, a group

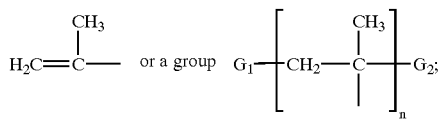

n has a value from 2 to 10;

$G_1$ and $G_2$ independently of one another are end-groups of the polymeric unit, in particular hydrogen or CH$_3$;

$R_{26}$ is hydroxyl, $C_1$–$C_{16}$alkoxy, morpholino, dimethylamino or —O(CH$_2$CH$_2$O)$_m$—$C_1$–$C_{16}$alkyl;

$R_{27}$ and $R_{28}$ independently of one another are hydrogen, $C_1$–$C_6$alkyl, phenyl, benzyl, $C_1$–$C_{16}$alkoxy or —O(CH$_2$CH$_2$O)$_m$—$C_1$–$C_{16}$alkyl, or $R_{27}$ and $R_{28}$ together with the carbon atom to which they are bonded form a cyclohexyl ring;

m is a number from 1–20;

where $R_{26}$, $R_{27}$ and $R_{28}$ are not all $C_1$–$C_{16}$alkoxy or —O(CH$_2$CH$_2$O)$_m$—$C_1$–$C_{16}$alkyl at the same time, and $R_{29}$ is hydrogen,

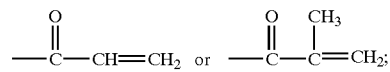

$R_{30}$ an $R_{32}$ independently of one another are hydrogen or methyl;

$R_{31}$ is hydrogen, methyl or phenylthio, where the phenyl ring of the phenylthio radical is unsubstituted or substituted by $C_1$–$C_4$alkyl in the 4-, 2-, 2,4- or 2,4,6-position;

$R_{33}$ and $R_{34}$ independently of one another are $C_1$–$C_{20}$alkyl, cyclohexyl, cyclopentyl, phenyl, naphthyl or biphenyl, where these radicals are unsubstituted or are substituted by halogen, $C_1$–$C_{12}$alkyl and/or $C_1$–$C_{12}$-alkoxy, or $R_{33}$ is an S- or N-containing 5- or 6-membered heterocyclic ring, or are

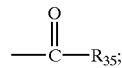

$R_{35}$ is cyclohexyl, cyclopentyl, phenyl, naphthyl or biphenyl, these radicals being unsubstituted or substituted by halogen, $C_1$–$C_4$alkyl and/or $C_1$–$C_4$alkoxy, or $R_{35}$ is an S- or N-containing 5- or 6-membered heterocyclic ring;

$R_{36}$ and $R_{37}$ independently of one another are unsubstituted cyclopentadienyl or cyclopentadienyl substituted once, twice or three times by $C_1$–$C_{18}$alkyl, $C_1$–$C_{18}$alkoxy, cyclopentyl, cyclohexyl or halogen; and $R_{38}$ and $R_{39}$ independently of one another are phenyl which is substituted in at least one of the two ortho positions relative to the titanium-carbon bond by fluorine atoms or CF$_3$, and which on the aromatic ring may contain, as further substituents, unsubstituted pyrrolinyl or pyrrolinyl substituted by one or two $C_1$–$C_{12}$alkyl, di($C_1$–$C_{12}$alkyl)aminomethyl, morpholinomethyl, $C_2$–$C_4$alkenyl, methoxymethyl, ethoxymethyl, trimethylsilyl, formyl, methoxy or phenyl; or polyoxaalkyl, or $R_{38}$ and $R_{39}$ are

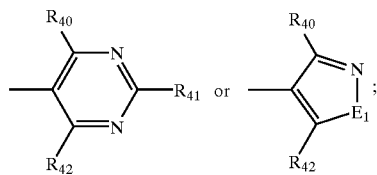

$R_{40}$, $R_{41}$ and $R_{42}$ independently of one another are hydrogen, halogen, $C_2$–$C_{12}$alkenyl, $C_1$–$C_{12}$alkoxy, $C_2$–$C_{12}$alkoxy interrupted by one to four O atoms, cycylohexyloxy, cyclopentyloxy, phenoxy, benzyloxy, unsubstituted phenyl or phenyl substituted by $C_1$–$C_4$alkoxy, halogen, phenylthio or $C_1$–$C_4$-alkylthio; or biphenyl, where $R_{40}$ and $R_{42}$ are not both hydrogen at the same time and in the radical

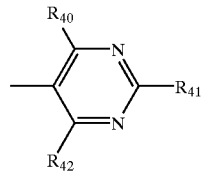

at least one radical $R_{40}$ or $R_{42}$ is $C_1$–$C_{12}$alkoxy, $C_2$–$C_{12}$alkoxy interrupted by one to four O atoms, cyclohexyloxy, cyclopentyloxy, phenoxy or benzyloxy;

$E_1$ is O, S or NR$_{43}$; and $R_{43}$ is $C_1$–$C_8$alkyl, phenyl or cyclohexyl.

$R_{25}$ as $C_1$–$C_{18}$alkyl can have the same meanings as described for the compounds of the formulae I, II or III. Also, $R_{27}$ and $R_{28}$ as $C_1$–$C_6$alkyl and $R_{26}$ as $C_1$–$C_4$alkyl can have the same meanings as described above apart from the respective number of carbon atoms.

$C_1$–$C_{18}$alkoxy is, for example, branched or unbranched alkoxy, for example methoxy, ethoxy, n-propoxy, isopropoxy, n-butoxy, isobutoxy, sec-butoxy, tert-butoxy, pentoxy, hexyloxy, heptyloxy, octyloxy, 2,4,4-trimethylpent-1-yloxy, 2-ethylhexyloxy, nonyloxy, decyloxy, dodecyloxy or octadecyloxy.

$C_2$–$C_{12}$alkoxy has the meanings given above apart from the corresponding number of carbon atoms.

$C_1$–$C_{16}$alkoxy has the same meanings as described above apart from the corresponding number of carbon atoms, and decyloxy, methoxy and ethoxy are preferred, in particular methoxy and ethoxy.

The radical —O(CH$_2$CH$_2$O)$_m$—$C_1$–$C_{16}$alkyl stands for 1 to 20 consecutive ethylene oxide units whose chain ends with a $C_1$–$C_{16}$alkyl. Preferably, m is 1 to 10, e.g. 1 to 8, in particular 1 to 6. Preferably, the ethylene oxide unit chain is terminated with a $C_1$–$C_{10}$alkyl, e.g. $C_1$–$C_8$alkyl, in particular with a $C_1$–$C_4$alkyl.

$R_{31}$ as a substituted phenylthio ring is, preferably, p-tolylthio.

$R_{33}$ and $R_{34}$ as $C_1$–$C_{20}$alkyl are linear or branched and are, for example, $C_1$–$C_{12}$alkyl, $C_1$–$C_8$alkyl, $C_1$–$C_6$alkyl or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl or icosyl. Preferably, $R_{33}$ as alkyl is $C_1$–$C_8$alkyl.

$R_{33}$, $R_{34}$ and $R_{35}$ as substituted phenyl are mono- to pentasubstituted, e.g. mono-, di- or trisubstituted, in particular tri- or disubstituted, on the phenyl ring. Substituted phenyl, naphthyl or biphenyl are substituted e.g. with a linear or branched $C_1$–$C_4$alkyl such as methyl, ethyl, n-propyl, isopropyl, n-butyl, isobutyl, s-butyl or t-butyl or with a linear or branched $C_1$–$C_4$alkoxy such as methoxy, ethoxy, n-propoxy, isopropoxy, n-butoxy, isobutoxy, s-butoxy or t-butoxy, preferably with methyl or methoxy.

If $R_{33}$, $R_{34}$ and $R_{36}$ are an S- or N-containing 5- or 6-membered heterocyclic ring, they are, for example, thienyl, pyrrolyl or pyridyl.

In the expression di($C_1$–$C_{12}$alkyl)aminomethyl, $C_1$–$C_{12}$alkyl has the same meanings as given above.

$C_2$–$C_{12}$alkenyl is linear or branched, can be mono- or polyunsaturated and is, for example, allyl, methallyl, 1,1-dimethylallyl, 1-butenyl, 2-butenyl, 1,3-pentadienyl, 1-hexenyl or 1-octenyl, in particular allyl.

$C_1$–$C_4$alkylthio is linear or branched and is, for example, methylthio, ethylthio, n-propylthio, isopropylthio, n-butylthio, isobutylthio, s-butylthio or t-butylthio, preferably methylthio.

$C_2$–$C_4$alkenyl is, for example, allyl, methallyl, 1-butenyl or 2-butenyl.

Halogen is fluorine, chlorine, bromine and iodine, preferably, fluorine, chlorine and bromine.

The term polyoxaalkyl includes $C_2$–$C_{20}$alkyl interrupted by 1 to 9 O atoms and stands, for example, for structural units such as $CH_3$—O—$CH_2$—, $CH_3CH_2$—O—$CH_2CH_2$—, $CH_3O[CH_2CH_2O]_y$—, where y=1–9,—$(CH_2CH_2O)_7CH_2CH_3$, —$CH_2$—$CH(CH_3)$—O—$CH_2$—$CH_2CH_3$.

Preference is given to compositions in which
$R_{25}$ is hydrogen, —$OCH_2CH_2$—$OR_{29}$, morpholino, $SCH_3$, a group

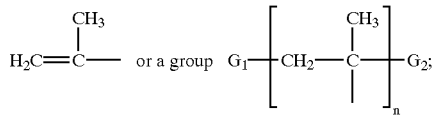

$R_{26}$ is hydroxyl, $C_1$–$C_{16}$alkoxy, morpholino or dimethylamino;
$R_{27}$ and $R_{28}$ independently of one another are $C_1$–$C_4$alkyl, phenyl, benzyl or $C_1$–$C_{16}$alkoxy, or
$R_{27}$ and $R_{28}$ together with the carbon atom to which they are bonded form a cyclohexyl ring;
$R_{29}$ is hydrogen or

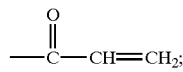

$R_{30}$, $R_{31}$ and $R_{32}$ are hydrogen;
$R_{33}$ is $C_1$–$C_{12}$alkyl, unsubstituted phenyl or phenyl substituted by $C_1$–$C_{12}$alkyl and/or $C_1$–$C_{12}$alkoxy;

$R_{34}$ is

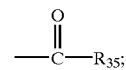

and
$R_{35}$ is phenyl which is substituted by $C_1$–$C_4$alkyl and/or $C_1$–$C_4$alkoxy.

Preferred compounds of the formulae VII, IX, X and XI are α-hydroxycyclohexyl phenyl ketone or 2-hydroxy-2-methyl-1-phenylpropanone, (4-methylthiobenzoyl)-1-methyl-1-morpholinoethane, (4-morpholinobenzoyl)-1-benzyl-1-dimethylaminopropane, benzil dimethyl ketal, (2,4,6-trimethylbenzoyl)phenylphosphine oxide, bis(2,6-dimethoxybenzoyl)(2,4,4-trimethyl-pent-1-yl)phosphine oxide, bis(2,4,6-trimethylbenzoyl)phenylphosphine oxide or bis(2,4,6-trimethylbenzoyl)(2,4-dipentoxyphenyl)phosphine oxide and dicyclopentadienyl-bis(2,6-difluoro-3-pyrrolo)titanium.

Preference is also given to compositions in which, in the formula VIII $R_{27}$ and $R_{28}$ independently of one another are $C_1$–$C_6$alkyl, or together with the carbon atom to which they are bonded form a cyclohexyl ring, and $R_{26}$ is hydroxyl.

The proportion of compounds of the formula II and/or III (photoinitiator component (b)) in the mixture with compounds of the formulae VII, IX, X and/or XI (=photoinitiator component (c)) is 5 to 99%, e.g. 20–80%, preferably 25 to 75%.

Also important are compositions in which, in the compounds of the formula VIII, $R_{27}$ and $R_{28}$ are identical and are methyl, and $R_{26}$ is hydroxyl or isopropoxy.

Likewise preferred are compositions comprising compounds of the formula II and/or III and compounds of the formula X in which
$R_{33}$ is unsubstituted or mono- to tri-$C_1$–$C_{12}$alkyl- and/or $C_1$–$C_{12}$alkoxy-substituted phenyl or $C_1$–$C_{12}$alkyl;
$R_{34}$ is the group

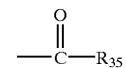

or phenyl; and
$R_{35}$ is phenyl substituted by one to three $C_1$–$C_4$alkyl or $C_1$–$C_4$alkoxy.

Of particular interest are compositions as described above which comprise photoinitiator mixtures of the formulae II, III, VII, IX, X and/or XI and are liquid at room temperature.

The preparation of the compounds of the formulae VII, IX, X and XI is generally known to the person skilled in the art and some of the compounds are available commercially. The preparation of oligomeric compounds of the formula VIII is described, for example, in EP 161463. A description of the preparation of compounds of the formula IX can, for example, be found in EP 209831. The preparation of compounds of the formula X is disclosed, for example, in EP 7508, EP 184095 and GB 2259704. The preparation of compounds of the formula XI is described, for example, in EP 318894, EP 318893 and EP 565488.

The photopolymerizable compositions advantageously comprise the photoinitiator in an amount of from 0.05 to 20% by weight, e.g. 0.05 to 15% by weight, preferably 0.1 to 5% by weight, based on the composition. The amount of photoinitiator stated is based on the total of all added photoinitiators if mixtures thereof are used, i.e. both on the photoinitiator (b) and on the photoinitiators (b)+(c).

Compounds according to the invention in which $Z_1$ or $Z_2$ are siloxane-containing radicals are particularly suitable as photoinitiators for surface coatings, in particular vehicle paints. These photoinitiators are not distributed as homogeneously as possible in the formulation to be cured, but enriched in a targeted manner on the surface of the coating to be cured, i.e. a targeted orientation of the initiator to the surface of the formulation takes place.

The photopolymerizable compositions can be used for various purposes, for example as printing inks, such as screen printing inks, flexographic printing inks or offset printing inks, as clearcoats, as colour coats, as white coats, e.g. for wood or metal, as powder coatings, as paints, inter alia for paper, water, metal or plastic, as daylight-curable coatings for marking buildings and roads, for photographic reproduction processes, for holographic recording materials, for image recording processes or for the production of printing plates which can be developed using organic solvents or aqueous-alkaline media, for the production of masks for screen printing, as dental filling materials, as adhesives, as pressure-sensitive adhesives, as laminating resins, as photoresists, e.g. galvanoresists, etch or permanent resists, both liquid and dry films, as photostructurable dielectrics, and as solder stopping masks for electronic circuits, as resists for the preparation of colour filters for any type of screen or for producing structures in the production process of plasma displays and electroluminescence displays, for the production of optical switches, optical gratings (interference gratings), for the preparation of three-dimensional objects by mass curing (UV curing in transparent moulds) or by the stereolithography process, as is described, for example, in U.S. Pat. No. 4,575,330, for the preparation of composite materials (e.g. styrenic polyesters which may contain glass fibres and/or other fibres and other auxiliaries) and other thick-layer materials, for the coating or sealing of electronic components or as coatings for optical fibres. The compositions are also suitable for the preparation of optical lenses, e.g. contact lenses and Fresnel lenses, and for the preparation of medical instruments, auxiliaries or implants.

The compositions are also suitable for the preparation of gels having thermotropic properties. Such gels are described, for example, in DE 19700064 and EP 678534.

Furthermore, the compositions can be used in dry-film paints, as are described, for example, in Paint & Coatings Industry, April 1997, 72 or Plastics World, Volume 54, No. 7, page 48(5).

The compounds according to the invention can also be used as initiators for emulsion, bead or suspension polymerizations or as initiators of a polymerization for the fixing of ordered states of liquid-crystalline mono- and oligomers, or as initiators for the fixing of dyes to organic materials.

In surface coatings, mixtures of a prepolymer with polyunsaturated monomers are often used which also contain a monounsaturated monomer. The prepolymer here is primarily responsible or the properties of the coating film, and variation thereof allows the person skilled in the art to influence the properties of the cured film. The polyunsaturated monomer functions as a crosslinking agent which renders the coating film insoluble. The monounsaturated monomer functions as a reactive diluent, by means of which the viscosity is reduced without the need to use a solvent.

Unsaturated polyester resins are mostly used in two-component systems together with a monounsaturated monomer, preferably with styrene. For photoresists, specific one-component systems are often used, for example polymaleimides, polychalcones or polyimides, as are described in DE 2308830.

The compounds according to the invention and mixtures thereof may also be used as free-radical photoinitiators or photoinitiating systems for radiation-curable powder coatings. The powder coatings may be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (e.g. methyl methacrylamide glycolate) and with a free-radical photoinitiator according to the invention, as described, for example, in the paper "Radiation Curing of Powder Coating", Conference Proceedings, Radtech Europe 1993 by M. Wittig and Th. Gohmann. Similarly, free-radically UV-curable powder coatings can be formulated by mixing unsaturated polyester resins with solid acrylates, methacrylates or vinyl ethers and with a photoinitiator (or photoinitiator mixture) according to the invention. The powder coatings can also comprise binders, as described, for example, in DE 4228514 and EP 636669. The UV-curable powder coatings can also comprise white or coloured pigments. Thus, for example, preferably rutile titanium dioxide may be used in concentrations of up to 50% by weight in order to obtain a cured powder coating with good coverage. The process normally involves electrostatic or tribostatic spraying of the powder onto the substrate, for example metal or wood, melting the powder by heating and, after a smooth film has formed, radiation-curing of the coating with ultraviolet and/or visible light, e.g. using medium-pressure mercury lamps, metal halide lamps or xenon lamps. A particular advantage of the radiation-curable powder coatings compared with their thermally curable counterparts is that the flow time after the melting of the powder particles can be extended as desired in order to ensure the formation of a smooth, high-gloss coating. In contrast to thermally curable systems, radiation-curable powder coatings can be formulated without the desired effect of a reduction in their service life such that they melt at relatively low temperatures. For this reason, they are also suitable as coatings for heat-sensitive substrates, for example wood or plastics.

In addition to the photoinitiators according to the invention, the powder coating formulations can also comprise UV absorbers. Appropriate examples have been listed above under points 1–8.

The photocurable compositions according to the invention are suitable, for example, as coating substances for substrates of all kinds, e.g. wood, textiles, paper, ceramic, glass, plastics such as polyesters, polyethylene terephthalate, polyolefins or cellulose acetate, in particular in the form of films, and also metals such as Al, Cu, Ni, Fe, Zn, Mg or Co and GaAs, Si or $SiO_2$, on which a protective coating or, for example by imagewise exposure, an image is to be applied.

The substrates can be coated by applying a liquid composition, a solution or suspension to the substrate. The choice of solvent and the concentration depend primarily on the type of composition and on the coating procedure. The solvent should be inert, i.e. it should not undergo any chemical reaction with the components and should be capable of being removed again after the coating operation, in the drying process. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

Using known coating processes, the formulation is applied to a substrate, e.g. by spincoating, dip coating, knife coating, curtain coating, brushing, spraying, especially, for example, by electrostatic spraying and reverse-roll coating, and by electrophoretic deposition. It is also possible to apply the photosensitive layer to a temporary, flexible support and then to coat the final substrate, e.g. a copper-laminated circuit board, by means of layer transfer via lamination.

The amount applied (layer thickness) and the type of substrate (layer support) are dependant on the desired field of application. The suitable layer thicknesses for the respective fields of application, e.g. in the photoresist field, printing ink field or paint field are known to the person skilled in the art. Depending on the field of application, the layer thickness range generally includes values from about 0.1 $\mu$m to more than 10 mm.

The radiation-sensitive compositions according to the invention are used, for example, as negative resists which have very high photosensitivity and can be developed in an aqueous-alkaline medium without swelling. They are suitable as photoresists for electronics, such as galvanoresists, etch resists, both in liquid and also dry films, solder stopping resists, as resists for the production of colour filters for any desired type of screen, or for the formation of structures in the manufacturing process of plasma displays and electroluminescence displays, for the production of printing plates, for example offset printing plates, for the production of printing formes for typographic printing, planographic printing, intaglio printing, flexographic printing or screen printing formes, the production of relief copies, e.g. for the production of texts in Braille, for the production of stamps, for use in moulding etching or use as microresists in the production of integrated circuits. The compositions may also be used as photostructurable dielectrics, for the encapsulation of materials or as insulator coating for the production of computer chips, printed circuits and other electrical or electronic components. The possible layer supports and the processing conditions of the coated substrates are varied accordingly.

The compounds according to the invention are also used for the production of single-layer or multilayer materials for image recording or image duplication (copies, reprography), which may be monotone or multicoloured. Furthermore, these materials can also be used as colour testing systems. In this technology, it is also possible to use formulations which contain microcapsules and, to generate the image, a thermal step can be connected downstream of the exposure step. Such systems and technologies and their applications are described, for example, in U.S. Pat. No. 5,376,459.

For photographic information recording, films made of polyester, cellulose acetate or plastic-coated papers, for example, are used, and for offset printing formes, specially treated aluminium, for example, is used, for the production of printed circuits, copper-faced laminates, for example, are used, and for the production of integrated circuits, silicon wafers are used. The usual layer thicknesses for photographic materials and offset printing forms are generally about 0.5 $\mu$m to 10 $\mu$m, and for printed circuits are from 1.0 $\mu$m to about 100 $\mu$m.

After the substrates have been coated, the solvent is usually removed by drying, to leave a layer of the photoresist on the support.

The term "imagewise" exposure encompasses both exposure via a photomask containing a predetermined pattern, for example a diapositive, exposure by a laser beam which is moved, for example under control by a computer, over the surface of the coated substrate, thereby generating an image, and irradiation with computer-controlled electron beams. It is also possible to use masks of liquid crystals which can be controlled pixel by pixel in order to generate digital images, as described, for example, by A. Bertsch, J. Y. Jezequel, J. C. Andre in Journal of Photochemistry and Photobiology A: Chemistry 1997, 107, p. 275–281 and by K.-P. Nicolay in Offset Printing 1997, 6, p. 34–37.

Conjugated polymers, for example polyanilines, can be converted from a semiconducting state to a conducting state by doping with protons. The photoinitiators according to the invention can also be used for the imagewise exposure of polymerizable compositions which contain such polymers in order to form conducting structures (in the irradiated zones) which are embedded in the insulating material (unexposed zones). Such materials can, for example, be used as wiring or connecting components for the production of electrical or electronic components.

Following the imagewise exposure of the material and prior to the developing, it may be advantageous to carry out a thermal treatment for a relatively short period. Here, only the exposed parts are thermally cured. The temperatures used are generally 50–150° C., preferably 80–130° C.; the thermal treatment time is usually between 0.25 and 10 minutes.

Furthermore, the photocurable composition can be used in a process for the production of printing formes or photoresists, as described, for example, in DE 4013358. Herein, prior to, simultaneously with or following the imagewise irradiation, the composition is briefly exposed to visible light having a wavelength of at least 400 nm without a mask. Following the exposure and the optional thermal treatment, the unexposed areas of the photoresist are removed using a developer in a manner known per se.

As already mentioned, the compositions according to the invention can be developed by aqueous-alkaline media. Suitable aqueous-alkaline developer solutions are, in particular, aqueous solutions of tetraalkylammonium hydroxides or of alkali metal silicates, phosphates, hydroxides and carbonates. Relatively small amounts of wetting agents and/or organic solvents can also be added to these solutions. Typical organic solvents which may be added to the developer liquids in small amounts are, for example, cyclohexanone, 2-ethoxyethanol, toluene, acetone and mixtures of such solutions.

Photocuring is of great importance for printing inks since the drying time of the binder is a crucial factor for the production rate of graphic products and should be in the order of magnitude of fractions of seconds. UV-curable inks are of importance particularly for screen, flexographic and offset printing.

As already mentioned, the mixtures according to the invention are also highly suitable for the production of printing plates. Here, mixtures of soluble linear polyamides or styrene/butadiene or styrene/isoprene rubber, polyacrylates or polymethyl methacrylates containing carboxyl groups, polyvinyl alcohols or urethane acrylates with photopolymerizable monomers, for example acryl- or methacrylamides or acrylic or methacrylic esters, and a photoinitiator, for example, are used. Films and plates made from these systems (wet or dry) are exposed via the negative (or positive) of the print original, and the uncured parts are subsequently washed out using a suitable solvent.

A further field of use for photocuring is the coating of metals, for example the coating of metal sheets and tubes, cans or bottlecaps, and the photocuring of plastic coatings, for example PVC-based floor or wall coverings. Examples of the photocuring of paper coatings are the colourless coating of labels, record sleeves or book covers.

Likewise of interest is the use of the compounds according to the invention for the curing of mouldings made from composite materials. The composite material consists of a self-supporting matrix material, e.g. a glass-fibre fabric, or else, for example, plant fibres [cf. K.-P. Mieck, T. Reussmann in Kunststoffe 85 (1995), 366–370], which is impregnated with the photocuring formulation. Mouldings made of composite materials produced using the compounds according to the invention have high mechanical stability and resistance. The compounds according to the invention can also be used as photocuring agents in moulding, impregnation or coating materials, as described, for example, in EP 7086. Such materials are, for example, fine coating resins, which are subject to strict requirements with regard to their curing activity and yellowing resistance, fibre-reinforced mouldings, for example planar or longitudinally or transversely corrugated light-diffusing panels. Processes for the production of such mouldings, for example hand lay-up techniques, fibre lay-up spraying, centrifugal or winding techniques, are described, for example, by P. H. Selden in "Glasfaserverstärkte Kunststoffe" [Glass-fibre-reinforced plastics], page 610, Springer Verlag Berlin-Heidelberg-New York 1967. Examples of articles which may be produced by this method are boats, chipboard or plywood panels coated on both sides with glass-fibre-reinforced plastic, pipes, sport articles, roof coverings, and containers etc. Further examples of moulding, impregnation and coating materials are UP resin fine coatings for mouldings containing glass fibres (GFP), e.g. corrugated sheets and paper laminates. Paper laminates may be based on urea or melamine resins. The fine coating is produced on a support (e.g. a film) prior to the production of the laminate. The photocurable compositions according to the invention can also be used for casting resins or for embedding articles, e.g. electronic components etc. Moreover, they can also be used for the lining of cavities and pipes. For curing, medium-pressure mercury lamps are used, as are customary in UV curing. However, less intensive lamps are also of particular interest, e.g. those of the type TL 40W/03 or TL40W/05. The intensity of these lamps corresponds approximately to that of sunlight. It is also possible to use direct sunlight for the curing. It is a further advantage that the composite material can be removed from the light source in a partially cured, plastic state and can be deformed. Curing is then carried out to completion.

The compositions and compounds according to the invention can also be used for the preparation of optical waveguides and optical switches, use being made of the generation of a difference in the refractive index between exposed and unexposed areas.

Also important is the use of photocurable compositions for imaging processes and for the optical production of information carriers. Here, as already described above, the coat (wet or dry) applied to the support is irradiated with UV or visible light via a photomask and the unexposed areas of the coat are removed by treatment with a solvent (=developer). The photocurable layer can also be applied to the metal by an electrodeposition technique. The exposed areas are crosslinked/polymeric and thus insoluble and remain on the support. Appropriate coloration produces visible images. If the support is a metallicized layer, then the metal can be removed from the unexposed areas by etching after exposure and developing, or can be strengthened by electroplating. Printed electronic circuits and photoresists can be produced in this way.

The photosensitivity of the compositions according to the invention generally ranges from about 200 nm to about 600 nm (UV range). Suitable radiation comprises, for example, sunlight or light from artificial light sources. Therefore, a large number of very different types of light sources can be used. Point sources and flat radiators (lamp carpets) are suitable. Examples are: carbon arc lamps, xenon arc lamps, medium-pressure, high-pressure and low-pressure mercury lamps, optionally doped with metal halides (metal halogen lamps), microwave-stimulated metal vapour lamps, excimer lamps, superactinic fluorescent tubes, fluorescent lamps, incandescent argon lamps, flashlights, photographic floodlight lamps, light-emitting diodes (LED), electron beams and X-rays. The distance between the lamp and the substrate to be exposed according to the invention can vary depending on the intended use and lamp type and intensity, e.g. between 2 cm and 150 cm. Of particular suitability are laser light sources, e.g. excimer lasers, such as krypton F lasers for exposure at 248 nm. It is also possible to use lasers in the visible region. Using this method it is possible to produce printed circuits in the electronics industry, lithographic offset printing plates or relief printing plates, and also photographic image recording materials.

The invention therefore also provides a process for the photopolymerization of nonvolatile monomeric, oligomeric or polymeric compounds having at least one ethylenically unsaturated double bond, which comprises irradiating a composition as described above with light in the range from 200 to 600 nm. The invention also provides for the use of the compounds of the formula II or III as photoinitiators for the photopolymerization of nonvolatile monomeric, oligomeric or polymeric compounds having at least one ethylenically unsaturated double bond by irradiation with light in the range from 200 to 600 nm.

The invention also provides for the use of the above-described composition or a process for the preparation of pigmented and unpigmented surface coatings, printing inks, for example screen printing inks, offset printing inks, flexographic printing inks, powder coatings, printing plates, adhesives, dental compositions, optical waveguides, optical switches, colour testing systems, composite materials, glass fibre cable coatings, screen printing stencils, resist materials, colour filters, use for the encapsulation of electrical and electronic components, for the production of magnetic recording materials, for the production of three-dimensional objects using stereolithography, for photographic reproductions, and for use as image recording material, in particular for holographic recordings, for decolouring materials, for decolouring materials for image recording materials, for image recording materials using microcapsules.

The invention likewise provides a coated substrate which has been coated on at least one surface with a composition as described above, and also a process for the photographic production of relief images in which a coated substrate is subjected to imagewise exposure and then the unexposed portions are removed with a solvent. The imagewise exposure can be carried out via a mask or by means of a laser beam. Of particular interest here is exposure by means of a laser beam.

The examples below illustrate the invention in more detail, although it is not intended that the invention be limited to the examples. Unless stated otherwise, parts and percentages are based, as elsewhere in the description and in the claims, on the weight. Wherever reference is made to alkyl or alkoxy radicals having more than three carbon atoms without stating the isomer, then the n-isomers are always intended.

EXAMPLE 1

2,4,6-Trimethylbenzoylisobutylphenylphosphine Oxide

At −20° C., 40 ml (0.064 mol) of butyllithium 1.6 M are slowly added dropwise to 9.5 g (0.058 mol) of isobutylphenylphosphine in 100 ml of tetrahydrofuran (THF). At the same temperature, 11.7 g (0.064 mol) of 2,4,6-trimethylbenzoyl chloride are then added dropwise. After the mixture has been allowed to warm to room temperature, the orange reaction suspension is concentrated using a rotary evaporator (Rotavap). The residue is taken up in 150 ml of toluene, and is treated with 13.1 g (0.116 mol) of hydrogen peroxide 30%. After the mixture has been stirred for 2 hours between 20–30° C., the reaction is complete. The reaction emulsion is poured onto water and washed with aqueous saturated sodium hydrogencarbonate solution, then dried over magnesium sulfate and filtered. The filtrate is concentrated using the Rotavap. The residue is purified over silica gel and dried under a high vacuum. 11.8 g of the title compound are obtained as a yellow viscous oil.

$^{31}$P-NMR: δ28.94 ppm $^{1}$H-NMR, measured in CDCl$_3$, δ [ppm]: 7.37–7.79 (m), 6.70 (s), 1.98–2.23 (m), 1.93 (s) and 0.87–1.02 (q)

EXAMPLE 2

2,4,6-Trimethylbenzoyl-(2,4,4-trimethylpentyl)phenylphosphine Oxide

The compound is prepared analogously to the method described in Example 1, but using 2,4,4-trimethylpentylphenylphosphine instead of isobutylphenylphosphine.

$^{31}$P-NMR: δ28.86 ppm $^{1}$H-NMR, measured in CDCl$_3$, δ [ppm]: 7.37–7.80 (m), 6.69 (s), 2.01–2.45 (m), 1.93–1.94 (d), 0.91–1.43 (m) and 0.71–0.80 (d)

EXAMPLE 3

Lithium (2,4,6-trimethylbenzoyl)phenylphosphine

Under argon and with the exclusion of moisture, 14.0 g of lithium (2.0 mol) are introduced into 250 ml of tetrahydrofuran at room temperature. Following the addition of 1.25 g of naphthalene, 44.8 g (0.25 mol) of dichlorophenylphosphine are added dropwise with stirring at 20–25° C. and, after stirring for 4 h, the black solution is filtered into a three-necked round flask through a frit (G2 porosity) with the exclusion of moisture and under argon as a protective gas. 47.2 g (0.258 mol) of 2,4,6-trimethylbenzoyl chloride are added dropwise at room temperature over the course of 30 minutes with stirring and cooling. Stirring for 2 hours gives the title compound as a red solution in tetrahydrofuran.

$^{31}$P-NMR δ98.4 ppm.

EXAMPLES 4–5

The compounds of Examples 4 and 5 are obtained analogously to the method described in Example 3 using the corresponding starting materials. The compounds and their spectroscopic data are given in Table 1 below.

EXAMPLE 6

2,4,6-Trimethylbenzoylphenylphosphine 35 ml (0.022 mol) of the solution described in Example 3 are added dropwise to a mixture of toluene/water and acetic acid. The organic phase is separated off, dried over magnesium sulfate and concentrated using the Rotavap under argon. A sample is distilled at 200° C. and 0.02 mbar by means of Kugelrohr oven distillation. The title compound is obtained as a yellow viscous oil.

$^{31}$P-NMR δ: −1.0 ppm $^{1}$H-NMR, measured in C$_6$D$_6$, [ppm]: 2.05 (s), 2.14 (s), 4.82(s)+5.61 (s) (1H on the P) 6.55 (s), 7.04 (m), 7.40 (m).

EXAMPLE 7

2,4,6-Trimethylbenzoyl-(2,6-dimethoxybenzoyl)phenylphosphine Oxide 4.4 g (0.022 mol) of 2,6-dimethoxybenzoyl chloride, dissolved in 20 ml of tetrahydrofuran, are added dropwise over the course of 20 min to 35 ml (0.022 mol) of the solution obtained according to Example 3 at 20–30° C. After the mixture has been afterstirred for 2 hours, the orange reaction suspension is concentrated using the Rotavap. The residue is taken up in 50 ml of toluene, and is treated with 5.7 g (0.05 mol) of hydrogen peroxide 30%. After the mixture has been stirred for 2 hours between 20–30° C., the reaction is complete. The reaction emulsion is poured onto water and washed with aqueous saturated sodium hydrogencarbonate solution, then dried over magnesium sulfate and filtered. The filtrate is concentrated using the Rotavap. The residue is purified over silica gel and dried under a high vacuum. 1.5 g of the title compound are obtained as a yellow solid with a melting point of 126–127° C.

$^{31}$ P-NMR δ6.89 ppm $^{1}$H-NMR, measured in CDCl$_3$, [ppm]: 7.33–8.05 (m), 6.82 (s), 6.50–6.53 (d), 3.60 (s), 2.27 (s) and 2.18 (s)

EXAMPLES 8–49

The compounds of Examples 8 to 49 are obtained analogously to the method described in Example 7 using the corresponding starting materials. The compounds and physical data are given in Table 2.

TABLE 1

| Example | Compound | δ $^{31}$P-NMR Starting material |
|---|---|---|
| 4 | 2,6-dimethoxybenzoyl-phenylphosphine lithium structure | −45.232 ppm 2,6-Dimethoxybenzoyl chloride |
| 5 | 2,6-dichlorobenzoyl-phenylphosphine lithium structure | 52.876 ppm 2,6-Dichlorobenzoyl chloride |

TABLE 2

| Example | Compound | Starting materials | δ NMR [ppm]*<br>Melting point |
|---|---|---|---|
| 8 | (structure: phenyl phosphine oxide with two 2,6-dimethoxyphenyl and 2,6-dichlorophenyl groups) | Lithium (2,6-dimethoxybenzoyl)phenylphosphine; 2,6-dichlorobenzoyl chloride | $^{31}$P-NMR 32.08; $^1$H-NMR 7.2(s), 7.23–8.05 (m), 6.46–6.49 (d) and 3.60 (s); m.p. 168–169° C. |
| 9 | (structure: phenyl phosphine oxide with 2,4,6-trimethylphenyl and 2,6-dichlorophenyl groups) | Lithium (2,6-dichlorobenzoyl)phenylphosphine; 2,4,6-trimethylbenzoyl chloride | $^{31}$P-NMR 5.78; $^1$H-NMR 7.33–7.94 (m), 7.13–7.16 (d), 6.68 (s), 2.11 (s) and 2.06 (s); m.p. 146–148° C. |
| 10 | (structure: phenyl phosphine oxide with 2,4,6-trimethylphenyl and tert-butyl groups) | Lithium (2,4,6-trimethylbenzoyl)phenylphosphine; pivaloyl chloride | $^{31}$P-NMR 32.552; $^1$H-NMR 7.43–7.92 (m), 6.78 (s), 2.236 (s), 2.18 (s) and 1.3 (s); — |
| 11 | (structure: phenyl phosphine oxide with 2,4,6-trimethylphenyl and anthracen-9-yl groups) | Lithium (2,4,6-trimethylbenzoyl)phenylphosphine; anthracene-9-carbonyl chloride | $^{31}$P-NMR 9.85; $^1$H-NMR 8.76 (s), 7.46–8.30 (m), 7.06 (s), 2.52 (s) and 2.37 (s); m.p. 181–182° C. |

TABLE 2-continued

| Example | Compound | Starting materials | δ NMR [ppm]* Melting point |
|---|---|---|---|
| 12 | (diphenylmethyl mesitoyl phenylphosphinate structure) | Lithium (2,4,6-trimethylbenzoyl)phenylphosphine; diphenylacetyl chloride | $^{31}$P-NMR 12.17 $^{1}$H-NMR 6.98–7.65 (m), 6.74 (s), 4.92 (s), 2.25 (s), and 1.94 (s) m.p. 148–149° C. |
| 13 | (1-naphthoyl mesitoyl phenylphosphinate structure) | Lithium (2,4,6-trimethylbenzoyl)phenylphosphine; 1-naphthoyl chloride | $^{31}$P NMR 13.04 $^{1}$H NMR 9.11–9.09 (d); 8.88–8.86 (d); 8.16–8.11 (m); 7.91–7.89 (m); 7.68–7.53 (m); 6.86 (s); 2.28 (s); 2.14 (s) — |
| 14 | (benzyl mesitoyl phenylphosphinate carbonate structure) | Lithium (2,4,6-trimethylbenzoyl)phenylphosphine; benzyl chloroformate | $^{31}$P NMR 8.66 $^{1}$H NMR 7.96–7.91 (m); 7.57–7.53 (m); 7.46–7.42 (m); 7.27 (s); 6.72 (s); 5.34–5.20 (q); 2.17 (s); 1.98 (s) — |
| 15 | (methyl mesitoyl phenylphosphinate carbonate structure) | Lithium (2,4,6-trimethylbenzoyl)phenylphosphine; methyl chloroformate | $^{31}$P NMR 8.45 $^{1}$H NMR 7.97–7.93 (m); 7.59–7.55 (m); 7.49–7.44 (m); 6.76 (s); 3.84 (s); 2.20 (s); 2.07 (s) |

TABLE 2-continued

| Example | Compound | Starting materials | δ NMR [ppm]* Melting point |
|---|---|---|---|
| 16 | | Lithium (2,4,6-trimethylbenzoyl) phenylphosphine; ethyl chloroformate | ³¹P NMR 8.5 ¹H NMR 1.35 (t), 2.15 (s), 2.27 (s) 4.41 (m), 6.84 (s), 7.53 (m.), 7.64 (t), 8.03 (dd) |
| 17 | | Lithium (2,4,6-trimethylbenzoyl) phenylphosphine; 2,4,6-trimethyl 1,5-dibenzoyl chloride | ³¹P NMR 8.30 ¹H NMR 7.18–7.80 (m), 7.31–7.47 (m), 6.71 (s), 2.11 (s), 2.05 (s) |
| 18 | | Lithium (2,4,6-trimethylbenzoyl) phenylphosphine; phthaloyl dichloride | ³¹P-NMR 13.12; ¹H-NMR 7.0–8.3 (m), 6.5 (s), 2.1 (s) and 1.6 (s); m.p. 202–203° C. |
| 19 | | Lithium (2,4,6-trimethyl-benzoyl) phenylphosphine; 3-(2-chlorphenyl-5-methylisoxazol-4-carbonyl chloride | ³¹P-NMR 9.16; ¹H-NMR 7.19–7.71 (m), 6.71 (s), 2.73 (s), 2.18 (s), 2.05 (s); — |

TABLE 2-continued

| Example | Compound | Starting materials | δ NMR [ppm]* Melting point |
|---|---|---|---|
| 20 | (structure) | Lithium (2,4,6-trimethyl-benzoyl)phenylphosphine; 2,4,6-triisopropyl-benzoyl chloride | ³¹P-NMR 8.62; ¹H-NMR 7.34–7.86 (m), 6.86 (s), 6.75 (s), 2.70–2.96 (m), 2.21 (s), 2.13 (s), 1.12–1.14 (d), 0.96–0.98 (d), 0.83–0.85 (d); — |
| 21 | (structure) | Lithium (2,4,6-trimethyl-benzoyl)phenylphosphine; 2-ethoxy-1-naphthoyl chloride | ³¹P-NMR 9.65; ¹H-NMR 7.71–7.90 (m), 7.28–7.48 (m), 6.99–7.03 (d), 6.72 (s), 3.94–4.06 (m), 3.62–3.72 (m), 2.19 (s), 2.06 (s), 1.07–1.12 (t); m.p. 138–139° C. |
| 22 | (structure) | Lithium (2,4,6-trimethyl-benzoyl)phenylphosphine; 2-acetoxy-isobutyryl chloride | ³¹P-NMR 8.88; ¹H-NMR 7.24–7.86 (m), 6.70 (s), 2.17 (s), 2.09 (s), 1.96 (s), 1.51 (s), 1.38 (s); — |
| 23 | (structure) | Lithium (2,4,6-trimethyl-benzoyl)phenylphosphine; 2-(trifluoromethyl)-benzoyl chloride | ³¹P-NMR 11.63; ¹H-NMR 7.04–8.27 (m), 6.74 (s), 2.19 (s), 2.04 (s); — |

TABLE 2-continued

| Example | Compound | Starting materials | δ NMR [ppm]*<br>Melting point |
|---|---|---|---|
| 24 | (structure with 2-iodophenyl group) | Lithium (2,4,6-tri-methyl-benzo-yl)phenylphos-phine; 2-iodbenzoyl chloride | ³¹P-NMR 11.53; ¹H-NMR 7.10–8.27 (m), 6.71 (s), 2.19 (s), 2.03 (s); — |
| 25 | (structure with 1-adamantyl group) | Lithium (2,4,6-tri-methyl-benzo-yl)phenylphos-phine; 1-adamantan-carbonyl chloride | ³¹P-NMR 10.66; ¹H-NMR 7.85–7.91 (m), 7.42–7.58 (m), 6.79 (s), 2.26 (s), 2.19 (s), 1.72–2.06 (m); — |
| 26 | (structure with C(CH₃)₂CH₂Cl group) | Lithium (2,4,6-tri-methyl-benzoyl) phenylphosphine; 3-chlorpivaloyl-chloride | —; ¹H-NMR 7.97–8.03 (m), 7.52–7.70 (m), 6.90 (s), 4.22–4.26 (d), 3.89–3.93 (d), 2.36 (s), 2.29 (s), 1.50 (s), 1.43 (s); — |
| 27 | (structure with N(C₂H₅)₂ group) | Lithium (2,4,6-tri-methyl-benzo-yl)phenylphos-phine; diethylcarbamyl-chloride | ³¹P-NMR 8.46; ¹H-NMR 7.94–8.00 (m), 7.40–7.58 (m), 6.78 (s), 3.74–4.03 (m), 3.25–3.49 (m), 2.24 (s), 1.08–1.18 (m); m.p. 109–110° C. |

TABLE 2-continued

| Example | Compound | Starting materials | δ NMR [ppm]* Melting point |
|---|---|---|---|
| 28 | (structure) | Lithium (2,4,6-tri-methyl-benzo-yl)phenylphos-phine; diphenylcarbamyl chloride | ³¹P-NMR 10.53; ¹H-NMR 7.69–7.75 (m), 7.10–7.49 (m), 6.78 (s), 2.24 (s), 2.20 (s); m.p. 153–154° C. |
| 29 | (structure) | Lithium (2,4,6-tri-methyl-benzo-yl)phenylphos-phine; 2-(benzoyl-oxy-methyl)-benzoyl chloride | ³¹P-NMR 13.48; ¹H-NMR 8.73–8.75 (d), 7.91–8.04 (m), 7.34–7.57 (m), 6.73 (s), 5.59 (s), 2.18 (s), 2.02 (s); — |
| 30 | (structure) | Lithium (2,4,6-tri-methyl-benzo-yl)phenylphos-phine; 2-methylbenzoyl chloride | ³¹P-NMR 13.57; ¹H-NMR 8.59–8.62 (d), 8.02–8.08 (m), 7.27–7.65 (m), 6.83 (s), 2.54 (s), 2.28 (s), 2.10 (s); — |

TABLE 2-continued

| Example | Compound | Starting materials | δ NMR [ppm]* Melting point |
|---|---|---|---|
| 31 | (structure) | Lithium (2,4,6-trimethyl-benzoyl)phenylphosphine; 2-fluor-6-(trifluormethyl)-benzoyl chloride | ³¹P-NMR 5.96; ¹H-NMR 7.97–8.31 (m), 7.09–7.88 (m), 6.83 (s), 2.27 (s), 2.18 (s); m.p. 109–110° C. |
| 32 | (structure) | Lithium (2,4,6-trimethyl-benzoyl)phenylphosphine; 2-(difluormethylthio)-benzoyl chloride | ³¹P-NMR 10.89; ¹H-NMR 8.20–8.23 (d), 7.35–8.17 (m), 6.74 (s), 2.19 (s), 2.08 (s), 2.04 (s); — |
| 33 | (structure) | Lithium (2,4,6-trimethyl-benzoyl)phenylphosphine; 9-fluorenylmethyl chlorformiate | ³¹P-NMR 8.37; ¹H-NMR 7.11–7.94 (m), 6.76 (s), 4.55–4.57 (d), 4.16–4.21 (t), 2.20 (s), 2.05 (s); — |
| 34 | (structure) | Lithium (2,4,6-trimethyl-benzoyl)phenylphosphine; phenyl chloroformiate | ³¹P-NMR 9.52; ¹H-NMR 8.00–8.04 (m), 7.07–7.81 (m), 6.75 (s), 2.20 (s), 2.12 (s); — |

TABLE 2-continued

| Example | Compound | Starting materials | δ NMR [ppm]* Melting point |
|---|---|---|---|
| 35 | [structure with isobutyl group: H₂C-O-C(=O)-P(=O)(phenyl)-C(=O)-mesityl, with CH(CH₃)CH₃] | Lithium (2,4,6-tri-methyl-benzoyl)phenylphosphine; isobutylchloroformiate | ³¹P-NMR 8.99; ¹H-NMR 7.92–7.97 (m), 7.44–7.56 (m), 6.75 (s), 4.02–4.10 (m), 2.19 (s), 2.07 (s), 1.94–1.99 (m), 0.84–0.93 (m); — |
| 36 | [structure with 2-ethylhexyl group: H₂C-O-C(=O)-P(=O)(phenyl)-C(=O)-mesityl, with CH(C₄H₉)(C₂H₅)] | Lithium (2,4,6-tri-methyl-benzoyl)phenylphosphine; 2-ethylhexyl chloroformiate | ³¹P-NMR 8.94; ¹H-NMR 7.91–7.96 (m), 7.42–7.56 (m), 6.75 (s), 4.14–4.24 (s), 2.18 (s), 2.09 (s), 1.56–1.60 (m), 1.18–1.30 (m), 0.77–0.82 (m); — |
| 37 | [structure with 2-bromoethyl group: H₂C-O-C(=O)-P(=O)(phenyl)-C(=O)-mesityl, with CH₂Br] | Lithium (2,4,6-tri-methyl-benzoyl)phenylphosphine; 2-bromoethyl chloroformiate | ³¹P-NMR 8.99; ¹H-NMR 7.93–7.98 (m), 7.46–7.59 (m), 6.77 (s), 4.50–4.61 (m), 3.43–3.52 (m), 2.20 (s), 2.09 (s); m.p. 73–75° C. |
| 38 | [structure with allyl group: H₂C-O-C(=O)-P(=O)(phenyl)-C(=O)-mesityl, with CH=CH₂] | Lithium (2,4,6-tri-methyl-benzoyl)phenylphosphine; allyl chloroformiate | ³¹P-NMR 8.56; ¹H-NMR 7.93–7.98 (m), 7.44–7.59 (m), 6.76 (s), 5.82–5.90 (m), 5.28 (d), 5.25 (d), 4.69–4.79 (m), 2.19 (s), 2.07 (s); — |

TABLE 2-continued

| Example | Compound | Starting materials | δ NMR [ppm]* Melting point |
|---|---|---|---|
| 39 | (structure: phenyl-P(=O)(C(=O)OC₄H₉) with 2,4,6-trimethylphenyl-C(=O)) | Lithium (2,4,6-trimethyl-benzoyl)phenylphosphine; butyl chloroformiate | ³¹P-NMR 8.81; ¹H-NMR 7.92–7.97 (m), 7.44–7.56 (m), 6.76 (s), 4.21–4.33 (m), 2.19 (s), 2.07 (s), 1.62 (quint.), 1.31 (sext.), 0.85 (t); — |
| 40 | (structure: phenyl-P(=O)(C(=O)OC₈H₁₇) with 2,4,6-trimethylphenyl-C(=O)) | Lithium (2,4,6-trimethyl-benzoyl)phenylphosphine; octyl chloroformiate | ³¹P-NMR 8.75; ¹H-NMR 7.92–7.97 (m), 7.43–7.57 (m), 6.76 (s), 4.22–4.32 (m), 2.19 (s), 2.07 (s), 1.63 (quint.), 1.18–1.28 (m), 0.80 (t); — |
| 41 | (structure: phenyl-P(=O)(C(=O)O-C(CH₃)₂-CCl₃) with 2,4,6-trimethylphenyl-C(=O)) | Lithium (2,4,6-trimethyl-benzoyl)phenylphosphine; 2,2,2-trichloro-1,1-dimethyl chloroformiate | ³¹P-NMR 9.95; ¹H-NMR 7.93–7.98 (m), 7.43–7.58 (m), 6.75 (s), 2.19 (s), 2.07 (s), 1.96 (s), 1.93 (s); m.p. 88–92° C. |
| 42 | (structure: phenyl-P(=O)(C(=O)O-CH₂-CCl₃) with 2,4,6-trimethylphenyl-C(=O)) | Lithium (2,4,6-trimethyl-benzoyl)phenylphosphine; 2,2,2-trichloroethyl chloroformiate | ³¹P-NMR 9.51; ¹H-NMR 7.95–8.00 (m), 7.46–7.61 (m), 6.77 (s), 4.88 (d), 4.83 (d), 2.20 (s), 2.09 (s); — |

TABLE 2-continued

| Example | Compound | Starting materials | δ NMR [ppm]* Melting point |
|---|---|---|---|
| 43 | (mesityl-P(=O)(Ph)-C(=O)-O-cholesteryl structure) | Lithium (2,4,6-tri-methyl-benzo-yl)phenylphos-phine; cholesterole chloroformiate | $^{31}$P-NMR 7.48; $^{1}$H-NMR 7.92–7.98 (m), 7.43–7.58 (m), 6.76 (s), 5.32–5.34 (m), 4.77–4.84 (m), 2.32–2.51 (m), 2.20 (s), 2.08 (s), 0.96–1.96 (m), 0.94 (s), 0.84 (d), 0.79 (d), 0.60 (s); m.p. 58–62° C. |
| 44 | (mesityl-P(=O)(Ph)-C(=O)-O-CH(CH₃)-CH₂Cl structure) | Lithium (2,4,6-tri-methyl-benzo-yl)phenylphos-phine; 1-chloro-2-methyl-propyl chloroformiate | $^{31}$P-NMR 8.82; $^{1}$H-NMR 7.91–7.99 (m), 7.45–7.61 (m), 6.77 (s), 6.36 (d), 2.07–2.25 (m), 2.18 (s), 2.10 (s), 0.91–1.00 (m); — |
| 45 | (mesityl-P(=O)(Ph)-C(=O)-O-p-tolyl structure) | Lithium (2,4,6-tri-methyl-benzo-yl)phenylphos-phine; p-tolyl chlorofor-miate | $^{31}$P-NMR 9.68; $^{1}$H-NMR 7.99–8.04 (m), 7.47–7.58 (m), 7.10 (d), 6.95 (d), 6.74 (s), 2.26 (s), 2.21 (s), 2.12 (s); — |

TABLE 2-continued

| Example | Compound | Starting materials | δ NMR [ppm]*<br>Melting point |
|---|---|---|---|
| 46 | (structure) | Lithium (2,4,6-trimethyl-benzoyl)phenylphosphine; isopropyl chloroformiate | $^{31}$P-NMR 8.49; $^1$H-NMR 7.92–7.97 9m), 7.43–7.57 (m), 6.76 (s), 5.22 (sept.), 2.22 (s), 2.07 (s), 1.26 (d); — |
| 47 | (structure) | Lithium (2,4,6-trimethyl-benzoyl)phenylphosphine; propargyl chloroformiate | $^{31}$P-NMR 8.53; $^1$H-NMR 7.93–7.98 (m), 7.42–7.59 (m), 6.76 (s), 4.75–4.87 (m), 2.47 (t), 2.19 (s), 2.09 (s); — |
| 48 | (structure) | Lithium (2,4,6-trimethyl-benzoyl)phenylphosphine; neopentyl chloroformiate | $^{31}$P-NMR 9.08; $^1$H-NMR 7.92–7.97 (m), 7.43–7.58 (m), 6.76 (s), 3.97 (s), 2.19 (s), 2.09 (s), 0.88 (s); — |
| 49 | (structure) | Lithium (2,4,6-trimethyl-benzoyl)phenylphosphine; (−)-menthyl chloroformiate | $^{31}$P-NMR 8.45; $^1$H-NMR 7.91–7.96 (m), 7.44–7.56 (m), 6.76 (s), 4.87–4.96 (m), 2.19 (s), 2.08 (s), 0.98–1.97 (m), 0.77–0.86 (m), 0.64–0.68 (m); — |

*$^1$H-NMR measured in CDCl$_3$

EXAMPLE 50

2,4,6-Trimethylbenzoylbenzylphenylphosphine Oxide

At 20–30° C., 8.5 g (0.05 mol) of benzyl bromide are added dropwise over the course of 20 min to 35 ml (0.022 mol) of the solution obtained according to Example 3. After the mixture has been afterstirred for 2 hours, the orange reaction suspension is concentrated using the Rotavap. The residue is taken up in 50 ml of toluene and, is treated with 5.7 g (0.05 mol) of hydrogen peroxide 30%. After the mixture has been stirred for 2 hours between 20–30° C., the reaction is complete. The reaction emulsion is poured onto water and washed with aqueous saturated sodium hydrogencarbonate solution, then dried over magnesium sulfate and filtered. The filtrate is concentrated using the Rotavap. The residue is purified over silica gel and dried under a high vacuum. 1.4 g of the title compound are obtained as a yellow solid with a melting point of 113–114° C.

$^{31}$P-NMR δ26.26 ppm $^{1}$H-NMR, measured in CDCl$_3$, [ppm]: 7.16–7.83 (m), 6.63(s), 3.43–3.88 (m), 2.13 (s) and 1.66 (s)

EXAMPLES 51–60

The compounds of Examples 51–60 are prepared analogously to the method described in Example 50 using the corresponding starting materials. The compounds and their physical data are given in Table 3.

TABLE 3

| Example | Compound | Starting materials | δ NMR [ppm]* |
|---|---|---|---|
| 51 | (structure) | Lithium (2,4,6-trimethylbenzoyl)-phenylphosphine; allyl bromide | $^{31}$P-NMR 26.60; $^{1}$H-NMR 7.36–7.78 (m), 6.69 (s), 5.74–5.78 (m), 5.12–5.23 (m) 3.0–3.30 (m), 2.18 (s) and 1.97 (s) |
| 52 | (structure) | Lithium (2,4,6-trimethylbenzoyl)-phenylphosphine; 2-ethylhexyl bromide | $^{31}$P-NMR 29.17; $^{1}$H-NMR 7.36–7.79 (m), 6.70 (s), 2.15–2.25 (m), 2.15 (s), 1.94 (s), 1.36–1.38 (m), 1.06–1.19 (m) and 0.68–0.80 (m) |
| 53 | (structure) | Lithium (2,4,6-trimethylbenzoyl)-phenylphosphine; n-propyl bromide | $^{31}$P-NMR 30.35; $^{1}$H-NMR 7.35–7.77 (m), 6.69 (s), 2.15–2.31 (m), 2.13 (s), 1.92 (s) 1.59–1.63 (m) and 0.94–0.97 (t) |
| 54 | (structure) | Lithium (2,4,6-trimethylbenzoyl)-phenylphosphine; n-butyl bromide | $^{31}$P-NMR 30.35; $^{1}$H-NMR 7.38–7.77 (m), 6.69 (s), 2.15–2.34 (m), 2.13 (s), 1.92 (s) 1.32–1.57 (m) and 0.80–0.84 (t) |
| 55 | (structure) | Lithium (2,4,6-trimethylbenzoyl)-phenylphosphine; tetrabromopentaerythritol | $^{31}$P-NMR 22.60; $^{1}$H-NMR 7.40–7.83 (m), 6.72 (s), 3.52–3.77 (q), 2.61–2.92 (m), 2.16 (s) and 1.94 (s) |

TABLE 3-continued

| Example | Compound | Starting materials | δ NMR [ppm]* |
|---|---|---|---|
| 56 | (2,4,6-trimethylbenzoyl)(phenyl)P(=O)–(CH₂)₂–C(=O)OCH₃ | Lithium (2,4,6-trimethylbenzoyl)-phenylphosphine; methyl 3-bromopropionate | $^{31}$P-NMR 27.96; $^{1}$H-NMR 7.42–7.78 (m), 6.72 (s), 3.60 (s), 2.50–2.65 (m), 2.19 (s) and 1.95 (s) |
| 57 | (2,4,6-trimethylbenzoyl)(phenyl)P(=O)–CH(CH₃)–C(=O)OC₈H₁₇ | Lithium (2,4,6-trimethylbenzoyl)-phenylphosphine; octyl 2-bromopropionate | $^{31}$P-NMR 18.63; $^{1}$H-NMR 7.20–7.78 (m), 6.72 (s), 3.96–4.03 (m), 3.48–3.54 (m), 2.17 (s), 2.06 (s), 1.02–1.58 (m) and 0.54–0.77 (m) |
| 58 | (2,4,6-trimethylbenzoyl)(phenyl)P(=O)–CH₂–C(=O)OCH₃ | Lithium (2,4,6-trimethylbenzoyl)-phenylphosphine; methylbromoacetate | $^{31}$P-NMR 22.29; $^{1}$H-NMR 7.32–7.74 (m), 6.65 (s), 3.18–3.74 (m), 2.09 (s) and 1.93 (s) |
| 59 | (2,4,6-trimethylbenzoyl)(phenyl)P(=O)–(CH₂)₃–Si(CH₃)₂–O–Si(CH₃)₂–(CH₂)₃–Cl | Lithium (2,4,6-trimethylbenzoyl)-phenylphosphine; 1,3-bis(chloropropyl)tetramethyldisiloxane | $^{31}$P-NMR 29.36; $^{1}$H-NMR 7.45–7.84 (m), 6.77 (s), 3.44–3.49 (t), 2.24–2.44 (m), 2.24 (s), 2.0 (s), 1.69–1.77 (m), 0.53–0.69 (m) and 0.0 (s) |
| 60 | (2,4,6-trimethylbenzoyl)(phenyl)P(=O)–CH₂–Si(CH₃)₂–O–Si(CH₃)₃ | Lithium (2,4,6-trimethylbenzoyl)-phenylphosphine; chloromethylpentamethyldisiloxane | $^{31}$P-NMR 28.32; $^{1}$H-NMR 7.47–7.86 (m), 6.78 (s), 2.25 (s), 2.01 (s), 1.69–1.98 (m), 0.22 (s), 0.05 (s) and 0.0 (s) |

EXAMPLE 61

2,4,6-Trimethylbenzoyl-(5-trifluoromethyl)pyrid-2-ylphenylphosphine Oxide

At 20–30° C., 4.0 g (0.022 mol) of 2-chloro-5-trifluoromethylpyridine, dissolved in 20 ml of tetrahydrofuran, are added dropwise over the course of 20 min to 35 ml (0.022 mol) of the solution obtained according to Example 3. After the mixture has been afterstirred for 2 hours, the orange reaction suspension is concentrated using the Rotavap. The residue is taken up in 50 ml of toluene, and is treated with 5.7 g (0.05 mol) of hydrogen peroxide 30%. After the mixture has been stirred for 2 hours between 20–30° C., the reaction is complete. The reaction emulsion is poured onto water and washed with aqueous saturated sodium hydrogencarbonate solution, then dried over magnesium sulfate and filtered. The filtrate is concentrated using the Rotavap. The residue is purified over silica gel and dried under a high vacuum. 1.5 g of the title compound are obtained as a yellow resin.

$^{31}$P-NMR: δ10.42 ppm $^{1}$H-NMR, measured in CDCl₃, δ [ppm]: 8.98 (s), 7.37–8.14 (m), 6.69 (s), 2.15 (s) and 2.01 (s)

EXAMPLES 62–63

The compounds of Examples 62 and 63 are obtained analogously to the method described in Example 61 using the corresponding starting materials. The compounds and their physical data are given in Table 4.

TABLE 4

| Example | Compound | Starting materials | δ NMR [ppm]* Melting point |
|---|---|---|---|
| 62 | (structure: 2,4,6-trimethylbenzoyl-phenylphosphinoyl group attached to a dichlorothioxanthone) | Lithium (2,4,6-trimethylbenzoyl)-phenylphosphine; 2,3,5-trichloro-thioxanthone | $^{31}$P-NMR 29.03; $^1$H-NMR 7.33–8.39 (m), 6.69 (s), 2.20 (s) and 2.15 (s); m.p. 172–173° C. |
| 63 | (structure: 2,4,6-trimethylbenzoyl-phenylphosphinoyl group attached to a 4,6-bis(2,4-dimethylphenyl)-1,3,5-triazine) | Lithium (2,4,6-trimethylbenzoyl)-phenylphosphine; 2-chloro-4,6-bis-(2,4-dimethyl-phenyl)-[1,3,5]-triazine | $^{31}$P NMR 14.65 $^1$H NMR 8.11–8.17 (m), 7.51–7.66 (m), 7.10–7.14 (m), 6.84 (s), 2.56 (s), 2.38 (s), 2.28 (s), 2.15 (s) m.p. 153–154° C. |

EXAMPLE 64

Phenyl-(2,4,6-trimethylbenzoyl)thiophosphinic S-(4-methylphenyl)ester

At 20–30° C., 4.8 g (0.025 mol) of 4-toluenesulfonyl chloride, dissolved in 20 ml of toluene, are added dropwise over the course of 20 min to 35 ml (0.025 mol) of the solution described in Example 3. The yellow-brown reaction suspension is heated to 40° C. and, after the mixture has been afterstirred for 2 hours, it is concentrated using the Rotavap. The residue is taken up in 50 ml of toluene and washed with water and aqueous saturated sodium hydrogencarbonate solution, then dried over magnesium sulfate and filtered. The filtrate is concentrated using the Rotavap. The residue is purified over silica gel and dried under a high vacuum. The title compound is obtained as a yellow resin.

$^{31}$P NMR: 34.79

$^1$H NMR: 7.80–7.86 (m), 7.31–7.48 (m), 6.96–6.99 (d), 6.67 (s), 2.21 (s), 2.13 (s), 1.84 (s)

EXAMPLE 65

A UV-curable white coat is prepared by mixing
67.5 parts of polyester acrylate oligomer ($^{RTM}$EBECRYL 830, UCB, Belgium)
5.0 parts of hexanediol diacrylate
2.5 parts of trimethylolpropane triacrylate
25.0 parts of rutile titanium dioxide ($^{RTM}$R-TC2, Tioxide, France)
2.0 parts of the photoinitiator from Example 7.

The coating is applied to a coil-coated aluminium sheet using a 100 μm slotted doctor knife and then cured. Curing is carried out by conveying the sample twice, on a conveyor belt which is moving at a speed of 10 m/min, beneath an 80 W/cm medium-pressure mercury lamp (Hanovia, USA). The pendulum hardness is then determined in accordance with König (DIN53157) in [s]. The pendulum hardness is a measure of the through-curing of the composition. The higher the values, the more effective the curing which has been carried out. A value of 161 s is achieved. After the first pendulum hardness determination, the sample is after-exposed under low-pressure mercury lamps of the type TL 40W/03 (Philips; Emission maximum of 430 nm), and after 15 minutes the pendulum hardness is determined again. Following after-exposure, a value of 181 s is obtained.

EXAMPLE 66

Two parts of the compound according to Example 65 are incorporated instead of the photoinitiator compound from Example 7 into a photocurable formulation described as in Example 58, and the formulation is applied to a coil-coated aluminium sheet as described in Example 65. Curing is carried out by conveying the sample four times, on a conveyor belt which is moving at a speed of 10 m/min, beneath an 80 W/cm medium-pressure mercury lamp (Hanovia, USA). The yellowness index of the sample cured in this way is determined in accordance with ASTMD 1925-88. A value of 2.0 is obtained.

What is claimed is:

1. A photocurable composition comprising
    (a) at least one ethylenically unsaturated photopolymerizable compound and
    (b) at least one compound of the formula II or III as photoinitiator,

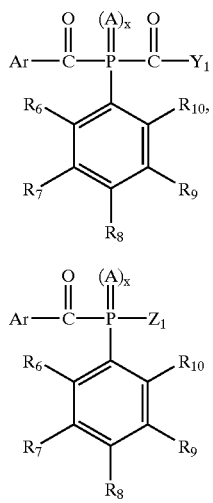

(II)

(III)

wherein in each formula (II) and (III)
Ar is a group

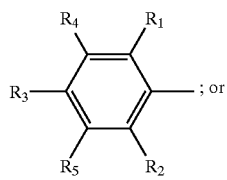; or

Ar is cyclopentyl, cyclohexyl, naphthyl, biphenylyl, anthracyl or an O—, S— or N-containing 5- or 6-membered heterocyclic ring, where the radicals cyclopentyl, cyclohexyl, naphthyl, biphenylyl, anthracyl or O—, S— or N-containing 5- or 6-membered heterocyclic ring are unsubstituted or substituted by halogen, $C_1$–$C_4$alkyl and/or $C_1$–$C_4$alkoxy;

$R_1$ and $R_2$ independently of one another are $C_1$–$C_{20}$alkyl, $OR_{11}$, $CF_3$ or halogen; and $R_3$, $R_4$ and $R_5$ independently of one another are hydrogen, $C_1$–$C_{20}$alkyl, $OR_{11}$ or halogen; or in each case two of the radicals $R_1$, $R_2$, $R_3$, $R_4$ and/or $R_5$ together form $C_2$–$C_{20}$alkylene, which optionally is interrupted by O, S or $NR_{14}$; and in formula (II)

A is O or S;

x is 1;

$R_6$, $R_7$, $R_8$, $R_9$ and $R_{10}$ independently of one another are hydrogen, $C_1$–$C_{20}$alkyl; $C_2$–$C_{20}$alkyl, which is interrupted once or more than once by nonconsecutive O atoms and which is unsubstituted or substituted by OH and/or SH; or $R_6$, $R_7$, $R_8$, $R_9$ and $R_{10}$ are $OR_{11}$, phenyl or halogen;

$R_{11}$ is hydrogen, $C_1$–$C_{20}$alkyl, $C_2$–$C_{20}$alkenyl, $C_3$–$C_8$cycloalkyl, phenyl, benzyl or $C_2$–$C_{20}$alkyl which is interrupted once or more than once by nonconsecutive O atoms and which is unsubstituted or substituted by OH and/or SH;

$Y_1$ is $C_1$–$C_{18}$alkyl which is unsubstituted or substituted by one or more phenyl; $C_1$–$C_{18}$-halogenoalkyl; $C_2$–$C_{18}$alkyl which is interrupted once or more than once by O or S and which is unsubstituted or substituted by OH and/or SH; unsubstituted $C_3$–$C_{18}$cycloalkyl or $C_3$–$C_{18}$cycloalkyl substituted by $C_1$–$C_{20}$alkyl, $OR_{11}$, $CF_3$ or halogen; $C_2$–$C_{18}$alkenyl; naphthyl, biphenylyl, anthracyl or an O—, S or N-containing 5- or 6-membered heterocyclic ring, where the radicals naphthyl, biphenylyl, anthracyl or O—, S— or N-containing 5- or 6-membered heterocyclic ring are unsubstituted or are substituted by halogen, $C_1$–$C_4$alkyl and/or $C_1$–$C_4$alkoxy;

or $Y_1$ is $OR_{11}$, $N(R_{16})(R_{17})$,

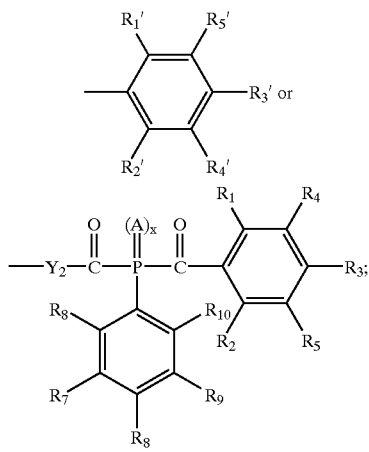

$Y_2$ is a direct bond, unsubstituted $C_1$–$C_{18}$alkylene or $C_1$–$C_{18}$alkylene substituted by phenyl; unsubstituted $C_4$–$C_{18}$-cycloalkylene or $C_4$–$C_{18}$cycloalkylene substituted by $C_1$–$C_{12}$alkyl, $OR_{11}$, halogen and/or phenyl; unsubstituted $C_5$–$C_{18}$cycloalkenylene or $C_5$–$C_{18}$cycloalkenylene substituted by $C_1$–$C_{12}$alkyl, $OR_{11}$, halogen and/or phenyl; unsubstituted phenylene or phenylene substituted one to four times by $C_1$–$C_{12}$alkyl, $OR_{11}$, halogen, —(CO)$OR_{14}$, —(CO)N$(R_{12})(R_{13})$ and/or phenyl;

or $Y_2$ is a radical

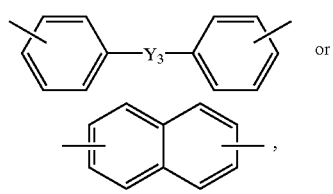

where these radicals are unsubstituted or are substituted one to four times on one or both aromatic ring(s) by $C_1$–$C_{12}$alkyl, $OR_{11}$, halogen and/or phenyl;

Y3 is O, S, SO, $SO_2$, $CH_2$, $C(CH_3)_2$, $CHCH_3$, $C(CF_3)_2$, (CO), or a direct bond;

$R_{12}$ and $R_{13}$ independently of one another are hydrogen, $C_1$–$C_{20}$alkyl, $C_3$–$C_8$cycloalkyl, phenyl, benzyl or $C_2$–$C_{20}$alkyl which is interrupted once or more than once by O or S and which is unsubstituted or substituted by OH and/or SH; or $R_{12}$ and $R_{13}$ together are $C_3$–$C_5$alkylene which optionally is interrupted by O, S or $NR_{14}$;

$R_{14}$ is hydrogen, phenyl, $C_1$–$C_{12}$alkyl or $C_2$–$C_{12}$alkyl which is interrupted once or more than once by O or S and which is unsubstituted or substituted by OH and/or SH;

$R_1'$ and $R_2'$ independently of one another have the same meanings as given for $R_1$ and $R_2$; and R$_3$', R$_4$' and R$_5$' independently of one another have the same meanings as given for R$_3$, R$_4$ and R$_5$; with the proviso that
if Y$_1$ is a radical

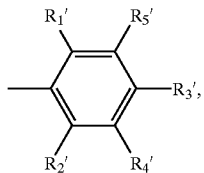

naphthyl, biphenylyl, anthracyl or an O—, S— or N-containing 5- or 6-membered heterocyclic ring, the benzoyl group made up by the Y$_1$ radical is not identical to the other benzoyl group on the phosphorus atom; and in formula (III)

A is O or S;
x is 1;
R$_6$, R$_7$, R$_8$, R$_9$ and R$_{10}$ independently of one another are hydrogen, C$_1$–C$_{20}$alkyl; C$_2$–C$_{20}$alkyl which is interrupted once or more than once by nonconsecutive O atoms and which is unsubstituted or substituted by OH and/or SH; or R$_6$, R$_7$, R$_8$, R$_9$ and R$_{10}$ are OR$_{11}$, halogen; or unsubstituted phenyl or phenyl substituted once or more than once by C$_1$–C$_4$alkyl;
R$_{11}$ is hydrogen, C$_1$–C$_{20}$alkyl, C$_2$–C$_{20}$alkenyl, C$_3$–C$_8$cycloalkyl, phenyl, benzyl or C$_2$–C$_{20}$alkyl which is interrupted once or more than once by nonconsecutive O atoms and which is unsubstituted or substituted by OH and/or SH;
Z$_1$ is C$_1$–C$_{24}$alkyl which is unsubstituted or substituted once or more than once by OR$_{15}$, SR$_{15}$, N(R$_{16}$)(R$_{17}$), phenyl, halogen, CN, NCO,

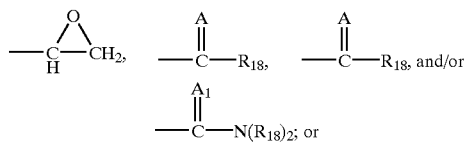

Z$_1$ is C$_2$–C$_{24}$alkyl which is interrupted once or more than once by O, S or NR$_{14}$ and which is unsubstituted or substituted by OR$_{15}$, SR$_{15}$, N(R$_{16}$)(R$_{17}$), phenyl, halogen,

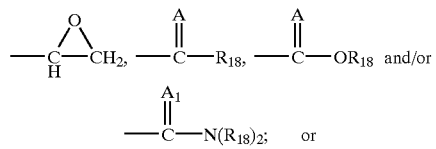

Z$_1$ is C$_1$–C$_{24}$alkoxy which is substituted once or more than once by phenyl, CN, NCO,

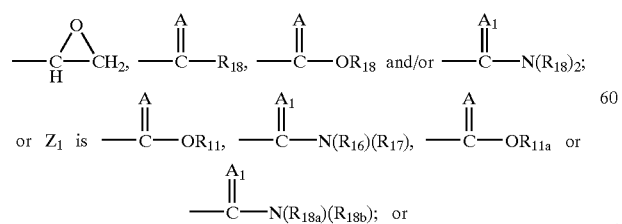

Z$_1$ is unsubstituted C$_3$–C$_{24}$-cycloalkyl or C$_3$–C$_{24}$cycloalkyl substituted by C$_1$–C$_{20}$alkyl, OR$_{11}$, CF$_3$ or halogen; or Z$_1$ is unsubstituted C$_2$–C$_{24}$alkenyl or C$_2$–C$_{24}$-alkenyl substituted by C$_6$–C$_{12}$aryl, CN, (CO)OR$_{15}$ or (CO)N(R$_{18}$)$_2$; or Z$_1$ is C$_3$–C$_{24}$cycloalkenyl or is one of the radicals

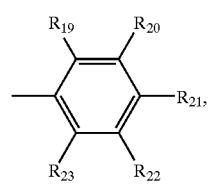
(f)

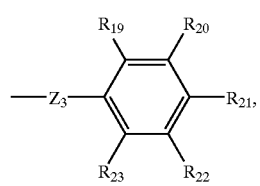
(g)

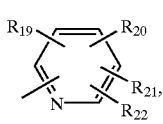
(h)

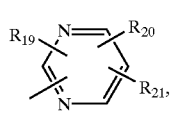
(i)

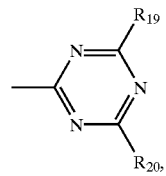
(k)

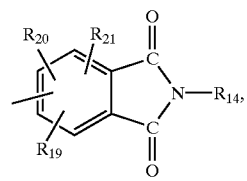
(l)

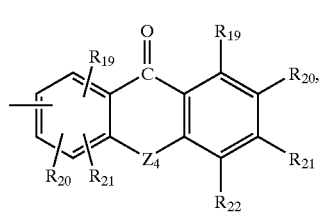
(m)

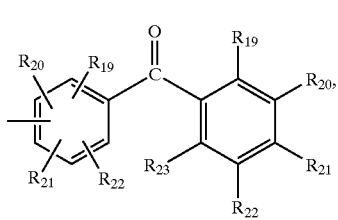
(n)

-continued

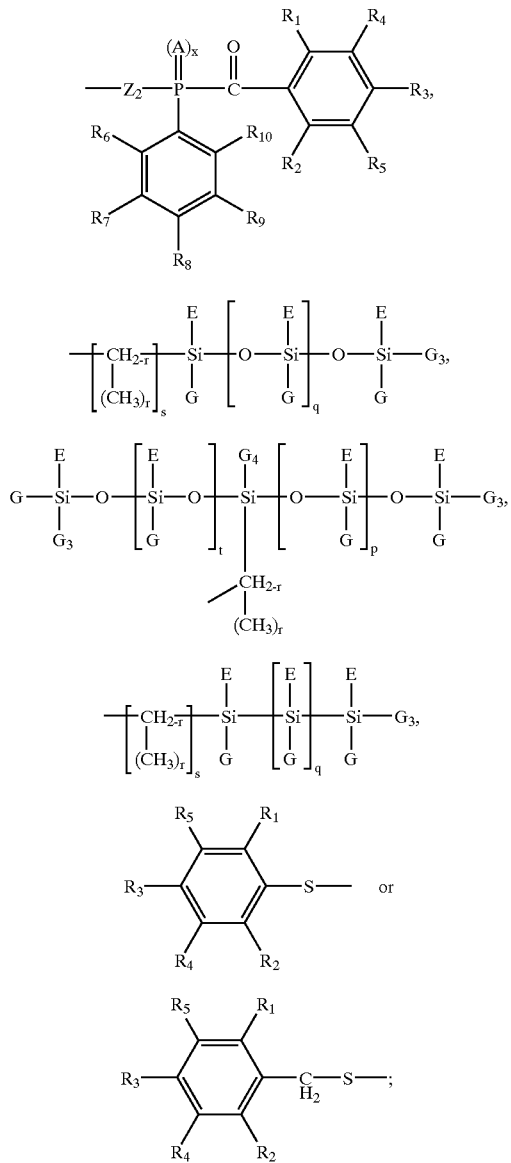

or $Z_1$ is $C_1$–$C_{24}$alkylthio, in which the alkyl radical is uninterrupted or is interrupted once or more than once by nonconsecutive O or S, and is unsubstituted or substituted by $OR_{15}$, $SR_{15}$ and/or halogen;

$A_1$ is O, S or $NR_{18a}$;

$Z_2$ is $C_1$–$C_{24}$alkylene; $C_2$–$C_{24}$alkylene interrupted once or more than once by O, S, or $NR_{14}$; $C_2$–$C_{24}$alkenylene, optionally interrupted once or more than once by O, S, or $NR_{14}$; $C_3$–$C_{24}$cycloalkylene, optionally interrupted once or more than once by O, S, or $NR_{14}$; $C_3$–$C_{24}$cycloalkenylene, optionally interrupted once or more than once by O, S, or $NR_{14}$;

where the radicals $C_1$–$C_{24}$alkylene, $C_2$–$C_{24}$alkylene, $C_2$–$C_{24}$alkenylene, $C_3$–$C_{24}$cycloalkylene and $C_3$–$C_{24}$cycloalkenylene are unsubstituted or are substituted by $OR_{11}$, $SR_{11}$, $N(R_{12})(R_{13})$ and/or halogen; or $Z_2$ is one of the radicals

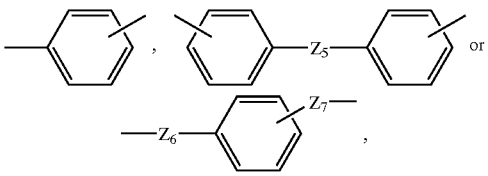

where these radicals are unsubstituted or are substituted on the aromatic ring by $C_1$–$C_{20}$alkyl; by $C_2$–$C_{20}$alkyl which is interrupted once or more than once by nonconsecutive O atoms and which is unsubstituted or substituted by OH and/or SH; or are substituted by $OR_{11}$, $SR_{11}$, $N(R_{12})(R_{13})$, phenyl, halogen, $NO_2$, CN, (CO)—$OR_{18}$, (CO)—$R_{18}$, (CO)—$N(R_{18})_2$, $SO_2R_{24}$, $OSO_2R_{24}$, $CF_3$ and/or $CCl_3$;

or $Z_2$ is a group $Z_3$ is $CH_2$, $CHCH_3$ or $C(CH_3)_2$;
$Z_4$ is S, O, $CH_2$, C=O, $NR_{14}$ or a direct bond;
$Z_5$ is S, O, $CH_2$, $CHCH_3$, $C(CH_3)_2$, $C(CF_3)_2$, CO, SO or $SO_2$;
$Z_6$ and $Z_7$ independently of one another are $CH_2$, $CHCH_3$ or $C(CH_3)_2$;
r is 0, 1 or 2;
s is a number from 1 to 12;
q is a number from 0 to 50;
t and p are each a number from 0 to 20;
E, G, $G_3$ and $G_4$ independently of one another are unsubstituted $C_1$–$C_{12}$alkyl or $C_1$–$C_{12}$alkyl substituted by halogen, or are unsubstituted phenyl or phenyl substituted by one or more $C_1$–$C_4$alkyl;
$R_{11a}$ is $C_1$–$C_{20}$alkyl substituted once or more than once by $OR_{15}$, halogen or $$-\underset{H}{\overset{O}{C}}-CH_2;$$

or is $C_2$–$C_{20}$alkyl interrupted once or more than once by nonconsecutive O atoms which optionally is substituted once or more than once by $OR_{15}$, halogen or $$-\underset{H}{\overset{O}{C}}-CH_2;$$

or is $C_2$–$C_{20}$alkenyl or $C_3$–$C_{12}$alkynyl; or is $C_3$–$C_{12}$cycloalkyl substituted once or more than once by $C_1$–$C_6$alkyl or halogen; or is unsubstituted $C_6$–$C_{12}$aryl or $C_6$–$C_{12}$aryl substituted once or more than once by halogen, $NO_2$, $C_1$–$C_6$alkyl, $OR_{11}$ or $C(O)OR_{18}$; or is $C_7$–$C_{16}$arylalkyl or $C_8$–$C_{16}$arylcycloalkyl;

$R_{14}$ is hydrogen, phenyl, $C_1$–$C_{12}$alkoxy, $C_1$–$C_{12}$alkyl or $C_2$–$C_{12}$alkyl which is interrupted once or more than once by O or S and which is unsubstituted or substituted by OH and/or SH;

$R_{15}$ has one of the meanings given for $R_{11}$ or is a radical

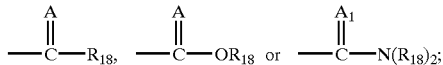

$R_{16}$ and $R_{17}$ independently of one another have one of the meanings given for $R_{12}$ or are a radical

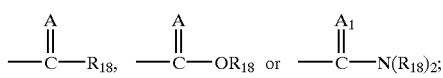

$R_{18}$ is hydrogen, $C_1$–$C_{24}$alkyl, $C_2$–$C_{12}$alkenyl, $C_3$–$C_8$cycloalkyl, phenyl, benzyl; $C_2$–$C_{20}$alkyl which is interrupted once or more than once by O or S and which is unsubstituted or substituted by OH;

$R_{18a}$ and $R_{18b}$ independently of one another are hydrogen, $C_1$–$C_{20}$alkyl which is substituted once or more than once by $OR_{15}$, halogen, styryl, methylstyryl, —N=C=A or

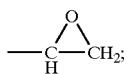

or are $C_2$–$C_{20}$alkyl which is interrupted once or more than once by nonconsecutive O atoms and which optionally is substituted once or more than once by $OR_{15}$, halogen, styryl, methylstyryl or

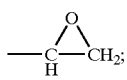

or are $C_2$–$C_{12}$alkenyl; or are $C_5$–$C_{12}$cycloalkyl substituted by —N=C=A or —$CH_2$—N=C=A and optionally additionally once or more than once substituted by $C_1$–$C_4$alkyl; or are $C_6$–$C_{12}$aryl optionally once or more than once substituted by halogen, $NO_2$, $C_1$–$C_6$alkyl, $C_2$–$C_4$alkenyl, $OR_{11}$, —N=C=A, —$CH_2$—N=C=A or $C(O)OR_{18}$; or are $C_7$–$C_{16}$arylalkyl; or both groups $R_{18a}$ and $R_{18b}$ together are $C_8$–$C_{16}$arylcycloalkyl; or $R_{18a}$ and $R_{18b}$ independently of one another are

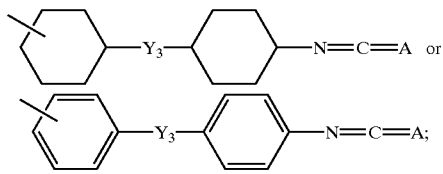

$Y_3$ is O, S, SO, $SO_2$, $CH_2$, $C(CH_3)_2$, $CHCH_3$, $C(CF_3)_2$, (CO), or a direct bond;

$R_{19}$, $R_{20}$, $R_{21}$, $R_{22}$ and $R_{23}$ have one of the meanings given for $R_6$ or are $NO_2$, CN, $SO_2R_{24}$, $OSO_2R_{24}$, $CF_3$, $CCl_3$ or halogen; and $R_{24}$ is $C_1$–$C_{12}$alkyl, halogen-substituted $C_1$–$C_{12}$alkyl, phenyl, or phenyl substituted by $OR_{15}$ and/or $SR_{15}$;

with the proviso that if $Z_1$ is a radical

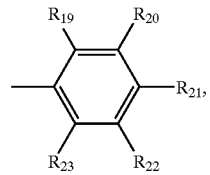

this is not identical to the other aromatic radical

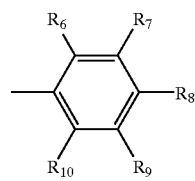

on the phosphorus atom.

2. A photocurable composition according to claim 1, comprising, in addition to components (a) and (b), further photoinitiators (c) and/or further additives (d).

3. A photocurable composition as claimed in claim 2, comprising, as further photoinitiator (c), at least one compound of the formula VIII, IX, X, XI

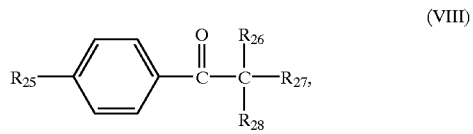
(VIII)

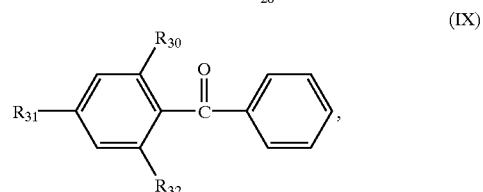
(IX)

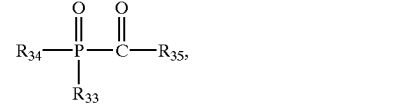
(X)

(XI)

in which $R_{25}$ is hydrogen, $C_1$–$C_{18}$alkyl, $C_1$–$C_{18}$alkoxy, —$OCH_2CH_2$—$OR_{29}$, morpholino, $SCH_3$;

a group

or a group

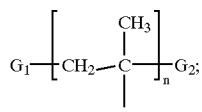

n has a value from 2 to 10;

$G_1$ and $G_2$ independently of one another are end-groups of the polymeric unit, in particular hydrogen or $CH_3$;

$R_{26}$ is hydroxyl, $C_1$–$C_{16}$alkoxy, morpholino, dimethylamino or —O(CH$_2$CH$_2$O)$_m$—C$_1$–C$_{16}$alkyl;

$R_{27}$ and $R_{28}$ independently of one another are hydrogen, $C_1$–$C_6$alkyl, phenyl, benzyl, $C_1$–$C_{16}$alkoxy or —O(CH$_2$CH$_2$O)$_m$—C$_1$–C$_{16}$alkyl, or $R_{27}$ and $R_{28}$ together with the carbon atom to which they are bonded form a cyclohexyl ring;

m is a number from 1–20;

where $R_{26}$, $R_{27}$ and $R_{28}$ are not all $C_1$–$C_{16}$alkoxy or —O(CH$_2$CH$_2$O)$_m$—C$_1$–C$_{16}$alkyl at the same time, and $R_{29}$ is hydrogen,

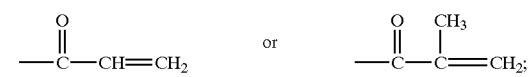

$R_{30}$ and $R_{32}$ independently of one another are hydrogen or methyl;

$R_{31}$ is hydrogen, methyl or phenylthio, where the phenyl ring of the phenylthio radical is unsubstituted or substituted by $C_1$–$C_4$alkyl in the 4-, 2-, 2,4- or 2,4,6- position;

$R_{33}$ and $R_{34}$ independently of one another are $C_1$–$C_{20}$alkyl, cyclohexyl, cyclopentyl, phenyl, naphthyl or biphenyl, where these radicals are unsubstituted or are substituted by halogen, $C_1$–$C_{12}$alkyl and/or $C_1$–$C_{12}$alkoxy, or $R_{33}$ is an S— or N-containing 5- or 6-membered heterocyclic ring, or are

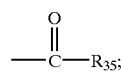

$R_{35}$ is cyclohexyl, cyclopentyl, phenyl, naphthyl or biphenyl, these radicals being unsubstituted or substituted by halogen, $C_1$–$C_4$alkyl and/or $C_1$–$C_4$alkoxy, or $R_{35}$ is an S— or N-containing 5- or 6-membered heterocyclic ring;

$R_{36}$ and $R_{37}$ independently of one another are unsubstituted cyclopentadienyl or cyclopentadienyl substituted once, twice or three times by $C_1$–$C_{18}$alkyl, $C_1$–$C_{18}$alkoxy, cyclopentyl, cyclohexyl or halogen; and $R_{38}$ and $R_{39}$ independently of one another are phenyl which is substituted in at least one of the two ortho positions relative to the titanium-carbon bond by fluorine atoms or $CF_3$, and which on the aromatic ring may contain, as further substituents, unsubstituted pyrrolinyl or pyrrolinyl substituted by one or two $C_1$–$C_{12}$alkyl, di($C_1$–$C_{12}$alkyl)aminomethyl, morpholinomethyl, $C_2$–$C_4$alkenyl, methoxymethyl, ethoxymethyl, trimethylsilyl, formyl, methoxy or phenyl; or polyoxaalkyl, or $R_{38}$ and $R_{39}$ are

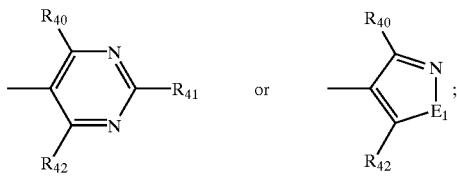

$R_{40}$, $R_{41}$ and $R_{42}$ independently of one another are hydrogen, halogen, $C_2$–$C_{12}$alkenyl, $C_1$–$C_{12}$alkoxy, $C_2$–$C_{12}$alkoxy interrupted by one to four O atoms, cyclohexyloxy, cyclopentyloxy, phenoxy, benzyloxy, unsubstituted phenyl or phenyl substituted by $C_1$–$C_4$alkoxy, halogen, phenylthio or $C_1$–$C_4$-alkylthio; or biphenyl, where $R_{40}$ and $R_{42}$ are not both hydrogen at the same time and in the radical

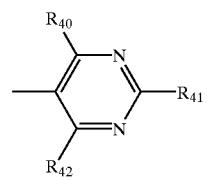

at least one radical $R_{40}$ or $R_{42}$ is $C_1$–$C_{12}$alkoxy, $C_2$–$C_{12}$alkoxy interrupted by one to four O atoms, cyclohexyloxy, cyclopentyloxy, phenoxy or benzyloxy;

$E_1$ is O, S or $NR_{43}$; and $R_{43}$ is $C_1$–$C_8$alkyl, phenyl or cyclohexyl.

4. A coated substrate which has been coated on at least one surface with a composition according to claim 1.

5. A process for the photographic production of relief images in which a coated substrate according to claim 4 is subjected to imagewise exposure and then the unexposed portions are removed with a solvent.

6. A composition according to claim 1, wherein the compounds of formula (II) and (III) in each formula (II) and (III)

Ar is a group

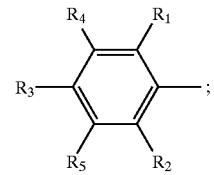

$R_1$ and $R_2$ independently of one another are $C_1$–$C_4$alkyl, $C_1$–$C_4$alkoxy or halogen;

$R_3$, $R_4$ and $R_5$ independently of one another are hydrogen or $C_1$–$C_4$alkyl;

$R_6$, $R_7$, $R_8$, $R_9$ and $R_{10}$ are hydrogen, $C_1$–$C_4$alkyl, $OR_{11}$ or phenyl;

$R_{11}$ is $C_1$–$C_4$alkyl, $C_2$–$C_8$alkenyl or benzyl;

in formula (II)

A is O or S;

x is 1;

$Y_1$ is $C_1$–$C_4$alkyl which is unsubstituted or substituted by one or more phenyl; or $Y_1$ is naphthyl, anthracyl, $OR_{11}$, $N(R_{16})(R_{17})$, $OR_{11a}$, $N(R_{18a})(R_{18b})$,

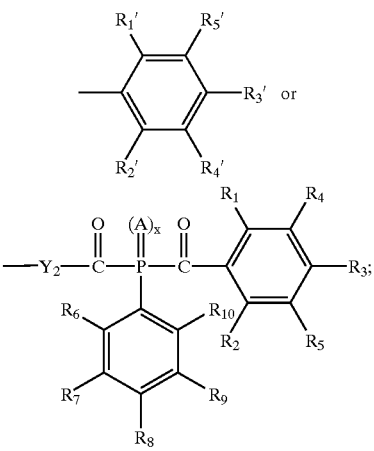

Y$_2$ is unsubstituted phenylene or phenylene substituted one to four times by C$_1$–C$_4$alkyl;

R$_1$' and R$_2$' independently of one another have the same meanings as given for R$_1$ and R$_2$; and R$_3$', R$_4$' and R$_5$' independently of one another have the same meanings as given for R$_3$, R$_4$ and R$_5$;

with the proviso that if Y$_1$ is a radical

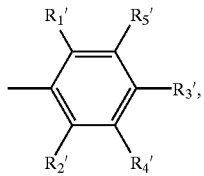

naphthyl or anthracyl, the benzoyl group made up by the Y$_1$ radical is not identical to the other benzoyl group on the phosphorus atom;

in formula (III)

A is O or S;

x is 1;

Z$_1$ is C$_1$–C$_{12}$alkyl; C$_1$–C$_4$alkyl which is substituted by phenyl, halogen or

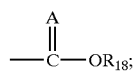

or Z$_1$ is unsubstituted C$_2$–C$_8$alkenyl or C$_2$–C$_8$alkenyl substituted by C$_6$–C$_{12}$aryl, CN (CO)OR$_{15}$ or (CO)N(R$_{18}$)$_2$ or (g)

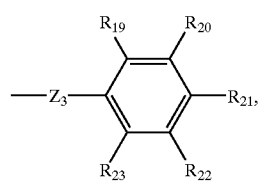

(h)

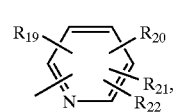

(k)

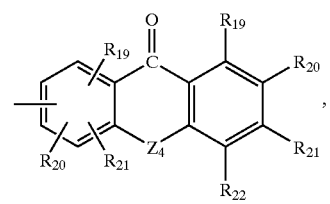

(m)

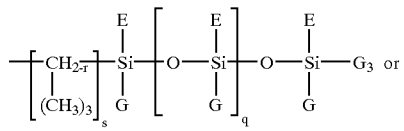

(p)

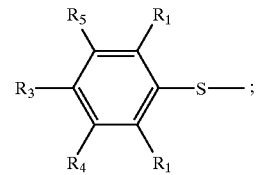

(v)

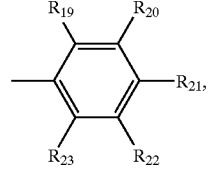

with the proviso that if Z$_1$ is a radical

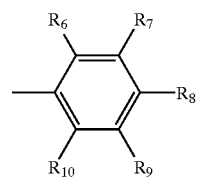

this is not identical to the other aromatic radical on the phosphorus atom;

Z$_3$ is CH$_2$;

Z$_4$ is S;

r is 0;

s is a number from 1 to 4;

q is a number from 0 to 4;

E, G, G$_3$ and G$_4$ independently of one another are unsubstituted C$_1$–C$_4$alkyl or are C$_1$–C$_4$alkyl substituted by chlorine;

R$_{11a}$ is C$_1$–C$_8$alkyl substituted by OR$_{15}$, halogen or

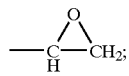

or is C$_2$–C$_6$alkenyl, C$_3$–C$_6$cycloalkyl or C$_7$–C$_{12}$arylalkyl; or is C$_6$–C$_{10}$aryl optionally once or more than once substituted by C$_1$–C$_4$alkyl;

R$_{15}$ is C$_1$–C$_8$alkyl or (CO)R$_{18}$;

R$_{16}$ and R$_{17}$ independently of one another are hydrogen, C$_1$–C$_8$alkyl; C$_2$–C$_6$alkenyl, C$_3$–C$_6$cycloalkyl, phenyl or benzyl; or R$_{16}$ and R$_{17}$ together are C$_3$–C$_5$alkylene optionally interrupted by O, S or NR$_{18}$;

R$_{18}$ is C$_1$–C$_8$alkyl or C$_1$–C$_8$alkenyl;

R$_{18a}$ and R$_{18b}$ independently of one another are C$_1$–C$_8$alkyl substituted by OR$_{15}$, halogen, —N=C=A or

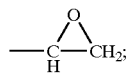

or are C$_2$–C$_8$alkenyl; or are C$_5$–C$_{12}$cycloalkyl substituted by —N=C=A or —CH$_2$—N=C=A and optionally additionally once or more than once substituted by methyl; or are C$_6$–C$_{10}$aryl optionally substituted by C$_1$–C$_4$alkyl and/or —N=C=A; or are C$_7$–C$_{12}$arylalkyl;

R$_{19}$, R$_{20}$, R$_{21}$, R$_{22}$ and R$_{23}$ are hydrogen, CF$_3$, CCl$_3$ or halogen.

7. A process for the photopolymerization of nonvolatile monomeric, oligomeric or polymeric compounds having at least one ethylenically unsaturated double bond, which comprises irradiating a composition according to claim 1 with light in the range from 200 to 600 nm.

8. A process according to claim 7 for the preparation of pigmented and nonpigmented surface coatings, printing inks, screen printing inks, offset printing inks, flexographic printing inks, powder coatings, printings plates, adhesives, dental materials, optical waveguides, optical switches, colour testing systems, composite materials, glass-fibre cable coatings, screen printing stencils, resist materials, colour filters, for the encapsulation of electrical and electronic components, for the preparation of magnetic recording materials, of three-dimensional objects by means of stereolithography, of photographic reproductions, image recording material, in particular for holographic recordings, for the preparation of decolouring materials, in particular decolouring materials for image recording materials, for the preparation of image recording materials using microcapsules.

* * * * *